US012691167B2

(12) United States Patent
Burkhardt et al.

(10) Patent No.: US 12,691,167 B2
(45) Date of Patent: *Jul. 28, 2026

(54) **PROTEINS AND IMMUNIZING COMPOSITIONS CONTAINING *KLEBSIELLA* PROTEINS AND METHODS OF USE**

(71) Applicant: VAXXINOVA US, INC., Willmar, MN (US)

(72) Inventors: Douglas T. Burkhardt, Dassel, MN (US); Daryll Emery, New London, MN (US); Darren Straub, New London, MN (US)

(73) Assignee: Vaxxinova US, Inc., Willmar, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,348

(22) Filed: Dec. 6, 2023

(65) Prior Publication Data

US 2024/0216494 A1 Jul. 4, 2024

Related U.S. Application Data

(63) Continuation of application No. 17/226,761, filed on Apr. 9, 2021, now Pat. No. 11,872,273, which is a continuation of application No. 15/741,574, filed as application No. PCT/US2016/041614 on Jul. 8, 2016, now Pat. No. 11,000,582.

(60) Provisional application No. 62/190,947, filed on Jul. 10, 2015.

(51) Int. Cl.
| | |
|---|---|
| *A61K 39/108* | (2006.01) |
| *A61K 39/00* | (2006.01) |
| *A61K 39/116* | (2006.01) |
| *A61K 39/40* | (2006.01) |
| *C07K 14/26* | (2006.01) |

(52) U.S. Cl.
CPC ........ *A61K 39/0266* (2013.01); *A61K 39/116* (2013.01); *A61K 39/40* (2013.01); *C07K 14/26* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 6,027,736 | A | 2/2000 | Emery |
| 6,610,836 | B1 | 8/2003 | Breton |
| 11,000,582 | B2 | 5/2021 | Burkhardt |
| 2005/0186217 | A1 | 8/2005 | Emery |

FOREIGN PATENT DOCUMENTS

| | | |
|---|---|---|
| CA | 2029906 A1 | 9/1990 |
| JP | 03143388 A | 6/1991 |
| WO | WO 90/11349 | 10/1990 |
| WO | WO 95/21627 | 8/1995 |
| WO | WO 96/01620 A1 | 1/1996 |
| WO | WO 01/37810 A2 | 5/2001 |
| WO | WO 02/053180 | 7/2002 |
| WO | WO 2006/088803 | 8/2006 |
| WO | WO 2008/135446 | 11/2008 |
| WO | WO 2010/111273 | 9/2010 |
| WO | WO 2011125015 A2 * | 10/2011 |

OTHER PUBLICATIONS

McGuinness et al. Lancet 337: 514-517, 1991.*
McGuinness et al. McGuiMol. Microbiol. 7: 505-514, 1993.*
Pajon et al. Infect. Immun. 80: 2667-2677, 2012.*
Ellis RW. Vaccines, (Eds) Plotkin et al., W.B. Saunders Company, Philadelphia, Chapter 29, 568-575, 1988.*
PCT Patent Application No. US2016/041614, filed Jul. 8, 2016; International Preliminary Report on Patentability issued Jan. 25, 2018; 15 pages.
PCT Patent Application No. US2016/041614, filed Jul. 8, 2016; International Search Report and Written Opinion issued Mar. 6, 2017; 27 pages.
Baghal et al., Production and Immunogenicity of Recombinant Ferric Enterobactin Protein (FepA), *International Journal of Infectious Diseases*, 14S (2010) pp. 166-170.
Biegel Carson et al., "Ferric Enterobactin Binding and Utilization by Neisseria Gonorrhoeae", Journal of Bacteriology, vol. 181, No. 9, May 1, 1999, pp. 2895-2901.
Bouchet et al., "Immunological Variants of the Aerobactin-Cloacin DF13 Outer Membrane Protein Receptor IUTA Among Enteric Bacteria", *Infection and Immunity*, vol. 62, No. 7, Jul. 1, 1994, pp. 3017-3021.
Boulianne, "Production of functional chimaeric mouse/human antibody" 1984 *Nature*, 312(5995):643-6.
Brisse, "The genus *Klebsiella*" in Dworkin, Ed., *The prokaryotes*, 3rd ed, vol. 6, Springer: New York, NY; 2006. Cover page, title page, table of contents, pp. 159-196.
Bruggeman, "Production of human antibody repertoires in transgenic mice" 1997 *Curr. Opin. Biotechnol.*, 8(4):455-8.
Budzikiewicz, "Siderophore from bacteria and from fungi" in *Iron uptake and homeostasis in Microorganisms. 1st ed.*, Cornelis , ed., Caister Academic Press: Poole, UK; 2010. Cover page, publisher's page, and Chapter 1.
Chander, "Differentiation of Klebsiella pneumoniae and Klebsiella oxytoca by multiplex poly-merase chain reaction" 2011 *Intern J Appl Res Vet Med.*, 9:138-142.
Cryz, "Experimental Klebsiella pneumoniae burn wound sepsis: role of capsular polysaccharide" Jan. 1984 *J Infect Dis*, 150(1):817-822.

(Continued)

*Primary Examiner* — S. Devi

(74) *Attorney, Agent, or Firm* — Mueting Raasch Group

(57) ABSTRACT

Provided herein are isolated proteins isolatable from a *Klebsiella* spp. Also provided are compositions that include one or more of the proteins, and methods for making and methods for using the proteins.

2 Claims, 33 Drawing Sheets

Specification includes a Sequence Listing.

(56) References Cited

OTHER PUBLICATIONS

Cryz, "Purification and vaccine potential of Klebsiella capsular polysaccharides" 1985 *Infect Immun*, 50:225-230.
Cryz, "Seroepidemiology of Klebsiella bacteremic isolates and implications for vaccine development" 1986 *J Clin Microbiol*, 23:687-690.
Daugherty, "Polymerase chain reaction facilitates the cloning, CDR grafting, and rapid expression of a murine monoclonal antibody directed against the CD18 component of leukocyte integrins" 1991 *Nucleic Acids Res.*, 19(9): 2471-6.
Goujon, "A new bioinformatics analysis tools framework at EMBL-EBI" 2010 Nucleic acids research Jul. 2010, 38 Suppl: W695-9.
Greenspan et al., Nature Biotechnology 17: 936-937, 1999.
Grohn, "Effect of pathogen-specific clinical mastitis on milk yield in dairy cows" 2004 *J. Dairy Sci.*, 87:3358-3374.
Harlow, Ed., *Antibodies, A Laboratory Manual*, Cold Spring Harbor Laboratory: Cold Spring Harbor, NY; 1988. Cover page, title page, table of contents, and Chapter 5.
Hoblet, "Costs associated with selected preventive practices and with episodes of clinical mastitis in nine herds with low somatic cell counts" Jul. 1991 *J. Am Vet Med. Assoc.*, 199(2):190-196.
Hogan et al., "Iron Uptake and Growth Responses by *Escherichia coli* Cultured with Antibodies from Cows Immunized with High Affinity Ferric Receptors," Mastitis in Dairy Production: Current Knowledge and Future Solutions Wageningen Academic Publishers, Postbus 220, 6700 AE Wageningen, Netherlands, 4th IDF International Mastitis Conference, Maastricht, Netherlands, Jun. 12-15, 2005, pp. 297-301.
Houghten et al., New Approaches to Immunization, Vaccine86, Cold Spring Harbor Laboratory, pp. 21-25, 1986.
Jeannin, "Outer membrane protein A (OmpA): a new pathogen-associated molecular pattern that interacts with antigen presenting cells-impact on vaccine strategies" 2002 *Vaccine 20*, Suppl. 4: A23-A27.
Jones, "Replacing the complementarity-determining regions in a human antibody with those from a mouse" 1986 *Nature*, 321(6069):522-5.
Jurkevitch, "Differential Siderophore Utilization and Iron Uptake by Soil and Rhizosphere Bacteria" 1992 *Appl Environ Microbiol.*, 58(1):119.
Keler, "Metachromatic Assay for the Quantitative Determination of Bacterial Endotoxins" 1986 *Analyt. Biochem.*, 156, 189.
Kurupati et al., "Identification of Vaccine Candidate Antigens of an ESBL Producing *Klebsiella pneumoniae* Clinical Strain by Immunoproteome Analysis," *Proteomics*, (2006), 6, pp. 836-844.
Kurupati, "Protective Efficacy of DNA Vaccines Encoding Outer Membrane Protein A and OmpK36 of Klebsiella pneumoniae in Mice" Jan. 2011 *Clinical Vaccine Immunol.*, 18(1):82-88.
Lazar et al., Mol. Cellular Biol. 8: 1247-1252, 1988.
Libon, "*Streptococcus pneumoniae* polysaccharides conjugated to the outer membrane protein A from Klebsiella pneumoniae elicit protective antibodies" May 2002 *Vaccine*, 20:2174-2180.
Lin et al., "Immunization of Cows with Ferric Enterobactin Receptor from Coliform Bacteria," *Journal of Dairy Science*, American Dairy Science Association, U.S., vol. 81, No. 8, (1998), pp. 2151-2158.
Lin et al., "Inhibition of In Vitro Growth of Coliform Bacteria by a Monoclonal Antibody Directed Against Ferric Enterobactin Receptor FepA", *Journal of Dairy Science*, vol. 81, No. 5, May 1, 1998, pp. 1267-1274.
Lobuglio, "Mouse/human chimeric monoclonal antibody in man: Kinetics and immune response" Jun. 1989 *Proc. Natl. Acad. Sci. USA*, 86(11):4220-4.
Lodge, "Influence of Growth Rate and Iron Limitation on the Expression of Outer Membrane Proteins and Enterobactin by Klebsiella pneumoniae Grown in Continuous Culture" Feb. 1986 *Journal of Bacteriology*, 165(2):353-356.
Lonberg, "Antigen-specific human antibodies from mice comprising four distinct genetic modifications" 1994 *Nature*, 368:856-9.

Lonberg, "Human Antibodies from Transgenic Mice" 1995 *Int. Rev. Immunol.*, 13(1):65-93.
Lundberg, "Identification and characterization of antigens as vaccine candidates against Klebsiella pneumoniae" 2013, *Human Vaccines Immunotherapeutics*, 9(3):497-505.
Lyczak, "Lung infections associated with cystic fibrosis" 2002 *Clinical microbiology reviews* 15.2:194-222.
Meno, "The Surface Hydrophobicity and Avirulent Character of an Encapsulated Strain of Klebsiella pneumoniae" 1991 *Microbiol. Immuniol.*, 35(10):841-848.
Miethke, "Siderophore-based iron acquisition and pathogen control" 2007 *Microbiol Mol Rev*, 71(3):413-451.
Morrison, "Chimeric human antibody molecules: Mouse antigen-binding domains with human constant region domains" 1984 *Proc. Natl. Acad. Sci. USA*, 81(21):6851-5.
Murphy et el., "Surface Topology of the *Escherichia coli* K-12 Ferric Enterobactin Receptor", *Journal of Bacteriology*, vol. 172, No. 5, May 1, 1990, pp. 2736-2746.
Nikaido, "Outer Membrane" in: *Escherichia coli* and *Salmonella typhimurium*, Cellular and Molecular Biology, Neidhardt, (ed.); American Society for Microbiology: Washington, D.C.; 1987. Cover page, title page, table of contents, and pp. 7-22.
Parchuri, "Extended spectrum beta-lactamase-producing Klebsiella pneumoniae chronic ambulatory peritoneal dialysis peritonitis treated successfully with polymyxin B" 2005 *Heart lung*, 5:360-363.
Perkins, "Probability-based protein identification by searching sequence databases using mass spectrometry data" 1999 *Electrophoresis* 20, 3551-3567.
Pinzon-Sanchez, "Decision tree analysis of treatment strategies for mild and moderate cases of clinical mastitis occurring in early lactation" 2011 *J. Dairy Sci.*, 94:1873-1892.
Podschun, "*Klebsiella* spp. as nosocomial pathogens: epidemiology, taxonomy, typing methods, and pathogenicity factors" 1998 *Clin. Microbiol. Rev.* 11(4):589-603.
Queen, "A humanized antibody that binds to the interleukin 2 receptor" 1989 *Proc. Natl. Acad. Sci. USA*, 86(24):10029-33.
Rabsch, "Role of Receptor Proteins for Enterobactin and 2,3-Dihydroxybenzoylserine in Virulence of *Salmonella enterica*" Dec. 2003 *Infect Immun.*, 12:6953-6961.
Riechmann, "Reshaping human antibodies for therapy" 1988 *Nature*, 332(6162):323-7.
Roberts et al., "Inhibition of Biological Activities of the Aerobactin Receptor Protein in Rough Strains of *Escherichia coli* by Polyclonal Antiserum Raised Against Native Protein", Journal of General Microbiology, vol. 135, Jan. 1, 1989, pp. 2387-2398.
Rudinger et al., In: Peptide Hormones. (Ed) JA Parsons, University Park Press, pp. 1-7, 1979.
Sanchez, Jan. 2013 *Emerg Infect Dis.*, 19(1):133-6.
Shand, "In Vivo Evidence That Bacteria in Urinary Tract Infection Grow Under Iron-Restricted Conditions" Apr. 1985 *Infection and Immunity*, 48(1):35-39.
Sievers, "Fast, scalable generation of high-quality protein multiple sequence alignments using Clustal Omega" *Molecular Systems Biology* 7:539.
Skolnick et al., Trends in Biotechnology, 18: 34-39, 2000.
Stamm, "Comparison of endemic and epidemic nosocomial infections" in Dixon (ed.), *Nosocomial infections*, Yorke Medical Books: Atlanta, GA; 1981. Cover page, title page, table of contents, and pp. 9-13.
Tatusova, "Blast 2 Sequences, a new tool for comparing protein and nucleotide sequences" 1999 *FEMS Microbiol Lett*, 174, 247-250.
Taylor, "A transgenic mouse that expresses a diversity of human sequence heavy and light chain immunoglobulins" Dec. 1992 *Nucleic Acids Res.*, 20:6287-94.
Toky, "Establishment of a sepsis model following implantation of Klebsiella pneumoniae-infected fibrin clot into the peritoneal cavity of mice" 2003 *Folia Microbiol (Praha)*, 48(5):665-669.
Traxler. "Interspecies modulation of bacterial development through iron competition and siderophore piracy" Nov. 2012 *Mol. Microbiol.*, 86:628-644.
Tuntufye et al., *Escherichia coli* Ghosts or Live *E. coli* Expressing the Ferri-Siderophore Receptors FepA, FhuE, IroN and IutA Do Not

(56)          References Cited

OTHER PUBLICATIONS

Protect Boiler Chickens Against Avian Pathogenic *E. coli* (APEC), *Veterinary Microbiology*, 159 (2012) pp. 470-478.

Ueda, "In Vitro and In Vivo Antibacterial Activities of SM-216601, a New Broad-Spectrum Parenteral Carbapenem" Oct. 2005 *Antimicrob Agents Chemother*, 49:4185-4196.

Vered, "Susceptibility to klebsiella pneumonaie infection in collaborative cross mice is a complex trait controlled by at least three loci acting at different time points" 2014, *BMC Genomics*, 15:865.

Verhoeyen, "Reshaping human antibodies: grafting an antilysozyme activity" 1988 *Science*, 239(4847):1534-6.

Watson, Ed., *Endotoxins and Their Detection With the Limulus Amebocyte Lystate Test*, Alan R. Liss, Inc.: New York, NY; 1982. Cover page, title page and table of contents.

Williams, "Expression of high affinity iron uptake systems by clinical isolates of Klebsiella" Nov. 1987 *FEMS Microbiol Lett.*, 44:407-412.

Wolf et al., "Iron Uptake by *Escherichia coli* Cultured with Antibodies from Cows Immunized with High-Affinity Ferric Receptors," *Journal of Dairy Science*, 87 (2004) pp. 2103-2107.

Wu, "Identification of a novel cephalosporinase (DHA-3) in Klebsiella pneumoniae isolated in Taiwan" 2005 *Clin Microbiol Infect*, 11: 893-897.

Yadav, "Lipopolysaccharide-mediated protection againstKlebsiella pneumoniae-induced lobar pneumonia: Intranasalvs. intramuscular route of immunization" Jan. 2005 *Folia Microbiologica*, 50:83-86.

Yu, "Virulence characteristics of Klebsiella and clinical manifestations of K. pneumoniae bloodstream infections" 2007 *Emerg. Inf. Dis.* 13:986-993.

Zhou et al., "Binding Characterization of the Iron Transport Receptor from the Outer Membrane of *Escherichia coli* (FepA): Differentiation Between FepA and FecA", Biometals, vol. 8, No. 2, Apr. 1, 1995, pp. 129-136.

Chu et al., "Siderphore Uptake in Bacteria and the Battle for Iron with the Host; a Bird's Eye View," Biometals (2010) 23:601-611.

Office Action issued in Mexico for Application No. MX/a/2018/000395 dated Aug. 22, 2022 (7 pages).

* cited by examiner

| Organism | Target Gene | Product Size (bp) |
|---|---|---|
| *Klebsiella oxytoca* | pehX | 343 |
| *Klebsiella pneumoniae* | rpoB | 108 |

SDS-PAGE

Western Blot

Fig. 7

| Klebsiella pneumoniae 1571 FecA (Ferric Citrate Receptor) Gene Sequence. SEQ ID NO:1 |
|---|
| ATGACGCCGTTACGCGTTTTTCGTAAAACAACTCCTTTGGTTAACGCCATTCGCCTGAGCCTGCTGCCGCTGGCC<br>GGTCTCTCGTTTTCCGCTTTTGCTGCACAGGTTGATATCGCACCGGGGATCGCTCGACAAAGCGCTCAATCAGTAT<br>GCCGCACACAGCGGAATTACCCTCTCGGTTGACGCCAGCCTGACGCGCGGCAAGCAGAGCAACGGCCTGCACGGA<br>GATTACGACGTCGAGAGCGGCCTGCAACAGCTGCTGGACGGCAGCGGACTGCAGGTAAAACCGCTGGGAAATAAC<br>AGCTGGACGCTGGAGCCCGCGCCCGCGCCAAAAGAAGATGCCCTGACCGTGGTCGGCGACTGGCTGGGCGATGCG<br>CGTGAAAACGACGTATTTGAACATGCTGGCGCGCGTGACGTGATCCGCCGTGAGGATTTCGCCAAAACCGGCGCA<br>ACCACCATGCGTGAGGTGCTTAACCGCATCCCTGGCGTCAGCGCGCCGGAAAACAACGGCACCGGCAGCCACGAC<br>CTGGCGATGAACTTTGGCATCCGGGGCCTGAACCCACGCCTCGCCAGCCGCTCGACCGTCCTGATGGACGGCATC<br>CCCGTCCCCTTTGCCCCTTACGGTCAGCCGCAGCTTTCACTGGCTCCCGTTTCGCTCGGCAACATGGATGCCATT<br>GACGTGGTGCGCGGTGGTGGTGCGGTGCGTTACGGACCGCAGAGCGTGGGCGGCGTGGTGAACTTTGTTACCCGC<br>GCCATTCCGCAGGACTTTGGTATCGAGGCGGGGGTGGAAGGTCAGCTCAGCCCAACCTCTTCACAAAACAACCCG<br>AAAGAGACGCACAACCTGATGGTGGGCGGCACAGCGGACAACGGTTTTGGCACCGCGCTGCTCTACTCCGGCACG<br>CGCGGCAGTGACTGGCGCGAGCACAGCGCCACCCGCATCGACGACCTGATGCTGAAAAGCAAATATGCGCCGAAT<br>GAGGTGCACACCTTCAACAGCCTGCTGCAATATTACGATGGTGAAGCCGACATGCCCGGCGGCCTGTCCGCGCG<br>GATTACGACGCCGATCGCTGGCAATCCACCCGCCCGTATGACCGCTTCTGGGGCCGTCGCAAGCTGGCGAGCCTG<br>GGCTACCAGTTCCAGCCGGACAGCCAGCATAAATTCAACATTCTGGGGTTCTACACCCAAACCCTGCGCAGCGGC<br>TACCTGGAGCAAGGCAAACGCATCACCCTCTCGCCGCGTAACTACTGGGTGCGCGGTATTGAGCCACGCTACAGC<br>CAGAGCTTTATGATCGGCCCTTCCGCGCACGAAGTGGGCGTGGGCTATCGCTATGTGAATGAATCAACGCATGAA<br>ATGCGTTACTACACCGCCACCAGCAGCGGGCAGTTGCCGTCCGGCTCAAGCCCTTACGACCGCGACACGCGTTCC<br>GGCACCGAGGCGCACGCCTGGTATCTGGATGACAAAATCGACATCGGCAACTGGACCATCACGCCGGGTATGCGT<br>TTCGAACATATCGAGTCATACCAGAACAACGCCATCAAAGGCACGCACGAAGAGGTAAGCTATAACGCACCGCTT<br>CCGGCGTTGAACGTGCTCTATCACCTGACTGACAGCTGGAATCTTTATGCAAACACTGAAGGCTCGTTCGGCACC<br>GTACAGTACAGCCAGATTGGCAAGGCTGTGCAAAGCGGCAATGTGGAACCGGAAAAAGCGCGAACCTGGGAACTC<br>GGTACCCGCTACGACGACGGCGCGCTGACGGCGGAAATGGGGCTGTTCCTGATTAACTTTAACAATCAGTACGAC<br>TCCAACCAGACCAACGACACCGTCACTGCACGTGGCAAAACGCGCCATACCGGGCTGGAAACGCAGGCACGTTAC<br>GACCTGGGTACGCTAACGCCAACGCTTGATAACGTTTCCGTCTACGCCAGCTATGCGTATGTGAACGCGGAAATC<br>CGCGAGAAAGGCGACACCTATGGCAATCAGGTGCCATTCTCCCCGAAACATAAAGGCACGCTGGGCGTGGACTAC<br>AAGCCGGGCAACTGGACGTTCAATCTGAACAGCGATTTCCAGTCCAGCCAGTTTGCGGATAACGCCAATACGGTG<br>AAAGAGAGCGCCGACGGCAGTACCGGCCGCATTCCCGGCTTCATGCTCTGGGGCGCACGCGTGGCGTATGACTTT<br>GGCCCGCAGATGGCAGATCTGAACCTGGCGTTCGGTGTGAAAAACATCTTCGACCAGGACTACTTCATCCGCTCT<br>TATGACGACAACAACAAAGGCATCTACGCAGGCCAGCCGCGCACGCTGTATATGCAGGGTCGTTGAAGTTCTGA |
| Klebsiella pneumoniae 1571 FecA (Ferric Citrate Receptor) AA Sequence, SEQ ID NO:2. Underlined sequence is the signal sequence. Sequence of protein without signal sequence is SEQ ID NO:41, and the calculated molecular weight is 81.6 kDa. |
| MTPLRVFRKTTPLVNAIRLSLLPLAGLSFSAFAAQVDIAPGSLDKALNQYAAHSGITLSVDASLTRGKQSNGLHG<br>DYDVESGLQQLLDGSGLQVKPLGNNSWTLEPAPAPKEDALTVVGDWLGDARENDVFEHAGARDVIRREDFAKTGA<br>TTMREVLNRIPGVSAPENNGTGSHDLAMNFGIRGLNPRLASRSTVLMDGIPVPFAPYGQPQLSLAPVSLGNMDAI<br>DVVRGGAVRYGPQSVGGVVNFVTRAIPQDFGIEAGVEGQLSPTSSQNNPKETHNLMVGGTADNGFGTALLYSGT<br>RGSDWREHSATRIDDLMLKSKYAPNEVHTFNSLLQYYDGEADMPGGLSRADYDADRWQSTRPYDRFWGRRKLASL<br>GYQFQPDSQHKFNILGFYTQTLRSGYLEQGKRITLSPRNYWVRGIEPRYSQSFMIGPSAHEVGVGYRYVNESTHE<br>MRYYTATSSGQLPSGSSPYDRDTRSGTEAHAWYLDDKIDIGNWTITPGMRFEHIESYQNNAIKGTHEEVSYNAPL<br>PALNVLYHLTDSWNLYANTEGSFGTVQYSQIGKAVQSGNVEPEKARTWELGTRYDDGALTAEMGLFLINFNNQYD<br>SNQTNDTVTARGKTRHTGLETQARYDLGTLTPTLDNVSVYASYAYVNAEIREKGDTYGNQVPFSPKHKGTLGVDY<br>KPGNWTFNLNSDFQSSQFADNANTVKESADGSTGRIPGFMLWGARVAYDFGPQMADLNLAFGVKNIFDQDYFIRS<br>YDDNNKGIYAGQPRTLYMQGSLKF |

Fig. 8

| Klebsiella pneumoniae 1571 FhuA (Ferrichrome Receptor) Gene Sequence. SEQ ID NO:3. |
|---|
| ATGGCGCGTCCAAAAACTGCTCAGCCAAATCACTCGCTGCGTAAAGTCGCAGCTGTAGTAGCCACGGCGGTTAGC<br>GGCATGTCTGTCTACGCACAGGCAGCAGAACAACCGAAGCAAGAAGAAACCATCACCGTCGTTGCCGCCCCGGCC<br>GCCCAGGAAAACGCCTGGGGACCGGCGCCGACTATCGCGGCAAAACGCTCCGCCACGGCGACCAAAACCGATACC<br>CCGATTGAAAAAACGCCGCAGTCTGTGTCGGTGGTGACGCGCCATGAGATGGAGATGCGCCAGCCGACGACGGTA<br>AAAGAGGCGCTCTCCTATACGCCAAGCGTCTTCTCCACTCGCGGCAGTTCGACCACCTATGACGTGGTCACCATT<br>CGCGGCTTCACCACCTCGACGACCGTCAACACCAACCAGTATCTGGACGGCATGAAGCTGCAGGGGAATAACTAC<br>TCTGAAGTCTCCATGGATCCTTACTTCCTCGAGCGTGTGGAAGTGATGCGCGGGCCAACCTCGGTGCTGTACGGC<br>AACAGCAACCCGGGCGGTATCGTCAGCATGGTCAGCAAGCGCCCGACTACCGAGCCGCTGAAAGAAGTGCAGTTT<br>AAGATGGGCACCGACAATCTGTGGCAGACCGGGTTTGACTTTAGCGACGCCATTGATGATGCCGGCGTCTGGTCG<br>TATCGCCTGACCGGCCTTGGCCGCAGTCAGGATGCCCAGCAGCAGATGGCGAAATCGACTCGCTACGCGGTGGCG<br>CCCTCCTTTAGCTGGCGTCCGGACGATAAAACCGACTTCACCTTCCTGAGCAACTTCCAGAATGACCCGGATGCG<br>GGCTACTACGGCTGGCTGCCGCGCGAAGGCACCGTGGTGCCGTATTACGACGCCAACGGTAAGGCGCACAAGCTG<br>CCGACCGATTTCAACGAAGGCGAGTCCGATAATAAAATCTCCCGCCGCCAGAAGATGGTGGGCTACAGCTTCTCC<br>CATCAGTTCGATGACACCTTTACCGTGCGGCAGAACCTGCGCTATGCCGATGTGCATACGCTCTATCGTTCGGTA<br>TACGGCAACGGCTATGTCGCGCCGGGCTACATGAATCGCGCCTACGTGCGCTCCGACGAGCACCTGAACACCTTC<br>ACCGTCGATACCCAGCTGCAGTCTGATTTCGCCACCGGCGCGGTCAGCCATACGCTGCTGACCGGCGTGGACTAC<br>TCGCGGATGCGTAACGATGTGGATGCCGACTACGGGACGGCGGATCCTATCAGCATGAGCAATCCGCAGTACGGC<br>AATCCGAATATTCAGGTCACCTTCCCGTACGCGGTCCTCAACCGGATGGAGCAGACCGGCCTGTACGCGCAGGAT<br>CAGATGGAGTGGGATAAATGGGTGATGACCCTGGGCGGCCGTTACGATTACGCCACGACCTCAACGTTAACCCGC<br>GCCACCAACAGCCTGGCGGAGAATCACGACCAGCAGTTCAGCTGGCGCGGCGGCATCAACTACCTGTTCGATAAC<br>GGCATCTCGCCGTACTTCAGCTACAGCGAATCGTTTGAACCGGTATCGGGTTCCAACAGCCGCGGCCAGCCGTTC<br>GATCCGTCGCGCGGTAAGCAGTATGAAGCCGGCGTGAAATACGTGCCGAAAGATATGCCGGTGGTGGTCACCGCG<br>GCGGTCTATCAGCTGACCAAAGACAAGAACCTGACGGCTGATCCGGCTAACCAGGCGTTCAGCATCCAGACCGGC<br>GAGATCCGCTCCCGCGGCCTTGAGCTGGAGGCGAAGGCGGCGGTGAACGCCAATATTAACGTCACCGCGGCCTAC<br>AGCTACACCGATGCGGAGTACACTCACGATACGGTGTTCAACGGCAAACGTCCGGCGGAAGTGCCGCGTAACATG<br>GCCTCCCTGTGGGCGGATTATACCTTCCACGAAACCGCGCTGAGCGGTCTGACGATTGGGGCCGGGGCGCGCTAT<br>ATCGGTTCAACGGTCAGCTACTACAAAAATGACACCAGCACCGGTAAGAAAAATGATGCCTTTAGTGTGGCCGGT<br>TATGCGCTGATGGATGCGACGGTGAAATACGATCTGGCGCGCTTTGGCCTGCCGGGATCGTCGGTCGGCGTCAAC<br>GTCAACAACCTGTTCGACCGCGAATATGTCTCCAGTTGCTACAGCGAATACGCCTGCTACTGGGGCGCCGGACGT<br>CAGGTCGTCGCCACCGCCACCTTCCGTTTCTAA |
| Klebsiella pneumoniae 1571 FhuA (Ferrichrome Receptor) AA Sequence, 735 aa, SEQ ID NO:4. Underlined sequence is the signal sequence. Sequence of protein without signal sequence is SEQ ID NO:42, and the calculated molecular weight is 78 kDa. |
| <u>MARPKTAQPNHSLRKVAAVVATAVSGMSVYAQAAEQPKQEET</u>ITVVAAPAAQENAWGPAPTIAAKRSATATKTDT<br>PIEKTPQSVSVVTRHEMEMRQPTTVKEALSYTPSVFSTRGSSTTYDVVTIRGFTTSTTVNTNQYLDGMKLQGNNY<br>SEVSMDPYFLERVEVMRGPTSVLYGNSNPGGIVSMVSKRPTTEPLKEVQFKMGTDNLWQTGFDFSDAIDDAGVWS<br>YRLTGLGRSQDAQQQMAKSTRYAVAPSFSWRPDDKTDFTFLSNFQNDPDAGYYGWLPREGTVVPYYDANGKAHKL<br>PTDFNEGESDNKISRRQKMVGYSFSHQFDDTFTVRQNLRYADVHTLYRSVYGNGYVAPGYMNRAYVRSDEHLNTF<br>TVDTQLQSDFATGAVSHTLLTGVDYSRMRNDVDADYGTADPISMSNPQYGNPNIQVTFPYAVLNRMEQTGLYAQD<br>QMEWDKWVMTLGGRYDYATTSTLTRATNSLAENHDQQFSWRGGINYLFDNGISPYFSYSESFEPVSGSNSRGQPF<br>DPSRGKQYEAGVKYVPKDMPVVVTAAVYQLTKDKNLTADPANQAFSIQTGEIRSRGLELEAKAAVNANINVTAAY<br>SYTDAEYTHDTVFNGKRPAEVPRNMASLWADYTFHETALSGLTIGAGARYIGSTVSYYKNDTSTGKKNDAFSVAG<br>YALMDATVKYDLARFGLPGSSVGVNVNNLFDREYVSSCYSEYACYWGAGRQVVATATFRF |

Fig. 9

| Table 5.  Klebsiella pneumoniae 1571 CirA (Colicin I Receptor) Gene Sequence. SEQ ID NO:5. |
|---|
| ATGTTCAGGTTAAACCCTTTTATCCGGGCGGGATTGTCTGCGTCCGTCGTATCGTTGGCGTTTCCGGCTCTGGCC<br>GATGTGAATGAAGAAACGCTGGTGGTGACCGCCTCGGCCACTGAACAGAATGTCAAAGACGCGCCGGCGAGCATC<br>AGCGTCATCACCCAACAGGATTTACAACGCAAGCCTGTTCAGAACCTGAAAGACGTGCTGCGCGATGTGCCTGGG<br>GTCCAGCTCACCAACGAAGGGGATAACCGCAAGGGCGTTAGCATCCGCGGTCTGAGCAGCAGCTATACCCTGATC<br>CTGGTCGACGGCAAGCGCGTTAACTCGCGGAACGCCGTCTTCCGCCACAATGACTTCGACCTTAACTGGATCCCG<br>GTGGATGCTATTGAGCGTATCGAAGTGGTGCGCGGCCCGATGTCCTCCCTTTACGGCTCCGATGCGCTCGGTGGG<br>GTGGTCAACATTATTACCAAAAAAATCGGCCAGAAATGGACCGGGACGCTGAGTGCTGATACCACTATTCAGGAG<br>CACCGCGATCGCGGGGATACCTATAACGGCCAGTTCTTCACCAGCGGCCCGCTGATCGACGGCGTACTTGGAATG<br>AAGGCCTACGGCAGCCTGGCAAAACGCGCCAAGGACGATCCGCAGTCATCCAGTAATGCCACCGGCGAGACGCCG<br>CGCATCGAGGGCTTCACCAGCCGCGATGGCAATGTTGAATTCGCCTGGACGCCGAACGAAAACCACGATTTTACC<br>GCAGGCTACGGCTTTGACCGTCAGGATCGCGATTCCGATTCCCTTGACCGCAACCGCCTTGAGCGGGAGAACTAC<br>TCTCTGAGCCATAACGGCCGCTGGGATATTGGCAATAGCGAGCTCAAGTTCTACGGCGAAAAGGTGGATAACAAA<br>AATCCAGGGCAGAGCGGGACTATTACCTCGGAAAGCAATGCCATCGACGGCAAGTATGTCCTGCCGCTGGGCATG<br>ATTAACCAGCTGGTGACCTTCGGCGGCGAATGGCGCCACGACAAACTGAAAGATCCGGTCAACCTGAGCAGCGGC<br>GGCCAGTCAACGTCGGCCAGCCAGTACGCCCTGTTTATCGAAGACGAATGGCGCATCATCGAGCCGCTGGCGCTG<br>ACCACCGGCATTCGTATGGACGACCATCAGACCTATGGCGATCACTGGAGCCCGCGCGCCTATCTGGTGTATAAC<br>GCCACCGATACCGTCACCGTCAAAGGCGGCTGGGCGACGGCGTTTAAAGCCCCGTCGCTGCTGCAGCTTAACCCC<br>GACTGGACCACCAACTCCTGCCGCGGCTCGTGCAGCATCGTCGGTAACCCGGATCTGAAACCGGAAACCAGCGAA<br>AGCTTCGAGCTCGGTCTCTACTACCGCGGGGAAGAGGGCTGGCTTGAAAATGTCGAAGGCAGCATCACCACCTTC<br>CAGAATAATGTCGACGACATGATCGATGTTCTGCGCACCTCCAGCGCCAGCGAAGCGCCGGGCTACCCGAACTTT<br>GTCGGCTGGAAAACCGTCAACGGCAAGCGCGTGCCGATCTTCCGCTATTTCAACGTCAACAAAGCCCGCATCAAA<br>GGGGTGGAGACGGAGGTGAAGATCCCGTTTGGCGATGAGTGGAAGCTGACGGTGAACTACACATACAACGATGGT<br>CGCGATCTGAGCAATGGCGGCGACAAACCGCTGCAGACGCTGCCGTTCCATACCGCCAACGGCACGCTCGACTGG<br>AAACCGCTGGACGATTGGTCCTTCTACGTGACGGCCAACTATACCGGCCAGCAGCGCGCGGTGAGCGCCACCGGC<br>AAAACGCCGGGCGGCTACACCCTGTTTGACGTTGGCGCGGCATGGCAGGTGACCAAAAACGTGAAACTGCGCTCC<br>GGGGTGCAGAACGTGGGTGATAAAGATCTGAGCCGGGACGACTACAGCTATACCGAAGAAGGCCGTCGCTACTTT<br>ATGGCGGTGGATTATCGCTTCTGA |
| Klebsiella pneumoniae 1571 CirA (Colicin I Receptor) AA Sequence, SEQ ID NO:6.  Underlined sequence is the signal sequence.  Sequence of protein without signal sequence is SEQ ID NO:43, and the calculated molecular weight is 70.4 kDa. |
| MFRLNPFIRAGLSASVVSLAFPALADVNEETLVVTASATEQNVKDAPASISVITQQDLQRKPVQNLKDVLRDVPG<br>VQLTNEGDNRKGVSIRGLSSSYTLILVDGKRVNSRNAVFRHNDFDLNWIPVDAIERIEVVRGPMSSLYGSDALGG<br>VVNIITKKIGQKWTGTLSADTTIQEHRDRGDTYNGQFFTSGPLIDGVLGMKAYGSLAKRAKDDPQSSSNATGETP<br>RIEGFTSRDGNVEFAWTPNENHDFTAGYGFDRQDRDSDSLDRNRLERENYSLSHNGRWDIGNSELKFYGEKVDNK<br>NPGQSGTITSESNAIDGKYVLPLGMINQLVTFGGEWRHDKLKDPVNLSSGGQSTSASQYALFIEDEWRIIEPLAL<br>TTGIRMDDHQTYGDHWSPRAYLVYNATDTVTVKGGWATAFKAPSLLQLNPDWTTNSCRGSCSIVGNPDLKPETSE<br>SFELGLYYRGEEGWLENVEGSITTFQNNVDDMIDVLRTSSASEAPGYPNFVGWKTVNGKRVPIFRYFNVNKARIK<br>GVETEVKIPFGDEWKLTVNYTYNDGRDLSNGGDKPLQTLPFHTANGTLDWKPLDDWSFYVTANYTGQQRAVSATG<br>KTPGGYTLFDVGAAWQVTKNVKLRSGVQNVGDKDLSRDDYSYTEEGRRYFMAVDYRF |

Fig. 10

Klebsiella pneumoniae 1571 FepA (Ferrienterobactin Receptor) Gene Sequence.
SEQ ID NO:7.    N refers to A, T, G, or C.

```
ATGAATAACAGGATCAAATCCCTGGCCTTGCTGGTCAATCTGGGAATTTACGGGGGTTGCTTTTCCGTTAAGCGCA
GCGGAAACCGCCACCGACGATAAAAACAGCGCCGCTGAAGAGACCATGGTGGTCACCGCCGCCGAGCAGAACCTG
CAGGCGCCGGGCGTCTCCACCATCACCGCCGATGAGATCCGCAAACGCCCCCCGGCGCGCGACGTCTCGGAGATC
ATTCGCACCATGCCGGGAGTCAACCTGACCGGCAACTCCACCAGCGGCCAGCGCGGCAACAACCGCCAGATTGAT
ATCCGCGGCATGGGCCCGGAAAATACCCTGATCCTGATCGACGGCAAGCCGGTCACCAGCCGCAACTCCGTGCGC
CTTGGCTGGCGCGGCGAGCGCGACACCCGCGGCGATACCAGCTGGGTGCCGCCGGAGATAATCGAACGTATCGAA
GTGATTCGCGGCCCGGCCGCCGCCCGCTACGGCAACGGCGCCGCCGGCGGCGTGGTGAATATCATCACCAAAAAA
ACCGGCGATGAGTGGCACGGCTCATGGAACACCTATATGAACGCCCCGGAGCACAAGGATGAAGGCTCCACCAAA
CGCACTAACTTCAGCCTCAGCGGCCCGCTGGGCGGCGATTTTAGCTTCCGCCTGTTCGGTAACCTCGACAAAACG
CAGGCCGACGCCTGGGATATCAACCAGGGCCATCAGTCCGAGCGTACCGGGATCTATGCCGATACTCTGCCGGCC
GGGCGCGAAGGGGTGAAAAACAAAAACATCGATGGTCTGGTGCGCTGGGAATTCGCTCCGATGCAGTCGCTGGAG
TTTGAGGCCGGCTACAGCCGCCAGGGCAACCTCTACGCCGGCGACACCCAGAACACCAACTCCAACGACCTGGTA
AAAGAGAACTACGGCAAAGAGACCAACCGTCTGTATCGCAACACCTACTCGGTTACCTGGAACGGCGCCTGGGAC
AACGGGGTGACCACCAGCAACTGGGCGCAGTACGAACGCACCCGCAACTCGCGCAAAGGCGAAGGCCTGGCCGGC
GGCACCGAGGGGGATCTTTAACAGCAACCAGTTCACGGATATCGATCTGGCGGATGTGATGCTGCACAGCGAAGTC
AGCATTCCCTTCGACTATCTGGTTAATCAGAACCTGACGCTGGGCAGCGAGTGGAATCAACAGCGGATGAAGGAT
AACGCGTCCAACACCCAGGCGCTGTCGGGAGGCGGAATTCCGGGCTACGACAGCACCGGCCGCAGCCCGTACTCG
CAGGCGGAAATCTTCTCGCTGTTCGCCGAGAACAACATGGAGCTGACCGACACCACCATGCTGACTCCGGCGCTG
CGTTTCGATCATCACAGCATTGTCGGCAATAACTGGAGCCCGTCCCTCAACCTGTCGCAGGGCCTGTGGGATGAC
TTCACGCTGAAGANNNNNNNNCCCGCGCCTATAAAGCGCCGAGCCTGTATCAGACCAACCCGAACTACATTCTC
TACAGTAAAGGCCAGGGCTGCTACGCCAGTAAAGACGGCTGCTATCTGCAGGGTAATGACGACTTAAAAGCCGAG
ACCAGCATCAACAAAGAGATTGGCCTCGAGTTTAAACGCGACGGCTGGCTGGCGGGCGTCACCTGGTTCCGCAAC
GACTACCGCAACAAGATTGAAGCGGGCTATGCCCCGGTCTATCAAAACAATAAAGGTACCGATCTCTACCAGTGG
GAAAACGTGCCGAAAGCGGTGGTGGAAGGTCTGGAGGGGACGTTGAACGTTCCGGTGAGCGAGACCGTCAACTGG
ACCAACAACATCACCTATATGCTGCAGAGTAAGAACAAAGAGACCGGCGATCGTCTGTCGATTATCCCGGAATAC
ACGCTGAACTCCACCCTGAGCTGGCAGGTTCGCGATGACGTTTCGCTGCAGTCGACCTTCACCTGGTACGGCAAG
CAGGAGCCGAAGAAGTACAACTACAAGGGTCAACCGGTCACCGGCAGCGAGAAGAACGAGGTTAGCCCCTACAGC
ATCCTCGGCCTGAGCGCGACCTGGGACGTCACCAAATACGTCAGTCTGACCGGCGGCGTGGATAACGTCTTCGAT
AAGCGCCACTGGCGCGCGGGCAACGCCCAGACCACCGGGGGCGCCACCGGCACGATGTACGGCGCCGGCGCCGAG
ACCTACAATGAATCGGGCCGCACCTGGTACCTGAGCGTCAACACCCACTTCTGA
```

Klebsiella pneumoniae 1571 FepA (Ferrienterobactin Receptor) AA Sequence,
SEQ ID NO:8.    Underlined sequence is the signal sequence.    Sequence of
protein without signal sequence is SEQ ID NO:44, and the calculated
molecular weight is estimated to be 79.7 kDa based on an average of 110
Daltons per amino acid depicted as X.    X refers to any amino acid.

```
MNNRIKSLALLVNLGIYGVAFPLSAAETATDDKNSAAEETMVVTAAEQNLQAPGVSTITADEIRKRPPARDVSEI
IRTMPGVNLTGNSTSGQRGNNRQIDIRGMGPENTLILIDGKPVTSRNSVRLGWRGERDTRGDTSWVPPEIIERIE
VIRGPAAARYGNGAAGGVVNIITKKTGDEWHGSWNTYMNAPEHKDEGSTKRTNFSLSGPLGGDFSFRLFGNLDKT
QADAWDINQGHQSERTGIYADTLPAGREGVKNKNIDGLVRWEFAPMQSLEFEAGYSRQGNLYAGDTQNTNSNDLV
KENYGKETNRLYRNTYSVTWNGAWDNGVTTSNWAQYERTRNSRKGEGLAGGTEGIFNSNQFTDIDLADVMLHSEV
SIPFDYLVNQNLTLGSEWNQQRMKDNASNTQALSGGGIPGYDSTGRSPYSQAEIFSLFAENNMELTDTTMLTPAL
RFDHHSIVGNNWSPSLNLSQGLWDDFTLKXXXXRAYKAPSLYQTNPNYILYSKGQGCYASKDGCYLQGNDDLKAE
TSINKEIGLEFKRDGWLAGVTWFRNDYRNKIEAGYAPVYQNNKGTDLYQWENVPKAVVEGLEGTLNVPVSETVNW
TNNITYMLQSKNKETGDRLSIIPEYTLNSTLSWQVRDDVSLQSTFTWYGKQEPKKYNYKGQPVTGSEKNEVSPYS
ILGLSATWDVTKYVSLTGGVDNVFDKRHWRAGNAQTTGGATGTMYGAGAETYNESGRTWYLSVNTHF
```

Fig. 11

| Klebsiella pneumoniae 1571 BtuB (Vitamin B12 Transporter) Gene Sequence. SEQ ID NO:9. N refers to A. T, G. or C. |
|---|
| ATGATTAAAAAAGCTTCGCTGATGACGGCCTTATCCGTCACGGCATTTTCCGGCTGGGCGCAGGATAGCAATTCA GATACGTTGGTGGTGACAGCAAACCGTTTTCAACAGCCGGTCAATACCGTGCTGGCGCCGACCGACATTGTGACG CGCGATGACATCGACCGCTGGCAGTCCAAAGATTTAAACGATGTCATGCGTCGTCTTCCCGGGGTCGATATTGCC CGCAACGGCGGCATGGGGCAGAGCGCTTCGCTGTATGTTCGGGGGACGGAGGCTCGTCACGTGCTGGTGCTGATC GACGGTGTGCCGATGGCGCGTCCGGGGATCTCCAACGGCGTAGATATCAGTCAGATCCCTATCTCACTGGTCCAG CGGGTGGAATACATCCGCGGCCCCGCGCTCCGCGGTGTANNNNNNNNNNNNNNNNNNNNNNNNNNNNNNNNNNNNNN NNNNNNACCGACGCTGAGCGTTCGCAAATCAACGCCGGCGCGGGCACGAACGGCTATCAGTCCTATGACGGCGCC TTTAACAAGCGGTTTGGCAACACGCTGGTTACCGCTGCTGGCGCCTATCAGACCACCAAAGGGTTTAACGTCCAG CCGAATTCCTCTTATAGCGGCGACAGCGATCGCGACGGCTACCGCAATAAAATGCTGTGGGGCGGGGTACAGCAT CAGTTCGATGACAACTTCTCGGGGTTCTTCCGCGGCTATGGTTATTCCGCCAACGCTGACTATGACCAGGGTAAC TGGGGCTACGCAGGTGGAAACGATGAAGATCAATCCTATACCCAATCCTGGGATACCGGTCTGCACTACCACTCC GGAATTTACTCCTCCCAGCTGATTGCTAACTATCAGCGCATCAAAGATTACAACTACAGCAGCGACGCTGGCCGC TATGCCGCGGGCACCACCCTGGATGATATGGAACAGCGCTATATCCAGTGGGGAAATAATGTTGTGGTAGGCCAT GGGGCAGTGAGCGGCGGCGTTGACTGGAAACAAGAGAAGCTGAAATCCAGCGGAACGACCAGTACCGACGTGTAT AAGCGTGACACCACCGGTCTTTATCTGACGGGACAGCAGCAGATTGACAGCGTGACGCTGGAAGCTTCCGGCCGT GAGGATCATGACGAGCAGTTTGGCTGGCACGGTACCTGGCAGACGGCCGCAGGCTGGGAATTTATCGACGGTTAT CGGACAACGCTCTCGTACGGCACAGGATTCCTCGCCCCCTCCCTCGGGCAGCAGTACGGCGCAGAACGCTTTGGC ATCGCCTCTAACCCGAATCTGAAGCCAGAGGAGTCGAAGCAATGGGAAGCGGGCCTTGAAGGGTTAACGGGGCCG GTCGACTGGCGCCTCTCCGCATATCGCTATGAGATTCAAAACCTCATCGATTACGACAACAACGCCTATTACAAC GTCAAGTCGGCGACGATTAAGGGGCTGGAGTGGACGGGGAATATAACCACCGGGCCGGTGGAGCACCATCTGACG CTGCAGTATGTTGACCCTCGCGATGATGAAACCAATAAGATCCTCTATCGCCGGGCGAAGCAGCAGGTGAAATAC GAGCTGAACGGCCAGGTCTACGATCTGGGGTGGGATGTGACGTATCACTACATCGGCAAGCGTTACGATTATGAC TACGACAACTCGCGTACCGTCAATATGGGTGGGTTGAGCCTCTGGGATGTCGGTTTATCGTATCCCGTCACCTCA CACCTGACAGTTCGTGGTAAAATAGCCAACCTGTTCGATAAAGATTACGAGACAGTTTATGGCTACCAATCTGCA GGACGGGAATACACCTTGTCTGGCAGCTACACCTTC |
| Klebsiella pneumoniae 1571 BtuB (Vitamin B12 Transporter) AA Sequence, SEQ ID NO:10 Underlined sequence is the signal sequence. Sequence of protein without signal sequence is SEQ ID NO:45, and the calculated molecular weight is estimated to be 66.2 kDa based on an average of 110 Daltons per amino acid depicted as X. X is any amino acid. |
| MIKKASLMTALSVTAFSGWAQDSNSDTLVVTANRFQQPVNTVLAPTDIVTRDDIDRWQSKDLNDVMRRLPGVDIA RNGGMGQSASLYVRGTEARHVLVLIDGVPMARPGISNGVDISQIPISLVQRVEYIRGPRSAVXXXXXXXXXXXXXX XXTDAERSQINAGAGTNGYQSYDGAFNKRFGNTLVTAAGAYQTTKGFNVQPNSSYSGDSDRDGYRNKMLWGGVQH QFDDNFSGFFRGYGYSANADYDQGNWGYAGGNDEDQSYTQSWDTGLHYHSGIYSSQLIANYQRIKDYNYSSDAGR YAAGTTLDDMEQRYIQWGNNVVVGHGAVSGGVDWKQEKLKSSGTTSTDVYKRDTTGLYLTGQQQIDSVTLEASGR EDHDEQFGWHGTWQTAAGWEFIDGYRTTLSYGTGFLAPSLGQQYGAERFGIASNPNLKPEESKQWEAGLEGLTGP VDWRLSAYRYEIQNLIDYDNNAYYNVKSATIKGLEWTGNITTGPVEHHLTLQYVDPRDDETNKILYRRAKQQVKY ELNGQVYDLGWDVTYHYIGKRYDYDYDNSRTVNMGGLSLWDVGLSYPVTSHLTVRGKIANLFDKDYETVYGYQSA GREYTLSGSYTF |

Fig. 12

| Klebsiella pneumoniae 1571 YbiL (catecholate siderophore receptor) NT Sequence. SEQ ID NO:11. |
|---|
| ATGGAAAAAAACGCTTCTCTGCCTTTCGGCAGTTTCAACTCATTGGCATTGTTTACAGGTCTGTGTCTGGGAGCC TCGCCGGCAGCAGGCATCGCAGCGGAAAATTCGGTCAAAAATAGTGAAGAGACGCTGGTAGTGGAAGCCGCTCCG CCTTCACTCTACTCCCCCGGCGCTTCCGCCGATCCCAAGTTCAATAAACCGCTGGTCGATACCACCCGCACCATC ACCGTGATCCCGGAACAGGTGATTAAAGATCAGGGCGTCACCAACCTGACTGACGCCCTCAAAAACGTTCCCGGC GTGGGGGCGTTTTATGCCGGGGAGAATGGCAGCTCAACCACCGGGGATGCCATCTTTATGCGCGGCGTGGATACC TCTAACAGCATCTATGTGGACGGCATTCGCGACATCGGCAGCGTGACGCGCGATACCTTCAATACCCAGCAGGTG GAAGTCATCAAAGGGCCCGCCGGCACGGACTATGGCCGCAGCGCGCCCTCCGGCTCGATCAATATGATCAGCAAG CAGCCGCGCCTTGACTCCGGGATCGACGGCTCGGCCAGCATCGGCAGCGCCTGGTCGCGCCGGGGCACTCTCGAC CTGAACCAGGCGTTTAGCGACAACGCTGCGTTCCGTCTGAACCTGATGGGGGAAAAAACCCATGACGCTGGTCGG GACCGCATTGAAAACGAACGCTATGGCATCGCACCGTCGCTGGCCTTCGGCCTTGATACCCCAACTCGTCTGTAT CTGAACTATCTGCACGTCCGGCAGAACAACACCCCGGATGGCGGGATCCCTACCGTCGGCCTGCCGGGCTATTCG GCGCCTTCGCCGAAGTATGCCGCACTCAACTCCACCGGGAAGGTCGATACCAGCAATTTCTATGGCACCGACTCC GATTACGATAAATCTACTACCGACAGCGGTACCCTGCGCTTCGAACACGATCTGACAGAGAGCACCACCGTGCGC AATACCACCCGCTGGTCGCGCGAGTGAAACAGGAGTATCTTTTGACCGCGGTGATGGGCGGCGCGAACAATATCACC GCCCCCGATATCAATGACGTCAACACCTGGAGCTGGTCGCGTCTGGTTAATACCAAAGATGTCAGCAACCGCATT CTGACCAACCAGACCAATATCACCTCGACCTTCGATACTGGCTCGATAGGCCATGACGTCAGCGCCGGCGTGGAG TTTACCCGGGAAAACCAGACCAACTATGGCGTTAACGCCAGGACCGCGCCGGCGGTGAATCTCTACCATCCGGTG AGCAACCTGTCGATTGGCGGGCTGGACAGAAACGGGGCGAACGCCAACGGCCAGACCGATACCTTCGGGATTTAT GCCTTTGATACGCTGACGCTGACCGAGCGGATTGAGATCAACGGCGGGCTGCGTCTCGACAATTACCATACCAAA TATGACAGCGCCACCGCCTGCGGCGGCAGCGGACGCGGGGCTATCGCCTGCCCGCCCGGACAGTCGACCGGCAGC CCGGTCACCACTGTCGATACCGCTAAATCCGGCAATCTGGTTAACTGGAAAGCCGGGGCGCTGTACCGCTTAACC GAGCAGGGCAATGTCTACGTCAACTACGCCATCTCACAGCAGCCGCCGGGAGGCAGCAGCTTCGCCCTGGCCGCC AGCGGCAGCGGCAACAGCGCTAACCGAACCGACTTTAAGCCGCAGAAGGCAAAATCCAGCGAGCTGGGCACCAAG TGGCAAATCTTCGACAACCGTCTGCTGCTCAGCGCGGCGTTATTCCGCACCGATATTGAAACGAAGTGGCCGCC AACGATGACGGAACCTGGTCGCAGTACGGCAAAAAGCGCGTGGAGGGGTATGAACTCTCCGCGACCGGAAACCTG ACCCCGGACTGGACGATTATCGCCGGCTACACTCAGCAGCATGCGACAGTGACGGAGGGACAGAACGTTGCACAG GATGGATCTTCCGCCCTGGCCTACACCCCGAAACATGCCTTTACGCTGTGGACGCAGTATCAGGCCACCAGCGAT CTGTCCGTCGGCGGCGGTGTGCGCTATGTCGGAAGCCTGCGCCGGGGCAGCGATGGTGCAGTCGGTACCCCGGAT CACACCGAGGGCTACTGGGTTGCCGACGCCAAACTGGGCTATCGGGTCAACAGCAACCTCGATCTGCAGCTCAAT ATGTATAACCTGTTTGATACCGATTACGTGGCCTCCATCAACAAGAGCGGCTATCGCTATCATCCGGGCGAACCC CGGACCTTTATGCTGACGGCGAACGTCCATTTC |
| Klebsiella pneumoniae 1571 YbiL (catecholate siderophore receptor) AA Sequence, SEQ ID NO:12. Underlined sequence is the signal sequence. Sequence of protein without signal sequence is SEQ ID NO:46, and the calculated molecular weight is 78.4 kDa. |
| MEKNASLPFGSFNSLALFTGLCLGASPAAGIAAENSVKNSEETLVVEAAPPSLYSPGASADPKFNKPLVDTTRTI TVIPEQVIKDQGVTNLTDALKNVPGVGAFYAGENGSSTTGDAIFMRGVDTSNSIYVDGIRDIGSVTRDTFNTQQV EVIKGPAGTDYGRSAPSGSINMISKQPRLDSGIDGSASIGSAWSRRGTLDLNQAFSDNAAFRLNLMGEKTHDAGR DRIENERYGIAPSLAFGLDTPTRLYLNYLHVRQNNTPDGGIPTVGLPGYSAPSPKYAALNSTGKVDTSNFYGTDS DYDKSTTDSGTLRFEHDLTESTTVRNTTRWSRVKQEYLLTAVMGGANNITAPDINDVNTWSWSRLVNTKDVSNRI LTNQTNITSTFDTGSIGHDVSAGVEFTRENQTNYGVNARTAPAVNLYHPVSNLSIGGLDRNGANANGQTDTFGIY AFDTLTLTERIEINGGLRLDNYHTKYDSATACGGSGRGAIACPPGQSTGSPVTTVDTAKSGNLVNWKAGALYRLT EQGNVYVNYAISQQPPGGSSFALAASGSGNSANRTDFKPQKAKSSELGTKWQIFDNRLLLSAALFRTDIENEVAA NDDGTWSQYGKKRVEGYELSATGNLTPDWTIIAGYTQQHATVTEGQNVAQDGSSALAYTPKHAFTLWTQYQATSD LSVGGGVRYVGSLRRGSDGAVGTPDHTEGYWVADAKLGYRVNSNLDLQLNMYNLFDTDYVASINKSGYRYHPGEP RTFMLTANVHF |

Fig. 13

| Klebsiella pneumoniae 1571 YncD (Probable TonB Dependent Receptor) Gene Sequence. SEQ ID NO:13. |
|---|
| ATGAAAATCCTGTCCGTGCGTCACGCCGCCCTCCCGGCCCTGCTCTTGCCGCTCATTGCCGCAGCCCAGGCCGCT<br>GATGAACAAACCATGGTGGTGACCGCCGCGCCAACCACGGTTTCTGAACTGGATACCCCCGCCGCCGTCAGCGTG<br>GTGAATGGGGATGAGATGCGCCAGGCCGCGCCGCGCGTCAATCTCTCTGAATCGCTGGGCGCCGTGCCGGGCCTG<br>CAGGTGCAGAACCGGCAAAACTATGCCCAGGATCTGCAGCTGTCGATTCGCGGCTTTGGCTCGCGCTCAACCTAT<br>GGCGTGCGCGGACTACGCATCTATGTGGATGGCATTCCGGCCACCATGCCCGACGGCCAGGGGCAGACCTCAAAT<br>ATTGATATCGGCAGCGTTGACACCATTGAGGTGCTGCGCGGCCCCTTCTCTGCCCTGTACGGTAACTCGTCCGGC<br>GGGGTGATCAACGTCACCAGCCAGACCGGCACCCAGCCGCCCACCGTGGAAGCCAGCAGCTACTATGGCAGCTTC<br>GGCACCTGGCACTACGGGATGAAAGCCACTGGCGCCGTTGGCGACGGCAGCCACGCAGGCGATGTGGATTACACG<br>GTCTCAACCAATCGCTTCACCACCCATGGCTATCGCGATCACAGCGGCGCGCGCAAAAATCTGGCGAACGCCCGG<br>CTGGGGGTGCGCATCAACGACGTCAGTAAGCTGACTCTGCTGCTGAATAGCGTGGATATCAAAGCCAATGACGCC<br>GGTGGCCTGACCGCCGATGAATGGCGCGATAACCCGCGCCAGTCGCCGCGCGGCGACCAGTATAATACCCGCAAG<br>AATACCCGACAGACCCAGGCCGGCCTGCGCTATGAGCGCCAGCTCAGTGCCCAGGACGATCTCAGCGTATG |
| Klebsiella pneumoniae 1571 YncD (Probable TonB Dependent Receptor) AA Sequence, SEQ ID NO:14. Underlined sequence is predicted to be the signal sequence. |
| MKILSVRHAALPALLLPLIAAAQAADEQTMVVTAAPTTVSELDTPAAVSVVNGDEMRQAAPRVNLSESLGAVPGL<br>QVQNRQNYAQDLQLSIRGFGSRSTYGVRGLRIYVDGIPATMPDGQGQTSNIDIGSVDTIEVLRGPFSALYGNSSG<br>GVINVTSQTGTQPPTVEASSYYGSFGTWHYGMKATGAVGDGSHAGDVDYTVSTNRFTTHGYRDHSGARKNLANAR<br>LGVRINDVSKLTLLLNSVDIKANDAGGLTADEWRDNPRQSPRGDQYNTRKNTRQTQAGLRYERQLSAQDDLSV |

Fig. 14

| Klebsiella pneumoniae 1571 IroN Gene Sequence. SEQ ID NO:15. N is A, T, G, or C. |
|---|
| GTCGATTATCACGGCTGAGGATATTGCTAAGCAGCCGCCGGTCAACGATCTCTCAGACATCATCCGTAAAATGCC CGGGGGTGAACTTGACCGGCAACAGCGCCAGCGGCAGTCGGGGCAACAACCGCCAGATTGATATCCGCGGCATGGG GCCGGAGAACACCCTGATCCTGATAGATGGGGTACCGGTCACGTCACGTAACGCGGTTCGCTATAGCTGGCGCGG CGAACGCGATACCCGGGGCGACAGCAACTGGGTACCTGCCGAAATGGTCGAACGGATTGAAGTTCTNNNNNNNNNN NNNNNNNNNNNNNNNNNNNNNNNNNNNNNNNNNNNNNNNGGAGTGGTCAATATCATTACCAAACGTCCGACCAACACCTG GCACGGTTCGCTGTCTTTCTTCACCAACCAGCCGGAAAACAACAAAGAAGGCACGACCAATCGCGCTAACTTCAA TCTCAGCGGCCCACTGGCCGGCGAGGCGCTGACGATGCGCCTGTATGGCAATATCAATAAAACGGAACCCGACGC CTGGGATATTAACCATGCGCAAAACGGCTCTTACGCTGCGGGGCGCGAAGGGGTCCGCAATAAAGACATTAACGC GCTACTGTCATGGAAAATGACCCCGCAACAAATTCTCGATTTCAGCTACGCCTATAGCCGTCAGGGGAATATCTA TGCTGGCGATACCCAGTACAGCAACGGCAATCTTAGCCCGAACGGGCTGGTGGACTCCCTGTACGGCCACGAAAC AAATCGCCTCTATCGCCAGTCCTGGGGACTCACCTACAACGGTCTATGGGATTGGGGTCAGTCCAAAGCCGGTGT TTACTACGAGAAAACCAACAATACCCGCCTGCAGGAAGGCTCTACCGGCCGCGTCGAAGGCATGATCAACAGTGA AGATTATGCCACCAGCCGTCTGGAATCCTGGCGTACTACCTCGGAATTCAATGTGCCTTTCTTCTGGCTGGCGGA CCAGACGCTGACGCTGGGAATGGAATGGAACCATGATCAGCTTGACGACCCGGCATCAATGCAGGCCACTAACAG CAACGGCGAGACTATCCCTGGGACCTCGGGCGACCCTACGCAACGCAGTACCAAAAACAGCGCCACCCTCACCGG TATCTATCTGGAAGATAATATCGAAGCCGTGCCCGGCACCAACCTGATCCCCGGCATTCGCTTCGATTATCATAA TCAGTTTGGCAGTAACTGGAGCCCCAGCCTCAATCTGTCCCAGGAGCTCGGCGATATGTTCACGCTGAAGGCCGG TATCGCGCGCGTGTTTAAAGCGCCAAACCTCTATCAATCCAGTAAAGGCTATTTGCTCTCCACCCGCGGCAACGG TTGTCCAAACACGATCGCTGAAGGCAGCTGCTACCTGCTGGGTAACCCTGACCTCGACCCGGAGATCAGTATCAA CAAAGAGATCGGTATCGAATTTAACCTTAATGGTTACGCTGCCGGAGTCACCTGGTTTCGCAACGATTACAAAAA CAAAATCGTCTCCGGAACAGAGGTACTGGGCTATACCTCCAGCGGCAATAATATTTTGCAATGGCAGAACGGCGG CAAAGCCGTGGTCGAGGGGCTGGAAGGAAATCTGCTGATCCCGGTGCTGAGAGATGTCCTCAGCTGGCGGACCAA TGCCACCTGGATGCTCAAATCTGAAAGTAAAGAGACTGGCAACCCGCTGTCGGTTATCCCGAAATATACCGTTAA CACGATGCTTGACTGGCAGGTAAACGACGCCCTGTCTGCGAATGTGAACTGGACGCTTTATGGCCGTCAGAAGCC GCGTCAGTATGCGGAGATCCGCAACGAAACCGGGACCCTTGCCACCACCGAGGTTGGCGCCTATTCCATCGTGGG TATTGGTACTCAGTATCAGCTAAACCGGGATATTCGCCTGAATGCCGGAATAAGTAATCTATTTGATAAGCAACT GTATCGCGAAAATGCCGGCGCCTCGACCTACAATGAGCCTGGCCGCGCGTATTACGCCGGCGTTACCCTCTCCTT CTGA |

| Klebsiella pneumoniae 1571 IroN AA Sequence, 675 aa, SEQ ID NO:16     X is any amino acid. |
|---|
| SIITAEDIAKQPPVNDLSDIIRKMPGVNLTGNSASGSRGNNRQIDIRGMGPENTLILIDGVPVTSRNAVRYSWRG ERDTRGDSNWVPAEMVERIEVLXXXXXXXXXXXXXXXXGVVNIITKRPTNTWHGSLSFFTNQPENNKEGTTNRANFN LSGPLAGEALTMRLYGNINKTEPDAWDINHAQNGSYAAGREGVRNKDINALLSWKMTPQQILDFSYAYSRQGNIY AGDTQYSNGNLSPNGLVDSLYGHETNRLYRQSWGLTYNGLWDWGQSKAGVYYEKTNNTRLQEGSTGRVEGMINSE DYATSRLESWRTTSEFNVPFFWLADQTLTLGMEWNHDQLDDPASMQATNSNGETIPGTSGDPTQRSTKNSATLTG IYLEDNIEAVPGTNLIPGIRFDYHNQFGSNWSPSLNLSQELGDMFTLKAGIARVFKAPNLYQSSKGYLLSTRGNG CPNTIAEGSCYLLGNPDLDPEISINKEIGIEFNLNGYAAGVTWFRNDYKNKIVSGTEVLGYTSSGNNILQWQNGG KAVVEGLEGNLLIPVLRDVLSWRTNATWMLKSESKETGNPLSVIPKYTVNTMLDWQVNDALSANVNWTLYGRQKP RQYAEIRNETGTLATTEVGAYSIVGIGTQYQLNRDIRLNAGISNLFDKQLYRENAGASTYNEPGRAYYAGVTLSF |

Fig. 15

| Klebsiella pneumoniae 1571 IutA (Ferric Aerobactin). Gene Sequence. SEQ ID NO:17. |
|---|
| ATGAAAAAGCGCCTCTGGGTGCTCCACCCTCTGCTGCTGGCCAGCACGCTGCCTGCGCTGGCGGCTCAGTCTGAT GAAGACAGCATCATCGTTAGCGCAAACCGCACCCATCGCACCGTGGCCGAAATGGCCCAAACCACCTGGGTCATT GAGGGCCAGGAGATTGAGCAGCAGGTCCAGGGCGGGAAAGAGTTCAAAGACGTGCTGGCGCAGCTGATCCCCGGC ATCGACGTCAGCAGCCAGGGGCGGACCAACTATGGGATGAACATGCGCGGGCGCGCGATCGTCGTGCTGATTGAC GGCGTCCGGCTCAACTCCTCACGCACCGACAGCCGCCAGCTCGACGCCATCGATCCATTCAACATCGAACATATC GAAGTGATCTCCGGAGCGACCTCGCTGTACGGCGGGGGCAGTACCGGCGGGCTTATCAACATCGTTACCAAAAAG GGGCAGCAGGATCGTCAGGTCGATCTTGAGGTGGGCAGCAAGAGCGGTTTTGCGAACAGCAACGATCATGATGAG CGCGTCGCGGCGGCCGTCAGCGGCGGAACAGACCACGCATCCGGCCGCTTGTCGGTAGCCTATCAGCGTTTCGGC GGCTGGTACGACGGCAATACCGATGCGCTGATCCTCGATAATACCCAAACGGGGCTCCAGCATTCTGACCGCCTC GACGTGATGGGGACGGGGACGATTGAGATCGATAATAACCGCCAGCTGCAGTTGGTCACCCAGTATTATAAAAGC CAGGGCGATGATGACTACGGTCTGTGGCTCGGGAAGAACATGTCCGCGGTCACCAGCGGCGGCAAAGCGTATACC ACCGACGGGCTCAATTCCGACCGTATCCCCGGCACCGAACGCCATCTGATCAGCCTCCAGTACTCTGATGCCGAC TTTTTCGGCCAGAATCTGGTGAGCCAGGTGTACTATCGCGATGAGTCCCTCACCTTCTATCCGTTCCCGACGCTC ACGAAAGGTCAGGTCAGTAGCTTCTCCTCGTCGCAGCAGGATACCGATCAGTATGGGGCCAAGCTGACCCTCAAC AGCCAACCGCTGGCGGGGGTGGGATCTCACCTGGGGTCTCGACGCCGATCATGAGACCTTTAATGCCAACCAAATG TTCTTCGATCTGCCACAATCGATGGCCTCCGGCGGGTTGCACAACGAATCGATCTACACAACCGGCCGCTACCCG GGATACAGTATTTCCAATGTCGCGCCATTCCTGCAGTCCAGCTACGATCTGAACGATATCTTTACCGTCAGCGGC GGGGTACGCTACCAGTGGACCGAAAACCGGGTCGACGACTTTGTCGGCTACGCCCAGCAGCAGGATATCGCCAAC GGCAAAGCGCGCTCCGCCGACGCCATCAAAGGCGGCAAAACCGATTACGATAACTTCCTGTTTAACGCCGGGATC GTGGCCCACCTGACCGAGCGTCAACAAACCTGGTTTAACTTCTCGCAGGGCGTCGAGCTACCGGACCCTGGTAAA TACTATGGCATCGGTAAATATGGCGCTGCGGTGAATGGTCATCTGCCGCTGATCTCCAGCGTCAACGTCGATGAC TCGCCGCTGCAGGGGATCAAAGTTAACTCGTACGAGCTGGGCTGGCGCTACACCGGCGATAACCTGCGCACCCAG CTGGCGGCGTACTACTCGACCTCAGATAAGACCATTGTCGTCAACCGCACCGACATGACCATCGACGTTCAGTCC GACAAACGGCGTATTTACGGCGTTGAGGGGCGGTCGACTACTTTATTCCGGATAGCGACTGGAGCGTCGGCGGT AACTTCAACGTGCTGAAATCCCAGGTGCAGACCGACGGCCGCTGGCAAAAATGGGACGTCACCCTCGCCTCGCCG TCTAAAGCCACCGCCTGGGTGGGCTGGGCGCCGGATCCGTGGAGCCTGCGCGTGCAGAGTCAGCAGGTATTTGAC CTCAGCGATGCCGCCGGCAACAAGCTGGAAGGCTATAACACCGTCGATTTTATCGGTAGTTACGCGCTGCCGGTG GGGAAACTGACCTTCAGTATCGAAAACCTGCTTAACGAAGACTATGTGACTATATGGGGCCAGCGCGCGCCGCTG CTCTACAGCCCAACCTACGGCAGTTCATCGCTGTATGAGTACAAAGGTCGTGGCCGCACCTTTGGTCTGAACTAC GCCTTAACCT |
| Klebsiella pneumoniae 1571 IutA (Ferric Aerobactin) AA Sequence, SEQ ID NO:18  Underlined sequence is the signal sequence.  Sequence of protein without signal sequence is SEQ ID NO:49, and the calculated molecular weight is 78 kDa. |
| MKKRLWVLHPLLLASTLPALAAQSDEDSIIVSANRTHRTVAEMAQTTWVIEGQEIEQQVQGGKEFKDVLAQLIPG IDVSSQGRTNYGMNMRGRAIVVLIDGVRLNSSRTDSRQLDAIDPFNIEHIEVISGATSLYGGGSTGGLINIVTKK GQQDRQVDLEVGSKSGFANSNDHDERVAAAVSGGTDHASGRLSVAYQRFGGWYDGNTDALILDNTQTGLQHSDRL DVMGTGTIEIDNNRQLQLVTQYYKSQGDDDYGLWLGKNMSAVTSGGKAYTTDGLNSDRIPGTERHLISLQYSDAD FFGQNLVSQVYYRDESLTFYPFPTLTKGQVSSFSSSQQDTDQYGAKLTLNSQPLAGWDLTWGLDADHETFNANQM FFDLPQSMASGGLHNESIYTTGRYPGYSISNVAPFLQSSYDLNDIFTVSGGVRYQWTENRVDDFVGYAQQQDIAN GKARSADAIKGGKTDYDNFLFNAGIVAHLTERQQTWFNFSQGVELPDPGKYYGIGKYGAAVNGHLPLISSVNVDD SPLQGIKVNSYELGWRYTGDNLRTQLAAYYSTSDKTIVVNRTDMTIDVQSDKRRIYGVEGAVDYFIPDSDWSVGG NFNVLKSQVQTDGRWQKWDVTLASPSKATAWVGWAPDPWSLRVQSQQVFDLSDAAGNKLEGYNTVDFIGSYALPV GKLTFSIENLLNEDYVTIWGQRAPLLYSPTYGSSSLYEYKGRGRTFGLNYALT |

Fig. 16

Klebsiella pneumoniae 1571 FitA (ferric coprogen receptor). SEQ ID NO:19.

```
CCCGCCGCGGCTTCGGCGCCAACCGCGACGGCTCGATCATGACCAACGGCCTGCGCACCGTGCTGCCGCGCAGCT
TTAACGCCGCCACCGAACGGGTGGAAGTCCTGAAGGGGCCCGCCTCGACGCTGTACGGTATCCTCGACCCCGGCG
GGCTGATCAACGTCATCACTAAACGGCCGGAGCGGCAGTTCTCCGGTTCGGTTTCCGGGACCTCCACCAGCTTTG
GCGGCGGCACCGGCAGCGTCGACATCACCGGCCCCATCGAAGGCACAAATCTGGCGTACCGACTGATCGGCGAAT
ATCAGAATGAGGATTACTGGCGCAATTTCGGTAAAAACAAAAGCAGCTTTATCGCCCCTTCCCTGACCTGGTTTG
GCGAGCGGGCAACGGTGACCGCGTCCTATTCGCACCGCGACTACAGCGCCCCCTTTGATCGCGGAACTATCTTCG
ATCTGAATACCGGCCATGCGGTTAACGTCGATCGCAAAACCCGCTTCGATGAAGCGTTTAATATTACCGATGGCT
ATTCCGATCTCGCTCAGCTCAACGCCGAGTATCGCCTTAACGACGCCTGGACCGCGCGCTTCGACTACAGCTACA
GCCAGGATCATTACAACGATAACCAGGCGCGGGTAATGGCCTATGATTCGGCGACCGGCAACCTCCCCCGCCGGG
TCGATGGTACCCACGGTTCAACGCAGAAGATGCACTCCACCCGCGCCGACCTGCAGGGCAACGTGGTAGTGGGCG
GCTTTTATAACGAGCTGCTGACCGGCGTCGCCTATGAGAATTACGATCTGCTGCGCACCGATATGCTGCGCTGTA
AGAACGTTAAAGGCTTTAACATCTATCATCCGGTCTACGGCACTCTCGACACCTGTAATACCGTCTCCGCCTCCG
ACAGCGACCAGCGCATTCAGCAGGAGAGCTATGCCGCATACGTGCAGGACGCGCTGTACCTGACCGACAACTGGA
TCGCCGTCGCCGGCGTGCGCTACCAGTACTACACCCAGTACGCCGGTAAAGGCCGACCGTTTAACGTCAATACCG
ACAGCCGCGATGAGAAATGGACGCCGAAAGCCGGCCTGGTCTACAAGGTCACGCCGAACGTCTCCCTGTTCGCCA
ACGTCGCCCAGTCGTTTATGCCGCAGTCGTCGATCGCCAGCTATATCGGCGAGCTGCCGCCGGAAGAGTCCACCT
CTTACGAAGTGGGCGCCAAATTCGACCTGTTAAACGGCATTACCGCCAATATCGCGTTGTTTGATATTCATAAGC
GTAACGTGCTGTACACCGAGAGCATTGGCGATGAGACGGTGGCCAAAACGGCGGGCAAAGTGCGTTCCCAGGGCG
TGGAAGTGGATCTGGCGGGGGTCCATCACCGATAACCTCAGCGTGATCGCCAGCTACGGCTACACCGACGCCAAAG
TGCTGGAAGATCCGGATTACGCCGGGAAACCGCTGCCAAACGTACCGAAACATACCGGTTCGCTGTTCCTGACCT
ATGACATTCATAACGTCTATAACAGCAACACCCTGACCGTCGGCGGCGGCGGCCACGCGGTCAGCAAGCGTTCCG
GCACCAACGGCGCGGATTATTATTTGCAGGGGTATGCGGTGGCGGATGTGTTTGCTGCCTATAAGATGAAGCTGC
AGTATCCGGTGACGCTGCAGGTGAATGTGAAGAACCTGTTTGATAAGACCTATTACACTTCCTCGATCGGCACCA
ATAATCTCGGCAACCAGATTGGCGACCCGCGCGAAGTGCAGTTCACGGTGAAGATGGATTTTTAA
```

Klebsiella pneumoniae 1571 FitA AA Sequence, SEQ ID NO:20.

```
RRGFGANRDGSIMTNGLRTVLPRSFNAATERVEVLKGPASTLYGILDPGGLINVITKRPERQFSGSVSGTSTSFG
GGTGSVDITGPIEGTNLAYRLIGEYQNEDYWRNFGKNKSSFIALSLTWFGERATVTASYSHRDYSAPFDRGTIFD
LNTGHAVNVDRKTRFDEAFNITDGYSDLAQLNAEYRLNDAWTARFDYSYSQDHYNDNQARVMAYDSATGNLPRRV
DGTHGSTQKMHSTRADLQGNVVVGGFYNELLTGVAYENYDLLRTDMLRCKNVKGFNIYHPVYGTLDTCNTVSASD
SDQRIQQESYAAYVQDALYLTDNWIAVAGVRYQYYTQYAGKGRPFNVNTDSRDEKWTPKAGLVYKVTPNVSLFAN
VAQSFMPQSSIASYIGELPPEESTSYEVGAKFDLLNGITANIALFDIHKRNVLYTESIGDETVAKTAGKVRSQGV
EVDLAGSITDNLSVIASYGYTDAKVLEDPDYAGKPLPNVPKHTGSLFLTYDIHNVYNSNTLTVGGGGHAVSKRSG
TNGADYYLQGYAVADVFAAYKMKLQYPVTLQVNVKNLFDKTYYTSSIGTNNLGNQIGDPREVQFTVKMDF
```

Fig. 17

```
Klebsiella pneumoniae 1571 FcuA (Ferrichrome receptor) SEQ ID NO:21

ATGGGGCAAATTATGCACACCACGCACTATTCATCCTTCCCGCTGCGTAAAACGCTGCTGGCCTTAGCCATCGGC
GCCGCCAGTCAAACGGCGATGGCCGCGGACGCTGCCGCCGCGAAGCAGCCTGGCGAAGAGACCCTCATCGTCGAG
GCTAACGAAACCAGCGATTTTAAATCCGGCGGTGACCTGGTGGTTCCGGCATTCCTCGATGGCCAGATCGCCCAC
GGCGGCCGTCTGGGGATGCTTGGCGAACAAAAAGCGATGGACGTCCCGTTTAACGTCATCGGCTATACCTCGAAG
CTGATTCAGGATCAGCAGGCGAAAACTATCGCCGATGTCGTCAGTAACGACGCTGGCGTGCAGGCCGTACAGGGC
TACGGCAACTTCGCCGAGACCTATCGAATCCGCGGGTTTAAGCTCGATGGCGATGACATGACGATGGGCGGCCTG
GCGGGCGTGGTGCCGCGTCAGGTGATGGACACCCAGATGCTGGAGCGCGTTGAAATTTTCAAAGGGGCTAACAGC
CTGCTTAACGGCGCGGCCAGCAGCGGTGTCGGCGGGGTGATTTACCTCGAGCCGAAGCGGGCGGAAGATCTGCCG
ACCGCACGCGTTGGCGTCGACTATACCTCTGATTCTCAGGTGGGCGGCACCCTCGACCTGGGGCGCCGTTTCGGC
GACAACAACCAGTTCGGCGCCCGGGTCAACCTGGTGCACCGCGAGGGTGAAGGCGCTATCGATAATGATAAACGC
CGTACCACGCTGGCCTTCGCTGGGGCTTGATTACCGCGGCGACCGTTTCCGCTCCTCGCTCGATTTCGGCTATCAG
AAGAAAACGTTCCACGGCGGTACGATGGGCGTCAATATCAGCGGCGTGGATTTCGTTCCGGCGCTGCCGGACAAC
AGCAAAAACTACAGCCAGAAGTGGGGCTATAGCGATATTGAAAGCGAGTTTGGCATGGCGAAGGCAGAATATGAC
CTGACCGATAGCTGGACGGTATACAGCGCCCTCGGCGGCCAGCATTCGCATGAAATTGGTACCTACAGCGCGCCG
AAGCTTCTGAATAAAAACGGCGATGCGACGGTGGGCCGCCTGGATACTAACCGCATTATCGACGCGATCAGCGGC
ATGGGCGGGGTACGCGGCGATTTCAATACCGGCGCGATTTCGCATACGGTGAACCTCGGCTATGCGGCGCAGGTG
CATACCGATGCGACCGCCTGGCGGATGTCGGCCAGGAACCCGACCACTAATATCTATGACAACCATGATGTGGCG
ATGCCGGATAACGCCTATTTTGGCGGCAACTACCACGATCCGCTGGTCACCTCGCGCAGCCGTACGCAGGGCTGG
CTGTTGAGTGATACCCTCGGCTTCTTTAACGATAAAGTGCTGTTTACCGCCGCTGCTCGTCATCAGAAAGTGGTT
GTGCGCAACTACAGCAACGCCACCGGGCTGGAAGATACCTCTTCGCGTTATACCCAAAGCCGCTGGATGCCGACG
TTTGGCCTGGTGTACAAGCCGTGGGAGCAGCTGTCGCTGTATGCTAACCATACCGAAGCGCTGCAGCCGGGCTCT
GTGGCGCCGACGACGGCGGCCAATGCCGGGCAGAGTACCGGGATCGCGCACTCGAAGCAGGACGAAGTGGGCGTC
AAGATCGACTACGGTACGATCGGAGGATCGCTGGCGCTGTTTGAAATCAAAAAACCGAACGCCATTTCCGATACC
GCTGGCAATTACGGCCTCGACGGCGAGCAGCGTAACCGCGGCGTAGAGATGAACGTCTTTGGCGAGCCGATGCTG
GGACTGCGTCTTAACGCCAGTACCGTCTGGCTGGATGCCAAACAGACTAAAACCGCTGAAGGCGCAACCGACGGT
AAAGATGCCATCGGGGTGGCTAACTTCTACGCGGTACTCGGCGCCGAATATGACATCAAGCCGGTGGAAGGCCTG
ACCGCCACCGCGCGCGTCAATCATAGCGGCTCGCAGTATGCCGATGCGGCCAATACCAAGAAGCTGGATAGCTAC
ACCACCCTGGATTTAGGCCTGCGCTATCGTATGCGTCTGAACGCCGACCAGAACGAAATGATCTGGCGCGTCGGG
GTGACCAACGTGACCAACGAGAAGTACTGGTCTGGCATTGACGATACCGGTACTTACCTGTTCGAAGGCGATCCG
CGTACCGTCCGCGTCTCAATGAGCTACGACTTCTGA
```

Klebsiella pneumoniae 1571 FcuA AA sequence, SEQ ID NO:22. Underlined sequence is the signal sequence. Sequence of protein without signal sequence is SEQ ID NO:51, and the calculated molecular weight is 76.2 kDa.

MGQIMHTTHYSSFPLRKTLLALAIGAASQTAMAADAAAAKQPGEETLIVEANETSDFKSGGDLVVPAFLDGQIAH
GGRLGMLGEQKAMDVPFNVIGYTSKLIQDQQAKTIADVVSNDAGVQAVQGYGNFAETYRIRGFKLDGDDMTMGGL
AGVVPRQVMDTQMLERVEIFKGANSLLNGAASSGVGGVIYLEPKRAEDLPTARVGVDYTSDSQVGGTLDLGRRFG
DNNQFGARVNLVHREGEGAIDNDKRRTTLASLGLDYRGDRFRSSLDFGYQKKTFHGGTMGVNISGVDFVPALPDN
SKNYSQKWGYSDIESEFGMAKAEYDLTDSWTVYSALGGQHSHEIGTYSAPKLLNKNGDATVGRLDTNRIIDAISG
MGGVRGDFNTGAISHTVNLGYAAQVHTDATAWRMSARNPTTNIYDNHDVAMPDNAYFGGNYHDPLVTSRSRTQGW
LLSDTLGFFNDKVLFTAAARHQKVVVRNYSNATGLEDTSSRYTQSRWMPTFGLVYKPWEQLSLYANHTEALQPGS
VAPTTAANAGQSTGIAHSKQDEVGVKIDYGTIGGSLALFEIKKPNAISDTAGNYGLDGEQRNRGVEMNVFGEPML
GLRLNASTVWLDAKQTKTAEGATDGKDAIGVANFYAVLGAEYDIKPVEGLTATARVNHSGSQYADAANTKKLDSY
TTLDLGLRYRMRLNADQNEMIWRVGVTNVTNEKYWSGIDDTGTYLFEGDPRTVRVSMSYDF*

Fig. 18

Klebsiella pneumoniae 1571 Ferric Enterbactin Colicin B/D receptor. SEQ ID
NO:23

ATGTACAAATCGACTCCGTCAGCAGCATGGTGTAAAAAACGCCTGCTGGTGACCTCTTTGTTTGCAGCAATTTAT
CAGACTTCTGCCATCGCAGCAGATACTTCCGCCGTTAGCGGCGAGGCGGTGGATGACACCTCGGAACAAATGACC
GTCACCGCCCCCGCGCCGGTGCAGAAAGCCGGTAGCGAACATAGCATCAGCGCCCGGGAGCTGGAGAATAAAGGC
GCTAACGATTTCGGCTCAATCATGCGCTATGAGCCGCTCATCAGCGCCACCGGGGCCAGCGGCGGCTCCGGCAAC
GGCAAAAGCGGCTTCGACCGCGGAGGTTACACCGGCTACAACATTCGCGGTATGGAGAGCAACCGCGTCGGCATC
GACGTGGACGGTATCGCGCAACCCAACGCCACCGGCCGCGGCTACGTCGGCCGCGCCGGGCTCAACACCTTCGGC
ATCGGCCGCGATTATATCGACCCGTATATGTACGGCAGCGTGGATATCCAGTCCGGCGCCACCTCGACGGAAACG
GCCAACAGCGCTATCGGGGGGAATGTCTCCTTCCGCCCCGAAATCAGCGGATGATTACCTGCGCCCGGGCAAGACC
AGCGCCTTCGGCTACCGCAGCGGTTACGACTCTGCGGATCGCAGCTGGCACAACGGGGTGACCGTCGCCGGCGGC
GATGAGTTCCTGCGCGGGATTTTGGTCTATAGCCGCCGTGACGGCCAGGAAACCGAAAACAACAGCGGCACCGTC
GACGCCTACCCGGCGAACTGGCACTCCGATGCTTTTCTGGCCTCCGGGATCTGGCAGCCTAACGATGAGCACAAG
CTGACCAGCACCTTCGACTATTACCATAAAACCAACCACACCCACTACGATACCTGGGACTCCAGCGGCAACAGC
ACCATCGGCACCGCCAACCAGACCAGCCAGACCCGGCGCTGGGGCCTGAGCCTGAAGGATGACTGGACGCCGATG
AACGACTACCTCGACAGCGTCTCCACAAAAATCTACTACCAGCATACCGAAGCCCATGACTGGACTTATATGCCG
GACAGCGTCACCCGCAGAATGCAGACGGTGAACTCTAACTACGATACCGACACCTGGGGCCTGCAGACCGCGCTG
GCGAAAACCCTGGGCCGCCACGATCTGAGCGCCGGTTTCAACGCCAGCACCAGCAAAACCCAGCGGCCGTTCAGC
CAGTCGCCGATCCCCAGCGTTTACAGCGAGATCATGCAGCCGGAGGCAGACAGCCGCAGCTACACCCTCGGCGGC
TTTGTCCAGGATAAGATCAACTTCGACCTTGATAGCCACAACTTCGCCGTTATTCCCGGCGTGCGCGTGGTGCAT
CAATCGACTAAGCCGGAAAATCTGTCCGATCTCGCCGCCAACAGCAGCGTGCTGAGCGAATCGTCGGTGGCGAAT
CTGTACGGCAAAAACAGCGATACCCAGGTTCTGCCGTCGTTGACCTTCCAGTACGACCTCACCCCGCGCCTGATG
ACCTACCTGCAGTACCAGCGCGGGGCGCAGTTCCCCAACGCCAGCCAGCTGTATGGCTCCTGGAACCTCGGCTCC
AGCTACGCCGGCAGCCAGCAGTATGCCCTGATCGGCAATACCGATCTGAAGACGGAAACCAGCGATAATCTCGAG
TGGGGGCTGAAGGGGGAAGTTACCGAAGGCATCACCCTGCGCACGGCGCTGTTCTACAACAGCTATAAGAACTTT
ATCGCCTATACCCGCTATACCCGCGCCAACAATCCGGGCCAGTTCACGAATGTGCCGTCGAACATCTACACCATT
TATCAGGCGGAAAACCGCGATAAAGCCTATATCTACGGCGGTGAGATTAGCACCAAATTTAACTTTGGCACCTGG
TTTGAGCAGGTGGACGGCCTGAGCGCCACCCTCGCCCTCGGCTATAGCGAAGGGAAATCGAAATCCAGCTACAGC
GGCGATAAATACGTCGACCTCGACAGCGTGGCGCCAATGAAAGCCATCGTCGGCGTGGCGTGGGACGATCCGGCG
AAACGCTACGGCACCGCCCTGACGGCGACCTTTGTCAAAGGGAAACAGGCGACCGCCACCAACCGCGAAAGCTAC
AGCAACAGCGGATCCGCCATCACCGATGCCAGTAGCGACTATATGCGCGTGCCGGGCTACGGCATGCTGGACTGG
ACCGCGTACTGGCAGGTGGCGAAAAACGTGCGCCTCAATGGCGGGGTCTACAACCTCACCGATCGTAAATACTGG
GATTACCTGAGCAGCCGCAATATCGAGACCGGCACCAACCAGGACGCCAACGATAAAGCGCTGGCGGTGATGCCG
GGCCGCACCTGGCAGCTGGGCGTCAACGTCGACTTCTGA

Klebsiella pneumoniae 1571 Ferric Enterbactin Colicin B/D receptor AA
sequence.  SEQ ID NO:24.  Underlined sequence is the signal sequence.
Sequence of protein without signal sequence is SEQ ID NO:52, and the
calculated molecular weight is 83 kDa.

MYKSTPSAAWCKKRLLVTSLFAAIYQTSAIAADTSAVSGEAVDDTSEQMTVTAPAPVQKAGSEHSISARELENKG
ANDFGSIMRYEPLISATGASGGSGNGKSGFDRGGYTGYNIRGMESNRVGIDVDGIAQPNATGRGYVGRAGLNTFG
IGRDYIDPYMYGSVDIQSGATSTETANSAIGGNVSFRPKSADDYLRPGKTSAFGYRSGYDSADRSWHNGVTVAGG
DEFLRGILVYSRRDGQETENNSGTVDAYPANWHSDAFLASGIWQPNDEHKLTSTFDYYHKTNHTHYDTWDSSGNS
TIGTANQTSQTRRWGLSLKDDWTPMNDYLDSVSTKIYYQHTEAHDWTYMPDSVTRRMQTVNSNYDTDTWGLQTAL
AKTLGRHDLSAGFNASTSKTQRPFSQSPIPSVYSEIMQPEADSRSYTLGGFVQDKINFDLDSHNFAVIPGVRVVH
QSTKPENLSDLAANSSVLSESSVANLYGKNSDTQVLPSLTFQYDLTPRLMTYLQYQRGAQFPNASQLYGSWNLGS
SYAGSQQYALIGNTDLKTETSDNLEWGLKGEVTEGITLRTALFYNSYKNFIAYTRYTRANNPGQFTNVPSNIYTI
YQAENRDKAYIYGGEISTKFNFGTWFEQVDGLSATLALGYSEGKSKSSYSGDKYVDLDSVAPMKAIVGVAWDDPA
KRYGTALTATFVKGKQATATNRESYSNSGSAITDASSDYMRVPGYGMLDWTAYWQVAKNVRLNGGVYNLTDRKYW
DYLSSRNIETGTNQDANDKALAVMPGRTWQLGVNVDF*

Fig. 19

Klebsiella pneumoniae 1571 FoxA SEQ ID NO:25

```
TTGGTTCAGGATGATCTTATGAACGTGGCTATTTCTCGAAAACGCCCGGGGCTGCTGTATGCCCTTGCGGTCACA
CTCCCCTTCACCGCGCAAGCCGAAGAGACGGTGGTGGTCACTGCCACCCCGCCGGCGTCCGCCAGCGCGCCGACG
GAGGGCTACAGCGCCAGCACCTCGCTCGGGGCGACGAAAACCGACCAGCCGTTAATCACTACCGCCCAGTCGGTG
TCGGTGGTCACCCGCCAGCAGATGGCGGATCAGGGGGCGAATACCATCAGCCAGGCGCTGGAATATACCCCGGGG
GTCTACTCCAGCTTCGGCGGCGGCGCCACCCGGTTCGACGCCATCTCCCTGCGCGGCTACCACGGCGGCGACGTC
GATAACCTGTTCCTCGACGGCATGCGCCTGATGAGCGACGGCGGCAGCCATAACGTACTGCAAATCGACCCGTGG
TTTATCGAACGCGTGGATGTGATCCGCGGCCCCTCCTCCGCGCTCTACGGGCAGAGCGTGCCGGGCGGCGTGGTC
AACCTGACTTCCAAACGTCCGCAGTTCAGCCAGCAGGGCCACATCCGCCTGACCGGCGGCACGCAAAATACCAAA
GGCGCGGCCTTCGATTACACCGACGCCATCAATGACCAGTGGGCATGGCGGCTGATCGGGATGACCCGCAGCAGC
GACACGCAGTATGACCATACCCGCGAAGAGCGCTACGCGATTTCGCCTTCCCTGCTGTGGCAGCCGGACAGCGAC
ACCTCGCTGCTGCTGCGCGCCTATCTGCAAAAAGATCCTTCCGGCGGCTACCACGGCTCTTTGCCGCTGGACGGC
ACCCGCTACGCGCACAATGGCCGTAAGCTCTCCCCCAGCACCAACGAAGGCGATCCGGGAGATGGCTATCAGCGC
CGCCAGCAGATCTACAGCTATGAGTTTGACCACCAGTTCACCGACGTCTGGTCGGTCTATTCCGCCGGGAGCTAC
ACCCATACCAACGTCTCCCTCGATCAGGTCTACCAGGTCGGCTGGATAGATGAAAGCGACATGCTGGCCCGCGGC
TACAGCGGTTCGCGCGGTTCGCTGGACGGCTGGTCAACCGATAACCGCCTGCGCGCCGATTTCAATACAGGCGAC
CTGGCGCACACCCTGATCCTCGGCGCCGAATATCATCGCTTCCGTAACGACCTGTGGACCGGCGCCGGCGGCGCG
GCGCCCCTTAACCCGTTTAGCGGCTATACCGAGCAGACCGGACATACCGTTACCTACAGCGACGACAATAATCGC
CGCTATTACCAGACCGGGCTGTATCTGCAGGATGAGATGGTCTGGAACCGCTGGCATGTGGATGTTTCCGCCCGC
TACGACCGCATCGTTTCCCAGCAGGTCAGCGATACCCAGGGGACCTCAAACCGCCGTTCAGACGACCATATCAGC
GGCCGCGCCTCGCTGTTGTACGCCCTGGACAACGGTCTGTCGCCCTACCTGAGCTACAGCCAGGCGATCACTCCG
GCGATGCTGCCGGGCGCGGACGGCAAACCGTTGAAACCGACCACCGCCGAACAGGTTGAAGCCGGCCTGAAGTTC
CAGCCGCCGGGCAGCAGCGATCTCTATAGCATCGCGATTTACGACCTGACGCAAAAGGATGTCGCCACTCGCGAC
CCGAACATCGCCACCGCCACCTATATTCCGGCGGGTAAGGTCCATTCCCAGGGCGTTGAGCTGGAAGCGCACCAC
CAGATCACCCCGCAGCTGAGTACTATCGCCTCGTATACCTGGAATCGTCTGCGTTTCCAGGACACCCAAGACGGG
ACCGACAATAACACGCCGCAGCTGACCCCGGATCAGATGGCCTCCTTCTGGGCGCGCTATCAGTTCCCGGCGGGG
ATCTCCGTTGGCGCCGGCGTCCGCTACATCGGTAAACAGTGGGCGGATGATGCCAACACCGCGCGGCTGCCGTCG
GTCACGTTGATGGACGCCATGATGCGGGCCGACCTCGGCGTCTGGTCGCCAACGCTGAAAGGCGCTTATGTGCAG
GTTAACGCCAACAATATCGGCGACCGCGAGTATATTTCCGGCTGCTATGGCACCGGCAACTGTTACTGGGGAGCA
GAGCGCAGCGTTATAGCCACCGTGGGCTACGATTTCTGA
```

Klebsiella pneumoniae 1571 FoxA AA sequence, SEQ ID NO:26. Underlined
sequence is the signal sequence.  Sequence of protein without signal
sequence is SEQ ID NO:53, and the calculated molecular weight is 74.7 kDa.

MVQDDLMNVAISRKRPGLLYALAVTLPFTAQAEETVVVTATPPASASAPTEGYSASTSLGATKTDQPLITTAQSV
SVVTRQQMADQGANTISQALEYTPGVYSSFGGGATRFDAISLRGYHGGDVDNLFLDGMRLMSDGGSHNVLQIDPW
FIERVDVIRGPSSALYGQSVPGGVVNLTSKRPQFSQQGHIRLTGGTQNTKGAAFDYTDAINDQWAWRLIGMTRSS
DTQYDHTREERYAISPSLLWQPDSDTSLLLRAYLQKDPSGGYHGSLPLDGTRYAHNGRKLSPSTNEGDPGDGYQR
RQQIYSYEFDHQFTDVWSVYSAGSYTHTNVSLDQVYQVGWIDESDMLARGYSGSRGSLDGWSTDNRLRADFNTGD
LAHTLILGAEYHRFRNDLWTGAGGAAPLNPFSGYTEQTGHTVTYSDDNNRRYYQTGLYLQDEMVWNRWHVDVSAR
YDRIVSQQVSDTQGTSNRRSDDHISGRASLLYALDNGLSPYLSYSQAITPAMLPGADGKPLKPTTAEQVEAGLKF
QPPGSSDLYSIAIYDLTQKDVATRDPNIATATYIPAGKVHSQGVELEAHHQITPQLSTIASYTWNRLRFQDTQDG
TDNNTPQLTPDQMASFWARYQFPAGISVGAGVRYIGKQWADDANTARLPSVTLMDAMMRADLGVWSPTLKGAYVQ
VNANNIGDREYISGCYGTGNCYWGAERSVIATVGYDF*

Fig. 20

| Klebsiella pneumoniae 1571 OmpC gene sequence. SEQ ID NO:27 |
|---|
| ATGAAAGTTAAAGTACTGTCCCTCCTGGTACCGGCTCTGCTGGTAGCAGGCGCAGCAAATGCGGCTGAAATTTAT<br>AACAAAGACGGCAACAAATTAGACCTGTACGGTAAAATTGACGGTCTGCACTACTTCTCTGACGACAAGAGCGTC<br>GACGGCGACCAGACCTACATGCGTGTAGGCGTGAAAGGCGAAACCCAGATCAACGACCAGCTGACCGGTTACGGC<br>CAGTGGGAATACAACGTTCAGGCGAACAACACTGAAAGCTCCAGCGATCAGGCATGGACTCGTCTGGCATTCGCA<br>GGCCTGAAATTTGGCGACGCGGGCTCTTTCGACTACGGTCGTAACTACGGCGTAGTATACGACGTAACGTCCTGG<br>ACCGACGTTCTGCCGGAATTCGGCGGCGACACCTACGGTTCTGACAACTTCCTGCAGTCCCGTGCTAACGGCGTT<br>GCAACCTACCGTAACTCTGATTTCTTCGGTCTGGTTGACGGCCTGAACTTTGCTCTGCAGTATCAGGGTAAAAAC<br>GGCAGCGTCAGCGGCGAAGGCGCTCTGTCTCCTACCAACAACGGTCGTACCGCCTTGAAACAGAACGGCGACGGT<br>TACGGTACTTCTCTGACCTATGACATCTATGATGGCATCAGCGCTGGTTTCGCATACTCTAACTCCAAACGTCTT<br>GGCGACCAGAACAGCAAGCTGGCACTGGGTCGTGGCGACAACGCTGAAACCTACACCGGCGGTCTGAAATACGAT<br>GCGAACAACATCTACCTGGCCACTCAGTACACCCAGACCTACAACGCGACCCGCGCCGGTTCCCTGGGCTTTGCT<br>AACAAAGCGCAGAACTTCGAAGTGGTTGCTCAGTACCAGTTCGACTTCGGTCTGCGTCCGTCCGTGGCTTACCTG<br>CAGTCTAAAGGTAAGGATCTGGAAGGCTACGGCGACCAGGACATCCTGAAATATGTTGACGTTGGCGCGACCTAC<br>TACTTCAACAAAAACATGTCCACCTATGTTGACTACAAAATCAACCTGCTGGACGACAACAGCTTCACCCACAAC<br>GCCGGTATCTCTACCGACGACGTGGTTGCACTGGGCCTGGTTTACCAGTTCTAA |
| Klebsiella pneumoniae 1571 OmpC amino acid sequence. SEQ ID NO:28.<br>Underlined sequence is the signal sequence.　Sequence of protein without<br>signal sequence is SEQ ID NO:54. |
| MKVKVLSLLVPALLVAGAANAAEIYNKDGNKLDLYGKIDGLHYFSDDKSVDGDQTYMRVGVKGETQINDQLTGYG<br>QWEYNVQANNTESSSDQAWTRLAFAGLKFGDAGSFDYGRNYGVVYDVTSWTDVLPEFGGDTYGSDNFLQSRANGV<br>ATYRNSDFFGLVDGLNFALQYQGKNGSVSGEGALSPTNNGRTALKQNGDGYGTSLTYDIYDGISAGFAYSNSKRL<br>GDQNSKLALGRGDNAETYTGGLKYDANNIYLATQYTQTYNATRAGSLGFANKAQNFEVVAQYQFDFGLRPSVAYL<br>QSKGKDLEGYGDQDILKYVDVGATYYFNKNMSTYVDYKINLLDDNSFTHNAGISTDDVVALGLVYQF |

Fig. 21

| Klebsiella pneumoniae 1571 OmpA gene sequence. SEQ ID NO:29 |
|---|
| ATGAAAAAGACAGCTATCGCGATTGCAGTGGCACTGGCTGGCTTCGCTACCGTAGCGCAGGCCGCTCCGAAAGAT<br>AACACCTGGTATGCAGGTGGTAAACTGGGTTGGTCCCAGTATCACGACACCGGTTTCTACGGTAACGGTTTCCAG<br>AACAACAACGGTCCGACCCGTAACGATCAGCTTGGTGCTGGTGCGTTCGGTGGTTACCAGGTTAACCCGTACCTC<br>GGTTTCGAAATGGGTTATGACTGGCTGGGCCGTATGGCATATAAAGGCAGCGTTGACAACGGTGCTTTCAAAGCT<br>CAGGGCGTTCAGCTGACCGCTAAACTGGGTTACCCGATCACTGACGATCTGGACATCTACACCCGTCTGGGCGGC<br>ATGGTTTGGCGCGCTGACTCCAAAGGCAACTACGCTTCTACCGGCGTTTCCCGTAGCGAACACGACACTGGCGTT<br>TCCCCAGTATTTGCTGGCGGCGTAGAGTGGGCTGTTACTCGTGACATCGCTACCCGTCTGGAATACCAGTGGGTT<br>AACAACATCGGCGACGCGGGCACTGTGGGTACCCGTCCTGATAACGGCATGCTGAGCCTGGGCGTTTCCTACCGC<br>TTCGGTCAGGAAGATGCTGCACCGGTTGTTGCTCCGGCTCCGGCTCCGGAAGTGGCTACCAAGCACTTC<br>ACCCTGAAGTCTGACGTTCTGTTCAACTTCAACAAAGCTACCCTGAAACCGGAAGGTCAGCAGGCTCTGGATCAG<br>CTGTACACTCAGCTGAGCAACATGGATCCGAAAGACGGTTCCGCTGTTGTTCTGGGCTACACCGACCGCATCGGT<br>TCCGAAGCTTACAACCAGCAGCTGTCTGAGAAACGTGCTCAGTCCGTTGTTGACTACCTGGTTGCTAAAGGCATC<br>CCGGCTGGCAAAATCTCCGCTCGCGGCATGGGTGAATCCAACCCGGTTACTGGCAACACCTGTGACAACGTGAAA<br>GCTCGCGCTGCCCTGATCGATTGCCTGGCTCCGGATCGTCGTGTAGAGATCGAAGTTAAAGGCTACAAAGAAGTT<br>GTAACTCAGCCGGCGGCTTAA |
| Klebsiella pneumoniae 1571 OmpA amino acid sequence. SEQ ID NO:30.<br>Underlined sequence is the signal sequence.　Sequence of protein without<br>signal sequence is SEQ ID NO:55. |
| MKKTAIAIAVALAGFATVAQAAPKDNTWYAGGKLGWSQYHDTGFYGNGFQNNNGPTRNDQLGAGAFGGYQVNPYL<br>GFEMGYDWLGRMAYKGSVDNGAFKAQGVQLTAKLGYPITDDLDIYTRLGGMVWRADSKGNYASTGVSRSEHDTGV<br>SPVFAGGVEWAVTRDIATRLEYQWVNNIGDAGTVGTRPDNGMLSLGVSYRFGQEDAAPVVAPAPAPAPEVATKHF<br>TLKSDVLFNFNKATLKPEGQQALDQLYTQLSNMDPKDGSAVVLGYTDRIGSEAYNQQLSEKRAQSVVDYLVAKGI<br>PAGKISARGMGESNPVTGNTCDNVKARAALIDCLAPDRRVEIEVKGYKEVVTQPAA |

| E. coli CFT073 CirA Gene Sequence, SEQ ID NO:56 |
|---|
| ATGAGAGGATCGCATCACCATCACCATCACGGATCTGGCTCTGGATCTGGTATCGAGGGAAGGCCTGTCGAT GATGATGGCGAAACGATGGTTGTCACTGCATCTTCCGTTGAACAAAACCTTAAAGATGCTCCCGCCAGTATCA GCGTCATTACCCAGGAAGACCTGCAGCGAAAACCGGTACAGAATCTGAAGGATGTCCTCAAAGAAGTGCCTG GCGTACAACTGACGAACGAAGGGGATAACCGTAAGGGCGTAAGTATTCGTGGTCTGGACAGCAGCTACACCC TGATTCTTGTCGACGGTAAACGCGTTAACTCCCGCAATGCCGTCTTCCGCCACAATGATTTCGATCTGAACTGG ATCCCGGTCGATTCCATCGAACGTATTGAAGTGGTTCGTGGCCCGATGTCGTCGCTGTACGGTTCCGATGCGC TCGGCGGTGTAGTGAATATCATCACCAAAAAAATCGGTCAGAAATGGTCGGGCACCGTTACCGTCGATACCAC CGTTCAGGAACATCGCGATCGCGGTGATACCTATAACGGTCAATTCTTTACCAGCGGACCATTAATTGACGGC GTGCTGGGAATGAAAGCTTACGGCAGCCTGGCAAAACGTGAAAAGGATGACCCGCAAACTCAACGACCACC GATACCGGAGAAACGCCGCGTATTGAAGGATTCTCCAGCCGCGACGGCAATGTCGAATTTGCCTGGACACCG AATCAAAATCACGATTTTACTGCCGGATACGGTTTCGACCGTCAGGATCGTGATTCCGACTCGCTGGACAAAA ACCGCCTGGAACGCCAGAACTACTCCGTCAGCCATAATGGGCGTTGGGATTACGGCACCAGCGAACTGAAAT ACTACGGTGAGAAAGTCGAGAACAAAAACCCTGGCAACAGCAGCCCGATAACTTCCGAAAGCAATACGGTCG ACGGCAAATACACGTTGCCGCTGACGGCGATTAATCAGTTTCTCACGGTTGGCGGTGAATGGCGTCACGACA AACTTAGCGATGCGGTGAACCTGACCGGGGGAACCAGCTCCAAAACGTCTGCCAGCCAGTACGCGCTGTTTG TGGAAGATGAATGGCGGATCTTCGAGCCGCTGGCGCTGACGACCGGCGTGCGTATGGACGATCACGAAACCT ACGGTGAACACTGGAGTCCGCGTGCCTACCTGGTTTATAACGCCACCGACACCGTAACGGTGAAAGGGGGCT GGGCGACGGCATTTAAAGCCCCTTCTCTGTTGCAACTTAGCCCTGACTGGACGAGCAATTCCTGCCGTGGCGC ATGTAAGATTGTGGGTAGCCCGGATCTGAAACCAGAAACCAGCGAAAGTTGGGAGCTGGGGCTTTACTACAT GGGTGAAGAAGGCTGGCTGGAAGGGGTTGAATCCAGCGTTACCGTTTTCCGTAACGATGTGAAAGATCGTAT CAGCATTAGCCGTACGTCTGACGTCAATGCTGCACCGGGCTACCAAAACTTTGTCGGTTTTGAGACGGGCGCT AACGGACGGCGCATACCGGTATTTAGCTACTACAACGTTAACAAAGCTCGTATTCAGGGCGTGGAAACCGAA CTGAAAATTCCGTTCAACGATGAATGGAAACTGTCGATCAACTACACCTACAACGATGGTCGTGATGTCAGCA ACGGCGAAAACAAACCGCTATCCGATCTGCCGTTCCATACTGCTAACGGTACGCTGGACTGGAAACCGCTGGC GCTGGAAGACTGGTCATTCTATGTTTCTGGTCACTATACCGGGCAGAAACGCGCCGACAGCGCGACGGCTAA AACACCGGGCGGTTATACCATCTGGAATACCGGCGCGGCCTGGCAGGTGACTAAAGACGTCAAACTGCGCGC AGGCGTGCTGAACCTTGGCGACAAGGATCTCAGTCGTGACGACTACAGCTATAACGAAGACGGACGTCGTTA CTTTATGGCAGTGGATTATCGCTTCTGA |

| E. coli CFT073 CirA amino acid sequence. SEQ ID NO:57. Amino acids 1-22 are a His tag and Xa protease cleavage site. Sequence of protein without His tag and Xa protease cleavage site is SEQ ID NO:58. |
|---|
| MRGSHHHHHHGSGSGSGIEGRPVDDDGETMVVTASSVEQNLKDAPASISVITQEDLQRKPVQNLKDVLKEVPGV QLTNEGDNRKGVSIRGLDSSYTLILVDGKRVNSRNAVFRHNDFDLNWIPVDSIERIEVVRGPMSSLYGSDALGGVV NIITKKIGQKWSGTVTVDTTVQEHRDRGDTYNGQFFTSGPLIDGVLGMKAYGSLAKREKDDPQNSTTTDTGETPRI EGFSSRDGNVEFAWTPNQNHDFTAGYGFDRQDRDSDSLDKNRLERQNYSVSHNGRWDYGTSELKYYGEKVENK NPGNSSPITSESNTVDGKYTLPLTAINQFLTVGGEWRHDKLSDAVNLTGGTSSKTSASQYALFVEDEWRIFEPLALTT GVRMDDHETYGEHWSPRAYLVYNATDTVTVKGGWATAFKAPSLLQLSPDWTSNSCRGACKIVGSPDLKPETSES WELGLYYMGEEGWLEGVESSVTVFRNDVKDRISISRTSDVNAAPGYQNFVGFETGANGRRIPVFSYYNVNKARIQ GVETELKIPFNDEWKLSINYTYNDGRDVSNGENKPLSDLPFHTANGTLDWKPLALEDWSFYVSGHYTGQKRADSA TAKTPGGYTIWNTGAAWQVTKDVKLRAGVLNLGDKDLSRDDYSYNEDGRRYFMAVDYRF |

Fig. 37

| E. coli CFT073 FepA Gene Sequence, SEQ ID NO:59. |
|---|
| ATGAGAGGATCGCATCACCATCACCATCACGGATCTGGCTCTGGATCTGGTATCGAGGGAAGGCCTCAAGAG CCGACCGATACTCCTGTTTCACATGACGATACCATTGTCGTTACCGCCGCCGAGCAGAACTTGCAGGCGCCTG GCGTTTCGACCATTACCGCAGATGAAATCCGCAAAAACCCGGTTGCCCGCGATGTATCGGAGATCATTCGTAC CATGCCTGGCGTTAACCTGACCGGTAACTCCACCAGTGGTCAGCGTGGTAATAACCGCCAGATTGATATTCGC GGCATGGGTCCGGAAAACACGCTGATTTTGATTGACGGCAAGCCGGTAAGCAGCCGTAACTCTGTGCGTCAG GGCTGGCGTGGCGAGCGCGATACCCGTGGTGATACCTCCTGGGTGCCGCCTGAAATGATTGAACGTATTGAA GTTCTGCGTGGTCCGGCAGCTGCGCGTTATGGCAACGGCGCGGCGGGGCGGCGTGGTTAACATCATTACCAAA AAAGGCAGCGGTGAGTGGCACGGCTCCTGGGATGCTTATTTCAATGCGCCAGAACATAAAGAGGAAGGTGC CACCAAACGCACCAACTTCAGCCTGACCGGTCCGCTGGGCGACGAATTCAGCTTCCGCTTGTATGGCAACCTC GACAAAACCCAGGCTGACGCGTGGGATATCAACCAGGGCCATCAGTCCGCGCGTGCCGGAACGTATGCCACG ACGTTACCAGCCGGGCGCGAAGGGGTGATCAACAAAGATATTAATGGCGTGGTGCGCTGGGACTTCGCGCCT CTGCAGTCACTCGAACTGGAAGCGGGCTACAGCCGCCAGGGTAACCTGTATGCGGGTGATACGCAGAACACC AACTCTGACGCTTACACTCGATCGAAATATGGCGATGAAACCAACCGCCTGTATCGCCAGAACTACTCGCTGA CCTGGAACGGTGGCTGGGATAACGGCGTGACCACCAGCAACTGGGTGCAGTACGAACACACCCGTAACTCGC GTATTCCGGAAGGTCTGGCGGGCGGTACCGAAGGGAAATTTAACGAAAAGCGGCACAGGATTTTGTAGAT ATCGATCTTGATGACGTGATGCTGCACAGCGAAGTTAACCTGCCGATTGATTTCCTCGTAAACCAAACGCTGA CGCTGGGTACAGAGTGGAATCAGCAACGGATGAAGGACTTAAGTTCCAACACCCAGGCGCTGACCGGGACG AATACCGGCGGTGCTATTGATGGTGTGAGTGCCACCGACCGTAGCCCGTATTCAAAAGCAGAAATTTTCTCGC TGTTTGCCGAAAACAATATGGAGCTGACTGACAGCACCATCGTAACGCCGGGGCTGCGTTTCGATCATCACAG TATTGTCGGCAATAACTGGAGCCCGGCGCTGAACATATCGCAAGGTTTAGGCGATGACTTCACGCTGAAAATG GGCATCGCCCGCGCCTATAAAGCGCCGAGCCTGTACCAGACTAACCCAAACTACATTCTCTACAGTAAAGGTC AGGGCTGCTATGCCAGCGCGGGCGGCTGCTATCTGCAAGGTAATGATGACCTGAAAGCAGAAACCAGCATCA ACAAGGAGATTGGTCTGGAGTTCAAACGCGACGGTTGGCTGGCGGGCGTGACCTGGTTCCGTAACGATTATC GCAATAAGATTGAAGCGGGCTATGTGGCTGTAGGGCAAACGCAGTCGGCACCGATCTCTATCAGTGGGATA ACGTACCGAAAGCGGTGGTTGAAGGTCTGGAAGGATCGTTAAACGTACCGGTTAGCGAAACGGTGATGTGG ACCAATAACATCACTTATATGCTGAAGAGTGAAAACAAAACCACGGGCGACCGTTTGTCGATCATCCCGGAGT ATACGTTGAACTCAACGCTGAGCTGGCAGGCACGGGAAGATTTGTCGATGCAAACGACCTTCACCTGGTACG GCAAACAGCAGCCGAAGAAGTACAACTATAAAGGTCAGCCAGCGGTTGGACCGGAAACCAAAGAAATCAGT CCGTACAGCATTGTTGGCCTGAGCGCGACCTGGGATGTGACGAAGAATGTCAGTCTGACCGGCGGCGTGGAC AACCTGTTCGACAAACGTTTGTGGCGTGCGGGTAATGCCCAGACCACGGGCGATCTGGCAGGGGCCAACTAT ATCGCCGGTGCCGGTGCGTATACCTATAACGAGCCGGGACGTACGTGGTATATGAGCATTAATACTCACTTCT GA |
| E. coli CFT073 FepA amino acid sequence. SEQ ID NO:60. Amino acids 1-22 are a His tag and Xa protease cleavage site. Sequence of protein without His tag and Xa protease cleavage site is SEQ ID NO:61. |
| MRGSHHHHHHGSGSGSGIEGRPQEPTDTPVSHDDTIVVTAAEQNLQAPGVSTITADEIRKNPVARDVSEIIRTMP GVNLTGNSTSGQRGNNRQIDIRGMGPENTLILIDGKPVSSRNSVRQGWRGERDTRGDTSWVPPEMIERIEVLRGP AAARYGNGAAGGVVNIITKKGSGEWHGSWDAYFNAPEHKEEGATKRTNFSLTGPLGDEFSFRLYGNLDKTQADA WDINQGHQSARAGTYATTLPAGREGVINKDINGVVRWDFAPLQSLELEAGYSRQGNLYAGDTQNTNSDAYTRSK YGDETNRLYRQNYSLTWNGGWDNGVTTSNWVQYEHTRNSRIPEGLAGGTEGKFNEKAAQDFVDIDLDDVMLH SEVNLPIDFLVNQTLTLGTEWNQQRMKDLSSNTQALTGTNTGGAIDGVSATDRSPYSKAEIFSLFAENNMELTDSTI VTPGLRFDHHSIVGNNWSPALNISQGLGDDFTLKMGIARAYKAPSLYQTNPNYILYSKGQGCYASAGGCYLQGND DLKAETSINKEIGLEFKRDGWLAGVTWFRNDYRNKIEAGYVAVGQNAVGTDLYQWDNVPKAVVEGLEGSLNVPV SETVMWTNNITYMLKSENKTTGDRLSIIPEYTLNSTLSWQAREDLSMQTTFTWYGKQQPKKYNYKGQPAVGPETK EISPYSIVGLSATWDVTKNVSLTGGVDNLFDKRLWRAGNAQTTGDLAGANYIAGAGAYTYNEPGRTWYMSINTH F |

Fig. 38

| E. coli CFT073 IutA Gene Sequence, SEQ ID NO:62. |
|---|
| ATGAGAGGATCGCATCACCATCACCATCACGGATCTGGCTCTGGATCTGGTATCGAGGGAAGGCCTCAGCAA AACGATGATAATGAGATCATAGTGTCTGCCAGCCGCAGCAATCGAACTGTAGCGGAGATGGCGCAAACCACC TGGGTTATCGAAAATGCCGAACTGGAGCAGCAGATTCAGGGCGGTAAAGAGCTGAAAGACGCACTGGCTCA GTTAATCCCCGGCCTTGATGTCAGCAGCCAGAGCCGAACCAACTACGGTATGAACATGCGTGGCCGCCCGCTG GTTGTCCTGATTGACGGTGTGCGCCTCAACTCTTCACGTTCCGACAGCCGACAACTGGACTCTGTCGATCCTTT TAATATCGACCATATTGAAGTGATCTCCGGCGCGACGGCCCTGTACGGTGGCGGGAGTACCGGAGGGTTGAT CAACATCGTGACCAAAAAGGCCAGCCGGAAACCATGATGGAGTTTGAGGCTGGCACAAAAGTGGCTTTAA CAGCAGTAAAGATCACGATGAGCGCATTGCCGGTGCTGTCTCCGGCGGAAATGACCATATCTCCGGACGTCTT TCCGTGGCATATCAGAAATTTGGCGGCTGGTTTGACGGTAACGGCGATGCCACCCTGCTTGATAACACCCAGA CCGGCCTGCAGCACTCCAATCGGCTGGACATCATGGGAACCGGTACGCTGAACATCGATGAATCCCGGCAGC TTCAACTGATAACGCAGTACTATAAAGTCAGGGGGACGACAATTACGGGCTTAATCTCGGGAAAGGCTTTTC CGCCATCAGCGGGAGCAGCACACCATACGTCAGTAAGGGGCTGAATTCTGACCGCATTCCCGGCACTGAGCG GCATTTGATCAGCCTGCAGTACTCTGACAGTGATTTCCTGAGACAGGAACTGGTCGGTCAGGTTTACTACCGC GATGAGTCGTTGCGGTTCTACCCGTTCCCGACGGTAAATGCGAATAAACAGGCGACGGCTTTCTCCTCGTCAC AGCAGGATACCGACCAGTACGGCATGAAACTGACTCTGAACAGCCAACTTATGGACGGCTGGCAAATCACCT GGGGGCTGGATGCTGAGCATGAGCGCTTTACCTCCAACCAGATGTTCTTCGATCTGGCTCAGGCAAGTGCTTC CGGAGGGCTGAACAACCATAAGATTTACACCACCGGGCGCTATCCGTCATATGACATCACCAATCTGGCGGCC TTCCTGCAATCCAGCTATGACATTAATGATATTTTTACCGTTAGCGGTGGCGTACGCTATCAGTATACTGAGAA CAGGGTAGATGATTTCATCGACTACACGCAGCAACAGAAGATTGCTGCCGGGAAGGCGATATCTGCCGACGC CATTCCTGGTGGTTCGGTAGATTACGATAACTTTCTGTTCAATGCTGGTCTGCTGATGCACATCACCGAACGTC AGCAGGCATGGTTCAATTTTTCCCAGGGGGTGGCATTGCCGGATCCGGGGAAATATTATGGTCGCGGCATCT ATGGTGCAGCAGTGAACGGCCATCTTCCCCTGACAAAGAGCGTGAACGTCAGCGACAGTAAGCTGGAAGGC GTGAAAGTCGATTCTTATGAACTGGGCTGGCGCTTTACCGGTGACAACCTGCGGACTCAAATCGCGGCATATT ACTCGCTTTCCAATAAGAGCGTGGAAAGGAATAAGATCTGACCATCAGTGTGAAGGACGACAGGCGCCGTA TTTACGGCGTGGAAGGTGCGGTGGACTACCTGATCCCGGATACTGACTGGAGTACCGGTGTGAACTTCAATG TGCTGAAAACCGAGTCGAAAGTGAACGGTCAATGGCAAAAATATGACGTGAAGGAATCAAGTCCATCGAAAG CGACAGCTTACATTAACTGGGCGCCGGAACCGTGGAGTCTGCGTGTACAGAGCACCACTTCTTTCGACGTAAG CGATGCAGAGGGTAACGATATTAATGGTTACACTACCGTCGATTTTATCAGTAGTTGGCAGCTTCCGGTGGGA ACACTCAGCTTCAGCGTTGAGAACCTCTTCGACCGTGACTATACCACTGTCTGGGGACAGCGTGCACCTCTGTA CTACAGCCCGGGTTACGGCCCTGCTTCACTGTACGACTACAAAGGCCGGGGCCGAACCTTTGGTCTGAACTAC TCAGTGCTGTTCTGA |

| E. coli CFT073 IutA amino acid sequence. SEQ ID NO:63.  Amino acids 1-22 are a His tag and Xa protease cleavage site.  Sequence of protein without His tag and Xa protease cleavage site is SEQ ID NO:64. |
|---|
| MRGSHHHHHHGSGSGSGIEGRPQQNDDNEIIVSASRSNRTVAEMAQTTWVIENAELEQQIQGGKELKDALAQLI PGLDVSSQSRTNYGMNMRGRPLVVLIDGVRLNSSRSDSRQLDSVDPFNIDHIEVISGATALYGGGSTGGLINIVTKK GQPETMMEFEAGTKSGFNSSKDHDERIAGAVSGGNDHISGRLSVAYQKFGGWFDGNGDATLLDNTQTGLQHSN RLDIMGTGTLNIDESRQLQLITQYYKSQGDDNYGLNLGKGFSAISGSSTPYVSKGLNSDRIPGTERHLISLQYSDSDFL RQELVGQVYYRDESLRFYPFPTVNANKQATAFSSSQQDTDQYGMKLTLNSQLMDGWQITWGLDAEHERFTSNQ MFFDLAQASASGGLNNHKIYTTGRYPSYDITNLAAFLQSSYDINDIFTVSGGVRYQYTENRVDDFIDYTQQQKIAAG KAISADAIPGGSVDYDNFLFNAGLLMHITERQQAWFNFSQGVALPDPGKYYGRGIYGAAVNGHLPLTKSVNVSDS KLEGVKVDSYELGWRFTGDNLRTQIAAYYSLSNKSVERNKDLTISVKDDRRRIYGVEGAVDYLIPDTDWSTGVNFN VLKTESKVNGQWQKYDVKESSPSKATAYINWAPEPWSLRVQSTTSFDVSDAEGNDINGYTTVDFISSWQLPVGTL SFSVENLFDRDYTTVWGQRAPLYYSPGYGPASLYDYKGRGRTFGLNYSVLF |

SEQUENCE LISTING

```
Sequence total quantity: 64
SEQ ID NO: 1            moltype = DNA   length = 2325
FEATURE                 Location/Qualifiers
source                  1..2325
                        mol_type = unassigned DNA
                        organism = Klebsiella pneumoniae
SEQUENCE: 1
atgacgccgt tacgcgtttt tcgtaaaaca actcctttgg ttaacgccat tcgcctgagc   60
ctgctgccgc tggccggtct ctcgttttcc gcttttgctg cacaggttga tatcgcaccg  120
ggatcgctcg acaaagcgct caatcagtat gccgcacaca gcggaattac cctctcggtt  180
gacgccagcc tgacgcgcgg caagcagagc aacggcctgc acggagatta cgacgtcgag  240
agcggcctgc aacagctgct ggacggcagc ggactgcagg taaaaccgct gggaaataac  300
agctggacgc tggagcccgc gcccgcgcca aaagaagatg ccctgaccgt ggtcggcgac  360
tggctgggcg atgcgcgtga aaacgacgta tttgaacatg ctggcgcgcg tgacgtgatc  420
cgccgtgagg atttcgccaa aaccggcgca accaccatgc gtgaggtgct taaccgcatc  480
cctgcgtca gcgcgccgga aaacaacggc accggcagcc acgacctggc gatgaacttt  540
ggcatccggg gcctgaaccc acgcctcgcc agccgctcga ccgtcctgat ggacggcatc  600
cccgtcccct ttgcccctta cggtcagccg cagctttcac tggctcccgt ttcgctcggc  660
aacatggatg ccattgacgt ggtgcgcggt ggtggtgcgg tgcgttacgg accgcagagc  720
gtgggcggcg tggtgaactt tgttacccgc gccattccgc aggactttgg tatcgaggcg  780
ggggtggaag gtcagctcag cccaacctct tcacaaaaca acccgaaaga gacgcacaac  840
ctgatggtgg gcggcacagc ggacaacggt tttggcaccg cgctgctcta ctccggcacg  900
cgcggcagtg actggcgcga gcacagcgcc acccgcatcg acgacctgat gctgaaaagc  960
```

-continued

```
aaatatgcgc cgaatgaggt gcacaccttc aacagcctgc tgcaatatta cgatggtgaa    1020
gccgacatgc ccggcggcct gtcccgcgcg gattacgacg ccgatcgctg gcaatccacc    1080
cgcccgtatg accgcttctg gggccgtcgc aagctggcga gcctgggcta ccagttccag    1140
ccggacagcc agcataaatt caacattctg gggttctaca cccaaaccct gcgcagcggc    1200
tacctggagc aaggcaaacg catcaccctc tcgccgcgta actactgggt gcgcggtatt    1260
gagccacgct acagccagag ctttatgatc ggccchttccg cgcacgaagt gggcgtgggc    1320
tatcgctatg tgaatgaatc aacgcatgaa atgcgttact acaccgccac cagcagcggg    1380
cagttgccgt ccggctcaag cccttacgac cgcgacacgc gttccggcac cgaggcgcac    1440
gcctggtatc tggatgacaa aatcgacatc ggcaactgga ccatcacgcc gggtatgcgt    1500
ttcgaacata tcgagtcata ccagaacaac gccatcaaag gcacgcacga agaggtaagc    1560
tataacgcac cgcttccggc gttgaacgtg ctctatcacc tgactgacag ctggaatctt    1620
tatgcaaaca ctgaaggctc gttcggcacc gtacagtaca gccagattgg caaggctgtg    1680
caaagcggca atgtggaacc ggaaaaagcg cgaacctggg aactcggtac ccgctacgac    1740
gacggcggca tgacggcgga aatggggctg ttcctgatta actttaacaa tcagtacgac    1800
tccaaccaga ccaacgacac cgtcactgca cgtggcaaaa cgcgccatac cgggctggaa    1860
acgcaggcac gttacgacct gggtacgcta acgccaacgc ttgataacgt ttccgtctac    1920
gccagctatg cgtatgtgaa cgcggaaatc cgcgagaaag cgcacaccta tggcaatcag    1980
gtgccattct ccccgaaaca taaaggcacg ctgggcgtga actacaagcc gggcaactgg    2040
acgttcaatc tgaacagcga tttccagtcc agccagtttg cggataacgc caatacggtg    2100
aaagagagcg ccgacggcag taccggccgc attcccggct tcatgctctg gggcgcacgc    2160
gtggcgtatg actttggccc gcagatggca gatctgaacc tggcgttcgg tgtgaaaaac    2220
atcttcgacc aggactactt catccgctct tatgacgaca acaacaaagg catctacgca    2280
ggccagccgc gcacgctgta tatgcagggg tcgttgaagt tctga                     2325
```

```
SEQ ID NO: 2              moltype = AA  length = 774
FEATURE                   Location/Qualifiers
source                    1..774
                          mol_type = protein
                          organism = Klebsiella pneumoniae
SEQUENCE: 2
MTPLRVFRKT TPLVNAIRLS LLPLAGLSFS AFAAQVDIAP GSLDKALNQY AAHSGITLSV    60
DASLTRGKQS NGLHGDYDVE SGLQQLLDGS GLQVKPLGNN SWTLEPAPAP KEDALTVVGD    120
WLGDARENDV FEHAGARDVI RREDFAKTGA TTMREVLNRI PGVSAPENNG TGSHDLAMNF    180
GIRGLNPRLA SRSTVLMDGI PVPFAPYGQP QLSLAPVSLG NMDAIDVVRG GGAVRYGPQS    240
VGGVVNFVTR AIPQDFGIEA GVEGQLSPTS SQNNPKETHN LMVGGTADNG FGTALLYSGT    300
RGSDWREHSA TRIDDLMLKS KYAPNEVHTF NSLLQYYDGE ADMPGGLSRA DYDADRWQST    360
RPYDRFWGRR KLASLGYQFQ PDSQHKFNIL GFYTQTLRSG YLEQGKRITL SPRNYWVRGI    420
EPRYSQSFMI GPSAHEVGVG YRYVNESTHE MRYYTATSSG QLPSGSSPYD RDTRSGTEAH    480
AWYLDDKIDI GNWTITPGMR FEHIESYQNN AIKGTHEEVS YNAPLPALNV LYHLTDSWNL    540
YANTEGSFGT VQYSQIGKAV QSGNVEPEKA RTWELGTRYD DGALTAEMGL FLINFNNQYD    600
SNQTNDTVTA RGKTRHTGLE TQARYDLGTL TPTLDNVSVY ASYAYVNAEI REKGDTYGNQ    660
VPFSPKHKGT LGVDYKPGNW TFNLNSDFQS SQFADNANTV KESADGSTGR IPGFMLWGAR    720
VAYDFGPQMA DLNLAFGVKN IFDQDYFIRS YDDNNKGIYA GQPRTLYMQG SLKF           774
```

```
SEQ ID NO: 3              moltype = DNA  length = 2208
FEATURE                   Location/Qualifiers
source                    1..2208
                          mol_type = unassigned DNA
                          organism = Klebsiella pneumoniae
SEQUENCE: 3
atggcgcgtc caaaaactgc tcagccaaat cactcgctgc gtaaagtcgc agctgtagta    60
gccacggcgg ttagcggcat gtctgtctac gcacaggcag cagaacaacc gaagcaagaa    120
gaaaccatca ccgtcgttgc cgccccggcc gcccaggaaa acgcctgggg accggcgccg    180
actatcgcgc aaaacgctc cgccacggcg accaaaaccg ataccccgat tgaaaaaacg    240
ccgcagtctg tgtcggtggt gacgcgccat gagatgaaa tgcgccagcc gacgacggta    300
aaagaggcgc tctcctatac gccaagcgtc ttctccactc gcggcagttc gaccacctat    360
gacgtggtca ccattcgcgg cttcaccacc tcgacgaccg tcaacaccaa ccagtatctg    420
gacggcatga agctgcaggg gaataactac tctgaagtct ccatggatcc ttacttcctc    480
gagcgtgtgg aagtgatgcg cgggccaacc tcggtgctgt acggcaacag caacccgggc    540
ggtatcgtca gcatggtcag caagcgcccg actaccgagc cgctgaaaga agtgcagttt    600
aagatgggca ccgacaatct gtggcagacc gggtttgact ttagcgacgc cattgatgat    660
gccggcgtct ggtcgtatcg cctgaccggc cttggccgca gtcaggatgc ccagcagcag    720
atggcgaaat cgactcgcta cgcggtggcg ccctcctta gctggcgtcc ggacgataaa    780
accgacttca ccttcctgag caacttccag aatgacccgg gcgggctca ctacggctgg    840
ctgccgcgcg aaggcaccgt ggtgccgtat tacgacgcca acggtaaggc gcacaagctg    900
ccgaccgatt caacgaagg cgagtccgat aataaaatct cccgccgcca gaagatggtg    960
ggctacagct ctcccatca gttcgatgac acctttaccg tgcggcagaa cctgcgctat    1020
gccgatgtgc atacgctcta tcgttcggta tacggcaacg gctatgtcgc gccgggctac    1080
atgaatcgcg cctacgtgcg ctccgacgag cacctgaaca ccttcaccgt cgataccgag    1140
ctgcagtctg atttcgccac cggcgcggtc agccatacg tgctgaccgg cgtggactac    1200
tcgcggatgc gtaacgatgt ggatgccgac tacgggacgg cggatcctat cagcatgagc    1260
aatccgcagt acggcaatcc gaatattcag gtcaccttcc gtacgcggt cctcaaccgg    1320
atggagcaga ccggcctgta cgcgcaggat cagatggagt gggataaatg ggtgatgacc    1380
ctgggcgatg gttacgatta cgccacgacc tcaacgttaa ccggcgccac caacagcctg    1440
gcggagaatc acgaccagca gttcagctgg cgcggcggca tcaactacct gttcgataac    1500
ggcatctcgc gtacttcag ctacagcgaa tcgtttgaac cggtatcggg ttccaacagc    1560
cgcggccagc cgttcgatcc gtcgcgcggt aagcagtatg aagccggcgt gaaatacgtg    1620
ccgaaagata tgccggtggt ggtcaccgcg gcggtctatc agctgaccaa agacaagaac    1680
ctgacggctg atccggctaa ccaggcgttc agcatccaga ccggcgagat ccgctcccgc    1740
```

-continued

```
ggccttgagc tggaggcgaa ggcggcggtg aacgccaata ttaacgtcac cgcggcctac   1800
agctacaccg atgcggagta cactcacgat acggtgttca acggcaaacg tccggcggaa   1860
gtgccgcgta acatggcctc cctgtgggcg gattatacct tccacgaaac cgcgctgagc   1920
ggtctgacga ttggggccgg ggcgcgctat atcggttcaa cggtcagcta ctacaaaaat   1980
gacaccagca ccggtaagaa aaatgatgcc tttagtgtgg gcggttatgc gctgatggat   2040
gcgacggtga aatacgatct ggcgcgcttt ggcctgccgg gatcgtcggt cggcgtcaac   2100
gtcaacaacc tgttcgaccg cgaatatgtc tccagttgct acagcgaata cgcctgctac   2160
tggggcgccg gacgtcaggt cgtcgccacc gccaccttcc gtttctaa              2208
```

SEQ ID NO: 4          moltype = AA  length = 735
FEATURE               Location/Qualifiers
source                1..735
                      mol_type = protein
                      organism = Klebsiella pneumoniae
SEQUENCE: 4
```
MARPKTAQPN HSLRKVAAVV ATAVSGMSVY AQAAEQPKQE ETITVVAAPA AQENAWGPAP   60
TIAAKRSATA TKTDTPIEKT PQSVSVVTRH EMEMRQPTTV KEALSYTPSV FSTRGSSTTY   120
DVVTIRGFTT STTVNTNQYL DGMKLQGNNY SEVSMDPYFL ERVEVMRGPT SVLYGNSNPG   180
GIVSMVSKRP TTEPLKEVQF KMGTDNLWQT GFDFSDAIDD AGVWSYRLTG LGRSQDAQQQ   240
MAKSTRYAVA PSFSWRPDDK TDFTFLSNFQ NDPDAGYYGW LPREGTVVPY YDANGKAHKL   300
PTDFNEGESD NKISRRQKMV GYSFSHQFDD TFTVRQNLRY ADVHTLYRSV YGNGYVAPGY   360
MNRAYVRSDE HLNTFTVDTQ LQSDFATGAV SHTLLTGVDY SRMRNDVDAD YGTADPISMS   420
NPQYGNPNIQ VTFPYAVLNR MEQTGLYAQD QMEWDKWVMT LGGRYDYATT STLTRATNSL   480
AENHDQQFSW RGGINYLFDN GISPYFSYSE SFEPVSGSNS RGQPFDPSRG KQYEAGVKYV   540
PKDMPVVVTA AVYQLTKDKN LTADPANQAF SIQTGEIRSR GLELEAKAAV NANINVTAAY   600
SYTDAEYTHD TVFNGKRPAE VPRNMASLWA DYTFHETALS GLTIGAGARY IGSTVSYYKN   660
DTSTGKKNDA FSVAGYALMD ATVKYDLARF GLPGSSVGVN VNNLFDREYV SSCYSEYACY   720
WGAGRQVVAT ATFRF                                                    735
```

SEQ ID NO: 5          moltype = DNA  length = 1974
FEATURE               Location/Qualifiers
source                1..1974
                      mol_type = unassigned DNA
                      organism = Klebsiella pneumoniae
SEQUENCE: 5
```
atgttcaggt taaacccttt tatccgggcg ggattgtctg cgtccgtcgt atcgttggcg   60
tttccggctc tggccgatgt gaatgaagaa acgctggtgg tgaccgcctc ggccactgaa   120
cagaatgtca aagacgcgcc ggcgagcatc agcgtcatca cccaacagga tttacaacgc   180
aagcctgttc agaacctgaa agacgtgctg cgcgatgtgc ctggggtcca gctcaccaac   240
gaaggggata accgcaaggg cgttagcatc cgcggtctgc gcagcagcta taccctgatc   300
ctggtcgacg gcaagcgcgt taactcgcgg aacgccgtct tccgccacaa tgacttcgac   360
cttaactgga tcccggtgga tgctattgag cgtatcgaag tggtgcgcgg cccgatgtcc   420
tcccttttacg gctccgatgc gctcgggtgg gtggtcaaca ttattaccaa aaaaatcggc   480
cagaaatgga ccgggacgct gagtgctgat accactattc aggagcaccg cgatcgcggg   540
gatacctata acgccagtt cttcaccagc ggcccgctga tcgacggcgt acttggaatg   600
aaggcctacg gcagcctggc aaaaacgcgcc aaggacgatc cgcagtcatc cagtaatgcc   660
accggcgaga cgccgcgcat cgagggcttc accagccgcg atggcaatgt tgaattcgcc   720
tggacgccga acgaaaacca cgattttacc gcaggctacg gctttgaccg tcaggatcgc   780
gattccgatt cccttgaccg caaccgcctt gagcgggaga actactctct gagccataac   840
ggccgctggg atattggcaa tagcgagctc aagttctacg gcgaaaaggt ggataacaaa   900
aatccaggc agagcgggac tattacctcg gaaagcaatt ccatcgacgg caagtatgtc   960
ctgccgctgg gcatgattaa ccagctggtg accttcggcg gcgaatggcg ccacgacaaa   1020
ctgaaagatc cggtcaacct gagcagcggc ggccagtcaa cgtcggccag ccagtacgcc   1080
ctgtttatcg aagacgaatg gcgcatcatc gagccgctgg cgctgaccac cggcattcgt   1140
atggacgacc atcagaccta tggcgatcac tggagccgtg gcgcctatct ggtgtataac   1200
gccaccgata ccgtcaccgt caaaggcggc tgggcgacgg cgtttaaagc ccgtcgctgt   1260
ctgcagctta accccgactg gaccaccaac tcctgccgcg gctcgtgcag catcgtcggt   1320
aacccggatc tgaaaccgga aaccagcgaa agcttcgagc tcggtctcta ctaccgcggg   1380
gaagagggct ggcttgaaaa tgtcgaaggc agcatccaca ccttccagaa taatgtcgaa   1440
gacatgatcg atgttctgcg cacctccagc gccagcgaag cgccgggcta cccgaacttt   1500
gtcggctgga aaaccgtcaa cggcaagcgc gtgccgatct tccgctattt caacgtcaac   1560
aaagcccgca tcaaaggggt ggagacggag gtgaagatcc cgtttggcga tgagtggaag   1620
ctgacggtga actacacata caacgatggt cgcgatctga gcaatggcgg cgacaaaccg   1680
ctgcagacgc tgccgttcca taccgccaac ggcacgtctc actggaaacc gctggaacgt   1740
tggtccttct acgtgacggc caactatacc ggccagcagc gcgcggtgag cgccaccggc   1800
aaaacgccgg cgcgctacac cctgtttgac gttggcgcgg catggcaggt gaccaaaaac   1860
gtgaaactgc gctccggggt gcagaacgtg ggtgataaag atctgagccg ggacgactac   1920
agctataccg aagaaggccg tcgctacttt atggcggtgg attatcgctt ctga         1974
```

SEQ ID NO: 6          moltype = AA  length = 657
FEATURE               Location/Qualifiers
source                1..657
                      mol_type = protein
                      organism = Klebsiella pneumoniae
SEQUENCE: 6
```
MFRLNPFIRA GLSASVVSLA FPALADVNEE TLVVTASATE QNVKDAPASI SVITQQDLQR   60
KPVQNLKDVL RDVPGVQLTN EGDNRKGVSI RGLSSSYTLI LVDGKRVNSR NAVFRHNDFD   120
LNWIPVDAIE RIEVVRGPMS SLYGSDALGG VVNIITKKIG QKWTGTLSAD TTIQEHRDRG   180
DTYNGQFFTS GPLIDGVLGM KAYGSLAKRA KDDPQSSSNA TGETPRIEGF TSRDGNVEFA   240
```

-continued

```
WTPNENHDFT AGYGFDRQDR DSDSLDRNRL ERENYSLSHN GRWDIGNSEL KFYGEKVDNK    300
NPGQSGTITS ESNAIDGKYV LPLGMINQLV TFGGEWRHDK LKDPVNLSSG GQSTSASQYA    360
LFIEDEWRII EPLALTTGIR MDDHQTYGDH WSPRAYLVYN ATDTVTVKGG WATAFKAPSL    420
LQLNPDWTTN SCRGSCSIVG NPDLKPETSE SFELGLYYRG EEGWLENVEG SITTFQNNVD    480
DMIDVLRTSS ASEAPGYPNF VGWKTVNGKR VPIFRYFNVN KARIKGVETE VKIPFGDEWK    540
LTVNYTYNDG RDLSNGGDKP LQTLPFHTAN GTLDWKPLDD WSFYVTANYT GQQRAVSATG    600
KTPGGYTLFD VGAAWQVTKN VKLRSGVQNV GDKDLSRDDY SYTEEGRRYF MAVDYRF       657
```

```
SEQ ID NO: 7              moltype = DNA   length = 2229
FEATURE                  Location/Qualifiers
misc_difference          1439..1447
                         note = modified_base - a, c, t or g
source                   1..2229
                         mol_type = unassigned DNA
                         organism = Klebsiella pneumoniae
SEQUENCE: 7
atgaataaca ggatcaaatc cctggccttg ctggtcaatc tgggaattta cggggttgct    60
tttccgttaa gcgcagcgga aaccgccacc gacgataaaa acagcgccgc tgaagagacc    120
atggtggtca ccgccgccga gcagaacctg caggcgccgg gcgtctccac catcaccgcc    180
gatgagatcc gcaaacgccc cccggcgcgc gacgtctcgg agatcattcg caccatgccg    240
ggagtcaacc tgaccggcaa ctccaccagc ggccagcgcg gcaacaaccg ccagattgat    300
atccgcggca tgggcccgga aaataccctg atcctgatcg acggcaagcc ggtcaccagc    360
cgcaactccg tgcgccttgg ctggcgcggc gagcgcgaca cccgcggcga taccagctac    420
gtgccgccgg agataatcga acgtatcgaa gtgattcgcg gcccggccgc cgcccgctac    480
ggcaacggcg ccgccggcgg cgtggtgaat atcatcacca aaaaaaccgg cgatgagtgg    540
cacggctcat ggaacaccta tatgaacgcc ccggagcaca aggatgaagg ctccaccaaa    600
cgcactaact tcagcctcag cggcccgctg ggcggccgatt ttagcttccg cctgttcggt    660
aacctcgaca aaacgcaggc cgacgcctgg gatatcaacc agggccatca gtccgagcgt    720
accgggatct atgccgatac tctgccggcc gggcgcgaag gggtgaaaaa caaaaacatc    780
gatggtctgg tgcgctggga attcgctccg atgcagtcgc tggagtttga ggccggctac    840
agccgccagg gcaacctcta cgccggcgac acccagaaca ccaactccaa cgacctggta    900
aaagagaact acggcaaaga gaccaaccgt ctgtatcgca acacctactc ggttacctgg    960
aacggcgcct gggacaacgg ggtgaccacc agcaactggg cgcagtacga acgcacccgc    1020
aactcgcgca aaggcgaagg cctggccggc ggcaccgagg ggatctttaa cagcaaccag    1080
ttcacggata tcgatctggc ggatgtgatg ctgcacagcg aagtcagcat tcccttcgac    1140
tatctggtta tcagaacct gacgctgggc agcgagtgga tcaacacgcg gatgaaggat    1200
aacgcgtcca cacccaggc gctgtcggga ggcggaattc cgggctacga cagcaccggc    1260
cgcagcccgt actcgcaggc ggaaatcttc tcgctgttcg ccgagaacaa catggagctg    1320
accgacacca ccatgctgac tccggccgctg cgtttcgatc atcacagct tgtcggcaat    1380
aactggagcc cgtccctcaa cctgtcgcag ggcctgtggg atgacttcac gctgaagann    1440
nnnnnnnccc gcgcctataa agcgccgagc ctgtatcaga ccaacccgaa ctacattctc    1500
tacagtaaag gccagggctg ctacgccagt aaagacggct gctatctgca gggtaatgac    1560
gacttaaaag ccgagaccag catcaacaaa gagattggcc tcgagtttaa acgcgacggc    1620
tggctggcgg gcgtcacctg gttccgcaac gactaccgca acaagattga agcgggctat    1680
gccccggtct atcaaacaa taaaggtacc gatctctacc agtgggaaaa cgtgccgaaa    1740
gcggtggtgg aaggtctgga ggggacgttg aacgttccgg tgagcgagac cgtcaactgg    1800
accaacaaca tcacctatat gctgcagagt aagaacaaag agaccggcga tcgtctgtcg    1860
attatcccgg aatacacgct gaactccacc ctgagctggc aggttcgcga tgacgtttcg    1920
ctgcagtcga ccttcacctg gtacggcaag caggagccga agaagtacaa ctacaagggt    1980
caaccggtca ccggcagcga gaagaacgag gttagcccct acagcatcct cggcctgagc    2040
gcgacctggg acgtcaccaa atacgtcagt ctgaccggcg gcgtggataa cgtcttcgat    2100
aagcgccact ggcgcgcggg caacgcccag accaccgggg gcgccaccgg cacgatgtac    2160
ggcgccggcg ccgagaccta caatgaatcg ggccgcacct ggtacctgag cgtcaacacc    2220
cacttctga                                                          2229
```

```
SEQ ID NO: 8              moltype = AA   length = 742
FEATURE                  Location/Qualifiers
VARIANT                  480..483
                         note = MOD_RES - Any amino acid
source                   1..742
                         mol_type = protein
                         organism = Klebsiella pneumoniae
SEQUENCE: 8
MNNRIKSLAL LVNLGIYGVA FPLSAAETAT DDKNSAAEET MVVTAAEQNL QAPGVSTITA    60
DEIRKRPPAR DVSEIIRTMP GVNLTGNSTS GQRGNNRQID IRGMGPENTL ILIDGKPVTS    120
RNSVRLGWRG ERDTRGDTSW VPPEIIERIE VIRGPAAARY GNGAAGGVVN IITKKTGDEW    180
HGSWNTYMNA PEHKDEGSTK RTNFSLSGPL GGDFSFRLFG NLDKTQADAW DINQGHQSER    240
TGIYADTLPA GREGVKNKNI DGLVRWEFAP MQSLEFEAGY SRQGNLYAGD TQNTNSNDLV    300
KENYGKETNR LYRNTYSVTW NGAWDNGVTT SNWAQYERTR NSRKGEGLAG GTEGIFNSNQ    360
FTDIDLADVM LHSEVSIPFD YLVNQNLTLG SEWNQQRMKD NASNTQALSG GGIPGYDSTG    420
RSPYSQAEIF SLFAENNMEL TDTTMLTPAL RFDHHSIVGN NWSPSLNLSQ GLWDDFTLKX    480
XXXRAYKAPS LYQTNPNYIL YSKGQGCYAS KDGCYLQGND DLKAETSINK EIGLEFKRDG    540
WLAGVTWFRN DYRNKIEAGY APVYQNNKGT DLYQWENVPK AVVEGLEGTL NVPVSETVNW    600
TNNITYMLQS KNKETGDRLS IIPEYTLNST LSWQVRDDVS LQSTFTWYGK QEPKKYNYKG    660
QPVTGSEKNE VSPYSILGLS ATWDVTKYVS LTGGVDNVFD KRHWRAGNAQ TTGGATGTMY    720
GAGAETYNES GRTWYLSVNT HF                                            742
```

```
SEQ ID NO: 9              moltype = DNA   length = 1836
FEATURE                  Location/Qualifiers
```

-continued

```
misc_difference         414..456
                        note = modified_base - a, c, t or g
source                  1..1836
                        mol_type = unassigned DNA
                        organism = Klebsiella pneumoniae
SEQUENCE: 9
atgattaaaa aagcttcgct gatgacggcc ttatccgtca cggcatttc cggctgggcg    60
caggatagca attcagatac gttggtggtg acagcaaacc gttttcaaca gccggtcaat   120
accgtgctgg cgccgaccga cattgtgacg cgcgatgaca tcgaccgctg gcagtccaaa   180
gatttaaacg atgtcatgcg tcgtcttccc ggggtcgata ttgcccgcaa cggcggcatg   240
gggcagagcg cttcgctgta tgttcggggg acggaggctc gtcacgtgct ggtgctgatc   300
gacggtgtgc cgatggcgcg tccggggatc tccaacggcg tagatatcag tcagatccct   360
atctcactgg tccagcgggt ggaatacatc cgcggcccgc gctccgcggt gtannnnnnn   420
nnnnnnnnn nnnnnnnnn nnnnnnnnn nnnnnaccg acgctgagcg ttcgcaaatc   480
aacgccggcg cgggcacgaa cggctatcag tcctatgacg gcgcctttaa caagcggttt   540
ggcaacacgc tggttaccgc tgctggcgcc tatcagacca ccaaagggtt taacgtccag   600
ccgaattcct cttatagcgg cgacagcgat cgcgacggct accgcaataa aatgctgtgg   660
ggcgggtac agcatcagtt cgatgacaac ttctccgcgg tcttccgcgg ctatggttat   720
tccgccaacg ctgactatga ccagggtaac tggggctacg caggtcggaa cgatgaagat   780
caatcctata cccaatcctg ggataccggt ctgcactacc actccggaat ttactcctcc   840
cagctgattg ctaactatca gcgcatcaaa gattacaact acagcagcga cgctggccgc   900
tatgccgcgg gcaccaccct ggatgatatg gaacagcgat atatccagtg gggaaataat   960
gttgtggtag ccatggggc agtgagcggc ggcgttgact ggaaacaaga gaagctgaaa  1020
tccagcggaa cgaccagtac cgacgtgtat aagcgtgaca ccaccggtct ttatctgacg  1080
ggacagcagc agattgacag cgtgacgctg gaagcttccg gccgtgagga tcatgacgag  1140
cagtttggct ggcacggtac ctggcagacg gccgcagacg gggaatttat cgacggttat  1200
cggacaacgc tctcgtacgg cacaggattc ctcgcccccc ccctcgggca gcagtacggc  1260
gcagaacgct ttggcatcgc ctctaaccc aatctgaagc cagaggagtc gaagcaatgg  1320
gaagcgggc ttgaagggtt aacgggccg gtcgactggc gcctctccgc atatcgctat  1380
gagattcaaa acctcatcga ttacgacaac aacgcctcat acaacgtcaa gtcggcgacg  1440
attaagggc tggagtggac ggggaatata accaccgggc cggtcggagca ccatctgacg  1500
ctgcagtatg ttgaccctcg cgatgatgaa accaataaga tcctctatcg ccgggcgaag  1560
cagcaggtga aatacgagct gaacggccag gtctacgatc tggggtggga tgtgacgtat  1620
cactacatcg gcaagcgtta cgattatgac tacgacaact cgcgtaccgt caatatgggt  1680
gggttgagcc tctgggatgt cggtttatcg tatcccgtca cctcacacct gacagttcgt  1740
ggtaaaatag ccaacctgtt cgataaagat tacgagacag tttatggcta ccaatctgca  1800
ggacgggaat acaccttgtc tggcagctac accttc                           1836

SEQ ID NO: 10          moltype = AA  length = 612
FEATURE                Location/Qualifiers
VARIANT                138..152
                       note = MOD_RES - Any amino acid
source                 1..612
                       mol_type = protein
                       organism = Klebsiella pneumoniae
SEQUENCE: 10
MIKKASLMTA LSVTAFSGWA QDSNSDTLVV TANRFQQPVN TVLAPTDIVT RDDIDRWQSK    60
DLNDVMRRLP GVDIARNGGM GQSASLYVRG TEARHVLVLI DGVPMARPGI SNGVDISQIP   120
ISLVQRVEYI RGPRSAVXXX XXXXXXXXXX XXTDAERSQI NAGAGTNGYQ SYDGAFNKRF   180
GNTLVTAAGA YQTTKGFNVQ PNSSYSGDSD RDGYRNKMLW GGVQHQFDDN FSGFFRGYGY   240
SANADYDQGN WGYAGGNDED QSYTQSWDTG LHYHSGIYSS QLIANYQRIK DYNYSSDAGR   300
YAAGTTLDDM EQRYIQWGNN VVVGHGAVSG GVDWKQEKLK SSGTTSTDVY KRDTTGLYLT   360
GQQQIDSVTL EASGREDHDE QFGWHGTWQT AAGWEFIDGY RTTLSYGTGF LAPSLGQQYG   420
AERFGIASNP NLKPEESKQW EAGLEGLTGP VDWRLSAYRY EIQNLIDYDN NAYYNVKSAT   480
IKGLEWTGNI TTGPVEHHLT LQYVDPRDDE TNKILYRRAK QQVKYELNGQ VYDLGWDVTY   540
HYIGKRYDYD YDNSRTVNMG GLSLWDVGLS YPVTSHLTVR GKIANLFDKD YETVYGYQSA   600
GREYTLSGSY TF                                                      612

SEQ ID NO: 11          moltype = DNA  length = 2283
FEATURE                Location/Qualifiers
source                 1..2283
                       mol_type = unassigned DNA
                       organism = Klebsiella pneumoniae
SEQUENCE: 11
atggaaaaaa acgcttctct gcctttcggc agtttcaact cattggcatt gtttacaggt    60
ctgtgtctgg gagcctcgcc ggcagcaggc atcgcagcgg aaaattcggt caaaaatagt   120
gaagagacgc tggtagtgga agccgctccg ccttcactct actcccccgg cgcttccgcc   180
gatcccaagt tcaataaacc gctggtcgat accacccgca ccatcaccgt gatcccggaa   240
caggtgatta aagatcaggg cgtcaccaac ctgactgacg ccctcaaaaa cgttcccggc   300
gtggggggcgt tttatgccgg ggagaatggc agctcaacca ccgggatgc catctttatg   360
cgcgcgctgg atacctctaa cagcatctat gtggacggca ttcgcgacat cggcagcgtg   420
acgcgcgata ccttcaatac ccagcaggtg gaagtcatca aagggcccgc cggcacggac   480
tatgccgca gcgcgccctc cggctcgatc aatatgatca gcaagcagcc gcgccttgac   540
tccgggatcg acggctcggc cagcatcggc agcgcctggc gcgcgcgggg cactctcgac   600
ctgaaccagg cgtttagcga caacgctgcg ttccgtctga acctgatggg ggaaaaaacc   660
catgacgctg gtcgggaccg cattgaaac gaacgctatg gcatcgcacc gtcgctggcc   720
ttcggcctta taccccaac tcgtctgtat ctgaactatc tgcacgtccg gcagaacaac   780
accccggatg gcgggatccc taccgtcggc ctgccgggct attcggcgcc ttcgccgaag   840
tatgccgcac tcaactccac cgggaaggtc gataccagca atttctatgg caccgactcc   900
```

```
gattacgata aatctactac cgacagcggt accctgcgct tcgaacacga tctgacagag      960
agcaccaccg tgcgcaatac cacccgctgg tcgcgagtga aacaggagta tcttttgacc     1020
gcggtgatgg gcggcgcgaa caatatcacc gcccccgata tcaatgacgt caacacctgg     1080
agctggtcgc gtctggttaa taccaaagat gtcagcaacc gcattctgac caaccagacc     1140
aatatcacct cgaccttcga tactggctcg ataggccatg acgtcagcgc cggcgtggag     1200
tttacccggg aaaaccagac caactatggc gttaacgcca ggaccgcgcc ggcggtgaat     1260
ctctaccatc cggtgagcaa cctgtcgatt ggcgggctgg acagaaacgg ggcgaacgcc     1320
aacggccaga ccgatacctt cgggatttat gcctttgata cgctgacgct gaccgagcgg     1380
attgagatca acggcgggct gcgtctcgac aattaccata ccaaatatga cagcgccacc     1440
gcctgcggcg gcagcggacg cgggggctatc gcctgcccgc ccggacagtc gaccggcagc     1500
ccggtcacca ctgtcgatac cgctaaatcc ggcaatctgg ttaactggaa agccgggggcg     1560
ctgtaccgct taaccgagca gggcaatgtc tacgtcaact acgccatctc acagcagccg     1620
ccgggaggca gcagcttcgc cctggccgcc agcggcagcg gcaacagcgc taaccgaacc     1680
gactttaagc cgcagaaggc aaaatccagc gagctggcgg ccaagtggca aatcttcgac     1740
aaccgtctgc tgctcagcgc ggcgttattc cgcaccgata ttgaaaacga agtggccgcc     1800
aacgatgacg gaacctggtc gcagtacggc aaaaagcgcg tggaggggta tgaactctcc     1860
gcgaccggaa acctgacccc ggactggacg attatcgccg gctacactca gcagcatgcg     1920
acagtgacgg agggacagaa cgttgcacag gatggatctt ccgccctggc ctacaccccg     1980
aaacatgcct ttacgctgtg gacgcagtat caggccacca gcgatctgtc cgtcggcggc     2040
ggtgtgcgct atgtcggaag cctgcgccgg ggcagcgatg tgtcagtcgg taccccggat     2100
cacaccgagg gctactgggt tgccgacgcc aaactgggct atcgggtcaa cagcaacctc     2160
gatctgcagc tcaatatgta taacctgttt gataccgatt acgtggcctc catcaacaag     2220
agcggctatc gctatcatcc gggcgaaccc cggaccttta tgctgacggc gaacgtccat     2280
ttc                                                                   2283
```

```
SEQ ID NO: 12              moltype = AA   length = 761
FEATURE                   Location/Qualifiers
source                    1..761
                          mol_type = protein
                          organism = Klebsiella pneumoniae
SEQUENCE: 12
MEKNASLPFG SFNSLALFTG LCLGASPAAG IAAENSVKNS EETLVVEAAP PSLYSPGASA      60
DPKFNKPLVD TTRTITVIPE QVIKDQGVTN LTDALKNVPG VGAFYAGENG SSTTGDAIFM     120
RGVDTSNSIY VDGIRDIGSV TRDTFNTQQV EVIKGPAGTD YGRSAPSGSI NMISKQPRLD     180
SGIDGSASIG SAWSRRGTLD LNQAFSDNAA FRLNLMGEKT HDAGRDRIEN ERYGIAPSLA     240
FGLDTPTRLY LNYLHVRQNN TPDGGIPTVG LPGYSAPSPK YAALNSTGKV DTSNFYGTDS     300
DYDKSTTDSG TLRFEHDLTE STTVRNTTRW SRVKQEYLLT AVMGGANNIT APDINDVNTW     360
SWSRLVNTKD VSNRILTNQT NITSTFDTGS IGHDVSAGVE FTRENQTNYG VNARTAPAVN     420
LYHPVSNLSI GGLDRNGANA NGQTDTFGIY AFDTLTLTER IEINGGLRLD NYHTKYDSAT     480
ACGGSGRGAI ACPPGQSTGS PVTTVDTAKS GNLVNWKAGA LYRLTEQGNV YVNYAISQQP     540
PGGSSFALAA SGSGNSANRT DFKPQKAKSS ELGTKWQIFD NRLLLSAALF RTDIENEVAA     600
NDDGTWSQYG KKRVEGYELS ATGNLTPDWT IIAGYTQQHA TVTEGQNVAQ DGSSALAYTP     660
KHAFTLWTQY QATSDLSVGG GVRYVGSLRR GSDGAVGTPD HTEGYWVADA KLGYRVNSNL     720
DLQLNMYNLF DTDYVASINK SGYRYHPGEP RTFMLTANVH F                         761
```

```
SEQ ID NO: 13              moltype = DNA   length = 896
FEATURE                   Location/Qualifiers
source                    1..896
                          mol_type = unassigned DNA
                          organism = Klebsiella pneumoniae
SEQUENCE: 13
atgaaaatcc tgtccgtgcg tcacgccgcc ctcccggccc tgctcttgcc gctcattgcc      60
gcagcccagg ccgctgatga acaaaccatg gtggtgaccg ccgcgccaac cacggtttct     120
gaactggata cccccgccgc cgtcagcgtg gtgaatgggg atgagatgcg ccaggccgcg     180
ccgcgcgtca atctctctga acgctatggc gccgtgccgg gcctgcaggt gcagaaccgg     240
caaaactatg cccaggatct gcagctgtcg attcgcggct ttggctcgcg ctcaacctat     300
ggcgtgcgcg gactacgcat ctatgtggat ggcattccgg ccaccatgcc cgacggccag     360
gggcagacct caaatattga tatcggcagc gttgacacca ttgaggtgct gcgcggcccc     420
ttctctgccc tgtacggtaa ctcgtccggc ggggtgatca acgtcaccag ccagaccggc     480
acccagccgc ccaccgtgga agccagcagc tactatggca gcttcggcac ctggcactac     540
gggatgaaag ccactggcgc cgttggcgac ggcagccacg caggcgatgt ggattacacg     600
gtctcaacca atcgcttcac cacccatggc tatcgcgatc acagcggcgc gcgcaaaaat     660
ctggcgaacg cccggctggg ggtgcgcatc aacgacgtca gtaagctgac tctgctgctg     720
aatagcgtgg atatcaaagc caatgacgcc ggtggcctga cgctggcctg atggccggat     780
aacccgcgcc agtcgccgcg cggcgaccag tataatcccg caagaatac ccgacagacc      840
caggccggcc tgcgctatga gcgccagctc agtgcccagg acgatctcag cgtatg         896
```

```
SEQ ID NO: 14              moltype = AA   length = 298
FEATURE                   Location/Qualifiers
source                    1..298
                          mol_type = protein
                          organism = Klebsiella pneumoniae
SEQUENCE: 14
MKILSVRHAA LPALLLPLIA AAQAADEQTM VVTAAPTTVS ELDTPAAVSV VNGDEMRQAA      60
PRVNLSESLG AVPGLQVQNR QNYAQDLQLS IRGFGSRSTY GVRGLRIYVD GIPATMPDGQ     120
GQTSNIDIGS VDTIEVLRGP FSALYGNSSG GVINVTSQTG TQPPTVEASS YYGSFGTWHY     180
GMKATGAVGD GSHAGDVDYT VSTNRFTTHG YRDHSGARKN LANARLGVRI NDVSKLTLLL     240
NSVDIKANDA GGLTADEWRD NPRQSPRGDQ YNTRKNTRQT QAGLRYERQL SAQDDLSV      298
```

```
SEQ ID NO: 15            moltype = DNA   length = 2029
FEATURE                 Location/Qualifiers
misc_difference         292..334
                        note = modified_base - a, c, t or g
source                  1..2029
                        mol_type = unassigned DNA
                        organism = Klebsiella pneumoniae
SEQUENCE: 15
gtcgattatc acggctgagg atattgctaa gcagccgccg gtcaacgatc tctcagacat   60
catccgtaaa atgcccgggg tgaacttgac cggcaacagc gccagcggca gtcgggcaa   120
caaccgccag attgatatcc gcggcatggg gccggagaac accctgatcc tgatagatgg   180
ggtaccggtc acgtcacgta acgcggttcg ctatagctgg cgcggcgaac gcgatacccg   240
gggcgacagc aactgggtac ctgccgaaat ggtcgaacgg attgaagttc tnnnnnnnnn   300
nnnnnnnnnn nnnnnnnnnn nnnnnnnnnn nnnnggagtg gtcaatatca ttaccaaacg   360
tccgaccaac acctggcacg gttcgctgtc tttcttcacc aaccagccgg aaaacaacaa   420
agaaggcacg accaatcgcg ctaacttcaa tctcagcggc ccactggccg gcgaggcgct   480
gacgatgcgc ctgtatggca atatcaataa aacggaaccc gacgcctggg atattaacca   540
tgcgcaaaac ggctcttacg ctgcgggggcg cgaagggtc cgcaataaag acattaacgc   600
gctactgtca tggaaaatga ccccgcaaca aattctcgat ttcagctacg cctatagccg   660
tcaggggaat atctatgctg gcgatacccc gtacagcaac ggcaatctta gcccgaacgg   720
gctggtggac tccctgtacg gccacgaaac aaatcgcctc tatcgccagt cctggggact   780
cacctacaac ggtctatggg attggggtca gtccaaagcc ggtgtttact acgagaaaac   840
caacaatacc cgcctgcagg aaggctctac cggccgcgtc gaaggcatga tcaacagtga   900
agattatgcc accagccgtc tggaatcctg gcgtactacc tcggaattca atgtgccttt   960
cttctggctg gcggaccaga cgctgacgct gggaatggaa tggaaccatg atcagcttga   1020
cgacccggca tcaatgcagg ccactaacag caacggcgga actatccctg ggacctcggg   1080
cgaccctacg caacgcagta ccaaaaacag cgccaccctc accggtatct atctggaaga   1140
taatatcgaa gccgtgcccg gcaccaacct gatcccggc attcgcttcg attatcataa   1200
tcagtttggc agtaactgga gccccagcct caatctgtcc caggagctcg gcgatatgtt   1260
cacgctgaag gccggtatcg cgcgcgtgtt taaagcgcca aacctctatc aatccagtaa   1320
aggctatttg ctctccaccc gcggcaacg ttgtccaaac acgatcgctg aaggcagctg   1380
ctacctgctg ggtaaccctg acctcgaccc ggagatcagt atcaacaaag agatcggtat   1440
cgaatttaac cttaatggtt acgctgccgg agtcacctgg tttcgcaacg attacaaaaa   1500
caaaatcgtc tccggaacag aggtactggg ctataccctc agcggcaata atattttgca   1560
atggcagaac ggcggcaaag ccgtggtcga ggggctggaa ggaaatctgc tgatcccggt   1620
gctgagagat gtcctcagct ggcggaccaa tgccacctgg atgctcaaat ctgaaagtaa   1680
agagactggc aacccgctgt cggttatccc gaaatatacc gttaacacga tgcttgactg   1740
gcaggtaaac gacgccctgt ctgcgaatgt gaactggacg ctttatggcc gtcagaagcc   1800
gcgtcagtat gcggagatcc gcaacgaaac cgggaccctt gccaccaccg aggttggcgc   1860
ctattccatc gtgggtattg gtactcagta tcagctaaac cgggatattc gcctgaatgc   1920
cggaataagt aatctatttg ataagcaact gtatcgcgaa aatgccggcg cctcgaccta   1980
caatgagcct ggccgcgcgt attacgccgg cgttacccctc tccttctga              2029

SEQ ID NO: 16            moltype = AA   length = 675
FEATURE                 Location/Qualifiers
VARIANT                 98..111
                        note = MOD_RES - Any amino acid
source                  1..675
                        mol_type = protein
                        organism = Klebsiella pneumoniae
SEQUENCE: 16
SIITAEDIAK QPPVNDLSDI IRKMPGVNLT GNSASGSRGN NRQIDIRGMG PENTLILIDG   60
VPVTSRNAVR YSWRGERDTR GDSNWVPAEM VERIEVLXXX XXXXXXXXXX XGVVNIITKR   120
PTNTWHGSLS FFTNQPENNK EGTTNRANFN LSGPLAGEAL TMRLYGNINK TEPDAWDINH   180
AQNGSYAAGR EGVRNKDINA LLSWKMTPQQ ILDFSYAYSR AGNIYAGDTQ YSNGNLSPNG   240
LVDSLYGHET NRLYRQSWGL TYNGLWDWGQ SKAGVYYEKT NNTRLQEGST GRVEGMINSE   300
DYATSRLESW RTTSEFNVPF FWLADQTLTL GMEWNHDQLD DPASMQATNS NGETIPGTSG   360
DPTQRSTKNS ATLTGIYLED NIEAVPGTNL IPGIRFDYHN QFGSNWSPSL NLSQELGDMF   420
TLKAGIARVF KAPNLYQSSK GYLLSTRGNG CPNTIAEGSC YLLGNPDLDP EISINKEIGI   480
EFNLNGYAAG VTWFRNDYKN KIVSGTEVLG YTSSGNNILQ WQNGGKAVVE GLEGNLLIPV   540
LRDVLSWRTN ATWMLKSESK ETGNPLSVIP KYTVNTMLDW QVNDALSANV NWTLYGRQKP   600
RQYAEIRNET GTLATTEVGA YSIVGIGTQY QLNRDIRLNA GISNLFDKQL YRENAGASTY   660
NEPGRAYYAG VTLSF                                                   675

SEQ ID NO: 17            moltype = DNA   length = 2185
FEATURE                 Location/Qualifiers
source                  1..2185
                        mol_type = unassigned DNA
                        organism = Klebsiella pneumoniae
SEQUENCE: 17
atgaaaaagc gcctctgggt gctccaccct ctgctgctgg ccagcacgct gcctgcgctg   60
gcgggctcagt ctgatgaaga cagcatcatc gttagcgcaa accgcaccca tcgcaccgtg   120
gccgaaatgg cccaaaccac ctgggtcatt gagggccagg agattgagca gcaggtccag   180
ggcgggaaag agttcaaaga cgtgctggcg cagctgatcc gcggcatcga cgtcagcagc   240
caggggcgga ccaactatgg gatgaacatg cgcgggcgcg cgatcgtcgt gctgattgac   300
ggcgtccggc tcaactcctc acgcaccgac agccgccagc tcgacgccat cgatccattc   360
aacatcgaac atatcgaagt gatctccgga gcgacctcgc tgtacggcgg gggcagtacc   420
ggcgggctta tcaacatcgt taccaaaaag gggcagcagg atcgtcaggt cgatcttgag   480
gtgggcagca agagcggttt tgcgaacagc aacgatcatg atgagcgcgt cgcggcgggcc   540
```

-continued

```
gtcagcggcg gaacagacca cgcatccggc cgcttgtcgg tagcctatca gcgtttcggc    600
ggctggtacg acggcaatac cgatgcgctg atcctcgata ataacccaaac ggggctccag   660
cattctgacc gcctcgacgt gatggggacg gggacgattg agatcgataa taaccgccag   720
ctgcagttgg tcacccagta ttataaaagc cagggcgatg atgactacgg tctgtggctc    780
gggaagaaca tgtccgcggt caccagcggc ggcaaagcgt ataccaccga cgggctcaat    840
tccgaccgta tccccggcac cgaacgccat ctgatcagcc tccagtactc tgatgccgac    900
ttttcggcc agaatctggt gagccaggtg tactatcgcg atgagtccct caccttctat     960
ccgttcccga cgctcacgaa aggtcaggtc agtagcttct cctcgtcgca gcaggatacc   1020
gatcagtatg gggccaagct gaccctcaac agccaaccgc tggcggggtg ggatctcacc   1080
tggggtctcg acgccgatca tgagaccttt aatgccaacc aaatgttctt cgatctgcca   1140
caatcgatgg cctccggcgg gttgcacaac gaatcgatct acacaaccgg ccgctacccg   1200
ggatacagta tttccaatgt cgcgccattc ctgcagtcca gctacgatct gaacgatatc   1260
tttaccgtca gcgggcgggt acgctaccag tggaccgaaa accgggtcga cgactttgtc   1320
ggctacgccc agcagcagga tatcgccaac ggcaaagcgc gctccgccga cgccatcaaa   1380
ggcggcaaaa ccgattacga taacttcctg tttaacgccg ggatcgtggc ccacctgacc   1440
gagcgtcaac aaacctggtt taacttctcg cagggcgtcg agctaccgga ccctggtaaa   1500
tactatggca tcggtaaata tggcgctgcg gtgaatggtc atctgccgct gatctccagc   1560
gtcaacgtcg atgactcgcc gctgcaggg atcaaagtta actcgtacga gctgggctgg    1620
cgctacaccg gcgataacct gcgcacccag ctggcggcgt actactcgac ctcagataag   1680
accattgtcg tcaaccgcac cgacatgacc atcgacgttc agtccgacaa acggcgtatt   1740
tacggcgttg aggggcggt cgactacttt attccggata gcgactggag cgtcggcggt    1800
aacttcaacg tgctgaaatc ccaggtgcag accgacgtc gctggcaaaa atgggacgtc   1860
accctcgcct cgccgtctaa agccaccgcc tgggtgggct gggcgccgga tccgtgggagc  1920
ctgcgcgtgc agagtcagca ggtatttgac ctcagcgatg ccgccggcaa caagctggaa   1980
ggctataaca ccgtcgattt tatcggtagt tacgcgctgc cggtggggaa actgaccttc   2040
agtatcgaaa acctgcttaa cgaagactat gtgactatat ggggccagcg cgcgccgctg   2100
ctctacagcc caacctacgg cagttcatcg ctgtatgagt acaaaggtcg tggccgcacc   2160
tttggtctga actacgcctt aacct                                         2185
```

```
SEQ ID NO: 18          moltype = AA  length = 728
FEATURE                Location/Qualifiers
source                 1..728
                       mol_type = protein
                       organism = Klebsiella pneumoniae
SEQUENCE: 18
MKKRLWVLHP LLLASTLPAL AAQSDEDSII VSANRTHRTV AEMAQTTWVI EGQEIEQQVQ    60
GGKEFKDVLA QLIPGIDVSS QGRTNYGMNM RGRAIVVLID GVRLNSSRTD SRQLDAIDPF   120
NIEHIEVISG ATSLYGGGST GGLINIVTKK GQQDRQVDLE VGSKSGFANS NDHDERVAAA   180
VSGGTDHASG RLSVAYQRFG GWYDGNTDAL ILDNTQTGLQ HSDRLDVMGT GTIEIDNNRQ   240
LQLVTQYYKS QGDDDYGLWL GKNMSAVTSG GKAYTTDGLN SDRIPGTERH LISLQYSDAD   300
FFGQNLVSQV YYRDESLTFY PFPTLTKGQV SSFSSSQQDT DQYGAKLTLN SQPLAGWDLT   360
WGLDADHETF NANQMFFDLP QSMASGGLHN ESIYTTGRYP GYSISNVAPF LQSSYDLNDI   420
FTVSGGVRYQ WTENRVDDFV GYAQQQDIAN GKARSADAIK GGKTDYDNFL FNAGIVAHLT   480
ERQQTWFNFS QGVELPDPGK YYGIGKYGAA VNGHLPLISS VNVDDSPLQG IKVNSYELGW   540
RYTGDNLRTQ LAAYYSTSDK TIVVNRTDMT IDVQSDKRRI YGVEGAVDYF IPDSDWSVGG   600
NFNVLKSQVQ TDGRWQKWDV TLASPSKATA WVGWAPDPWS LRVQSQQVFD LSDAAGNKLE   660
GYNTVDFIGS YALPVGKLTF SIENLLNEDY VTIWGQRAPL LYSPTYGSSS LYEYKGRGRT   720
FGLNYALT                                                            728
```

```
SEQ ID NO: 19          moltype = DNA  length = 1790
FEATURE                Location/Qualifiers
source                 1..1790
                       mol_type = unassigned DNA
                       organism = Klebsiella pneumoniae
SEQUENCE: 19
cccgccgcgg cttcggcgcc aaccgcgacg gctcgatcat gaccaacggc ctgcgcaccg    60
tgctgccgcg cagctttaac gccgccaccg aacgggtgga agtcctgaag gggcccgcct   120
cgacgctgta cggtatcctc gaccccggcg ggctgatcaa cgtcatcact aaacggccgg   180
agcggcagtt ctccggttcg gtttccggga cctccaccag ctttggcggc ggcaccggca   240
gcgtcgacat caccggcccc atcgaaggca caaatctggc gtaccgactg atcggcgaat   300
atcagaatga ggattactgg cgcaatttcg gtaaaaacaa aagcagcttt atcgcccctt   360
ccctgacctg gttggcgag cgggcaacgg tgaccgcgtc ctattcgcac cgcgactaca    420
gcgcccctt tgatcgcgga actatcttcg atctgaatac cggccatgcg gttaacgtcg    480
atcgcaaaac ccgcttcgat gaagcgttta atattaccga tggctattcc gatctcgctc   540
agctcaacgc cgagtatcgc cttaacgacg cctggaccgc gcgcttcgac tacagctaca   600
gccaggatca ttacaacgat aaccaggcgc gggtaatggc ctatgattcg gcgaccggca   660
acctcccccg ccgggtcgat ggtacccacg gttcaacgca gaagatgcac tccacccgcg   720
ccgacctgca gggcaacgtg gtagtgggcg gctttttataa cgagctgctg accggcgtcg   780
cctatgagaa ttacgatctg ctgcgcaccg atatgctgcg ctgtaagaac gttaaaggct   840
ttaacatcta tcatccggtc tacggcactc tcgacacctg taataccgtc tccgcctccg   900
acagcgacca gcgcattcag caggagagct atgccgcata cgtgcaggac gcgctgtacc   960
tgaccgacaa ctggatcgcc gtcgccgcg tgcgctacca gtactacacc cagtacgccg    1020
gtaaaggccg accgtttaac gtcaataccg acagccgcga tgagaaatgg acgccgaaag   1080
ccggcctggt ctacaaggtc acgccgaacg tctccctgtt cgccaacgtc gccagtcgt    1140
ttatgcgcca gtcgtcgatc gccagctata tcggcgagct gccgccggaa gagtccacct   1200
cttacgaagt gggcgccaaa ttcgacctgt taaacggcat taccgccaat atcgcgttgt   1260
ttgatattca taagcgtaac gtgctgtaca ccgagagcat tggcgatgag acggtggcca   1320
aaacggcggg caaagtgcgt tcccagggcg tggaagtgga tctggcgggg tccatcaccg   1380
ataacctcag cgtgatcgcc agctacggct acaccgacgc caaagtgctg gaagatccgg   1440
```

-continued

```
attacgccgg gaaaccgctg ccaaacgtac cgaaacatac cggttcgctg ttcctgacct    1500
atgacattca taacgtctat aacagcaaca ccctgaccgt cggcggcggc ggccacgcgg    1560
tcagcaagcg ttccggcacc aacggcgcgg attattattt gcaggggtat gcggtggcgg    1620
atgtgtttgc tgcctataag atgaagctgc agtatccggt gacgctgcag gtgaatgtga    1680
agaacctgtt tgataagacc tattacactt cctcgatcgg caccaataat ctcggcaacc    1740
agattggcga cccgcgcgaa gtgcagttca cggtgaagat ggattttaa                1790
```

SEQ ID NO: 20          moltype = AA  length = 595
FEATURE                Location/Qualifiers
source                 1..595
                       mol_type = protein
                       organism = Klebsiella pneumoniae
SEQUENCE: 20
```
RRGFGANRDG SIMTNGLRTV LPRSFNAATE RVEVLKGPAS TLYGILDPGG LINVITKRPE    60
RQFSGSVSGT STSFGGGTGS VDITGPIEGT NLAYRLIGEY QNEDYWRNFG KNKSSFIALS    120
LTWFGERATV TASYSHRDYS APFDRGTIFD LNTGHAVNVD RKTRFDEAFN ITDGYSDLAQ    180
LNAEYRLNDA WTARFDYSYS QDHYNDNQAR VMAYDSATGN LPRRVDGTHG STQKMHSTRA    240
DLQGNVVVGG FYNELLTGVA YENYDLLRTD MLRCKNVKGF NIYHPVYGTL DTCNTVSASD    300
SDQRIQQESY AAYVQDALYL TDNWIAVAGV RYQYYTQYAG KGRPFNVNTD SRDEKWTPKA    360
GLVYKVTPNV SLFANVAQSF MPQSSIASYI GELPPEESTS YEVGAKFDLL NGITANIALF    420
DIHKRNVLYT ESIGDETVAK TAGKVRSQGV EVDLAGSITD NLSVIASYGY TDAKVLEDPD    480
YAGKPLPNVP KHTGSLFLTY DIHNVYNSNT LTVGGGGHAV SKRSGTNGAD YYLQGYAVAD    540
VFAAYKMKLQ YPVTLQVNVK NLFDKTYYTS SIGTNNLGNQ IGDPREVQFT VKMDF          595
```

SEQ ID NO: 21          moltype = DNA  length = 2211
FEATURE                Location/Qualifiers
source                 1..2211
                       mol_type = unassigned DNA
                       organism = Klebsiella pneumoniae
SEQUENCE: 21
```
atggggcaaa ttatgcacac cacgcactat tcatccttcc cgctgcgtaa aacgctgctg    60
gccttagcca tcggcgccgc cagtcaaacg gcgatggccg cggacgctgc cgccgcgaag    120
cagcctggcg aagagaccct catcgtcgag gctaacgaaa ccagcgattt taaatccggc    180
ggtgacctgg tggttccggc attcctcgat ggccagatcg cccacggcgg ccgtctgggg    240
atgcttggcg aacaaaaagc gatggacgtc ccgtttaacg tcatcggcta tacctcgaag    300
ctgattcagg atcagcaggc gaaaactatc gccgatgtcg tcagtaacga cgctggcgtg    360
caggccgtac agggctacgg caacttcgcc gagacctatc gaatccgcgg gtttaagctc    420
gatggcgatg acatgacgat gggcggcctg gcgggcgtgg tgccgcgtca ggtgatggac    480
acccagatgc tggagcgcgt tgaaattttc aaaggggcta acagcctgct taacggcgcg    540
gccagcagcg gtgtcggcgg ggtgatttac ctcgagccga gcgggcgga agatctgccg    600
accgcacgcg ttggcgtcga ctatacctct gattctcagg tgggcggcac cctcgacctg    660
gggcgccgtt tcgcgacaa caaccagttc ggcgcccggg tcaacctggt gcaccgcgag    720
ggtgaaggcg ctatcgataa tgataaacgc cgtaccacgc tggcttcgct ggggcttgat    780
taccgcggcg accgtttccg ctcctcgctc gatttcggct atcagaagaa aacgttccac    840
ggcggtacga tgggcgtcaa tatcagcggc gtggatttcg ttccggcgct gccggacaac    900
agcaaaaact acagccagaa gtggggctat agcgatattg aaagcgagtt tggcatggcg    960
aaggcagaat atgacctgac cgatagctgg acggtataca cgccctcg cggccagcat    1020
tcgcatgaaa ttggtaccta cagcgcgccg aagcttctga ataaaaacg cgatgcgacg    1080
gtgggccgcc tggatactaa ccgcattatc gacgcgatca gcggcatggg cggggtacgc    1140
ggcgatttca taccggcgc gatttcgcat acggtgaacc tcggctatgc ggcgcaggtg    1200
cataccgatg cgaccgcctg gcggatgtcg gccaggaacc cgaccactaa tatctatgac    1260
aaccatgatg tggcgatgcc ggataacgcc tattttggcg gcaactacca cgatccgctg    1320
gtcacctcgc gcagccgtac gcagggctgg ctgttgagtg ataccctcgg cttctttaac    1380
gataaagtgc tgtttaccgc cgctgctcgt catcagaaag tggttgtgcg caactacagc    1440
aacgccaccg ggctggaaga tacctcttcg cgttataccc aaagccgctg gatgccgaccg    1500
tttggcctgg tgtacaagcc gtgggagcag ctgtcgctgt atgctaacca taccgaagcg    1560
ctgcagccgg gctctgtggc gccgacgacg gcggccaatg ccgggcagag taccgggatc    1620
gcgcactcga agcaggacga agtgggcgtc aagatcgact acggtacgat cggaggatcg    1680
ctggcgctgt ttgaaatcaa aaaaccgaac gccatttccg ataccgctgg caattacggc    1740
ctcgacggcg agcagcgtaa ccgcggcgta gagatgaacg tctttggcga gccgatgctg    1800
ggactgcgtc ttaacgccag taccgtctgg ctggatgcca aacagactaa aaccgctgaa    1860
ggcgcaaccg acggtaaaga tgccatcggg gtggctaact ctacgcggt actcggcgcc    1920
gaatatgaca tcaagccggt ggaaggcctg accgccaccg cgcgcgtcaa tcatagcggc    1980
tcgcagtatg ccgatgcggc caataccaag aagctgatca gctacaccac cctggattta    2040
ggcctgcgct atcgtatgcg tctgaacgcc gaccagaacg aaatgatctg cgcgtcggg    2100
gtgaccaacg tgaccaacga gaagtactgg tctggcattg acgataccgg tacttacctg    2160
ttcgaaggcg atccgcgtac cgtccgcgtc tcaatgagct acgacttctg a              2211
```

SEQ ID NO: 22          moltype = AA  length = 736
FEATURE                Location/Qualifiers
source                 1..736
                       mol_type = protein
                       organism = Klebsiella pneumoniae
SEQUENCE: 22
```
MGQIMHTTHY SSFPLRKTLL ALAIGAASQT AMAADAAAAK QPGEETLIVE ANETSDFKSG    60
GDLVVPAFLD GQIAHGGRLG MLGEQKAMDV PFNVIGYTSK LIQDQQAKTI ADVVSNDAGV    120
QAVQGYGNFA ETYRIRGFKL DGDDMTMGGL AGVVPRQVMD TQMLERVEIF KGANSLLNGA    180
ASSGVGVIY LEPKRAEDLP TARVGVDYTS DSQVGGTLDL GRRFGDNNQF GARVNLVHRE    240
GEGAIDNDKR RTTLASLGLD YRGDRFRSSL DFGYQKKTFH GGTMGVNISG VDFVPALPDN    300
```

```
SKNYSQKWGY SDIESEFGMA KAEYDLTDSW TVYSALGGQH SHEIGTYSAP KLLNKNGDAT    360
VGRLDTNRII DAISGMGGVR GDFNTGAISH TVNLGYAAQV HTDATAWRMS ARNPTTNIYD    420
NHDVAMPDNA YFGGNYHDPL VTSRSRTQGW LLSDTLGFFN DKVLFTAAAR HQKVVVRNYS    480
NATGLEDTSS RYTQSRWMPT FGLVYKPWEQ LSLYANHTEA LQPGSVAPTT AANAGQSTGI    540
AHSKQDEVGV KIDYGTIGGS LALFEIKKPN AISDTAGNYG LDGEQRNRGV EMNVFGEPML    600
GLRLNASTVW LDAKQTKTAE GATDGKDAIG VANFYAVLGA EYDIKPVEGL TATARVNHSG    660
SQYADAANTK KLDSYTTLDL GLRYRMRLNA DQNEMIWRVG VTNVTNEKYW SGIDDTGTYL    720
FEGDPRTVRV SMSYDF                                                   736

SEQ ID NO: 23            moltype = DNA  length = 2364
FEATURE                  Location/Qualifiers
source                   1..2364
                         mol_type = unassigned DNA
                         organism = Klebsiella pneumoniae
SEQUENCE: 23
atgtacaaat cgactccgtc agcagcatgg tgtaaaaaac gcctgctggt gacctctttg     60
tttgcagcaa tttatcagac ttctgccatc gcagcagata cttccgccgt tagcggcgag    120
gcggtggatg acacctcgga acaaatgacc gtcaccgccc ccgcgccggt gcagaaagcc    180
ggtagcgaac atagcatcag cgcccgggag ctggagaata aaggcgctaa cgatttcggc    240
tcaatcatgc gctatgagcc gctcatcagc gccaccgggg ccagcggcgg ctccggcaac    300
ggcaaaagcg gcttcgaccg cggaggttac accggctaca acattcgcgg tatggagagc    360
aaccgcgtcg gcatcgacgt ggacggtatc gcgcaaccca acgccaccgg ccgcggctac    420
gtcggccgcg ccgggctcaa caccttcggc atcggccgcg attatatcga cccgtatatg    480
tacggcagcg tggatatcca gtccggcgcc acctcgacgg aaacggccaa cagcgctatc    540
ggggggaatg tctccttccg cccgaaatca gcggatgatt acctgcgccc gggcaagacc    600
agcgccttcg gctaccgcag cggttacgac tctgcggatc gcagctggca caacggggtg    660
accgtcgccg gcggcgatga gttcctgcgc gggattttgg tctatagccg ccgtgacggc    720
caggaaaccg aaaacaacag cggcaccgtc gacgcctacc cggcgaactg gcactccgat    780
gcttttctgg cctccgggat ctggcagcct aacgatgagc acaagctgac cagcaccttc    840
gactattacc ataaaaccaa ccacacccac tacgatacct gggactccag cggcaacagc    900
accatcggca ccgccaacca gaccagccag acccggcgct ggggcctgag cctgaaggat    960
gactggacgc cgatgaacga ctacctcgac agcgtctcca caaaaatcta ctaccagcat   1020
accgaagccc atgactggac ttatatgccg gacagcgtca cccgcagaat gcagacggtg   1080
aactctaact acgataccga cacctggggc ctgcagaccg cgctggcgaa aaccctgggc   1140
cgccacgatc tgagcgccgg tttcaacgcc agcaccagca aaacccagcg gccgttcagc   1200
cagtcgccga tccccagcgt ttacagcgag atcatgcagc cggaggcaga cagccgcagc   1260
tacaccctcg gcgcctttgt ccaggataag atcaacttcg accttgatag ccacaacttc   1320
gccgttattc ccggcgtgcg cgtggtgcat caatcgacta gccggaaaa tctgtccgat   1380
ctcgccgcca acagcagcgt gctgagcgaa tcgtcggtgg cgaatctgta cggcaaaaac   1440
agcgataccc aggttctgcc gtcgttgacc ttccagtacg acctcacccc gcgcctgatg   1500
acctacctgc agtaccagcg cggggcgcag ttccccaacg ccagccagct gtatggctcc   1560
tggaacctcg gctccagcta cgccggcagc cagcagtatg ccctgatcgg caataccgat   1620
ctgaagacgg aaaccagcga taatctcgag tgggggctga aggggaagt taccgaaggc   1680
atcaccctgc gcacggcgct gttctacaac agctataaga actttatcgc ctatacccgc   1740
tatacccgcg ccaacaatcc gggccagttc acgaatgtgc cgtcgaacat ctacaccatt   1800
tatcaggcgg aaaaccgcga taagcctat atctacggcg gtgagattag caccaaattt   1860
aactttggca cctggtttga gcaggtggac ggcctgagcg ccaccctggc cctcggctat   1920
agcgaaggga aatcgaaatc cagctacagc ggcgataaat acgtcgacct cgacagcgtg   1980
gcgccaatga aagccatcgt cggcgtggcg tgggacgatc cggcgaaacg ctacggcacc   2040
gccctgacgg cgacctttgt caaagggaaa caggcgaccg ccaccaaccg cgaaagctac   2100
agcaacagcg gatccgccat caccgatgcc agtagcgact atatgcgcgt gccgggctac   2160
ggcatgctgg actggaccgc gtactggcag gtggcgaaaa acgtgcgcct caatggcggg   2220
gtctacaacc tcaccgatcg taaatactgg gattacctga gcagccgcaa tatcgagacc   2280
ggcaccaacc aggacgccaa cgataaagcg ctggcggtga tgccgggccg cacctggcag   2340
ctgggcgtca acgtcgactt ctga                                         2364

SEQ ID NO: 24            moltype = AA  length = 787
FEATURE                  Location/Qualifiers
source                   1..787
                         mol_type = protein
                         organism = Klebsiella pneumoniae
SEQUENCE: 24
MYKSTPSAAW CKKRLLVTSL FAAIYQTSAI AADTSAVSGE AVDDTSEQMT VTAPAPVQKA     60
GSEHSISARE LENKGANDFG SIMRYEPLIS ATGASGGSGN GKSGFDRGGY TGYNIRGMES    120
NRVGIDVDGI AQPNATGRGY VGRAGLNTFG IGRDYIDPYM YGSVDIQSGA TSTETANSAI    180
GGNVSFRPKS ADDYLRPGKT SAFGYRSGYD SADRSWHNGV TVAGGDEFLR GILVYSRRDG    240
QETENNSGTV DAYPANWHSD AFLASGIWQP NDEHKLTSTF DYYHKTNHTH YDTWDSSGNS    300
TIGTANQTSQ TRRWGLSLKD DWTPMNDYLD SVSTKIYYQH TEAHDWTYMP DSVTRRMQTV    360
NSNYDTDTWG LQTALAKTLG RHDLSAGFNA STSKTQRPFN QSPIPSVYSE IMQPEADSRS    420
YTLGGFVQDK INFDLDSHNF AVIPGVRVVH QSTKPENLSD LAANSSVLSE SSVANLYGKN    480
SDTQVLPSLT FQYDLTPRLM TYLQYQRGAQ FPNASQLYGS WNLGSSYAGS QQYALIGNTD    540
LKTETSDNLE WGLKGEVTEG ITLRTALFYN SYKNFIAYTR YTRANNPGQF TNVPSNIYTI    600
YQAENRDKAY IYGGEISTKF NFGTWFEQVD GLSATLALGY SEGKSKSSYS GDKYVDLDSV    660
APMKAIVGVA WDDPAKRYGT ALTATFVKGK QATATNRESY SNSGSAITDA SSDYMRVPGY    720
GMLDWTAYWQ VAKNVRLNGG VYNLTDRKYW DYLSSRNIET GTNQDANDKA LAVMPGRTWQ    780
LGVNVDF                                                            787

SEQ ID NO: 25            moltype = DNA  length = 2139
FEATURE                  Location/Qualifiers
```

-continued

```
source                 1..2139
                       mol_type = unassigned DNA
                       organism = Klebsiella pneumoniae
SEQUENCE: 25
ttggttcagg atgatcttat gaacgtggct atttctcgaa aacgcccggg gctgctgtat     60
gcccttgcgg tcacactccc cttcaccgcg caagccgaag agacggtggt ggtcactgcc    120
accccgccgg cgtccgccag cgcgccgacg gagggctaca gcgccagcac ctcgctcggg    180
gcgacgaaaa ccgaccagcc gttaatcact accgcccagt cggtgtcggt ggtcacccgc    240
cagcagatgg cggatcaggg ggcgaatacc atcagccagc cgctggaata tacccccgggg    300
gtctactcca gcttcggcgg cggcgccacc cggttcgacg ccatctccct gcgcggctac    360
cacggcggcg acgtcgataa cctgttcctc gacggcatgc gcctgatgag cgacggcggc    420
agccataacg tactgcaaat cgaccccgtgg tttatcgaac gcgtggatgt gatccgcggc    480
ccctcctccg cgctctacgg gcagagcgtg ccgggcggcg tggtcaacct gacttccaaa    540
cgtccgcagt tcagccagca gggccacatc cgcctgacgg gcgggcacgca aaataccaaa    600
ggcgcggcct tcgattacac cgacgccatc aatgaccagt gggcatggcg gctgatcggg    660
atgacccgca gcagcgacac gcagtatgac catacccgcg aagagcgcta cgcgatttcg    720
ccttccctgc tgtggcagcc ggacagcgac acctcgctgc tgctgcgcgc ctatctgcaa    780
aaagatcctt ccggcgggcta ccacggctct ttgccgctgg acggcacccg ctacgcgcac    840
aatggccgta agctctcccc cagcaccaac gaaggcgatc cgggagatgg ctatcagcgc    900
cgccagcaga tctacagcta tgagtttgac caccagttca ccgacgtctg gtcggtctat    960
tccgcccggga gctacaccca taccaacgtc tccctcgatc aggtctacca ggtcggctgg   1020
atagatgaaa gcgacatgct ggcccgcggc tacagcggtt cggtcggacgc gctggacggc   1080
tggtcaaccg ataaccgcct gcgcgccgat ttcaatacag gcgacctggc gcacaccctg   1140
atcctcggcg ccgaatatca tcgcttccgt aacgacctgt ggaccggcgc cggcggcgcg   1200
gcgcccctta acccgtttag cggctatacc gagcagaccg gacataccgt tacctacagc   1260
gacgacaata tcgccgcta ttaccagacc gggctgtatc tgcaggatga gatggtcggg   1320
aaccgctggc atgtggatgt ttccgcccgc tacgaccgca tcgtttccca gcaggtcagc   1380
gatacccagg ggacctcaaa ccgccgttca gacgaccata tcagcggccg cgcctcgctg   1440
ttgtacgccc tggacaacgg tctgtcgccc tacctgagct acagccaggc gatcactccg   1500
gcgatgctgc cggacgcggga cggcaaaccg ttgaaaccga ccaccgccga acaggttgaa   1560
gccggcctga agttccagcc gccgggcagc agcgatctct atagcatcgc gatttacgac   1620
ctgacgcaaa aggatgtcgc cactcgcgac ccgaacatcg ccaccgccac ctatattccg   1680
gcgggtaagg tccattccca gggcgttgag ctggaagcgc accaccagat caccccgcag   1740
ctgagtacta tcgcctcgta tacctggaat cgtctgcgtt tccaggacac ccaagacggg   1800
accgacaata acacgccgca gctgacccg gatcagatgg cctccttctg ggcgcgctat   1860
cagttcccgg cggggatctc cgttggcgcc ggcgtccgct acatcggtaa acagtgggcg   1920
gatgatgcca acaccgcgcg gctgccgtcg gtcacgttga tggacgccat gatgcgggcc   1980
gacctcggcg tctggtcgcc aacgctgaaa ggcgcttatg tgcaggttaa cgccaacaat   2040
atcggcgacc gcgagtatat ttccggctgc tatggcaccg gcaactgtta ctggggagca   2100
gagcgcagcg ttatagccac cgtgggctac gatttctga                          2139
```

```
SEQ ID NO: 26           moltype = AA   length = 712
FEATURE                 Location/Qualifiers
source                  1..712
                        mol_type = protein
                        organism = Klebsiella pneumoniae
SEQUENCE: 26
MVQDDLMNVA ISRKRPGLLY ALAVTLPFTA QAEETVVVTA TPPASASAPT EGYSASTSLG     60
ATKTDQPLIT TAQSVSVVTR QQMADQGANT ISQALEYTPG VYSSFGGGAT RFDAISLRGY    120
HGGDVDNLFL DGMRLMSDGG SHNVLQIDPW FIERVDVIRG PSSALYGQSV PGGVVNLTSK    180
RPQFSQQGHI RLTGGTQNTK GAAFDYTDAI NDQWAWRLIG MTRSSDTQYD HTREERYAIS    240
PSLLWQPDSD TSLLLRAYLQ KDPSGGYHGS LPLDGTRYAH NGRKLSPSTN EGDPGDGYQR    300
RQQIYSYEFD HQFTDVWSVY SAGSYTHTNV SLDQVYQVGW IDESDMLARG YSGSRGSLDG    360
WSTDNRLRAD FNTGDLAHTL ILGAEYHRFR NDLWTGAGGA APLNPFSGYT EQTGHTVTYS    420
DDNNRRYYQT GLYLQDEMVW NRWHVDVSAR YDRIVSQQVS DTQGTSNRRS DDHISGRASL    480
LYALDNGLSP YLSYSQAITP AMLPGADGKP LKPTTAEQVE AGLKFQPPGS SDLYSIAIYD    540
LTQKDVATRD PNIATATYIP AGKVHSQGVE LEAHHQITPQ LSTIASYTWN RLRFQDTQDG    600
TDNNTPQLTP DQMASFWARY QFPAGISVGA GVRYIGKQWA DDANTARLPS VTLMDAMMRA    660
DLGVWSPTLK GAYVQVNANN IGDREYISGC YGTGNCYWGA ERSVIATVGY DF            712
```

```
SEQ ID NO: 27           moltype = DNA   length = 1104
FEATURE                 Location/Qualifiers
source                  1..1104
                        mol_type = unassigned DNA
                        organism = Klebsiella pneumoniae
SEQUENCE: 27
atgaaagtta aagtactgtc cctcctggta ccggctctgc tggtagcagg cgcagcaaat     60
gcggctgaaa tttataacaa agacggcaac aaattagacc tgtacggtaa aattgacggt    120
ctgcactact tctctgacga caagagcgtc gacggcgacc agactacgat gcgtgtaggc    180
gtgaaaggcg aaacccagat caacgaccag ctgaccggtt acggccagtg ggaatacaac    240
gttcaggcga caacactga aagctccagc gatcaggcat ggactcgtct ggcattcgca    300
ggcctgaaat ttggcgacgc gggctctttc gactacggtc gtaactacgg cgtagtatac    360
gacgtaacgt cctggaccga cgttctgccg gaattcggcg cgcaccta cggttctgac    420
aacttcctgc agtcccgtgc taacggcgtt gcaacctacc gcaacctga tttcttcggt    480
ctggttgacg gcctgaactt tgctctgcag tatcagggta aaaacggcag cgtcagcggc    540
gaaggcgctc tgtctcctac caacaacggt cgtaccgcct tgaaacagaa cggcgacggt    600
tacggtactt ctctgaccta tgacatctat gatggcatca cgctggtt cgcatactct    660
aactccaaac gtcttggcga ccagaacagc aagctgcac tgggtcgtgg cgacaacgct    720
gaaacctaca ccggcggtct gaaatacgat gcgaacaaca tctacctggc cactcagtac    780
```

-continued

```
acccagacct acaacgcgac ccgcgccggt tccctgggct ttgctaacaa agcgcagaac    840
ttcgaagtgg ttgctcagta ccagttcgac ttcggtctgc gtccgtccgt ggcttacctg    900
cagtctaaag gtaaggatct ggaaggctac ggcgaccagg acatcctgaa atatgttgac    960
gttggcgcga cctactactt caacaaaaac atgtccacct atgttgacta caaaatcaac   1020
ctgctggacg acaacagctt cacccacaac gccggtatct ctaccgacga cgtggttgca   1080
ctgggcctgg tttaccagtt ctaa                                          1104
```

```
SEQ ID NO: 28            moltype = AA  length = 367
FEATURE                  Location/Qualifiers
source                   1..367
                         mol_type = protein
                         organism = Klebsiella pneumoniae
SEQUENCE: 28
MKVKVLSLLV PALLVAGAAN AAEIYNKDGN KLDLYGKIDG LHYFSDDKSV DGDQTYMRVG     60
VKGETQINDQ LTGYGQWEYN VQANNTESSS DQAWTRLAFA GLKFGDAGSF DYGRNYGVVY    120
DVTSWTDVLP EFGGDTYGSD NFLQSRANGV ATYRNSDFFG LVDGLNFALQ YQGKNGSVSG    180
EGALSPTNNG RTALKQNGDG YGTSLTYDIY DGISAGFAYS NSKRLGDQNS KLALGRGDNA    240
ETYTGGLKYD ANNIYLATQY TQTYNATRAG SLGFANKAQN FEVVAQYQFD FGLRPSVAYL    300
QSKGKDLEGY GDQDILKYVD VGATYYFNKN MSTYVDYKIN LLDDNSFTHN AGISTDDVVA    360
LGLVYQF                                                              367
```

```
SEQ ID NO: 29            moltype = DNA  length = 1071
FEATURE                  Location/Qualifiers
source                   1..1071
                         mol_type = unassigned DNA
                         organism = Klebsiella pneumoniae
SEQUENCE: 29
atgaaaaaga cagctatcgc gattgcagtg gcactggctg cttcgctac cgtagcgcag      60
gccgctccga aagataacac ctggtatgca ggtggtaaac tgggttggtc ccagtatcac    120
gacaccggtt tctacggtaa cggtttccag aacaacaacg gtccgacccg taacgatcag    180
cttggtgctg gtgcgttcgg tggttaccag gttaacccgt acctcggttt cgaaatgggt    240
tatgactggc tgggccgtat ggcatataaa ggcagcgttg acaacggtgc tttcaaagct    300
cagggcgttc agctgaccgc taaactgggt tacccgatca ctgacgatct ggacatctac    360
acccgtctgg gcggcatggt ttggcgcgct gactccaaag gcaactacgc ttctaccggc    420
gtttccgta gcgaacacga cactggcgtt tccccagtat ttgctggcgg cgtagagtgg     480
gctgttactc gtgacatcgc tacccgtctg gaataccagt gggttaacaa catcggcgac    540
gcgggcactg tgggtacccg tcctgataac ggcatgctga gctgggcgt ttcctaccgc     600
ttcggtcagg aagatgctgc accggttgtt gctccggctc cggctccggc tccggaagtg    660
gctaccaagc acttcacccct gaagtctgac gttctgttca acttcaacaa agctaccctg    720
aaaccggaag gtcagcaggc tctggatcag ctgtacactc agctgagcaa catggatccg    780
aaagacggtt ccgctgttgt tctgggctac accgaccgca tcggttccga agcttacaac    840
cagcagcgt ctgagaaacg tgctcagtcc gttgttgact acctggttgc taaaggcatc     900
ccggctggca aaatctccgc tcgcggcatg ggtgaatcca acccggttac tggcaacacc    960
tgtgacaacg tgaaagctcg cgctgccctg atcgattgcc tggctccgga tcgtcgtgta   1020
gagatcgaag ttaaaggcta caaagaagtt gtaactcagc cggcggctta a            1071
```

```
SEQ ID NO: 30            moltype = AA  length = 356
FEATURE                  Location/Qualifiers
source                   1..356
                         mol_type = protein
                         organism = Klebsiella pneumoniae
SEQUENCE: 30
MKKTAIAIAV ALAGFATVAQ AAPKDNTWYA GGKLGWSQYH DTGFYGNGFQ NNNGPTRNDQ     60
LGAGAFGGYQ VNPYLGFEMG YDWLGRMAYK GSVDNGAFKA QGVQLTAKLG YPITDDLDIY    120
TRLGGMVWRA DSKGNYASTG VSRSEHDTGV SPVFAGGVEW AVTRDIATRL EYQWVNNIGD    180
AGTVGTRPDN GMLSLGVSYR FGQEDAAPVV APAPAPAPEV ATKHFTLKSD VLFNFNKATL    240
KPEGQQALDQ LYTQLSNMDP KDGSAVVLGY TDRIGSEAYN QQLSEKRAQS VVDYLVAKGI    300
PAGKISARGM GESNPVTGNT CDNVKARAAL IDCLAPDRRV EIEVKGYKEV VTQPAA        356
```

```
SEQ ID NO: 31            moltype = DNA  length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 31
caacggtgtg gttactgacg                                                 20
```

```
SEQ ID NO: 32            moltype = DNA  length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 32
tctacgaagt ggccgttttc                                                 20
```

-continued

```
SEQ ID NO: 33            moltype = DNA  length = 24
FEATURE                  Location/Qualifiers
misc_feature             1..24
                         note = Description of Artificial Sequence: Synthetic primer
source                   1..24
                         mol_type = other DNA
                         organism = synthetic construct
SEQUENCE: 33
gatacggagt atgcctttac ggtg                                           24

SEQ ID NO: 34            moltype = DNA  length = 24
FEATURE                  Location/Qualifiers
misc_feature             1..24
                         note = Description of Artificial Sequence: Synthetic primer
source                   1..24
                         mol_type = other DNA
                         organism = synthetic construct
SEQUENCE: 34
tagcctttat caagcggata ctgg                                           24

SEQ ID NO: 35            moltype =    length =
SEQUENCE: 35
000

SEQ ID NO: 36            moltype =    length =
SEQUENCE: 36
000

SEQ ID NO: 37            moltype =    length =
SEQUENCE: 37
000

SEQ ID NO: 38            moltype =    length =
SEQUENCE: 38
000

SEQ ID NO: 39            moltype =    length =
SEQUENCE: 39
000

SEQ ID NO: 40            moltype =    length =
SEQUENCE: 40
000

SEQ ID NO: 41            moltype = AA  length = 741
FEATURE                  Location/Qualifiers
source                   1..741
                         mol_type = protein
                         organism = Klebsiella pneumoniae
SEQUENCE: 41
AQVDIAPGSL DKALNQYAAH SGITLSVDAS LTRGKQSNGL HGDYDVESGL QQLLDGSGLQ  60
VKPLGNNSWT LEPAPAPKED ALTVVGDWLG DARENDVFEH AGARDVIRRE DFAKTGATTM  120
REVLNRIPGV SAPENNGTGS HDLAMNFGIR GLNPRLASRS TVLMDGIPVP FAPYGQPQLS  180
LAPVSLGNMD AIDVVRGGGA VRYGPQSVGG VVNFVTRAIP QDFGIEAGVE GQLSPTSSQN  240
NPKETHNLMV GGTADNGFGT ALLYSGTRGS DWREHSATRI DDLMLKSKYA PNEVHTFNSL  300
LQYYDGEADM PGGLSRADYD ADRWQSTRPY DRFWGRRKLA SLGYQFQPDS QHKFNILGFY  360
TQTLRSGYLE QGKRITLSPR NYWVRGIEPR YSQSFMIGPS AHEVGVGYRY VNESTHEMRY  420
YTATSSGQLP SGSSPYDRDT RSGTEAHAWY LDDKIDIGNW TITPGMRFEH IESYQNNAIK  480
GTHEEVSYNA PLPALNVLYH LTDSWNLYAN TEGSFGTVQY SQIGKAVQSG NVEPEKARTW  540
ELGTRYDDGA LTAEMGLFLI NFNNQYDSNQ TNDTVTARGK TRHTGLETQA RYDLGTLTPT  600
LDNVSVYASY AYVNAEIREK GDTYGNQVPF SPKHKGTLGV DYKPGNWTFN LNSDFQSSQF  660
ADNANTVKES ADGSTGRIPG FMLWGARVAY DFGPQMADLN LAFGVKNIFD QDYFIRSYDD  720
NNKGIYAGQP RTLYMQGSLK F                                             741

SEQ ID NO: 42            moltype = AA  length = 702
FEATURE                  Location/Qualifiers
source                   1..702
                         mol_type = protein
                         organism = Klebsiella pneumoniae
SEQUENCE: 42
AEQPKQEETI TVVAAPAAQE NAWGPAPTIA AKRSATATKT DTPIEKTPQS VSVVTRHEME  60
MRQPTTVKEA LSYTPSVFST RGSSTTYDVV TIRGFTTSTT VNTNQYLDGM KLQGNNYSEV  120
SMDPYFLERV EVMRGPTSVL YGNSNPGGIV SMVSKRPTTE PLKEVQFKMG TDNLWQTGFD  180
FSDAIDDAGV WSYRLTGLGR SQDAQQQMAK STRYAVAPSF SWRPDDKTDF TFLSNFQNDP  240
DAGYYGWLPR EGTVVPYYDA NGKAHKLPTD FNEGESDNKI SRRQKMVGYS FSHQFDDTFT  300
VRQNLRYADV HTLYRSVYGN GYVAPGYMNR AYVRSDEHLN TFTVDTQLQS DFATGAVSHT  360
LLTGVDYSRM RNDVDADYGT ADPISMSNPQ YGNPNIQVTF PYAVLNRMEQ TGLYAQDQME  420
WDKWVMTLGG RYDYATTSTL TRATNSLAEN HDQQFSWRGG INYLFDNGIS PYFSYSESFE  480
PVSGSNSRGQ PFDPSRGKQY EAGVKYVPKD MPVVVTAAVY QLTKDKNLTA DPANQAFSIQ  540
```

```
TGEIRSRGLE LEAKAAVNAN INVTAAYSYT DAEYTHDTVF NGKRPAEVPR NMASLWADYT    600
FHETALSGLT IGAGARYIGS TVSYYKNDTS TGKKNDAFSV AGYALMDATV KYDLARFGLP    660
GSSVGVNVNN LFDREYVSSC YSEYACYWGA GRQVVATATF RF                       702

SEQ ID NO: 43              moltype = AA  length = 632
FEATURE                    Location/Qualifiers
source                     1..632
                           mol_type = protein
                           organism = Klebsiella pneumoniae
SEQUENCE: 43
DVNEETLVVT ASATEQNVKD APASISVITQ QDLQRKPVQN LKDVLRDVPG VQLTNEGDNR    60
KGVSIRGLSS SYTLILVDGK RVNSRNAVFR HNDFDLNWIP VDAIERIEVV RGPMSSLYGS    120
DALGGVVNII TKKIGQKWTG TLSADTTIQE HRDRGDTYNG QFFTSGPLID GVLGMKAYGS    180
LAKRAKDDPQ SSSNATGETP RIEGFTSRDG NVEFAWTPNE NHDFTAGYGF DRQDRDSDSL    240
DRNRLERENY SLSHNGRWDI GNSELKFYGE KVDNKNPGQS GTITSESNAI DGKYVLPLGM    300
INQLVTFGGE WRHDKLKDPV NLSSGGQSTS ASQYALFIED EWRIIEPLAL TTGIRMDDHQ    360
TYGDHWSPRA YLVYNATDTV TVKGGWATAF KAPSLLQLNP DWTTNSCRGS CSIVGNPDLK    420
PETSESFELG LYYRGEEGWL ENVEGSITTF QNNVDDMIDV LRTSSASEAP GYPNFVGWKT    480
VNGKRVPIFR YFNVNKARIK GVETEVKIPF GDEWKLTVNY TYNDGRDLSN GGDKPLQTLP    540
FHTANGTLDW KPLDDWSFYV TANYTGQQRA VSATGKTPGG YTLFDVGAAW QVTKNVKLRS    600
GVQNVGDKDL SRDDYSYTEE GRRYFMAVDY RF                                  632

SEQ ID NO: 44              moltype = AA  length = 717
FEATURE                    Location/Qualifiers
VARIANT                    455..458
                           note = MOD_RES - Any amino acid
source                     1..717
                           mol_type = protein
                           organism = Klebsiella pneumoniae
SEQUENCE: 44
AETATDDKNS AAEETMVVTA AEQNLQAPGV STITADEIRK RPPARDVSEI IRTMPGVNLT    60
GNSTSGQRGN NRQIDIRGMG PENTLILIDG KPVTSRNSVR LGWRGERDTR GDTSWVPPEI    120
IERIEVIRGP AAARYGNGAA GGVVNIITKK TGDEWHGSWN TYMNAPEHKD EGSTKRTNFS    180
LSGPLGGDFS FRLFGNLDKT QADAWDINQG HQSERTGIYA DTLPAGREGV KNKNIDGLVR    240
WEFAPMQSLE FEAGYSRQGN LYAGDTQNTN SNDLVKENYG KETNRLYRNT YSVTWNGAWD    300
NGVTTSNWAQ YERTRNSRKG EGLAGGTEGI FNSNQFTDID LADVMLHSEV SIPFDYLVNQ    360
NLTLGSEWNQ QRMKDNASNT QALSGGGIPG YDSTGRSPYS QAEIFSLFAE NNMELTDTTM    420
LTPALRFDHH SIVGNNWSPS LNLSQGLWDD FTLKXXXXRA YKAPSLYQTN PNYILYSKGQ    480
GCYASKDGCY LQGNDDLKAE TSINKEIGLE FKRDGWLAGV TWFRNDYRNK IEAGYAPVYQ    540
NNKGTDLYQW ENVPKAVVEG LEGTLNVPVS ETVNWTNNIT YMLQSKNKET GDRLSIIPEY    600
TLNSTLSWQV RDDVSLQSTF TWYGKQEPKK YNYKGQPVTG SEKNEVSPYS ILGLSATWDV    660
TKYVSLTGGV DNVFDKRHWR AGNAQTTGGA TGTMYGAGAE TYNESGRTWY LSVNTHF       717

SEQ ID NO: 45              moltype = AA  length = 592
FEATURE                    Location/Qualifiers
VARIANT                    118..132
                           note = MOD_RES - Any amino acid
source                     1..592
                           mol_type = protein
                           organism = Klebsiella pneumoniae
SEQUENCE: 45
QDSNSDTLVV TANRFQQPVN TVLAPTDIVT RDDIDRWQSK DLNDVMRRLP GVDIARNGGM    60
GQSASLYVRG TEARHVLVLI DGVPMARPGI SNGVDISQIP ISLVQRVEYI RGPRSAVXXX    120
XXXXXXXXXX XXTDAERSQI NAGAGTNGYQ SYDGAFNKRF GNTLVTAAGA YQTTKGFNVQ    180
PNSSYSGDSD RDGYRNKMLW GGVQHQFDDN FSGFFRGYGY SANADYDQGN WGYAGGNDED    240
QSYTQSWDTG LHYHSGIYSS QLIANYQRIK DYNYSSDAGR YAAGTTLDDM EQRYIQWGNN    300
VVVGHGAVSG GVDWKQEKLK SSGTTSTDVY KRDTTGLYLT GQQQIDSVTL EASGREDHDE    360
QFGWHGTWQT AAGWEFIDGY RTTLSYGTGF LAPSLGQQYG AERFGIASNP NLKPEESKQW    420
EAGLEGLTGP VDWRLSAYRY EIQNLIDYDN NAYYNVKSAT IKGLEWTGNI TTGPVEHHLT    480
LQYVDPRDDE TNKILYRRAK QQVKYELNGQ VYDLGWDVTY HYIGKRYDYD YDNSRTVNMG    540
GLSLWDVGLS YPVTSHLTVR GKIANLFDKD YETVYGYQSA GREYTLSGSY TF            592

SEQ ID NO: 46              moltype = AA  length = 729
FEATURE                    Location/Qualifiers
source                     1..729
                           mol_type = protein
                           organism = Klebsiella pneumoniae
SEQUENCE: 46
AENSVKNSEE TLVVEAAPPS LYSPGASADP KFNKPLVDTT RTITVIPEQV IKDQGVTNLT    60
DALKNVPGVG AFYAGENGSS TTGDAIFMRG VDTSNSIYVD GIRDIGSVTR DTFNTQQVEV    120
IKGPAGTDYG RSAPSGSINM ISKQPRLDSG IDGSASIGSA WSRRGTLDLN QAFSDNAAFR    180
LNLMGEKTHD AGRDRIENER YGIAPSLAFG LDTPTRLYLN YLHVRQNNTP DGGIPTVGLP    240
GYSAPSPKYA ALNSTGKVDT SNFYGTDSDY DKSTTDSGTL RFEHDLTEST TVRNTTRWSR    300
VKQEYLLTAV MGGANNITAP DINDVNTWSW SRLVNTKDVS NRILTNQTNI TSTFDTGSIG    360
HDVSAGVEFT RENQTNYGVN ARTAPAVNLY HPVSNLSIGG LDRNGANANG QTDTFGIYAF    420
DTLTLTERIE INGGLRLDNY HTKYDSATAC GGSRGAIAC PPGQSTGSPV TTVDTAKSGN    480
LVNWKAGALY RLTEQGNVYV NYAISQQPPG GSSFALAASG SGNSANRTDF KPQKAKSSEL    540
GTKWQIFDNR LLLSAALFRT DIENEVAAND DGTWSQYGKK RVEGYELSAT GNLTPDWTII    600
AGYTQQHATV TEGQNVAQDG SSALAYTPKH AFTLWTQYQA TSDLSVGGGV RYVGSLRRGS    660
```

```
DGAVGTPDHT EGYWVADAKL GYRVNSNLDL QLNMYNLFDT DYVASINKSG YRYHPGEPRT   720
FMLTANVHF                                                            729

SEQ ID NO: 47          moltype =   length =
SEQUENCE: 47
000

SEQ ID NO: 48          moltype =   length =
SEQUENCE: 48
000

SEQ ID NO: 49          moltype = AA  length = 707
FEATURE                Location/Qualifiers
source                 1..707
                       mol_type = protein
                       organism = Klebsiella pneumoniae
SEQUENCE: 49
AQSDEDSIIV SANRTHRTVA EMAQTTWVIE GQEIEQQVQG GKEFKDVLAQ LIPGIDVSSQ   60
GRTNYGMNMR GRAIVVLIDG VRLNSSRTDS RQLDAIDPFN IEHIEVISGA TSLYGGGSTG   120
GLINIVTKKG QQDRQVDLEV GSKSGFANSN DHDERVAAAV SGGTDHASGR LSVAYQRFGG   180
WYDGNTDALI LDNTQTGLQH SDRLDVMGTG TIEIDNNRQL QLVTQYYKSQ GDDDYGLWLG   240
KNMSAVTSGG KAYTTDGLNS DRIPGTERHL ISLQYSDADF FGQNLVSQVY YRDESLTFYP   300
FPTLTKGQVS SFSSSQQDTD QYGAKLTLNS QPLAGWDLTW GLDADHETFN ANQMFFDLPQ   360
SMASGGLHNE SIYTTGRYPG YSISNVAPFL QSSYDLNDIF TVSGGVRYQW TENRVDDFVG   420
YAQQQDIANG KARSADAIKG GKTDYDNFLF NAGIVAHLTE RQQTWFNFSQ GVELPDPGKY   480
YGIGKYGAAV NGHLPLISSV NVDDSPLQGI KVNSYELGWR YTGDNLRTQL AAYYSTSDKT   540
IVVNRTDMTI DVQSDKRRIY GVEGAVDYFI PDSDWSVGGN FNVLKSQVQT DGRWQKWDVT   600
LASPSKATAW VGWAPDPWSL RVQSQQVFDL SDAAGNKLEG YNTVDFIGSY ALPVGKLTFS   660
IENLLNEDYV TIWGQRAPLL YSPTYGSSSL YEYKGRGRTF GLNYALT                 707

SEQ ID NO: 50          moltype =   length =
SEQUENCE: 50
000

SEQ ID NO: 51          moltype = AA  length = 703
FEATURE                Location/Qualifiers
source                 1..703
                       mol_type = protein
                       organism = Klebsiella pneumoniae
SEQUENCE: 51
ADAAAAKQPG EETLIVEANE TSDFKSGGDL VVPAFLDGQI AHGGRLGMLG EQKAMDVPFN   60
VIGYTSKLIQ DQQAKTIADV VSNDAGVQAV QGYGNFAETY RIRGFKLDGD DMTMGGLAGV   120
VPRQVMDTQM LERVEIFKGA NSLLNGAASS GVGGVIYLEP KRAEDLPTAR VGVDYTSDSQ   180
VGGTLDLGRR FGDNNQFGAR VNLVHREGEG AIDNDKRRTT LASLGLDYRG DRFRSSLDFG   240
YQKKTFHGGT MGVNISGVDF VPALPDNSKN YSQKWGYSDI ESEFGMAKAE YDLTDSWTVY   300
SALGGQHSHE IGTYSAPKLL NKNGDATVGR LDTNRIIDAI SGMGGVRGDF NTGAISHTVN   360
LGYAAQVHTD ATAWRMSARN PTTNIYDNHD VAMPDNAYFG GNYHDPLVTS RSRTQGWLLS   420
DTLGFFNDKV LFTAAARHQK VVVRNYSNAT GLEDTSSRYT QSRWMPTFGL VYKPWEQLSL   480
YANHTEALQP GSVAPTTAAN AGQSTGIAHS KQDEVGVKID YGTIGGSLAL FEIKKPNAIS   540
DTAGNYGLDG EQRNRGVEMN VFGEPMLGLR LNASTVWLDA KQTKTAEGAT DGKDAIGVAN   600
FYAVLGAEYD IKPVEGLTAT ARVNHSGSQY ADAANTKKLD SYTTLDLGLR YRMRLNADQN   660
EMIWRVGVTN VTNEKYWSGI DDTGTYLFEG DPRTVRVSMS YDF                     703

SEQ ID NO: 52          moltype = AA  length = 756
FEATURE                Location/Qualifiers
source                 1..756
                       mol_type = protein
                       organism = Klebsiella pneumoniae
SEQUENCE: 52
ADTSAVSGEA VDDTSEQMTV TAPAPVQKAG SEHSISAREL ENKGANDFGS IMRYEPLISA   60
TGASGGSGNG KSGFDRGGYT GYNIRGMESN RVGIDVDGIA QPNATGRGYV GRAGLNTFGI   120
GRDYIDPYMY GSVDIQSGAT STETANSAIG GNVSFRPKSA DDYLRPGKTS AFGYRSGYDS   180
ADRSWHNGVT VAGGDEFLRG ILVYSRRDGQ ETENNSGTVD AYPANWHSDA FLASGIWQPN   240
DEHKLTSTFD YYHKTNHTHY DTWDSSGNST IGTANQTSQT RRWGLSLKDD WTPMNDYLDS   300
VSTKIYYQHT EAHDWTYMPD SVTRRMQTVN SNYDTDTWGL QTALAKTLGR HDLSAGFNAS   360
TSKTQRPFSQ SPIPSVYSEI MQPEADSRSY TLGGFVQDKI NFDLDSHNFA VIPGVRVVHQ   420
STKPENLSDL AANSSVLSES SVANLYGKNS DTQVLPSLTF QYDLTPRLMT YLQYQRGAQF   480
PNASQLYGSW NLGSSYAGSQ QYALIGNTDL KTETSDNLEW GLKGEVTEGI TLRTALFYNS   540
YKNFIAYTRY TRANNPGQFT NVPSNIYTIY QAENRDKAYI YGGEISTKFN FGTWFEQVDG   600
LSATLALGYS EGKSKSSYSG DKYVDLDSVA PMKAIVGVAW DDDPAKRYGTA LTATFVKGKQ   660
ATATNRESYS NSGSAITDAS SDYMRVPGYG MLDWTAYWQV AKNVRLNGGV YNLTDRKYWD   720
YLSSRNIETG TNQDANDKAL AVMPGRTWQL GVNVDF                             756

SEQ ID NO: 53          moltype = AA  length = 680
FEATURE                Location/Qualifiers
source                 1..680
                       mol_type = protein
                       organism = Klebsiella pneumoniae
SEQUENCE: 53
```

-continued

```
EETVVVTATP PASASAPTEG YSASTSLGAT KTDQPLITTA QSVSVVTRQQ MADQGANTIS  60
QALEYTPGVY SSFGGGATRF DAISLRGYHG GDVDNLFLDG MRLMSDGGSH NVLQIDPWFI  120
ERVDVIRGPS SALYGQSVPG GVVNLTSKRP QFSQQGHIRL TGGTQNTKGA AFDYTDAIND  180
QWAWRLIGMT RSSDTQYDHT REERYAISPS LLWQPDSDTS LLLRAYLQKD PSGGYHGSLP  240
LDGTRYAHNG RKLSPSTNEG DPGDGYQRRQ QIYSYEFDHQ FTDVWSVYSA GSYTHTNVSL  300
DQVYQVGWID ESDMLARGYS GSRGSLDGWS TDNRLRADFN TGDLAHTLIL GAEYHRFRND  360
LWTGAGGAAP LNPFSGYTEQ TGHTVTYSDD NNRRYYQTGL YLQDEMVWNR WHVDVSARYD  420
RIVSQQVSDT QGTSNRRSDD HISGRASLLY ALDNGLSPYL SYSQAITPAM LPGADGKPLK  480
PTTAEQVEAG LKFQPPGSSD LYSIAIYDLT QKDVATRDPN IATATYIPAG KVHSQGVELE  540
AHHQITPQLS TIASYTWNRL RFQDTQDGTD NNTPQLTPDQ MASFWARYQF PAGISVGAGV  600
RYIGKQWADD ANTARLPSVT LMDAMMRADL GVWSPTLKGA YVQVNANNIG DREYISGCYG  660
TGNCYWGAER SVIATVGYDF                                            680

SEQ ID NO: 54           moltype = AA  length = 346
FEATURE                 Location/Qualifiers
source                  1..346
                        mol_type = protein
                        organism = Klebsiella pneumoniae
SEQUENCE: 54
AEIYNKDGNK LDLYGKIDGL HYFSDDKSVD GDQTYMRVGV KGETQINDQL TGYGQWEYNV  60
QANNTESSSD QAWTRLAFAG LKFGDAGSFD YGRNYGVVYD VTSWTDVLPE FGGDTYGSDN  120
FLQSRANGVA TYRNSDFFGL VDGLNFALQY QGKNGSVSGE GALSPTNNGR TALKQNGDGY  180
GTSLTYDIYD GISAGFAYSN SKRLGDQNSK LALGRGDNAE TYTGGLKYDA NNIYLATQYT  240
QTYNATRAGS LGFANKAQNF EVVAQYQFDF GLRPSVAYLQ SKGKDLEGYG DQDILKYVDV  300
GATYYFNKNM STYVDYKINL LDDNSFTHNA GISTDDVVAL GLVYQF                346

SEQ ID NO: 55           moltype = AA  length = 335
FEATURE                 Location/Qualifiers
source                  1..335
                        mol_type = protein
                        organism = Klebsiella pneumoniae
SEQUENCE: 55
APKDNTWYAG GKLGWSQYHD TGFYGNGFQN NNGPTRNDQL GAGAFGGYQV NPYLGFEMGY  60
DWLGRMAYKG SVDNGAFKAQ GVQLTAKLGY PITDDLDIYT RLGGMVWRAD SKGNYASTGV  120
SRSEHDTGVS PVFAGGVEWA VTRDIATRLE YQWVNNIGDA GTVGTRPDNG MLSLGVSYRF  180
GQEDAAPVVA PAPAPAPEVA TKHFTLKSDV LFNFNKATLK PEGQQALDQL YTQLSNMDPK  240
DGSAVVLGYT DRIGSEAYNQ QLSEKRAQSV VDYLVAKGIP AGKISARGMG ESNPVTGNTC  300
DNVKARAALI DCLAPDRRVE IEVKGYKEVV TQPAA                           335

SEQ ID NO: 56           moltype = DNA  length = 1983
FEATURE                 Location/Qualifiers
source                  1..1983
                        mol_type = unassigned DNA
                        organism = Escherichia coli
SEQUENCE: 56
atgagaggat cgcatcacca tcaccatcac ggatctggct ctggatctgg tatcgaggga  60
aggcctgtcg atgatgatgg cgaaacgatg gttgtcactg catcttccgt tgaacaaaac  120
cttaaagatg ctcccgccag tatcagcgtc attacccagg aagacctgca gcgaaaaccg  180
gtacagaatc tgaaggatgt cctcaaagaa gtgcctggcg tacaactgac gaacgaaggg  240
gataaccgta agggcgtaag tattcgtggt ctggacagca gctacaccct gattcttgtc  300
gacggtaaac gcgttaactc ccgcaatgcc gtcttccgac acaatgattt cgatctgaac  360
tggatcccgg tcgattccat cgaacgtatt gaagtggttc gtggcccgat gtcgtcgctg  420
tacggttccg atgcgctcgg cggtgtagtg aatatcatca ccaaaaaaat cggtcagaaa  480
tggtcgggca ccgttaccgt cgataccacc gttcaggaac atcgcgatcg cggtgatacc  540
tataacggtc aattctttac cagcggacca ttaattgacg gcgtgctggg aatgaaagct  600
tacggcagcc tggcaaaacg tgaaaaggat gacccgcaaa actcaacgac caccgatacc  660
ggagaaacgc cgcgtattga aggattctcc agccgcgacg gcaatgtcga atttgcctgg  720
acaccgaatc aaaatcacga ttttactgcc ggatacggtt cgaccgtca ggatcgtgat  780
tccgactcgc tggacaaaaa ccgcctggaa cgccagaact actccgtcaca ccataatggg  840
cgttgggatt acggcaccag cgaactgaaa tactacggtg agaaagtcga gaacaaaaac  900
cctggcaaca gcagcccgat aacttccgaa agcaatacgg tcgacggcaa atacacgttg  960
ccgctgacgg cgattaatca gtttctcacg gttggcggtg aatggcgtca cgacaaactt  1020
agcgatgcgt tgaacctgac cggggggaacc agctccaaaa cgtctgccag ccagtacgcg  1080
ctgtttgtgg aagatgaatg gcggatcttc gagccgctaa gacgac cggcgtgaac  1140
atggacgatc acgaaaccta cggtgaacac tggagtccgc gtgcctacct ggtttataac  1200
gccaccgaca ccgtaacggt gaaagggggc tgggcgacgg catttaaagc cccttctctg  1260
ttgcaactta gccctgactg gacgagcaat tcctgccgtg gcgcatgtaa gattgtgggt  1320
agcccggatc tgaaaccaga aaccagcgaa agttgggagc tggggcttta ctacatgggt  1380
gaagaaggct ggctggaagg ggttgaatcc agcgttaccg ttttccgtaa cgatgtgaaa  1440
gatcgtatca gcattagccg tacgtctgac gtcaatgctg caccgggcta ccaaaacttt  1500
gtcggttttg agacgggcgc taacggaccg cgcataccgg tatttagcta ctacaacgtt  1560
aacaaagctc gtattcaggg cgtggaaacc gaactgaaaa ttccgttcaa cgatgaatgg  1620
aaactgtcga tcaactacac ctacaacgat ggtcgtgatg tcagcaacgg cgaaaacaaa  1680
ccgctatccg atctgccgtt ccatactgct aacggtacgg aagaaaccgcg  1740
ctggaagact ggtcattcta tgtttctggt cactataccg ggcagaaacg cgccgacagc  1800
gcgacggcta aaacaccggg cggttatacc atctggaata ccggcgcggc ctggcaggtg  1860
actaaagacg tcaaactgcg cgcaggcgtg ctgaaccttg cgacaagga tctcagtcgt  1920
gacgactaca gctataacga agacggacgt cgttacttta tggcagtgga ttatcgcttc  1980
tga                                                             1983
```

```
SEQ ID NO: 57          moltype = AA  length = 660
FEATURE                Location/Qualifiers
source                 1..660
                       mol_type = protein
                       organism = Escherichia coli
SEQUENCE: 57
MRGSHHHHHH GSGSGSGIEG RPVDDDGETM VVTASSVEQN LKDAPASISV ITQEDLQRKP  60
VQNLKDVLKE VPGVQLTNEG DNRKGVSIRG LDSSYTLILV DGKRVNSRNA VFRHNDFDLN  120
WIPVDSIERI EVVRGPMSSL YGSDALGGVV NIITKKIGQK WSGTVTVDTT VQEHRDRGDT  180
YNGQFFTSGP LIDGVLGMKA YGSLAKREKD DPQNSTTTDT GETPRIEGFS SRDGNVEFAW  240
TPNQNHDFTA GYGFDRQDRD SDSLDKNRLE RQNYSVSHNG RWDYGTSELK YYGEKVENKN  300
PGNSSPITSE SNTVDGKYTL PLTAINQFLT VGGEWRHDKL SDAVNLTGGT SSKTSASQYA  360
LFVEDEWRIF EPLALTTGVR MDDHETYGEH WSPRAYLVYN ATDTVTVKGG WATAFKAPSL  420
LQLSPDWTSN SCRGACKIVG SPDLKPETSE SWELGLYYMG EEGWLEGVES SVTVFRNDVK  480
DRISISRTSD VNAAPGYQNF VGFETGANGR RIPVFSYYNV NKARIQGVET ELKIPFNDEW  540
KLSINYTYND GRDVSNGENK PLSDLPFHTA NGTLDWKPLA LEDWSFYVSG HYTGQKRADS  600
ATAKTPGGYT IWNTGAAWQV TKDVKLRAGV LNLGDKDLSR DDYSYNEDGR RYFMAVDYRF  660

SEQ ID NO: 58          moltype = AA  length = 638
FEATURE                Location/Qualifiers
source                 1..638
                       mol_type = protein
                       organism = Escherichia coli
SEQUENCE: 58
VDDDGETMVV TASSVEQNLK DAPASISVIT QEDLQRKPVQ NLKDVLKEVP GVQLTNEGDN  60
RKGVSIRGLD SSYTLILVDG KRVNSRNAVF RHNDFDLNWI PVDSIERIEV VRGPMSSLYG  120
SDALGGVVNI ITKKIGQKWS GTVTVDTTVQ EHRDRGDTYN GQFFTSGPLI DGVLGMKAYG  180
SLAKREKDDP QNSTTTDTGE TPRIEGFSSR DGNVEFAWTP NQNHDFTAGY GFDRQDRDSD  240
SLDKNRLERQ NYSVSHNGRW DYGTSELKYY GEKVENKNPG NSSPITSESN TVDGKYTLPL  300
TAINQFLTVG GEWRHDKLSD AVNLTGGTSS KTSASQYALF VEDEWRIFEP LALTTGVRMD  360
DHETYGEHWS PRAYLVYNAT DTVTVKGGWA TAFKAPSLLQ LSPDWTSNSC RGACKIVGSP  420
DLKPETSESW ELGLYYMGEE GWLEGVESSV TVFRNDVKDR ISISRTSDVN AAPGYQNFVG  480
FETGANGRRI PVFSYYNVNK ARIQGVETEL KIPFNDEWKL SINYTYNDGR DVSNGENKPL  540
SDLPFHTANG TLDWKPLALE DWSFYVSGHY TGQKRADSAT AKTPGGYTIW NTGAAWQVTK  600
DVKLRAGVLN LGDKDLSRDD YSYNEDGRRY FMAVDYRF                          638

SEQ ID NO: 59          moltype = DNA  length = 2241
FEATURE                Location/Qualifiers
source                 1..2241
                       mol_type = unassigned DNA
                       organism = Escherichia coli
SEQUENCE: 59
atgagaggat cgcatcacca tcaccatcac ggatctggct ctggatctgg tatcgaggga  60
aggcctcaag agccgaccga tactcctgtt tcacatgacg ataccattgt cgttaccgcc  120
gccgagcaga acttgcaggc gcctggcgtt tcgaccatta ccgcagatga aatccgcaaa  180
aacccggttg cccgcgatgt atcggagatc attcgtacca tgcctggcgt taacctgacc  240
ggtaactcca ccagtggtca gcgtggtaat aaccgccaga ttgatattcg cggcatgggt  300
ccggaaaaca cgctgatttt gattgacggc aagccggtaa gcagccgtaa ctctgtgcgt  360
cagggctggc gtggcgagcg cgatacccgt ggtgatacct cctgggtgcc gcctgaaatg  420
attgaacgta ttgaagttct gcgtggtccg gcagctcgc gttatggcaa cggcgcggcg  480
ggcggcgtgg ttaacatcat taccaaaaaa ggcagcggtg agtggcacgg ctcctgggat  540
gcttatttca atgcgccaga acataaagag gaaggtgcca ccaaacgcac caacttcagc  600
ctgaccggtc cgctgggcga cgaattcagc ttccgcttgt atggcaacct cgacaaaacc  660
caggctgacg cgtgggatat caaccagggc catcagtccg cgcgtgccgg aacgtatgcc  720
acgacgttac cagccgggcg cgaagggggtg atcaacaaag atattaatgg cgtggtcgcg  780
tgggacttcg cgcctctgca gtcactcgaa ctggaagcgg gctacagccg ccagggtaac  840
ctgtatgcgg gtgatacgca gaacaccaac tctgacgctt cactcgatc gaaatatggc  900
gatgaaacca accgcctgta tcgccagaac tactcgctga cctggaacgg tggctgggat  960
aacggcgtga ccaccagcaa ctgggtgcag tacgaacaca cccgtaactc gcgtattccg  1020
gaaggtctgg cgggcggtac cgaagggaaa tttaacgaaa aagcggcaca ggattttgta  1080
gatatcgatc ttgatgacgt gatgctgcac agcgaagtta acctgccgat tgatttcctc  1140
gtaaaccaaa cgctgacgct gggtacgag tggaatcagc aacggatgaa ggacttaagt  1200
tccaacaccc aggcgctgac cgggacgaat accggcggtg ctattgatgg tgtgagtgcc  1260
accgaccgta gcccgtattc aaaagcagaa attttctcgc tgtttgccga aaacaatatg  1320
gagctgactg acagcaccat cgtaacgccg gggctgcgtt cgatcatca cagtattgtc  1380
ggcaataact ggagccccggc gctgaacata tcgcaaggtt taggcgatga cttcacgctg  1440
aaaatgggca tcgcccgcgc ctataaagcg ccgagcctgt accagactaa cccaaactac  1500
attctctaca gtaaaggtca gggctgctat gccagcgcg gcggctgcta tctgcaaggt  1560
aatgatgacc tgaaagcaga aaccagcatc aacaaggaga ttggtctgga gttcaaacgc  1620
gacggttggc tggcgggcgt gacctggttc cgtaacgatt atcgcaataa gattgaagcg  1680
ggctatgtgc tgtagggca aaacgcagtc ggcaccgatc tctatcagtg ggataacgta  1740
ccgaaagcgg tggttgaagg tctggaagga tcgttaaacg taccggttag cgaaacggtg  1800
atgtggacca ataacatcac ttatatgctg aagagtgaaa acaaaaccaa cggcgaccgt  1860
ttgtcgatca tccccggagta tacgttgaac tcaacgctga gctggcaggc acgggagaat  1920
ttgtcgatgc aaacgacctt cacctggtac ggcaaacagc agccgaagaa gtacaactat  1980
aaaggtcagc cagcggttgg accggaaacc aaagaaatca gtccgtacag cattgttggc  2040
ctgagcgcga cctgggatgt gacgaagaat gtcagtctga ccggcggcgt ggacaacctg  2100
ttcgacaaac gtttgtggcg tgcgggtaat gcccagacca cgggcgatct ggcagggggcc  2160
```

```
aactatatcg ccggtgccgg tgcgtatacc tataacgagc cgggacgtac gtggtatatg   2220
agcattaata ctcacttctg a                                              2241

SEQ ID NO: 60            moltype = AA   length = 746
FEATURE                  Location/Qualifiers
source                   1..746
                         mol_type = protein
                         organism = Escherichia coli
SEQUENCE: 60
MRGSHHHHHH GSGSGSGIEG RPQEPTDTPV SHDDTIVVTA AEQNLQAPGV STITADEIRK     60
NPVARDVSEI IRTMPGVNLT GNSTSGQRGN NRQIDIRGMG PENTLILIDG KPVSSRNSVR     120
QGWRGERDTR GDTSWVPPEM IERIEVLRGP AAARYGNGAA GGVVNIITKK GSGEWHGSWD     180
AYFNAPEHKE EGATKRTNFS LTGPLGDEFS FRLYGNLDKT QADAWDINQG HQSARAGTYA     240
TTLPAGREGV INKDINGVVR WDFAPLQSLE LEAGYSRQGN LYAGDTQNTN SDAYTRSKYG     300
DETNRLYRQN YSLTWNGGWD NGVTTSNWVQ YEHTRNSRIP EGLAGGTEGK FNEKAAQDFV     360
DIDLDDVMLH SEVNLPIDFL VNQTLTLGTE WNQQRMKDLS SNTQALTGTN TGGAIDGVSA     420
TDRSPYSKAE IFSLFAENNM ELTDSTIVTP GLRFDHHSIV GNNWSPALNI SQGLGDDFTL     480
KMGIARAYKA PSLYQTNPNY ILYSKGQGCY ASAGGCYLQG NDDLKAETSI NKEIGLEFKR     540
DGWLAGVTWF RNDYRNKIEA GYVAVGQNAV GTDLYQWDNV PKAVVEGLEG SLNVPVSETV     600
MWTNNITYML KSENKTTGDR LSIIPEYTLN STLSWQARED LSMQTTFTWY GKQQPKKYNY     660
KGQPAVGPET KEISPYSIVG LSATWDVTKN VSLTGGVDNL FDKRLWRAGN AQTTGDLAGA     720
NYIAGAGAYT YNEPGRTWYM SINTHF                                          746

SEQ ID NO: 61            moltype = AA   length = 724
FEATURE                  Location/Qualifiers
source                   1..724
                         mol_type = protein
                         organism = Escherichia coli
SEQUENCE: 61
QEPTDTPVSH DDTIVVTAAE QNLQAPGVST ITADEIRKNP VARDVSEIIR TMPGVNLTGN     60
STSGQRGNNR QIDIRGMGPE NTLILIDGKP VSSRNSVRQG WRGERDTRGD TSWVPPEMIE     120
RIEVLRGPAA ARYGNGAAGG VVNIITKKGS GEWHGSWDAY FNAPEHKEEG ATKRTNFSLT     180
GPLGDEFSFR LYGNLDKTQA DAWDINQGHQ SARAGTYATT LPAGREGVIN KDINGVVRWD     240
FAPLQSLELE AGYSRQGNLY AGDTQNTNSD AYTRSKYGDE TNRLYRQNYS LTWNGGWDNG     300
VTTSNWVQYE HTRNSRIPEG LAGGTEGKFN EKAAQDFVDI DLDDVMLHSE VNLPIDFLVN     360
QTLTLGTEWN QQRMKDLSSN TQALTGTNTG GAIDGVSATD RSPYSKAEIF SLFAENNMEL     420
TDSTIVTPGL RFDHHSIVGN NWSPALNISQ GLGDDFTLKM GIARAYKAPS LYQTNPNYIL     480
YSKGQGCYAS AGGCYLQGND DLKAETSINK EIGLEFKRDG WLAGVTWFRN DYRNKIEAGY     540
VAVGQNAVGT DLYQWDNVPK AVVEGLEGSL NVPVSETVMW TNNITYMLKS ENKTTGDRLS     600
IIPEYTLNST LSWQAREDLS MQTTFTWYGK QQPKKYNYKG QPAVGPETKE ISPYSIVGLS     660
ATWDVTKNVS LTGGVDNLFD KRLWRAGNAQ TTGDLAGANY IAGAGAYTYN EPGRTWYMSI     720
NTHF                                                                 724

SEQ ID NO: 62            moltype = DNA   length = 2193
FEATURE                  Location/Qualifiers
source                   1..2193
                         mol_type = unassigned DNA
                         organism = Escherichia coli
SEQUENCE: 62
atgagaggat cgcatcacca tcaccatcac ggatctggct ctggatctgg tatcgaggga     60
aggcctcagc aaaacgatga taatgagatc atagtgtctg ccagccgcag caatcgaact     120
gtagcggaga tggcgcaaac cacctgggtt atcgaaaatg ccgaactgga gcagcagatt     180
cagggcggta aagagctgaa agacgcactg gctcagttaa tccccggcct tgatgtcagc     240
agccagagcc gaaccaacta cggtatgaac atgcgtggcc gcccgctggt tgtcctgatt     300
gacggtgtgc gcctcaactc ttcacgttcc gacagccgac aactggactc tgtcgatcct     360
tttaatatcg accatattga agtgatctcc ggcgcgacgg ccctgtacgg tggcgggagt     420
accgagggt tgatcaacat cgtgaccaaa aaaggccagc cggaaccat gatggagttt     480
gaggctggca caaaaagtgg ctttaacagc agtaaagatc acgatgagcg cattgccggt     540
gctgtctccg gcgaaatga ccatatctcc ggacgtcttt ccgtggcata tcagaaattt     600
ggcggctggt ttgacggtaa cggcgatgcc accctgcttg ataacacca gaccggcctg     660
cagcactcca atcggctgga catcatggga accggtacgc tgaacatcga tgaatcccgg     720
cagcttcaac tgataacgca gtactataaa agtcaggggg acgacaatta cgggcttaat     780
ctcgggaaag gctttccgc catcagcggg agcagcacac catacgtcag taaggggctg     840
aattctgacc gcattcccgg cactgagcgg catttgatca gcccgcagta ctctgacagt     900
gatttcctga gacaggaact ggtcggtcag gtttactacc gcgatgagtc gttgcggttc     960
tacccgttcc cgacggtaaa tgcgaataaa caggcgacgg ctttctcctc gtcacagcag   1020
gataccgacc agtacggcat gaaactgact ctgaacagcc aacttatgga cggctggcaa   1080
atcaccctgg ggctggatgc tgagcgtgag cgctttacct ccaaccagat gttcttcgat   1140
ctggctcagg caagtgcttc cggagggctg aacaaccata agatttacac caccgggcgc   1200
tatccgtcat atgacatcac caatctggcg gccttcctgc aatccagcta tgacattaat   1260
gatatttta ccgttagcgg tggcgtacgc tatcagtata ctgagaacag ggtagatgat   1320
ttcatcgact acacgcagca acagaagatt gctgccggga aggcgatatc tgccgacgcc   1380
attcctggtg gttcggtaga ttacgataac tttctgttca atgctggtct gctgatgcac   1440
atcaccgaac gtcagcaggc atggttcaat ttttcccagg gggttcacga gggaggatcg   1500
gggaaatatt atggtcgcgg catctatggt gcagcagtga acggccatct tcccctgaca   1560
aagagcgtga acgtcagcga cagtaagctg gaaggcgtga aagtcgattc ttatgaactg   1620
ggctggcgct taccggtga caacctgcgg actcaaatcg cggcatatta ctcgctttcc   1680
aataagagcg tggaaggaa taaagatctg accatcagtg tgaaggacga caggcgccgt   1740
atttacggcg tggaaggtgc ggtggactac ctgatcccgg atactgactg gagtaccggt   1800
```

-continued

```
gtgaacttca atgtgctgaa aaccgagtcg aaagtgaacg gtcaatggca aaaatatgac   1860
gtgaaggaat caagtccatc gaaagcgaca gcttacatta actgggcgcc ggaaccgtgg   1920
agtctgcgtg tacagagcac cacttctttc gacgtaagcg atgcagaggg taacgatatt   1980
aatggttaca ctaccgtcga tttttatcagt agttggcagc ttccggtggg aacactcagc   2040
ttcagcgttg agaacctctt cgaccgtgac tataccactg tctggggaca gcgtgcacct   2100
ctgtactaca gcccggggtta cggccctgct tcactgtacg actacaaagg ccggggccga   2160
acctttggtc tgaactactc agtgctgttc tga                                2193
```

```
SEQ ID NO: 63              moltype = AA   length = 730
FEATURE                    Location/Qualifiers
source                     1..730
                           mol_type = protein
                           organism = Escherichia coli
SEQUENCE: 63
MRGSHHHHHH GSGSGSGIEG RPQQNDDNEI IVSASRSNRT VAEMAQTTWV IENAELEQQI   60
QGGKELKDAL AQLIPGLDVS SQSRTNYGMN MRGRPLVVLI DGVRLNSSRS DSRQLDSVDP   120
FNIDHIEVIS GATALYGGGS TGGLINIVTK KGQPETMMEF EAGTKSGFNS SKDHDERIAG   180
AVSGGNDHIS GRLSVAYQKF GGWFDGNGDA TLLDNTQTGL QHSNRLDIMG TGTLNIDESR   240
QLQLITQYYK SQGDDNYGLN LGKGFSAISG SSTPYVSKGL NSDRIPGTER HLISLQYSDS   300
DFLRQELVGQ VYYRDESLRF YPFPTVNANK QATAFSSSQQ DTDQYGMKLT LNSQLMDGWQ   360
ITWGLDAEHE RFTSNQMFFD LAQASASGGL NNHKIYTTGR YPSYDITNLA AFLQSSYDIN   420
DIFTVSGGVR YQYTENRVDD FIDYTQQQKI AAGKAISADA IPGGSVDYDN FLFNAGLLMH   480
ITERQQAWFN FSQGVALPDP GKYYGRGIYG AAVNGHLPLT KSVNVSDSKL EGVKVDSYEL   540
GWRFTGDNLR TQIAAYYSLS NKSVERNKDL TISVKDDRRR IYGVEGAVDY LIPDTDWSTG   600
VNFNVLKTES KVNGQWQKYD VKESSPSKAT AYINWAPEPW SLRVQSTTSF DVSDAEGNDI   660
NGYTTVDFIS SWQLPVGTLS FSVENLFDRD YTTVWGQRAP LYYSPGYGPA SLYDYKGRGR   720
TFGLNYSVLF                                                          730
```

```
SEQ ID NO: 64              moltype = AA   length = 708
FEATURE                    Location/Qualifiers
source                     1..708
                           mol_type = protein
                           organism = Escherichia coli
SEQUENCE: 64
QQNDDNEIIV SASRSNRTVA EMAQTTWVIE NAELEQQIQG GKELKDALAQ LIPGLDVSSQ   60
SRTNYGMNMR GRPLVVLIDG VRLNSSRSDS RQLDSVDPFN IDHIEVISGA TALYGGGSTG   120
GLINIVTKKG QPETMMEFEA GTKSGFNSSK DHDERIAGAV SGGNDHISGR LSVAYQKFGG   180
WFDGNGDATL LDNTQTGLQH SNRLDIMGTG TLNIDESRQL QLITQYYKSQ GDDNYGLNLG   240
KGFSAISGSS TPYVSKGLNS DRIPGTERHL ISLQYSDSDF LRQELVGQVY YRDESLRFYP   300
FPTVNANKQA TAFSSSQQDT DQYGMKLTLN SQLMDGWQIT WGLDAEHERF TSNQMFFDLA   360
QASASGGLNN HKIYTTGRYP SYDITNLAAF LQSSYDINDI FTVSGGVRYQ YTENRVDDFI   420
DYTQQQKIAA GKAISADAIP GGSVDYDNFL FNAGLLMHIT ERQQAWFNFS QGVALPDPGK   480
YYGRGIYGAA VNGHLPLTKS VNVSDSKLEG VKVDSYELGW RFTGDNLRTQ IAAYYSLSNK   540
SVERNKDLTI SVKDDRRRIY GVEGAVDYLI PDTDWSTGVN FNVLKTESKV NGQWQKYDVK   600
ESSPSKATAY INWAPEPWSL RVQSTTSFDV SDAEGNDING YTTVDFISSW QLPVGTLSFS   660
VENLFDRDYT TVWGQRAPLY YSPGYGPASL YDYKGRGRTF GLNYSVLF                708
```

PROTEINS AND IMMUNIZING COMPOSITIONS CONTAINING *KLEBSIELLA* PROTEINS AND METHODS OF USE

CROSS-REFERENCE TO RELATED APPLICATIONS

This application is continuation of U.S. application Ser. No. 17/226,761, filed Apr. 9, 2021 now U.S. Pat. No. 11,872,273, and which is a continuation of U.S. application Ser. No. 15/741,574, filed Jan. 3, 2018, now U.S. Pat. No. 11,000,582, and which is a § 371 U.S. National Stage of International Application No. PCT/US16/041614, filed Jul. 8, 2016, which claims the benefit of U.S. Provisional Application Ser. No. 62/190,947, filed Jul. 10, 2015, disclosures of which are incorporated by reference herein in their entireties.

SEQUENCE LISTING

This application contains a Sequence Listing electronically submitted to the United States Patent and Trademark Office via Patent Center as an XML file entitled "0293_000047US03_SL.xml" having a size of 111,608 kilobytes and created on Feb. 9, 2024. The information contained in the Sequence Listing is incorporated by reference herein.

BACKGROUND

Bacterial infections now account for some 1.7 million cases of hospital-acquired infections yearly in the United States (4.5 per 100 admissions), with an overall mortality rate in the range of 20% to 60% or 99,000 deaths directly associated with a hospital acquired infection. The economic impact due to such infections is estimated to cost between 5 billion to 10 billion dollars annually in the United States.

Gram negative bacterial infections and their sequelae are frequently lethal. It is estimated that over 700,000 patients become susceptible to bacterial infections each year in the United States alone. Of these, 160,000 actually develop septicemia, resulting in 50,000 deaths annually. The majority of these are hospital-acquired infections due to such gram negative bacilli as *E. coli* (most common pathogen isolated from patients with gram negative sepsis), followed in frequency by *Klebsiella pneumoniae* and *Pseudomonas aeruginosa*.

Infections caused by gram negative bacteria, including Enterobacteriaceae, continue to be a significant concern in both human healthcare and animal agricultural settings. Bacteria in the family Enterobacteriaceae are a large heterogeneous group whose natural habitat is the intestinal tract of both humans and animals. The family includes many genera and is subdivided into eight tribes including: Escherichieae, Edwardsielleae, Salmonelleae, Citrobactereae, Klebsielleae, Proteeae, Yersineae, and Erwineae. Many species of the Enterobacteriaceae family are often opportunistic pathogens with clinically relevant significance including *Escherichia* spp., *Klebsiella* spp., *Enterobacter* spp., *Proteus* spp., *Providencia* spp., *Serratia* spp., *Citrobacter* spp., *Morganella* spp., *Shigella* spp., and *Salmonella* spp., are among the top twenty organisms responsible for causing infection. When clinically important diseases do occur they are often caused by *E. coli*, but others can infect and cause debilitating disease. In most cases the bacteria become pathogenic when they reach tissues outside of their normal intestinal environment when normal host defenses are inadequate. This is particularly seen today in the young or elderly; often in terminal stages of a primary infection due to immunological incompetence or immunosuppression; allowing the organism to reach the blood stream to cause sepsis resulting in death or secondary sequelae.

*Klebsiella* species are rod shaped gram negative, facultative anaerobic bacteria belonging to the family Enterobacteriaceae. Today, 7 species are known with demonstrated similarities in DNA homology: *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*. *Klebsiella* are ubiquitous in nature. They are often found in a variety of environments such as soil, vegetation, water, and the intestinal tract of humans and animals. In both humans and animals *Klebsiella* may colonize the skin or hide, pharynx or gastrointestinal tract, and are often regarded as normal flora in many parts of the colon and the intestinal tract. *Klebsiella pneumoniae* and *Klebsiella oxytoca* are the two most clinically relevant species in both animal and human populations.

The pathogenicity of *Klebsiella* can be attributed to multiple virulence factors including production of a heat-stable enterotoxin, capsular polysaccharides (CPS), lipopolysaccharides, adhesins (type 1 and 3 pili, KPF-28 fimbria, CF29K and aggregative adhesin), and iron acquisition systems (Podschun et al., Clin. Microbiol. Rev. 11(4): 589-603. 1998; Yu et al., Emerg. Inf. Dis. 13:986-993, 2007).

*Klebsiella* in animals are an important cause of metritis and infertility in horses, mastitis in bovine species, hematogenous osteomyelitis originating in pulmonary lesions in cattle, accumulation of pus in the pyothorax in horses, bronchopneumonia in both cats and dogs and a sequelae of secondary infections often following immunosuppression resulting from drug therapy, malnutrition, stress, endocrine diseases and other infections including canine parvovirus and feline immunodeficiency virus infection.

Today agriculture is critical for human welfare as it contributes to food, one major necessity for global survival. A number of factors adversely affect the stability and health of animal populations, by far one of the most important is infectious diseases which can cause widespread death in adult and/or young animals. Bacterial infections in production animals may severely affect all aspects of animal health resulting in tremendous economic losses to all sectors. Today zoonotic and emerging infectious diseases pose a threat to human health. At least 61 percent of all human pathogens are transmissible between animals and humans. Zoonosis make up 75 percent of emerging infectious diseases. The increase in infectious diseases in production animals and zoonotic diseases is primarily due to agricultural intensification, particularly in cattle (beef and dairy), swine, and poultry sectors.

In humans the interactions of *Klebsiella* range from opportunistic pathogens (mainly in hospitalized patients and community acquired infections) to asymptomatic carriage that frequent the intestinal tract and less frequently the nasopharynx. As nosocomial infections, *Klebsiella* are mostly associated with infections of urinary and respiratory tracts as well as wound and soft tissue infections that can lead to fatal septicemia. The spectrum of clinical syndromes includes bacteremia, pneumonia, urinary tract infection (UTI), thrombophlebitis, upper respiratory tract infection, cholecystitis, wound infection, osteomyelitis, endogenous endophthalmitis, endophthalmitis; endocarditis, and meningitis. It is estimated that *Klebsiella* account for 8% of endemic hospital infection and 3-7% of epidemic outbreaks (Stamm et al., Comparison of endemic and epidemic nosocomial infections, pp 9-13. In R. E. Dixon (ed.), Nosocomial infections. Yorke Medical Books, Atlanta, G A. 1981). *Klebsiella* cause as many as 14% of cases of primary bacteremia, second only to *E. coli* as a cause of gram-negative sepsis. *Klebsiella* has been isolated from bronchial alveolar lavage samples of 21% of patients with cystic fibrosis (Lyczak et al. *Clinical microbiology reviews* 15.2 (2002): 194-222).

*K. rhinoscleroma* and *K. ozaenae* are less common and rarely induce clinical infection. *K. rhinoscleroma* can induce a chronic inflammatory process involving the nasopharynx, while *K. ozaenae* induces a chronic atrophic rhinitis characterized by necrosis of the nasal mucosa and mucopurulent nasal discharge.

*K. oxytoca* has been implicated in neonatal bacteremia among premature infants and in neonatal intensive care units.

The emergence of *K. pneumoniae* producing carbapenemases has become a global health concern with serious clinical significance in both animal and human health sectors. *K. pneumoniae* carbapenemases (KPCs) have been shown to confer resistance to multiple antimicrobial agents, including nearly all β-lactams, fluoroquinolones, and aminoglycosides. Carbapenems are a class of β-lactam antibiotics with a broad spectrum of antibacterial activity used to treat infections caused by Gram-negative bacteria such as *E. coli* and *K. pneumoniae* that produce extended-spectrum β-lactamases. Carbapenemases are enzymes produced by *K. pneumoniae* that are capable of inactivating Carbapenems and sometimes other classes of β-lactam. Carbapenemases are found in bacteria belonging to the family of Enterobacteriaceae, *Pseudomonas* spp, and *Acinetobacter* spp. This resistant mechanism limits the number of agents available for the treatment of *K. pneumoniae.*

In human populations *K. pneumoniae* infections are common in hospitals where they cause pneumonia (characterized by emission of bloody sputum) and urinary tract infections in catheterized patients. In fact, *K. pneumoniae* is second only to *E. coli* as a urinary tract pathogen. It accounts for 6 to 17 percent of all nosocomial urinary tract infection (UTI). *Klebsiella* infections are encountered far more often now than in the past, and this increased occurrence may be due to the bacterium's antibiotic resistance properties. *Klebsiella* species may contain resistance plasmids (R-plasmids) which confer resistance to such antibiotics as Ampicillin and Carbenicillin (Wu et al., Clin Microbial Infect, 11: 893-897. 2005). To make matters worse, the R-plasmids can be transferred to other enteric bacteria not necessarily of the same species. Hospital outbreaks of multidrug-resistant *Klebsiella* spp. are often caused by a new type of strain, an ESBL producer (extended spectrum beta lactamase). The incidence of ESBL-producing strains among clinical *Klebsiella* isolates has been steadily increasing over the past several years. Frequencies of up to 40% have been reported in certain regions. To treat *K. pneumoniae* infections, there are few antibiotics available like Cefepime, Polymyxin B, Carbapenem, Meropenem and Imipenem (Parchuri et al., Heart lung, 5: 360-363. 2005; Ueda et al., Antimicrob Agents Chemother, 49: 4185-4196. 2005; Sanchez et al. Emerg Infect Dis 19.1 (2013): 133-6).

An alternative to the use of antibiotics for controlling *K. pneumoniae* is to attempt immunological control through vaccination. Effective vaccines against *Klebsiella* would greatly alleviate the significant global morbidity and mortality caused by these bacteria. Safe and effective vaccines against *Klebsiella* have been attempted with limited success. A number of bacterial constituents have been evaluated as potential vaccine development strategies, and include adhesions and fimbriae, capsular polysaccharides, lipopolysaccharides (LPS), and outer membrane proteins. Anti-capsular polysaccharide antibodies were found to provide a high degree of protection against corresponding capsular serotypes (Cryz et al., J Infect Dis, 150: 817-822. 1984; Cryz et al J Clin Microbiol, 23: 687-690. 1986). A 24-valent *Klebsiella* capsular polysaccharide vaccine was evaluated in Phase 1 trials that indicated the vaccine was safe (Cryz et al., Infect Immun, 50: 225-230. 1985). Further evaluation of the vaccine revealed a problem faced by anticapsular vaccination was the variability of capsular antigens in the natural *Klebsiella* populations. The selection of vaccine serotypes in the 24-valent vaccine was based on the most prevalent serotypes derived from bacteremic patients found in Europe and the United States. However, the serotypes included in the vaccine represented only 29% of strains found in other geographical areas, and since these serotypes were not included resulted in lack of efficacy. In addition, it has been shown that active immunization with LPS-containing vaccines can result in the induction of adverse toxic reactions, which are caused by the endotoxin content (Yadav et al., Folia Microbiologica, 50: 83-86. 2005). Other vaccine candidates have been evaluated for controlling *Klebsiella* infections utilizing cytotoxin toxoids, hepta- or mono-valent bacterial extracts (Libon et al., Vaccine, 20: 2174-2180. 2002) and/or outer membrane proteins such as OmpA (Jeannin et al., Vaccine 20, Suppl. 4: A23-A27. 2002).

In mammals, it has been shown that the response to tissue injury or bacterial infection results in an acute inflammatory response. This response increases capillary permeability and phagocytic infiltration resulting in the clinical signs recognized as inflammation; swelling, fever, pain and redness. If left uncontrolled, this may lead to death. The activation of humoral factors and the release of cytokines mediate systemic events collectively known as the acute phase protein response which results in a cascade of physiological and biochemical events. The duration of this response is directly related to the severity of the injury and magnitude of the systemic infection. It has been well-documented that during bacterial sepsis, major surgery, burns and other bodily trauma there is an alteration in the concentration of a number of metal ions in serum such as, iron, copper, and zinc. For instance, during the acute phase of an infection there is a decrease in plasma levels of iron and zinc and an increase in copper. The alteration of these trace metal ions in serum may directly affect the severity or progression of any bacterial infection.

Metal ions such as iron have been shown to be an essential nutrient for most organisms due to its role in electron transport. Since iron has very low solubility at neutral pH, it must be kept in solution by association with specialized protein carriers such as transferrin in blood, lactoferrin in secretory fluids, ovotransferrin in albumin, and ferritin within cells. It has been recognized that the concentration of free iron normally present in mammalian hosts is not enough to support the growth of bacteria. Hence, the low availability of iron within host species is one of the first barriers to infection that microorganisms must overcome, and it is not surprising that bacteria have developed strategies for obtaining iron from their hosts.

One of the most studied bacterial systems for iron acquisition is that of siderophores, low molecular weight iron ligands that are able to compete with host protein carriers for ferric iron binding (Miethke et al., Microbiol Mol Rev, 71(3): 413-451. 2007). The chelated iron is actively transported into the bacterial periplasm when the siderophore interacts with specific receptor proteins on the cell surface. The energy required for this activity appears to be dependent on the proteins TonB, ExbB, and ExbD (Miethke et al., Microbiol Mol Rev, 71(3): 413-451. 2007). Once the iron has reached the periplasm, it is transported into the cytoplasm via an ATP binding cassette (ABC) transport system (Budzikiewicz et al., Siderophore from bacteria and from fungi. In: Iron uptake and homeostasis in Microorganisms. 1ˢᵗ ed. Caister Academic Press. Chapter 1, 2010. Once the siderophore-iron complex has entered the cytoplasm, the iron is unloaded and the siderophore is either recycled or degraded.

Most *Klebsiella* strains possess the genes encoding the siderophore receptor proteins FepA, IroN, CirA, FhuA, and FhuE (Williams et al., FEMS Microbiol Lett. 44: 407-412. 1987). A recent study evaluating the effects of single, double, and triple mutants of thefepA, IroN, and CirA proteins to study the specificity of the receptors (Rabsch et al., Infect Immun. 12: 6953-6961 2003). The results suggested that these receptors are not entirely specific; most can utilize the iron from various siderophores and several siderophores can be used by any of the three proteins. In addition, several of the siderophore receptor proteins (iron-regulated proteins) use siderophores produced by other species of bacteria or fungi, a mechanism of iron acquisition referred to as "siderophore piracy" (Jurkevitch et al., Appl Environ Microbiol 58: 119. 1992). The multitude and redundancy of iron uptake systems in *Klebsiella* underscores the importance that the bacteria give to obtaining iron under various conditions. There is considerable evidence that iron acquisition is an important facet of *Klebsiella* pathogenesis (Brisse et al., Prokaryotes, 6: 159-196. 2006).

Currently there are no prophylactic *Klebsiella* vaccines on the market or, according to publicly available information, in active preclinical or clinical development.

SUMMARY OF THE APPLICATION

Provided herein are compositions. In one embodiment, a composition includes at least two isolated proteins having molecular weights of 82 kDa, 78 kDa, 72 kDa, or 68 kDa. The proteins are isolatable from a *Klebsiella pneumoniae* when incubated in media comprising an iron chelator and not isolatable when grown in the media without the iron chelator. The composition protects an animal against infection with *K. pneumoniae*. In one embodiment, the animal is a mouse, a dairy cow, or a human. In one embodiment, at least one of the proteins includes an amino acid sequence that is structurally similar to, or has 100% identity with, SEQ ID NO:41, SEQ ID NO:42, SEQ ID NO:43, or SEQ ID NO:44.

In one embodiment, a composition includes at least two isolated proteins that are structurally similar to, or have 100% identity with, a protein selected from SEQ ID NO:41, SEQ ID NO:42, SEQ ID NO:43, and SEQ ID NO:44.

In one embodiment, a composition includes at least two proteins that are structurally similar to, or have 100% identity with, a protein selected from SEQ ID NO:41, SEQ ID NO:58, SEQ ID NO:61, and SEQ ID NO:64.

In one embodiment, a composition also includes one or two proteins having molecular weights of 35 kDa and 33 kDa that are also isolatable from a *Klebsiella pneumoniae*. In one embodiment, a composition also includes a protein having an amino acid sequence that is structurally similar to, or has 100% identity with, SEQ ID NO:45, SEQ ID NO:46, SEQ ID NO:49, SEQ ID NO:51, SEQ ID NO:52, SEQ ID NO:53, SEQ ID NO:58, SEQ ID NO:61, or SEQ ID NO:64. In one embodiment, the composition also includes an 87 kDa protein isolatable from a *K. pneumoniae* when incubated in media comprising an iron chelator. In one embodiment, a composition also includes a pharmaceutically acceptable carrier. In one embodiment, a composition also includes an adjuvant.

Also provided herein are methods. In one embodiment, a method includes administering to a subject an amount of the composition described herein effective to induce the subject to produce antibody that specifically binds to at least one protein of the composition. In one embodiment, a method includes administering an effective amount of the composition described herein to a subject having or at risk of having an infection caused by a gram negative microbe. In one embodiment, a method includes administering an effective amount of a composition described herein to a subject having or at risk of having an infection caused by a gram negative microbe. In one embodiment, a method includes administering an effective amount of a composition described herein to a subject colonized by a gram negative microbe. The gram negative microbe can be selected from *K. pneumoniae, K. oxytoca, E. coli, Enterobacter* spp., *Serratia* spp., *Proteus* spp., *Citrobacter* spp., or a combination thereof.

In one embodiment, a method is for treating a condition in a subject, and includes administering an effective amount of the composition described herein to a subject in need thereof. In one embodiment, the subject has or at risk of having an infection caused by a *Klebsiella* spp. In one embodiment, the condition is caused by *K. pneumoniae, K. oxytoca, E. coli, Enterobacter* spp., *Serratia* spp., *Proteus* spp., *Citrobacter* spp., or a combination thereof. In different embodiments, the condition can include mastitis, high somatic cell counts in a subject's milk, low milk production. or a combination thereof.

In one embodiment, the subject is a mammal, such as a human or a bovine. In one embodiment, the *Klebsiella* spp. is *K. pneumonia* or *K. oxytoca*. In one embodiment, at least 700 micrograms (μg) and no greater than 1,200 μg of protein is administered.

Also provided herein are kits. In one embodiment, a kit includes in separate containers, an isolated protein of a composition described herein, and a reagent that detects an antibody that specifically binds the protein. In one embodiment, a kit includes in separate containers, an antibody that specifically binds an isolated protein of a composition described herein, and a second reagent that specifically binds the protein.

Further provided herein is an isolated whole cell that includes a protein of a composition described herein, and isolated antibody that specifically binds to the whole cell.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by end-points include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 7-21. Amino acid sequences of proteins encoded by *Klebsiella. pneumoniae* 1571 and an example of a nucleotide sequence encoding the corresponding protein.

FIG. 34. Plot of daily milk production (pounds of milk per cow) beginning at 8 days in milk (saleable milk) to 90 days in milk.

FIGS. 36-38. Amino acid sequences encoded by *E. coli* strain CFT073 and an example of a nucleotide sequence encoding the corresponding protein.

DETAILED DESCRIPTION OF ILLUSTRATIVE EMBODIMENTS

Proteins

Provided herein are proteins and compositions including proteins. As used herein, "protein" refers broadly to a polymer of two or more amino acids linked by peptide bonds. Thus, for example, the terms peptide, oligopeptide, protein, and enzyme are included within the definition of protein. This term also includes post-expression modifications of the protein, such as glycosylations, acetylations, phosphorylations, and the like. The term protein does not connote a specific length of a polymer of amino acids. A protein may be isolatable directly from a natural source, or can be prepared with the aid of recombinant, enzymatic, or chemical techniques. In the case of a protein that is naturally occurring, such a protein is typically isolated.

An "isolated" protein is one that has been removed from its natural environment. For instance, an isolated protein is a protein that has been removed from the cytoplasm or from the membrane of a cell, and many of the proteins, nucleic acids, and other cellular material of its natural environment are no longer present.

can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence. Molecular weights of proteins described herein were determined by gel electrophoresis, by matrix assisted laser desorption/ionization time-of-flight spectrometry (MALDI-TOF MS, also referred to herein as MALDI), or by determining the molecular weight of a deduced protein sequence (see Table 1). Unless indicated otherwise, molecular weight refers to molecular weight as determined by resolving a protein using an SDS polyacrylamide gel having a stacking gel of about 4% and a resolving gel of about 10% under reducing and denaturing conditions. In one embodiment, the molecular weight of a protein identified by SDS-PAGE includes molecular weights of 1, 2, 3, 4, or 5 kDa above and below the stated value. In one embodiment, the molecular weight of a protein identified by SDS-PAGE includes molecular weights of 1, 2, 3, 4, or 5 kDa above and below the stated value.

TABLE 1

Comparison of molecular weights of proteins.

The Comparison of Molecular Weights in Kilodaltons (kDa) of the
Vaccine Composition of *Klebsiella pneumonia* 1571 as
Examined by SDS-PAGE and MALD-TOF

| Protein Analysis | Isolate ID | Light top band | FepA | FecA | FhuA | CirA | OmpC | OmpA |
|---|---|---|---|---|---|---|---|---|
| SDS-PAGE | 1571 | 87 | 82 | 78 | 72 | 68 | 35 | 33 |
| MALDI-TOF | 1571 | Not analyzed | 82 | 83 | 81 | 71 | 40 | 38 |
| Predicted MW based on AA Sequence of full length protein | 1571 | Not analyzed | 82.2 | 82.7 | 81.3 | 71 | 40 | 38 |

Figure 4:
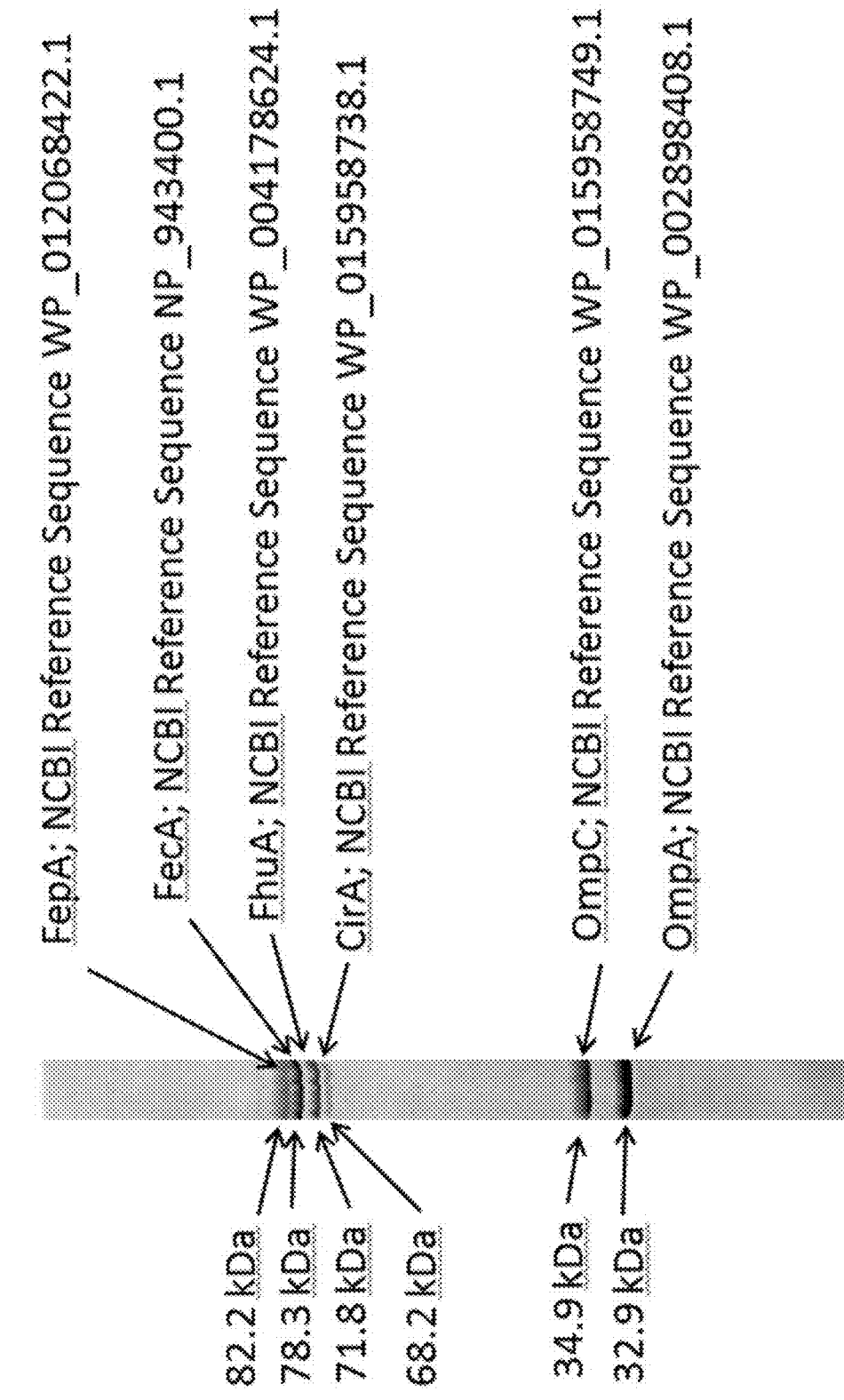
FIG. 4. *Klebsiella pneumoniae* 1571 LC/MS/MS. *Klebsiella pneumoniae* 1571 isolate showing siderophore receptor proteins CirA, FecA, FepA and FhuA, along with porin proteins OmpC and OmpA identified by LC/MS/MS.

Table 1. Protein Analysis: The molecular weights of the metal regulated proteins and porins of *Klebsiella pneumonia* were analyzed by single dimension SDS-PAGE, MALDI-TOF-MS, and the predicted molecular weight based on amino acid sequence.
Note:
there were 7 bands visualized in the SDS-PAFE Gel. The top band was light, and not analyzed by MALDI-TOF (FIG. 4). The other six bands have SDS-PAGE MW of 82, 78, 72, 68, 35 and 33 kDa. Six of the seven bands in the SDS-PAGE gel were excised and examined by MALDI-TOF-MS.

A protein characterized as "isolatable" from a particular source is a protein that, under appropriate conditions, is produced by the identified source, although the protein may be obtained from alternate sources using, for example, recombinant, chemical, or enzymatic techniques well known to those skilled in the art. Thus, characterizing a protein as "isolatable" from a particular source does not imply any specific source from which the protein must be obtained or any particular conditions or processes under which the protein must be obtained.

A "purified" protein is one that is at least 60% free, at least 75% free, or at least 90% free from other components with which it is naturally associated. Proteins that are produced outside the organism in which they naturally occur, e.g., through chemical or recombinant means, are considered to be isolated and purified by definition, since they were never present in a natural environment.

A protein described herein can be characterized by molecular weight, amino acid sequence, nucleic acid that encodes the protein, immunological activity, or any combination of two or more such characteristics. The molecular weight of a protein, typically expressed in kilodaltons (kDa), A protein of the present invention may be a metal-regulated protein. As used herein, a "metal-regulated protein" is a protein that is natively expressed by a microbe at a greater level when the microbe is grown in low metal conditions compared to growth of the same microbe in high metal conditions. Examples of metal-regulated proteins include siderophore receptor proteins. Low metal and high metal conditions are described herein. For instance, one class of metal-regulated protein produced by *Klebsiella* spp. is not expressed at detectable levels during growth of the microbe in high metal conditions but is expressed at detectable levels during growth in low metal conditions.

Examples of metal-regulated proteins isolatable from *K. pneumoniae* after growth in low iron conditions have molecular weights of between 100 kDa and 60 kDa, such as 97 kDa to 66 kDa. Specific examples of metal-regulated proteins isolatable from *K. pneumoniae* after growth in low iron conditions include proteins of 87 kDa, 82 kDa, 78 kDa, 72 kDa, and 68 kDa as determined by SDS-PAGE (Table 1). Examples of the proteins having molecular weights of 82 kDa, 78 kDa, 72 kDa, and 68 kDa, and nucleotide sequences encoding the proteins, are shown in FIGS. 7-10.

Other metal regulated proteins expected to be expressed by and isolatable from *K. pneumoniae* and expected to play a role in acquisition of metals include proteins having molecular weights of 83 kDa, 78 kDa, 78.4 kDa, 76.2 kDa, 74.7 kDa, and 66.2 kDa, where the molecular weight is determined from the deduced amino acid sequence. Examples of these proteins, and nucleotide sequences encoding the proteins, are shown in FIGS. 11, 12, 15, and 17-19. Additional examples of metal-regulated proteins include recombinantly-produced versions of proteins described herein. A recombinantly-produced protein may include the entire amino acid sequence translatable from an mRNA transcript. Alternatively, a recombinantly-produced metal-regulated protein can include a fragment of the entire translatable amino acid sequence. For example, a recombinantly-produced metal-regulated protein may lack a cleavable sequence at either end of the protein—e.g., a cleavable signal sequence at the amino terminus of the protein.

Other metal regulated proteins include the proteins shown at SEQ ID NO:58, SEQ ID NO:61, and SEQ ID NO:64 (FIGS. 36-38). Thus, a metal-regulated protein can be a protein that includes the amino acid sequence depicted in, for example, SEQ ID NO:41, SEQ ID NO:42, SEQ ID NO:43, SEQ ID NO:44, SEQ ID NO:45, SEQ ID NO:46, SEQ ID NO:49, SEQ ID NO:51, SEQ ID NO:52, SEQ ID NO:53, SEQ ID NO:58, SEQ ID NO:61, or SEQ ID NO:64.

Other metal regulated proteins expected to be expressed by and isolatable from *K. pneumoniae* and expected to play a role in acquisition of metals include proteins that include the amino acid sequences depicted in SEQ ID NO:14, SEQ ID NO:16, and SEQ ID NO:20.

Also provided herein are proteins that are not metal-regulated. Such proteins are expressed in the presence of a metal ion such as, for example, in the presence of ferric chloride, and also expressed when grown in low iron conditions. Examples of such proteins include porins. Examples of such proteins isolatable from *Klebsiella* spp., including *K. pneumoniae*, have molecular weights of between 26 kDa and 45 kDa. In one embodiment, non-metal regulated proteins produced by *Klebsiella* spp. are 35 kDa and 33 kDa as determined by SDS-PAGE. Examples of these proteins, and nucleotide sequences encoding the proteins, are shown in FIGS. 20 and 21.

Thus, a protein that is not metal-regulated can be a protein that includes the amino acid sequence depicted in, for example, SEQ ID NO:54, and SEQ ID NO:55 (FIGS. 20 and 21).

Whether a protein is a metal-regulated protein or not can be determined by methods useful for comparing the presence of proteins, including, for example, gel filtration, gel electrophoresis including sodium dodecyl sulfate-polyacrylamide gel electrophoresis (SDS-PAGE), capillary electrophoresis, mass spectrometry, and liquid chromatography including HPLC. Separate cultures of a microbe are grown under high metal conditions and under low metal conditions, proteins of the present invention are isolated as described herein, and the proteins present in each culture are resolved and compared. Typically, an equal amount of proteins from each culture is used. Preferably, the proteins are resolved using an SDS polyacrylamide gel having a stacking gel of about 4% and a resolving gel of about 10% under reducing and denaturing conditions. For instance, 30 micrograms (g) of total protein from each culture may be used and loaded into wells of a gel. After running the gel and staining the proteins with Coomasie Brilliant Blue, the two lanes can be compared. When determining whether a protein is or is not expressed at a detectable level, 30 µg of total protein from a culture is resolved on an SDS-PAGE gel and stained with Coomasie Brilliant Blue using methods known in the art. A protein that can be visualized by eye is considered to be expressed at a detectable level, while a protein that cannot be visualized by eye is considered to not be expressed at a detectable level.

Alternatively, whether a protein is metal-regulated or not can be determined using microarray-based gene expression analysis. Separate cultures of a microbe are grown under high metal conditions and under low metal conditions, RNA is extracted from cells of each culture, and differences in RNA expression in cells grown in high metal conditions versus RNA expression in cells grown in low metal conditions are detected and compared. For example, labeled cDNA can be prepared from 8-10 µg of bacterial RNA using known and routine methods. The labeled cDNA can be applied to a microarray of the *K. pneumoniae* genome. Such microarrays are commercially available and gene expression using such arrays is routine.

Proteins described herein may have immunological activity. "Immunological activity" refers to the ability of a protein to elicit an immunological response in an animal. An immunological response to a protein is the development in an animal of a cellular and/or antibody-mediated immune response to the protein. Usually, an immunological response includes but is not limited to one or more of the following effects: the production of antibodies, B cells, helper T cells, suppressor T cells, and/or cytotoxic T cells, directed to an epitope or epitopes of the protein. "Epitope" refers to the site on an antigen to which specific B cells and/or T cells respond so that antibody is produced. The immunological activity may be protective. "Protective immunological activity" refers to the ability of a protein to elicit an immunological response in an animal that prevents or inhibits infection by *Klebsiella* spp., for instance, *K. pneumoniae* or *K. oxytoca*. Whether a protein has protective immunological activity can be determined by methods known in the art such as, for example, methods described in Examples 11-14. For example, a protein described herein, or combination of proteins described herein, protects an animal against challenge with a *Klebsiella* spp. A protein of the present invention may have seroactive activity. "Seroactive activity" refers to the ability of a candidate protein to react with antibody present in convalescent serum from an animal infected with a *Klebsiella* spp., for instance, *K. pneumoniae* or *K. oxytoca*. In some aspects, the convalescent serum may be from an animal infected with *K. pneumoniae* or *K. oxytoca*. Proteins of the present invention may have immunoregulatory activity. "Immunoregulatory activity" refers to the ability of a protein to act in a nonspecific manner to enhance an immune response to a particular antigen. Methods for determining whether a protein has immunoregulatory activity are known in the art.

A protein described herein can have the characteristics of a reference protein. The characteristics can include, for example, molecular weight, amino acid sequence, activity, or any combination thereof. The reference protein can be one expressed by a gram negative microbe, such as a member of the family Enterobacteriacea, preferably, *Klebsiella* spp., more preferably, *K. pneumoniae*. An example of a *K. pneumoniae* strain is *K. pneumoniae* 1571.

A protein described herein can have an amino acid sequence that is structurally similar, as described below, to the amino acid sequence of SEQ ID NO:41, SEQ ID NO:42, SEQ ID NO:43, SEQ ID NO:44, SEQ ID NO:45, SEQ ID NO:46, SEQ ID NO:49, SEQ ID NO:50, SEQ ID NO:51, SEQ ID NO:52, SEQ ID NO:53, SEQ ID NO:54, SEQ ID NO:55, SEQ ID NO:58, SEQ ID NO:61, or SEQ ID NO:64. In one embodiment, a protein described herein can include a region of amino acids that is structurally similar, as described below, to the amino acid sequence of SEQ ID NO:14, SEQ ID NO:16, or SEQ ID NO:20.

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

Protein Sequence Similarity and Protein Sequence Identity

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference protein may be a protein described herein or any known metal-regulated protein, as appropriate. A candidate protein is the protein being compared to the reference protein. A candidate protein can be isolated, for example, from a microbe, or can be produced using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison WI). Alternatively, proteins may be compared using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$. Likewise, biologically active analogs of a protein containing deletions or additions of one or more contiguous or noncontiguous amino acids that do not eliminate a functional activity-such as, for example, immunological activity—of the protein are also contemplated.

Thus, as used herein, reference to a protein as described herein and/or reference to the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to a protein as described herein and/or reference to the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

As described in Example 9 and shown in Table 3, the metal regulated proteins described herein are conserved. Table 3 shows high levels of percent identity of different proteins present in *K. pneumoniae, E. coli,* and *Enterobacter.* A person of ordinary skill can easily align the amino acid sequences of a metal regulated protein that is expressed by different microbes using readily available algorithms, for instance CLUSTALW, and identify amino acids and regions that are conserved and amino acids and regions that are variable across the metal regulated proteins. A person of ordinary skill in the art can deduce from such data regions of the protein in which substitutions, particularly conservative substitutions, may be permitted without unduly affecting activity of the modified polypeptide.

Consequently, a protein described herein can include certain variants including, for example, homologous proteins that originate-biologically or recombinantly—from microbial species or strains other than the microbial species or strain from which the polypeptide was originally isolated and/or identified.

A protein as described herein also can be designed to provide one or more additional sequences such as, for example, the addition of coding sequences for added C-terminal and/or N-terminal amino acids that may facilitate purification by trapping on columns or use of antibodies. Such tags include, for example, histidine-rich tags that allow purification of proteins on nickel columns. Such gene modification techniques and suitable additional sequences are well known in the molecular biology arts.

A "modification" of a protein as described herein includes a protein (or an analog thereof such as, e.g., a fragment thereof) that is chemically or enzymatically derivatized at one or more constituent amino acid. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified proteins as described herein may retain the biological activity-such as, for example, immunological activity—of the unmodified protein or may exhibit a reduced or increased biological activity compared to the unmodified protein.

A protein as described herein (including a biologically active analog thereof and/or a modification thereof) can include a native (naturally occurring), a recombinant, a chemically synthesized, or an enzymatically synthesized protein. For example, a protein as described herein may be prepared by isolating the protein from a natural source or may be prepared recombinantly by conventional methods including, for example, preparation as fusion proteins in bacteria or other host cells.

A protein expressed by a reference microbe can be obtained by growing the reference microbe under low metal conditions as described herein and the subsequent isolation of a protein by the processes disclosed herein. Alternatively, a protein expressed by a reference microbe can be obtained by identifying coding regions expressed at higher levels when the microbe is grown in low metal conditions—e.g., metal-regulated. A metal-regulated coding region can be cloned and expressed, and the expressed metal-regulated protein may be identified by the processes described herein. A candidate protein can be isolatable from a microbe or identified from a microbe, preferably a gram negative microbe, more preferably, a member of the family Enterobacteriaceae, such as *Klebsiella* spp. such as, for example, *K. pneumoniae*, or *K. oxytoca*. A candidate protein may also be produced using enzymatic or chemical techniques.

Polynucleotide Sequence Similarity and Polynucleotide Sequence Identity

Proteins as described herein also may be identified in terms of the polynucleotide that encodes the protein. Thus, this disclosure provides polynucleotides that encode a protein as described herein or hybridize, under standard hybridization conditions, to a polynucleotide that encodes a protein as described herein, and the complements of such polynucleotide sequences.

As used herein, reference to a polynucleotide as described herein and/or reference to the nucleic acid sequence of one or more SEQ ID NOs can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides (for example, aligning the nucleotide sequence of the candidate sequence and a nucleotide sequence that includes, for example, a nucleotide sequence that encodes a protein or SEQ ID NO:41, 42, 43, 44, 45, 46, 49, 51, 52, 53, 54, 55, 58, 61, or 64) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence—e.g., a nucleotide sequence that includes the appropriate nucleotide sequence selected from, for example, the appropriate portion of SEQ ID NO:1, 3, 5, 7, 9, 11, 13, 15, 17, 19, 21, 23, 25, 27, or 29, that encodes a protein without the signal sequence. For example, two polynucleotide sequences can be compared using the Blastn program of the BLAST 2 search algorithm, as described by Tatiana et al., *FEMS Microbiol Lett.*, 1999; 174: 247-250, and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

This disclosure also provides whole cell preparations of a microbe, where the microbe expresses one or more of the proteins as described herein. The microbe can express the proteins naturally, or can be engineered to express one or more of the proteins described herein recombinantly. The cells present in a whole cell preparation may be inactivated such that the cells cannot replicate but the immunological activity of the proteins as described herein expressed by the microbe is maintained. Typically, the cells may be killed by exposure to agents such as glutaraldehyde, formalin, or formaldehyde.

Compositions

A composition as described herein may include at least one protein described herein, or a number of proteins that is an integer greater than one (e.g., at least two, at least three, at least four). Unless a specific level of sequence similarity and/or identity is expressly indicated herein (e.g., at least 80% sequence similarity, at least 90% sequence identity, etc.), reference to the amino acid sequence of an identified SEQ ID NO includes variants having the levels of sequence similarity and/or the levels of sequence identity described herein in the section headed "Protein sequence similarity and protein sequence identity." In one embodiment, a composition that includes the proteins described herein is a subset of proteins expressed by a microbe, such as a *K. pneumoniae*, under low metal conditions, such as low iron conditions, and is a combination of proteins does not naturally exist.

A recombinantly-produced protein may be expressed from a vector that permits expression of the protein when the vector is introduced into an appropriate host cell. A host cell may be constructed to produce one or more recombinantly-produced proteins as described herein and, therefore, can include one more vectors that include at least one polynucleotide that encodes a protein as described herein. Thus, each vector can include one or more polynucleotides as described herein—i.e., a polynucleotide that encodes a protein as described herein.

Certain compositions such as, for example, those including recombinantly-produced proteins, can include a maximum number of proteins. In some embodiments, the maximum number of proteins can refer to the maximum total number of proteins. Certain compositions can include, for example, no more than 50 proteins such as, for example, no more than 40 proteins, no more than 30 proteins, no more than 25 proteins, no more than 20 proteins, no more than 15 proteins, no more than 10 proteins, no more than nine proteins, no more than eight proteins, no more than seven proteins, no more than six proteins, no more than five proteins, no more than four proteins, no more than three proteins, no more than two proteins, or no more than one protein. In other embodiments, a maximum number of recombinantly-produced proteins may be specified in a similar manner. In still other embodiments, a maximum number of nonrecombinantly-produced proteins may be specified in a similar manner.

A composition can include proteins isolatable from one microbe, or can be isolatable from a combination of two or more microbes. For instance, a composition can include proteins isolatable from two or more *Klebsiella* spp., or from a *Klebsiella* spp. and a different microbe that is not a member of the genus *Klebsiella*.

In certain embodiments, a composition can include a whole cell preparation in which the whole cell expresses one or more of the proteins as described herein. In some of these embodiments, the whole cell can be a *Klebsiella* spp., in other embodiments, the whole cell is one genetically engineered to express one or more of the proteins. In some embodiments, a composition can include whole cell preparations from two, three, four, five, or six strains.

In one embodiment, a composition includes polypeptides expressed by a *Klebsiella* spp. during growth in low iron and at least one, at least two, at least three, or more recombinantly produced proteins. For instance, the *Klebsiella* spp. can be engineered to express at least one recombinant protein, or a composition isolated from a *Klebsiella* spp. can be supplemented with a least one recombinant protein expressed by a second cell. In one embodiment, such a composition is not naturally occurring.

Specific examples of compositions include, but are not limited to, the following. In one embodiment, a composition includes at least two metal regulated proteins having molecular weights selected from 82 kDa, 78 kDa, 72 kDa, and 68 kDa as determined by SDS-PAGE. For instance, a composition can include proteins having molecular weights of 82 kDa, 78 kDa, 72 kDa, and 68 kDa; 82 kDa, 78 kDa, and 72 kDa; 82 kDa, 78 kDa, and 68 kDa; 82 kDa, 72 kDa, and 68 kDa; 78 kDa, 72 kDa, and 68 kDa; 82 kDa and 78 kDa; 82 kDa and 68 kDa; or 72 kDa and 68 kDa. Optionally, a composition includes one or two proteins that are not metal regulated, where the proteins have molecular weights of 35 kDa and 33 kDa as determined by SDS-PAGE. Optionally, a composition includes a metal regulated protein having a molecular weight of 87 kDa as determined by SDS-PAGE. Optionally, a composition includes at least one metal regulated proteins expected to be expressed by and isolatable from *K. pneumoniae*, such as a protein having a molecular weight of 83 kDa, 78 kDa, 78.4 kDa, 76.2 kDa, 74.7 kDa, or 66.2 kDa, where the molecular weight is determined from the deduced amino acid sequence. Thus, in one embodiment a composition includes two, three, or four metal regulated proteins having molecular weights of 82 kDa, 78 kDa, 72 kDa, and 68 kDa, two proteins that are not metal regulated and have molecular weights of 35 kDa and 33 kDa, and a metal regulated protein having a molecular weight of 87 kDa.

In one embodiment, a composition includes at least two proteins that are structurally similar to proteins selected from SEQ ID NO:41, SEQ ID NO:42, SEQ ID NO:43, and SEQ ID NO:44. For instance, a composition can include proteins that are structurally similar to SEQ ID NO:41, SEQ ID NO:42, SEQ ID NO:43, and SEQ ID NO:44; SEQ ID NO:41, SEQ ID NO:42, and SEQ ID NO:43; SEQ ID NO:41, SEQ ID NO:42, and SEQ ID NO: 44; SEQ ID NO:41, SEQ ID NO:43, and SEQ ID NO:44; SEQ ID NO:42, SEQ ID NO 43, and SEQ ID NO:44; SEQ ID NO:41, SEQ ID NO:42; SEQ ID NO:41, and SEQ ID NO:44; SEQ ID NO:43, and SEQ ID NO:44. Optionally, a composition includes an additional two proteins that are structurally similar to SEQ ID NO:54 and SEQ ID NO:55. Optionally, a composition includes at least one protein that is structurally similar to a protein selected from SEQ ID NO:45, SEQ ID NO:46, SEQ ID NO:49, SEQ ID NO:51, SEQ ID NO:52, SEQ ID NO:53, SEQ ID NO:58, SEQ ID NO:61, and SEQ ID NO:64. Optionally, a composition includes at least one protein that is structurally similar to a protein that includes a region of amino acids that is structurally similar to the amino acid sequence of SEQ ID NO:14, SEQ ID NO:16, or SEQ ID NO:20.

In one embodiment, a composition includes at least two proteins that are structurally similar to proteins selected from SEQ ID NO:41, SEQ ID NO:58, SEQ ID NO:61, and SEQ ID NO:64. For instance, a composition can include proteins that are structurally similar to SEQ ID NO:41, SEQ ID NO:58, SEQ ID NO:61, and SEQ ID NO:64; SEQ ID NO:41, SEQ ID NO:58, and SEQ ID NO:61; SEQ ID NO:41, SEQ ID NO:58, and SEQ ID NO: 64; SEQ ID NO:41, SEQ ID NO:61, and SEQ ID NO:64; SEQ ID NO:58, SEQ ID NO:61, and SEQ ID NO:64; SEQ ID NO:41 and SEQ ID NO:58; SEQ ID NO:41 and SEQ ID NO:64; or SEQ ID NO:61, and SEQ ID NO:64. Optionally, a composition includes an additional two proteins that are structurally similar to SEQ ID NO:54 and SEQ ID NO:55. Optionally, a composition includes at least one protein that is structurally similar to a protein selected from SEQ ID NO:42, SEQ ID NO:43, and SEQ ID NO:44, SEQ ID NO:45, SEQ ID NO:46, SEQ ID NO:49, SEQ ID NO:51, SEQ ID NO:52, and SEQ ID NO:53. Optionally, a composition includes at least one protein that is structurally similar to a protein that includes a region of amino acids that is structurally similar to the amino acid sequence of SEQ ID NO:14, SEQ ID NO:16, or SEQ ID NO:20.

Optionally, a protein as described herein can be covalently bound or conjugated to a carrier protein to improve the immunological properties of the protein. Useful carrier proteins are known in the art. The chemical coupling of proteins as described herein can be carried out using known and routine methods. For instance, various homobifunctional and/or heterobifunctional cross-linker reagents such as bis(sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl) cycloheane-1-carboxylate, sulfosuccinimidyl 4-(p-maleimido-phenyl) butyrate and (1-ethyl-3-(dimethyl-aminopropyl) carbodiimide can be used (see, for instance, Harlow and Lane, Antibodies, A Laboratory Manual, generally and Chapter 5, Cold Spring Harbor Laboratory, Cold Spring Harbor, New York, NY (1988)).

A composition described herein can include low concentrations of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (0-specific chain, the outer and inner core) and the lipid A region. The lipid A component of LPS is the most biologically active component of the LPS structure and together induces a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scaring or blemishes of the tissue at the injection site.

The concentration of LPS can be determined using routine methods known in the art. Such methods typically include measurement of dye binding by LPS (see, for instance, Keler and Nowotny, *Analyt. Biochem.*, 156, 189 (1986)) or the use of a *Limulus* amebocyte lysate (LAL) test (see, for instance, Endotoxins and Their Detection With the *Limulus* Amebocyte Lystate Test, Alan R. Liss, Inc., 150 Fifth Avenue, New York, NY (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOX-ATE (Sigma Chemical Co., St. Louis, MO; see Sigma Technical Bulletin No. 210), and PYROTELL (Associates of Cape Cod, Inc., East Falmouth, MA). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for 1 hour undisturbed at 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE), U.S. Pharmacopeia (Rockville, MD, Catalog No. 235503), and Associates of Cape Cod, Inc., (Catalog No. E0005). In general, when a composition of the present invention is prepared by isolating polypeptides from a microbe by a method as described herein (e.g., a method that includes disrupting and solubilizing the cells, and collecting the insoluble polypeptides), the amount of LPS in a composition of the present invention is less than the amount of LPS present in a mixture of same amount of the same microbe that has been disrupted under the same conditions but not solubilized. Typically, the level of LPS in a composition described herein is decreased by, in increasing order of preference, at least 50%, at least 60%, at least 70%, at least 80%, at least 90%, at least 95%, or at least 99% relative to the level of LPS in a composition prepared by disrupting, but not solubilizing, the same microbe. In one embodiment, the level of LPS in a composition described herein is decreased by greater than 90%, greater than 95%, or greater than 99% compared to the level of LPS in a composition prepared by disrupting, but not solubilizing, the same microbe.

The compositions as described herein optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous; intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), in order to stimulate mucosal immunity, such as production of secretory IgA antibodies, throughout the animal's body.

A composition as described herein can also be administered via a sustained or delayed release implant. Implants suitable for use according to the invention are known and include, for example, those disclosed in Emery and Straub (WO 01/37810 (2001)), and Emery et al., (WO 96/01620 (1996)). Implants can be produced at sizes small enough to be administered by aerosol or spray. Implants also can include nanospheres and microspheres.

A composition as described herein may be administered in an amount sufficient to treat certain conditions as described herein. The amount of proteins or whole cells present in a composition as described herein can vary. For instance, the dosage of proteins can be between 0.01 micrograms (μg) and 300 mg, typically between 0.1 mg and 10 mg. In one embodiment, the dosage of proteins may be at least 700 μg, at least 900 μg, or at least 1,000 μg. In one embodiment, the dosage may be no greater than 1,800 μg, no greater than 1,600 μg, no greater than 1,400 μg, or no greater than 1,200 μg. When the composition is a whole cell preparation, the cells can be present at a concentration of, for instance, $10^2$ bacteria/ml, $10^3$ bacteria/ml, $10^4$ bacteria/ml, $10^5$ bacteria/ml, $10^6$ bacteria/ml, $10^7$ bacteria/ml, 108 bacteria/ml, or $10^9$ bacteria/ml. For an injectable composition (e.g. subcutaneous, intramuscular, etc.) the proteins may be present in the composition in an amount such that the total volume of the composition administered is 0.5 ml to 5.0 ml, typically 1.0 to 2.0 ml. When the composition is a whole cell preparation, the cells are preferably present in the composition in an amount that the total volume of the composition administered is 0.5 ml to 5.0 ml, typically 1.0 to 2.0 ml. The amount administered may vary depending on various factors including, but not limited to, the specific proteins chosen, the weight, physical condition and age of the animal, and the route of administration. Thus, the absolute weight of the protein included in a given unit dosage form can vary widely, and depends upon factors such as the species, age, weight and physical condition of the animal, as well as the method of administration. Such factors can be determined by one of skill in the art. Other examples of dosages suitable for the invention are disclosed in Emery et al., (U.S. Pat. No. 6,027,736).

The formulations may be conveniently presented in unit dosage form and may be prepared by methods well known in the art of pharmacy. Methods of preparing a composition with a pharmaceutically acceptable carrier include the step of bringing the active compound (e.g., a protein or whole cell as described herein) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyl dioctadecyl ammonium bromide (DDA), avridine, aluminum hydroxide, oils, saponins, alpha-tocopherol, polysaccharides, emulsified paraffins (including, for instance, those available from under the tradename EMULSIGEN from MVP Laboratories, Ralston, Nebraska), ISA-70, RIBI and other substances known in the art. It is expected that proteins as described herein will have immunoregulatory activity and that such proteins may be used as adjuvants that directly act as T cell and/or B cell activators or act on specific cell types that enhance the synthesis of various cytokines or activate intracellular signaling pathways. Such proteins are expected to augment the immune response to increase the protective index of the existing composition.

In another embodiment, a composition as described herein including a pharmaceutically acceptable carrier can include a biological response modifier, such as, for example, IL-2, IL-4 and/or IL-6, TNF, IFN-$\alpha$, IFN-$\gamma$, and other cytokines that effect immune cells. An immunizing composition can also include other components known in the art such as an antibiotic, a preservative, an anti-oxidant, or a chelating agent.

Methods of Making

The present invention also provides methods for obtaining the proteins described herein. The proteins and whole cells of the present invention may be isolatable from a member of the family Enterobacteriaceae. Microbes useful for obtaining proteins of the present invention and making whole cell preparations are commercially available from a depository such as American Type Culture Collection (ATCC). In addition, such microbes are readily obtainable by techniques routine and known to the art. The microbes may be derived from an infected animal as a field isolate, and used to obtain proteins and/or whole cell preparations of the present invention, or stored for future use, for example, in a frozen repository at $-20°$ C. to $-95°$ C., or $-40°$ C. to $-50°$ C., in bacteriological media containing 20% glycerol, and other like media.

When a protein of the present invention is to be obtained from a microbe, the microbe can be incubated under low metal conditions. As used herein, the phrase "low metal conditions" refers to an environment, typically bacteriological media, which contains amounts of a free metal that cause a microbe to express metal-regulated proteins at a detectable level. As used herein, the phrase "high metal conditions" refers to an environment that contains amounts of a free metal that cause a microbe to either not express one or more of the metal-regulated proteins described herein at a detectable level, or to express such a protein at a decreased level compared to expression of the metal-regulated protein under low metal conditions. In some cases, "high metal conditions" can include a metal-rich natural environment and/or culture in a metal-rich medium without a metal chelator. In contrast, in some cases, "low metal conditions" can include culture in a medium that includes a metal chelator, as described in more detail below. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron.

Low metal conditions are generally the result of the addition of a metal chelating compound to a bacteriological medium, the use of a bacteriological medium that contains low amounts of a metal, or the combination thereof. High metal conditions are generally present when a chelator is not present in the medium, a metal is added to the medium, or the combination thereof. Examples of metal chelators include natural and synthetic compounds. Examples of natural compounds include plant phenolic compounds, such as flavonoids. Examples of flavonoids include the copper chelators catechin and naringenin, and the iron chelators myricetin and quercetin. Examples of synthetic copper chelators include, for instance, tetrathiomolybdate, and examples of synthetic zinc chelators include, for instance, N,N,N',N'-Tetrakis (2-pyridylmethyl)-ethylene diamine. Examples of synthetic iron chelators include 2,2'-dipyridyl (also referred to in the art as $\forall,\forall'$-bipyridyl), 8-hydroxy-quinoline, ethylenediamine-di-O-hydroxyphenylacetic acid (EDDHA), desferrioxamine methanesulphonate (desferol), transferrin, lactoferrin, ovotransferrin, biological sidero-phores, such as, the catecholates and hydroxamates, and citrate. An example of a general divalent cation chelator is CHELEX resin. Preferably, 2,2'-dipyridyl is used for the chelation of iron. Typically, 2,2'-dipyridyl is added to the media at a concentration of at least 0.0025 micrograms/milliliter ($\mu g/ml$), at least 0.25 $\mu g/ml$, at least 25 $\mu g/ml$, at least 50 $\mu g/ml$, or higher amounts depending on the growth characteristics of the microbe.

It is expected that a *Klebsiella* spp. with a mutation in a fur gene will result in the constitutive expression of many, if not all, of the metal regulated proteins of the present invention. The production of a fur mutation in a *Klebsiella* spp. can be produced using routine methods including, for instance, transposon, chemical, or site-directed mutagenesis useful for generating gene knock-out mutations in gram negative bacteria.

The medium used to incubate the microbe and the volume of media used to incubate the microbe can vary. When a microbe is being evaluated for the ability to produce one or more of the proteins described herein, the microbe can be grown in a suitable volume, for instance, 10 milliliters to 1 liter of medium. When a microbe is being grown to obtain proteins for use in, for instance, administration to animals, the microbe may be grown in a fermenter to allow the isolation of larger amounts of proteins. Methods for growing microbes in a fermenter are routine and known to the art. The conditions used for growing a microbe preferably include a metal chelator, more preferably an iron chelator, for instance 2,2'-dipyridyl, a pH of between 6.5 and 7.5, preferably between 6.9 and 7.1, and a temperature of 37° C.

In some aspects of the invention, a microbe may be harvested after growth. Harvesting includes concentrating the microbe into a smaller volume and suspending in a medium different than the growth medium. Methods for concentrating a microbe are routine and known in the art, and include, for example, filtration or centrifugation. Typically, the concentrated microbe is suspended in an appropriate buffer. An example of a buffer that can be used contains Tris-base (7.3 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfo-nyl fluoride). Optionally and preferably, the concentrated microbe is frozen at $-20°$ C. or below until disrupted.

When the microbe is to be used as a whole cell preparation, the harvested cells may be processed using routine and known methods to inactivate the cells. Alternatively, when a microbe is to be used to prepare proteins described herein, the microbe may be disrupted using chemical, physical, or mechanical methods routine and known to the art, including, for example, boiling, French press, sonication, digestion of peptidoglycan (for instance, by digestion with lysozyme), or homogenization. An example of a suitable device useful for homogenization is a model C500-B AVESTIN homogenizer, (Avestin Inc, Ottawa Canada). As used herein, "disruption" refers to the breaking up of the cell. Disruption of a microbe can be measured by methods that are routine and known to the art, including, for instance, changes in optical density. Typically, when the percent transmittance of a 1:100 dilution of a microbe is 40%-60% prior to disruption, the percent transmittance is increased to 80% (increase of 20%-40%) following disruption. When physical or mechanical methods are used, the temperature during disruption is typically kept low, preferably at 4° C., to further minimize proteolytic degradation. When chemical methods are used the temperature may be increased to optimize for the cell disruption. A combination of chemical, physical, and mechanical methods may also be used to solubilize the cell wall of microbe. As used herein, the term "solubilize" refers to dissolving cellular materials (e.g., proteins, nucleic acids, carbohydrates) into the aqueous phase of the buffer in which the microbe was disrupted, and the formation of aggregates of insoluble cellular materials. Without intending to be limited by theory, the conditions for solubilization are believed to result in the aggregation of proteins of the present invention into insoluble aggregates that are large enough to allow easy isolation by, for instance, centrifugation.

The insoluble aggregates that include one or more of the proteins of the present invention may be isolated by methods that are routine and known to the art. In one embodiment, the insoluble aggregates are isolated by ultrafiltration. In one embodiment, the insoluble aggregates are isolated by centrifugation. Typically, centrifugation of proteins, such as membrane proteins, can be accomplished by centrifugal forces of 100,000×g. The use of such centrifugal forces requires the use of ultracentrifuges, and scale-up to process large volumes of sample is often difficult and not economical with these types of centrifuges. The methods described herein provide for the production of insoluble aggregates large enough to allow the use of continuous flow centrifuges, for instance T-1 Sharples (Alfa Laval Separations, Warminster, PA), which can be used with a flow rate of 250 ml/minute at 17 psi at a centrifugal force of 46,000×g to 60,000×g. Other large scale centrifuges can be used, such as the tubular bowl, chamber, and disc configurations. Such centrifuges are routinely used and known in the art, and are commercially available from such manufactures as Pennwalt, Westfalia and Alpha Laval.

The final harvested proteins are washed and/or dialyzed against an appropriate buffer using methods known in the art, for instance diafiltration, precipitation, hydrophobic chromatography, ion-exchange chromatography, or affinity chromatography, or ultrafiltration and washing the proteins, for instance, in alcohol, by diafiltration. After isolation, the proteins are suspended in buffer and stored at low temperature, for instance, −20° C. or below.

In those aspects of the present invention where a whole cell preparation is to be made, after growth a microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

In other aspects, an isolated protein of the invention may be prepared recombinantly. When prepared recombinantly, a polynucleotide encoding the protein may be identified and cloned into an appropriate expression host. The recombinant expression host may be grown in an appropriate medium, disrupted, and the proteins isolated as described above. Alternatively, when a recombinant protein forms inclusion bodies routine methods can be used to isolate and purify the recombinant protein. For instance, inclusion bodies can be extracted from the expression host and the protein present in the inclusion bodies solubilized. above.

Methods of Use

Also provided are methods of using the compositions described herein. The methods include administering to an animal an effective amount of a composition described herein. The animal can be, for instance, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, dogs or cats), members of the family Cervidae (including, for instance, deer, elk, moose, caribou and reindeer), or human.

In some aspects, the methods may further include additional administrations (e.g., one or more booster administrations) of the composition to the animal to enhance or stimulate a secondary immune response. A booster can be administered at a time after the first administration, for instance, one to eight weeks, preferably two to four weeks, after the first administration of the composition. Subsequent boosters can be administered one, two, three, four, or more times annually. Without intending to be limited by theory, it is expected that in some aspects of the present invention annual boosters will not be necessary, as an animal will be challenged in the field by exposure to microbes expressing proteins present in the compositions having epitopes that are identical to or structurally related to epitopes present on proteins of the composition administered to the animal.

In one aspect, the invention is directed to methods for making antibodies, for instance by inducing the production of antibody in an animal, or by recombinant techniques. The antibody produced includes antibody that specifically binds at least one protein present in the composition. In this aspect of the invention, an "effective amount" is an amount effective to result in the production of antibody in the animal. Methods for determining whether an animal has produced antibodies that specifically bind proteins present in a composition of the present invention can be determined as described herein. The present invention further includes antibody that specifically bind to a protein of the present invention, and compositions including such antibodies.

The method may be used to produce antibody that specifically binds proteins expressed by a microbe other than the microbe from which the proteins of the composition were isolated. As used herein, an antibody that can "specifically bind" a protein is an antibody that interacts with the epitope of the antigen that induced the synthesis of the antibody, or interacts with a structurally related epitope. At least some of the proteins present in the compositions of the present invention typically include epitopes that are conserved in the proteins of different species and different genera of microbes. Accordingly, antibody produced using a composition derived from one microbe is expected to bind to proteins expressed by other microbes and provide broad spectrum protection against gram negative organisms. Examples of gram negative microbes to which the antibody may specifically bind are members of the family Vibrionaceae (including, for instance, *Vibrio cholerae*), *Campylobacter* spp. (including, for instance, *C. jejuni*), members of the family Enterobacteriaceae (including, for instance, *Kleb-*

*siella* spp., *E. coli, Shigella* spp., *Salmonella* spp., *Proteus* spp., *Serratia* spp., and *Yersinia* spp.), members of the family Pasteurellaceae, preferably *Pasteurella* spp. (including, for instance, *P. multocida* and *P. haemolytica*), and members of the family Pseudomonadaceae, preferably *Pseudomonas* spp., (including, for instance, *Pseudomonas aeruginosa*). Examples of *Klebsiella* spp. include *K. pneumoniae* and *K. oxytoca*. Examples of *Salmonella* spp. include *Salmonella enterica* serovars, Bredeney, Dublin, Agona, Blockley, *Enteriditis, Typhimurium*, Hadar, Heidelberg, Montevideo, Muenster, Newport *senftenberg, Salmonella cholerasuis*, and *S. typhi*. Examples of strains of *E. coli* include, for example, *E. coli* serotypes O1a, 02a, 078, and 0157, different O:H serotypes including 0104, 0111, 026, 0113, 091, hemolytic strains of enterotoxigenic *E. coli* such as K88$^+$, F4$^+$, F18ab$^+$, and F18ac$^+$, and uropathogenic strains of *E. coli*. Therefore, antibody produced using a composition of proteins described herein may be used to identify and characterize proteins independent of the origin, source, and/or manner of obtaining the protein.

The present invention is also directed to the use of such antibody to target a microbe expressing a protein of the present invention or a protein having an epitope structurally related to an epitope present on a protein of the present invention. A compound can be covalently bound to an antibody, where the compound can be, for instance, a toxin. Likewise, such compounds can be covalently bound to a bacterial siderophore to target the microbe. The chemical coupling or conjugation of an antibody of the present invention, or a fragment thereof (such as a Fab fragment), can be carried out using known and routine methods.

In one aspect the invention is also directed to treating an infection in an animal, including a human, caused by a gram negative microbe. As used herein, the term "infection" refers to the presence of a gram negative microbe in an animal's body, which may or may not be clinically apparent. Treating an infection can be prophylactic or, alternatively, can be initiated after the animal is infected by the microbe. Treatment that is prophylactic—e.g., initiated before a subject is infected by a microbe or while any infection remains subclinical—is referred to herein as treatment of a subject that is "at risk" of infection. As used herein, the term "at risk" refers to an animal that may or may not actually possess the described risk. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered. The method includes administering an effective amount of the composition of the present invention to an animal having, or at risk of having, an infection caused by a gram negative microbe, and determining whether the number of microbes causing the infection has decreased. The gram negative microbe may be, for instance, a member of the family Vibrionaceae (including, for instance, *Vibrio cholerae*), *Campylobacter* spp. (including, for instance, *C. jejuni*), a member of the family Enterobacteriaceae (including, for instance, *Klebsiella* spp., *E. coli, Shigella* spp., *Salmonella* spp., *Proteus* spp., *Serratia* spp., *Yersinia* spp., *Enterobacter* spp. and *Citrobacter* spp.), a member of the family Pasteurellaceae, preferably *Pasteurella* spp. (including, for instance, *P. multocida* and *P. haemolytica*), or a member of the family Pseudomonadaceae. In one embodiment, the animal has, or is at risk of having, an infection caused by *K. pneumoniae* or *K. oxytoca*. In this aspect of the invention, an "effective amount" is an amount effective to reduce the number of the specified microbes in an animal or reduce the likelihood that the animal experiences a clinically-evident infection compared to an animal to which the composition is not administered. Methods for determining whether an infection is caused by a gram negative microbe, such as *K. pneumoniae* or *K. oxytoca*, are routine and known in the art, as are methods for determining whether the infection has decreased.

In another aspect, the present invention is directed to methods for treating one or more symptoms or clinical signs of certain conditions in an animal that may be caused by infection by a gram negative microbe. The method includes administering an effective amount of a composition of the present invention to an animal having or at risk of having a condition, or exhibiting symptoms and/or clinical signs of a condition, and determining whether at least one symptom and/or clinical sign of the condition is changed, preferably, reduced. The gram negative microbe may be, for instance, a member of the family Vibrionaceae (including, for instance, *Vibrio cholerae*), *Campylobacter* spp. (including, for instance, *C. jejuni*), a member of the family Enterobacteriaceae (including, for instance, *Klebsiella* spp., *E. coli, Shigella* spp., *Salmonella* spp., *Proteus* spp., *Serratia* spp., and *Yersinia* spp.), a member of the family Pasteurellaceae, preferably *Pasteurella* spp. (including, for instance, *P. multocida* and *P. haemolytica*), or a member of the family Pseudomonadaceae. In one embodiment, the animal has a condition caused by *K. pneumoniae* or *K. oxytoca*. In one embodiment, the animal has a condition caused by a uropathogenic *E. coli*. Examples of symptoms and/or clinical signs caused by a gram negative microbial infection are known to the person skilled in the art.

Treatment of symptoms and/or clinical signs associated with conditions caused by a gram negative infection can be prophylactic or, alternatively, can be initiated after the development of a condition described herein. As used herein, the term "symptom" refers to subjective evidence of a disease or condition experienced by the patient and caused by infection by a microbe. As used herein, the term "clinical sign" or, simply, "sign" refers to objective evidence of disease or condition caused by infection by a microbe. Symptoms and/or clinical signs associated with conditions referred to herein and the evaluations of such symptoms are routine and known in the art. Treatment that is prophylactic, for instance, initiated before a subject manifests symptoms or signs of a condition caused by a microbe, is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administration of a composition can be performed before, during, or after the occurrence of the conditions described herein. Treatment initiated after the development of a condition may result in decreasing the severity of the symptoms or signs of one of the conditions, or completely removing the symptoms or signs. In this aspect of the invention, an "effective amount" is an amount effective to prevent the manifestation of symptoms or signs of a disease, decrease the severity of the symptoms or signs of a disease, and/or completely remove the symptoms or signs. The successful treatment of a gram negative microbial infection in an animal is disclosed in Examples 11-19, which demonstrates the protection against disease caused by *K. pneumoniae* in a mouse model by administering a composition described herein. This mouse model is a commonly accepted model for the study of disease caused by *K. pneumoniae*.

In one embodiment, the condition is mastitis in a milk producing animal, such as a cow. The method includes administering an effective amount of a composition described herein to a milk producing animal having or at risk of having mastitis, and determining whether at least one symptom or sign of mastitis is reduced. Mastitis refers to inflammation of the mammary gland. Physical, chemical and usually bacteriological changes in the milk and pathological changes in the glandular tissue characterize it. These glandular changes often result in a number of symptomatic conditions such as, discoloration of the milk, the presence of clots and the presence of large numbers of leukocytes. Clinically, mastitis is seen as swelling, heat, pain and induration in the mammary gland often resulting in deformation of the udder. In many cases the diagnosis of subclinical infections has come to depend largely on indirect tests which depend on the leukocyte content of the milk or somatic cell count (SCC). The most common organisms that infect the udder are coliform bacteria, such as, *K. pneumoniae, K. oxytoca, E. coli, Enterobacter* spp., *Serratia* spp., *Proteus* spp., and *Citrobacter* spp. Other organisms that cause mastitis less frequently include *Pseudomonas* spp., *Brucella* spp., *Corynebacterium* spp., *Mycoplasma* spp., and *Pasteurella* spp.

In another embodiment, the condition is a high somatic cell count (SSC) in an animal's milk, such as a cow. The method includes administering an effective amount of a composition described herein to a milk producing animal having or at risk of having high somatic cell counts, and determining whether the somatic cell count in milk obtained from the animal contains reduced somatic cell counts compared to milk obtained from the animal before receiving the composition. In another embodiment, provided herein is a method for reducing somatic cell counts in an animal's milk. Somatic cells include leucocytes of the animal, and are typically present at low levels in normal milk. High levels of somatic cells in milk, for instance, greater than 200,000 cells per milliliter of milk. High levels of somatic cells in milk may be indicative of infection (mastitis), but may also be unassociated with infection. SCC is monitored, typically by milk processing plants, using methods that are routine to the art. The SCC is reduced to less than 750,000 cells/ml, less than 400,000 cells/ml, or less than 200,000 cells/ml.

In another embodiment, the condition is treating low milk production by a milk producing animal, such as a cow. The method includes administering an effective amount of the composition of the present invention to a milk producing animal having or at risk of having a low milk production, and determining whether milk production by the animal is increased compared to milk production by the animal before receiving the composition. Another embodiment is directed to a method for increasing milk production in a milk producing animal, such as a cow. The method includes administering a composition described herein to a milk producing animal, and determining whether milk production by the animal is increased compared to milk production by the animal before receiving the composition. The milk production by a milk producing animal after administration of composition described herein is increased by at least 0.1%, at least 0.5%, at least 1%, or at least 3%. Milk production by a cow is can be determined before administration and 2 weeks, 8 weeks, or 16 weeks after administration of the composition.

The present invention also provides methods for decreasing colonization by gram negative microbes, for instance blocking the attachment sites of gram negative microbes, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioles, alveoli), digestive system (for instance, mouth, salivary glands, esophagus, liver, stomach, large and small intestine), excretory system (for instance, kidney, ureter, bladder, and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like. In one embodiment, the gram negative microbe is *K. pneumoniae* or *K. oxytoca*.

Decreasing colonization in an animal may be performed prophylactically or, alternatively, can be initiated after the animal is colonized by the microbe. Treatment that is prophylactic—e.g., initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe and regardless of whether the animal may harbor a subcolonization number of the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition of the present invention to an animal colonized by, or at risk of being colonized by, a gram negative microbe. In this aspect of the invention, an "effective amount" is an amount sufficient to decrease colonization of the animal by the microbe, where decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art. For instance, colonization of an animal's intestinal tract by a microbe can be determined by measuring the presence of the microbe in the animal's feces. It is expected that decreasing the colonization of an animal by a microbe will reduce transmission of the microbe to other animals of the same or different species.

A composition of the invention can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare compositions (preferably containing antibody) from serum, plasma, blood, colostrum, etc. for passive immunization therapies. Antibody compositions including monoclonal antibodies and/or anti-idiotypes can also be prepared using known methods. Chimeric antibodies include human-derived constant regions of both heavy and light chains and murine-derived variable regions that are antigen-specific (Morrison et al., Proc. Natl. Acad. Sci. USA, 1984, 81(21):6851-5; LoBuglio et al., Proc. Natl. Acad. Sci. USA, 1989, 86(11):4220-4; Boulianne et al., Nature, 1984, 312(5995):643-6.). Humanized antibodies substitute the murine constant and framework (FR) (of the variable region) with the human counterparts (Jones et al., Nature, 1986, 321(6069):522-5; Riechmann et al., Nature, 1988, 332(6162):323-7; Verhoeyen et al., Science, 1988, 239(4847):1534-6; Queen et al., Proc. Natl. Acad. Sci. USA, 1989, 86(24):10029-33; Daugherty et al., Nucleic Acids Res., 1991, 19(9): 2471-6.). Alternatively, certain mouse strains can be used that have been genetically engineered to produce antibodies that are almost completely of human origin; following immunization the B cells of these mice are harvested and immortalized for the production of human monoclonal antibodies (Bruggeman and Taussig, Curr. Opin. Biotechnol., 1997, 8(4):455-8; Lonberg and Huszar, Int. Rev. Immunol., 1995; 13(1):65-93; Lonberg et al., Nature, 1994, 368:856-9; Taylor et al., Nucleic Acids Res., 1992, 20:6287-95.). Passive antibody compositions and fragments thereof, e.g., scFv, Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibodies useful for passive immunization may also be useful to conjugate to various drugs or antibiotics that could be directly targeted to bacteria expressing during a systemic or localized infection a protein of the present invention or a protein having an epitope structurally related to an epitope present on a protein of the present invention.

Animal models, in particular mouse models, are available for experimentally evaluating the compositions of the present invention. These mouse models (e.g., Meno and Amako, 1991, Microbiol. Immuniol., 35(10):841-848; Vered et al., 2014, BMC Genomics, 15:865; Kurupati et al., Clinical Vaccine Immunol., 18(1):82-88; Lundberg et al., 2013, Human Vaccines Immunotherapeutics, 9(3):497-505; and Toky et al., 2003, Folia Microbiol (Praha), 48(5):665-669) are commonly accepted models for the study of disease caused by members of the genus *Klebsiella*, and *K. pneumoniae* in particular. In those cases where a member of the genus *Klebsiella* causes disease in an animal, for instance a cow, the natural host can be used to experimentally evaluate the compositions described herein.

However, protection in a mouse model is not the only way to assess whether a composition can confer protection to an animal against infection by a *Klebsiella* spp. The adaptive immune response consists of two primary divisions: the humoral (antibody) response and the cellular (T cell) response. Following infection by a bacterial pathogen, dendritic cells at the infection site encounter microbial antigens and produce signaling molecules such as, for example, surface receptors and cytokines in response to conserved molecular patterns associated with the specific bacterium. These signals are shaped by the nature of the pathogen and ideally lead to the appropriate antibody and T cell responses that protect the host from disease. While some bacterial diseases are controlled primarily through antibody functions, others require T cell responses or both antibody and T cell responses for protection. The goal of vaccine biology is to identify the immune responses that provide protection and then design a vaccine to reproduce one or more of these responses in humans.

Antibodies can have many different functions in conferring protection against infection such as, for example, complement fixation, opsonization, neutralization, and/or agglutination. Moreover, some subclasses of antibodies are better than others at specific functions; for example, for complement fixation the following hierarchy exists for human IgG subclasses: IgG3>IgG1>IgG2>IgG4).

Antibody immunological functions can be studied in a variety of ways. For instance, Western blots are used to identify antigen-specific binding based on size of separated proteins, while the standard enzyme-linked immunosorbant assay (ELISA) is used to produce quantitative information about antibody titers within serum. Antibody surface binding studies are used to determine whether antibody in serum are able to recognize antigens on the surface of intact bacteria, an important indicator of whether the antibodies have the potential to work in vivo. Thus, one skilled in the art recognizes that antibody binding assays such as a Western blot, ELISA (e.g., using human antisera), and/or surface binding correlate positively with the specifically-bound antigens providing immunological activity against microbial infection. However, one skilled in the art further recognizes that a lack of antibody binding in an assay such as, for example, a Western blot, ELISA, or surface binding assay does not mean that the assayed antigen fails to provide immunological activity against microbial infection.

Antibodies can mediate bacterial death by blocking the acquisition of nutrients (e.g iron) or initiating complement-mediated membrane perforation that leads to osmotic lysis. Bactericidal antibodies can be assayed by mixing serum with live cultures and measuring for the presence of viable bacteria under appropriate conditions known to those skilled in the art. Techniques such as opsonophagocytosis assays (OPA), in which antibody and complement-bound bacteria are combined with human or mouse phagocytes to determine levels of bacterial killing, are useful for studying antibody function. A similar oxidative burst assay can be used to assess the level of reactive oxygen species (ROS) by fresh human or mouse neutrophils following interaction with antibody and complement-bound bacteria.

In some cases, one can determine that a candidate protein possesses cell-mediated immunological activity and, therefore, the candidate protein may exhibit immunological activity in the absence of inducing the production of antibodies. Cytotoxic or CD8 T cells primarily kill infected cells directly through various effector mechanisms, while helper CD4 T cells function to provide important signaling in the way of cytokines. These T cell classes can be further subdivided based on the cytokines they produce, and different subclasses are effective against different bacterial pathogens. T cells are often studied by assessing their phenotypes with flow cytometry, where antibodies are used to visualize the levels of specific surface markers that enable classification of the T cells as, for example, a recently activated CD4$^+$ T cell, a memory CD8$^+$ T cell, etc. In addition, cytokines and other products of T cells can be studied by isolating the T cells from lymphoid tissue and restimulating them with cognate antigen. Following antigen stimulation the T cells produce cytokines that may be visualized by, for example, intracellular cytokine staining coupled with flow cytometry, or collecting the cell supernatants and using Luminex bead technology to measure 15-25 cytokines simultaneously.

Thus, in addition to mouse models, those of ordinary skill in the art recognize that immunological activity commensurate with the methods described herein may correlate with any one or more of the following: Western blot data showing that serum from animals exposed to a microbial pathogen contains antibody that specifically binds to a candidate protein, cell surface binding assays demonstrating that antibody that specifically binds to a candidate protein specifically binds to a microbial pathogen, opsonophagocytosis data, and cytokine induction.

Another aspect of the present invention provides methods for detecting antibody that specifically binds proteins described herein. These methods are useful in, for instance, detecting whether an animal has antibody that specifically binds proteins described herein, and diagnosing whether an animal may have a condition caused by a microbe expressing proteins described herein, or expressing proteins that share epitopes with the proteins described herein. Such diagnostic systems may be in kit form. The methods include contacting an antibody with a preparation that includes a protein described herein to result in a mixture. The antibody may be present in a biological sample, for instance, blood, milk, or colostrum. The method further includes incubating the mixture under conditions to allow the antibody to specifically bind the protein to form a protein:antibody complex. As used herein, the term "protein:antibody complex" refers to the complex that results when an antibody specifically binds to a protein. The preparation that includes the proteins described herein may also include reagents, for instance a buffer, that provide conditions appropriate for the formation of the protein:antibody complex. The protein: antibody complex is then detected. The detection of antibodies is known in the art and can include, for instance, immunofluorescence or peroxidase. The methods for detecting the presence of antibodies that specifically bind to proteins described herein can be used in various formats that have been used to detect antibody, including radioimmunoassay and enzyme-linked immunosorbent assay.

Kits

The present invention also provides a kit for detecting antibody that specifically binds a protein described herein. The antibody detected may be obtained from an animal suspected to have an infection caused by a gram negative microbe, such as *K. pneumoniae* or *K. oxytoca*. In another embodiment, the present invention provides a kit for detecting a protein described herein.

The kit includes at least one of the proteins described herein (e.g., one, at least two, at least three, etc.), or an antibody described herein in a suitable packaging material in an amount sufficient for at least one assay. Optionally, other reagents such as buffers and solutions needed to practice the invention are also included. For instance, a kit may also include a reagent to permit detection of an antibody that specifically binds to a protein described herein, such as a detectably labeled secondary antibody designed to specifically bind to an antibody obtained from an animal. Instructions for use of the packaged proteins are also typically included. As used herein, the phrase "packaging material" refers to one or more physical structures used to house the contents of the kit. The packaging material is constructed by well known methods, generally to provide a sterile, contaminant-free environment. The packaging material may have a label which indicates that the proteins can be used for detecting antibody that specifically binds proteins of the present invention. In addition, the packaging material contains instructions indicating how the materials within the kit are employed to detect the antibody. As used herein, the term "package" refers to a container such as glass, plastic, paper, foil, and the like, capable of holding within fixed limits the proteins, and other reagents, for instance a secondary antibody. Thus, for example, a package can be a microtiter plate well to which microgram quantities of proteins have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like The present invention is illustrated by the following examples. It is to be understood that the particular examples, materials, amounts, and procedures are to be interpreted broadly in accordance with the scope and spirit of the invention as set forth herein.

Example 1

Isolation of Clinical Isolates of *Klebsiella* Pneumonia, *Klebsiella oxytoca* and *Enterobacter*

Isolates of *Klebsiella* pneumonia, *Klebsiella oxytoca* and *Enterobacter* were isolated from infected udders of cows on commercial dairy herds showing clinical signs of Coliform mastitis as diagnosed by the attending veterinarian (i.e. presence of abnormal milk; watery consistency, clots, blood, garget, pus, swelling of the udder and bacterial culture identification of milk samples). Master seed stocks of the *Klebsiella* pneumonia, *Klebsiella oxytoca* and *Enterobacter* were prepared by inoculating each of the isolates into 5000 ml of Tryptic Soy Broth (Difco Laboratories, Detroit, MI) containing 30 micrograms per milliliter (g/ml) of 2,2-dipyridyl (Sigma-Aldrich St. Louis, MO). The cultures were grown while stirring at 200 rpm for 6 hours at 37° C. The bacteria were collected by centrifugation at 10,000×g. The bacterial pellets from each isolate was resuspended into 500 ml Tryptic Soy Broth containing 20% glycerol, and sterilely dispensed into 2 ml cryogenic vials (1 ml per vial) and stored at −90° C. Each isolate was given an identification number designating it as a master seed. For example; seventeen *Klebsiella pneumonia* isolates were identified and designated as 1101, 1437, 1438, 1439, 1440, 1563, 1565, 1566, 1567, 1569, 1570, 1571, 1572, 1573, 1574, 1575, and 1576. *Klebsiella oxytoca* was designated as 1564 and *Enterobacter* was designated as 1568. The Bovine master seed number for *Klebsiella pneumoniae* was designated as 1571, the bovine master seed number for *Klebsiella oxytoca* was 1564, and the bovine master seed number for *Enterobacter* was 1568.

The master seed number for a human isolate of *Klebsiella pneumoniae* was prepared and designated LM21 (also referred to herein as 1748). A human UTI *E. coli* isolate used as a reference strain designated as CFT073. The master seeds of each isolate were expanded into working seeds that was then used for the production of metal regulated proteins. A small laboratory scale process was developed to examine initial metal-regulated protein expression of multiple *Klebsiella* isolates whereas a large-scale production process was developed involving fermentation, bacterial harvest, disruption, solubilization, concentration, diafiltration, and isolation of final vaccine antigens. Both the small and large scaled-up process for metal-regulated protein expression produced identical protein profiles when examined by single dimension SDS-PAGE.

Example 2

Identification and Differentiation of *Klebsiella pneumoniae* from *Klebsiella oxytoca* by Polymerase Chain Reaction (PCR)

Figure 1:
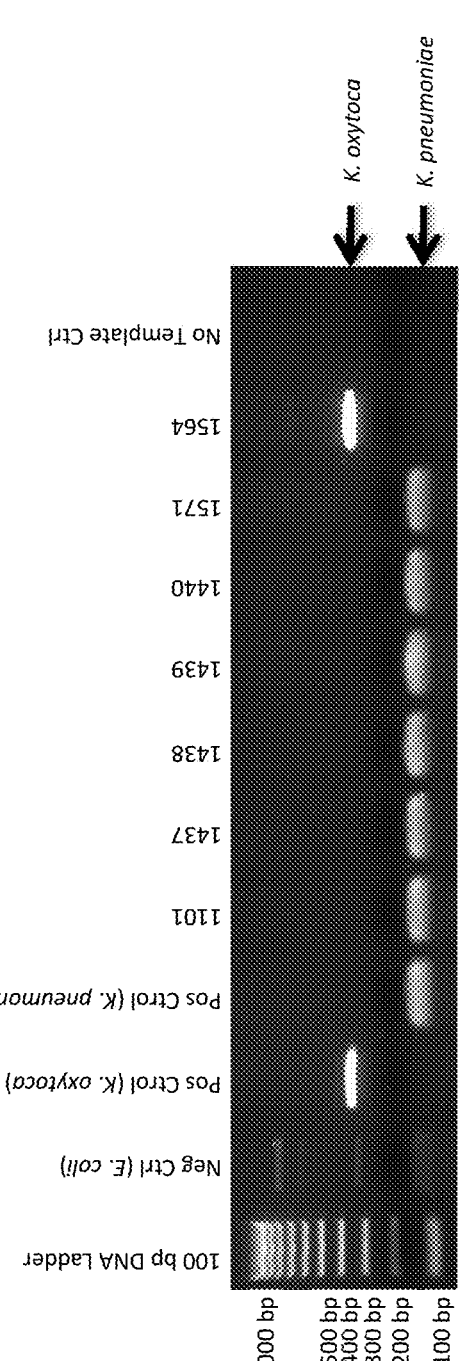
FIG. 1. *Klebsiella* multiplex PCR for identity confirmation of *Klebsiella pneumoniae, Klebsiella oxytoca* and *Escherichia coli*.

To differentiate *Klebsiella pneumoniae* 1571 from *Klebsiella oxytoca* 1564 isolates from both human and bovine species exhibiting clinical signs of disease, a multiplex polymerase chain reaction (PCR) was used with species specific primers as described by Chander et al. (2011, Intern J Appl Res Vet Med. 9:138-142). The position of bands on an agarose gel, 108 bp for *Klebsiella pneumoniae* 1571 and 343 bp for *K. oxytoca* 1564 confirmed strain identity (FIG. 1).

Primers and PCR Amplification: Working seeds of Example 1 were plated on blood agar in duplicate. The plates were incubated at 35-40° C. for 18-24 hours. After incubation the plates were visually examined and determined to be pure. A single, well isolated colony from one of the duplicate pure culture plates was suspended in 100 µL sterile water. The suspension was boiled for 10 minutes to lyse the cells, and allowed to cool at room temperature. The suspension was then centrifuged for 2 minutes at 13,000 rpm in a table top microcentrifuge. The supernatant containing the DNA Template was transferred to a new, sterile microcentrifuge tube and stored at −20° C. until use.

Species specific primers were used for the amplification of *K. pneumoniae* and *K. oxytoca* in a single reaction mixture (Table 2). Positive controls of *K. oxytoca* and *K. pneumoniae* were included in the assay. A no-primer negative control of *Escherichia coli* was also included. PCR reactions were set up using a Qiagen Multiplex PCR Kit according to the manufacturer's instructions. The reaction mixture consisted of: 25 µL 2× Qiagen Multiplex PCR Master Mix of each primer (forward and reverse); 5 µL 10× Primer Mix; 15 µL RNase-free water; 5 µL crude DNA template; and 50 µL total volume. The reaction conditions for PCR were as follows: initial denaturation at 95° C. for 15 minutes; 30 cycles of denaturation at 94° C. for 30 seconds; annealing at 55° C. for 1.5 minutes; and extension at 72° C. for 1.5 minutes.

TABLE 2

Sequences of primers used to identify and distinguish *Klebsiella pneumoniae* and *Klebsiella oxytoca*.

| Target Organism | Sequence (5'-3') | Product Size (bp) |
|---|---|---|
| *Klebsiella pneumoniae* | CAA CGG TGT GGT TAC TGA CG (SEQ ID NO: 31) TCT ACG AAG TGG CCG TTT TC (SEQ ID NO: 32) | 108 |
| *Klebsiella oxytoca* | GAT ACG GAG TAT GCC TTT ACG GTG (SEQ ID NO: 33) TAGCCTTTATCAAGCGGA TACTGG (SEQ ID NO: 34) | 343 |

The PCR products were visualized by electrophoresis on a 1% agarose gel (prestained with ethidium bromide) in 0.5× Tris/Boric Acid/EDTA (TBE) and UV trans-illumination. A 100 bp DNA ladder was used as molecular weight markers (FIG. 1).

Example 3

Process for Screening Metal Regulated Protein Expression of Multiple Isolates Grown Under Conditions of Metal Ion Restriction The screening of metal regulated proteins as well as the immunizing compositions used in the following examples were prepared using the proteins derived from *Klebsiella pneumoniae* originating from bovine species having clinical signs of disease.

Figure 2:
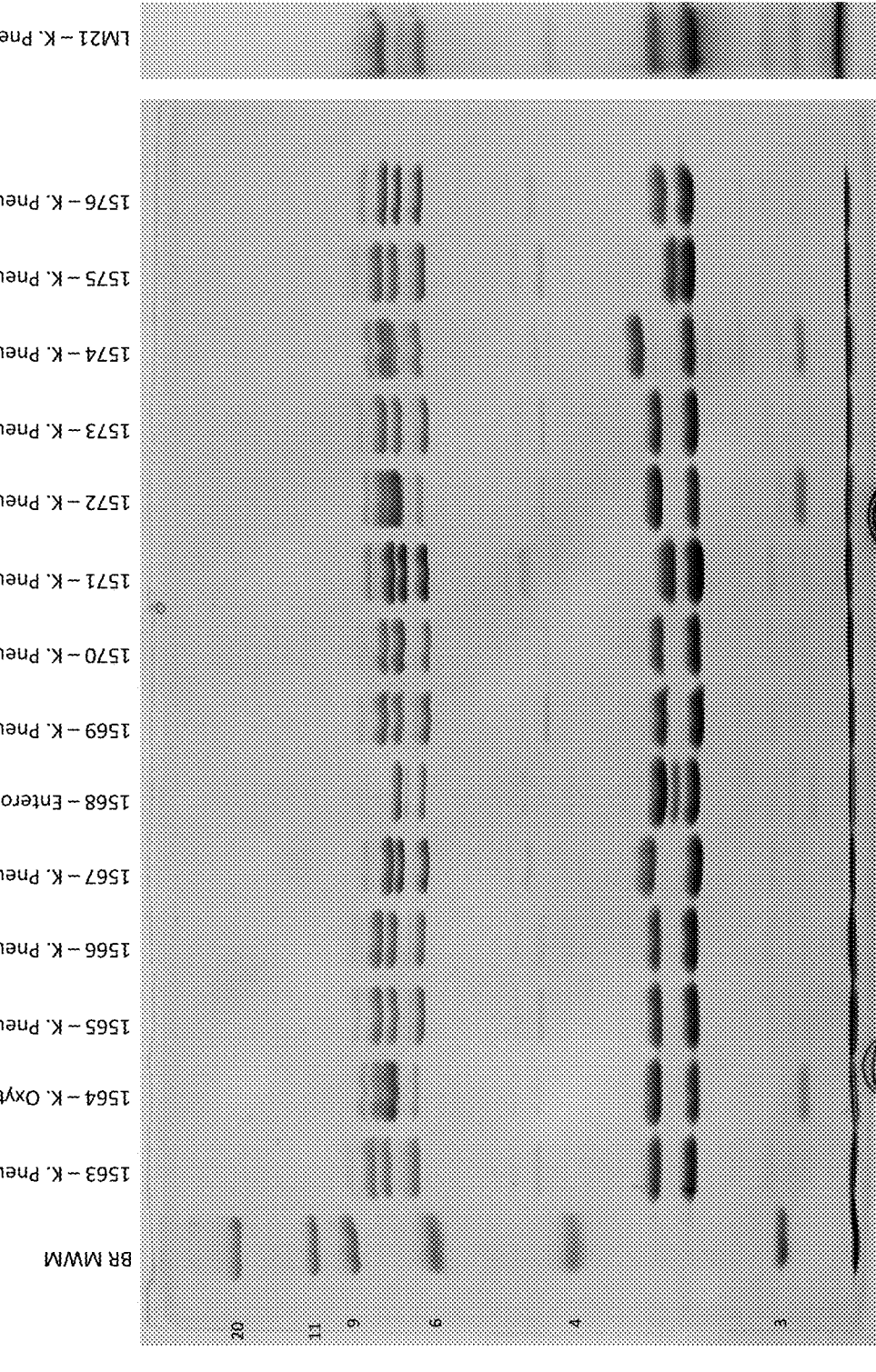
FIG. 2. Electrophoretic profile of bovine field isolates of *Klebsiella pneumonia, Klebsiella oxytoca,* and *Enterobacter* isolated from cows with mastitis and *Klebsiella pneumonia* human isolate LM21 showing the conservation of metal regulated protein profiles.

Multiple field isolates of *K. pneumoniae* 1563, 1565, 1566, 1567, 1569, 1570, 1571, 1572, 1573, 1574, 1575, and 1576 and single isolates of *K. oxytoca* 1564 and *Enterobacter* 1568 were collected from multiple Dairy herds showing clinical signs of mastitis. The human isolate of *K. pneumoniae* LM21 was also screened for metal regulated proteins. Each isolate was grown under conditions of iron restriction and the outer membrane profiles of proteins expressed under iron restriction was examined by SDS-PAGE (FIG. 2). Briefly, each of the isolates to be examined was inoculated into TSB containing 300 µM 2,2-diprydyl and incubated at 37° C. Following incubation for 12 hours, the cultures were subcultured (1:100) into 500 ml of iron-limiting media and incubated at 37° C. After 8 hours each culture was centrifuged at 10,000×g for 20 minutes, resuspended in 40 ml of osmotic shock buffer (7.3 g/l Tris Base; 1.86 g/l EDTA, pH 8.9, and disrupted by sonication, to yield a suspension. The suspensions were centrifuged at 32,000×g for 12 minutes to clarify or remove large cellular debris. The supernatants were collected and solubilized by the addition of 4% sodium lauroyl sarcosinate at 4° C. for 24 hours. The detergent-insoluble outer membrane protein-enriched fractions were collected by centrifugation at 32,000×g for 2.5 hours at 4° C. The protein pellets were resuspended in 200 µl Tris-buffer (pH 7.2).

The protein-enriched extracts derived from each isolate were size-fractionated on SDS-PAGE gels using a 4% stacking gel and 10% resolving gel. Samples for electrophoresis were prepared by combining 10 µl of sample with 30 µl of SDS reducing sample buffer (62.5 mM Tris-HCL pH 6.8, 20% glycerol, 2% SDS, 5% β-mercaptoethanol) and boiled for 4 minutes. Samples were electrophoresed at 18 mA constant current for 5 hours at 4° C. using a Protein II xi cell power supply (BioRad Laboratories, Richmond, CA, model 1000/500). The electrophoretic profiles comparing proteins derived from multiple isolates of *K. pneumonia, K. oxytoca Enterobacter* of bovine and human origin are shown in FIG. 2.

The SDS-PAGE patterns of the protein-enriched extracts showed a high degree of conservatism among all isolates examined, with the molecular weights ranging for the metal regulated proteins from 97 kDa to 66 kDa and non-metal regulated proteins, e.g., porins, ranging from 35 kDa to 33 kDa (Table 1). The electrophoretic profiles were analyzed using the Phoretix 1D Pro Gel Software (Total Lab; United Kingdom) to evaluate banding patterns and molecular weight calibration between each strain.

Example 4

Analysis of Metal-Regulated Proteins Under Iron Replete and Iron Deplete by Single Dimension SDS-PAGE To obtain a better perspective of the up-regulation of metal-regulated proteins of *Klebsiella pneumoniae* 1571, the isolate was grown in iron replete and iron deplete media conditions. Briefly, the organism was grown from a frozen master seed stock, previously prepared by sub-culturing into two separate 500 ml bottles. One bottle contained of 200 ml of sterile TSB containing 300 µM 2,2-diprydyl (Sigma-Aldrich St. Louis, MO) while the second bottle contained 200 ml of Tryptic Soy broth containing 200 µM ferric chloride (Sigma-Aldrich St. Louis, MO). Cultures were incubated for 12 hours with continuous stirring at 200 rpm at 37° C. Following the 12 hour incubation period, the cultures were sub-cultured (1:100) into 500 ml of either the iron-replete and/or the iron-deplete media and incubated at 37° C. for 8 hours. After 8 hours each culture was centrifuged at 10,000×g for 20 minutes, and resuspended in 40 ml of osmotic shock buffer (7.3 g/l Tris Base; 1.86 g/l EDTA), pH 8.9. The suspensions were centrifuged at 32,000×g for 12 minutes to clarify or remove large cellular debris. The supernatants were collected and solubilized by the addition of 4% sodium lauroyl sarcosinate at 4° C. for 24 hours. The detergent-insoluble outer membrane protein-enriched fractions were collected by centrifugation at 32,000×g for 2.5 hours at 4° C. The protein pellets were resuspended in 200 µl Tris-buffer (pH 7.2).

Figure 3:
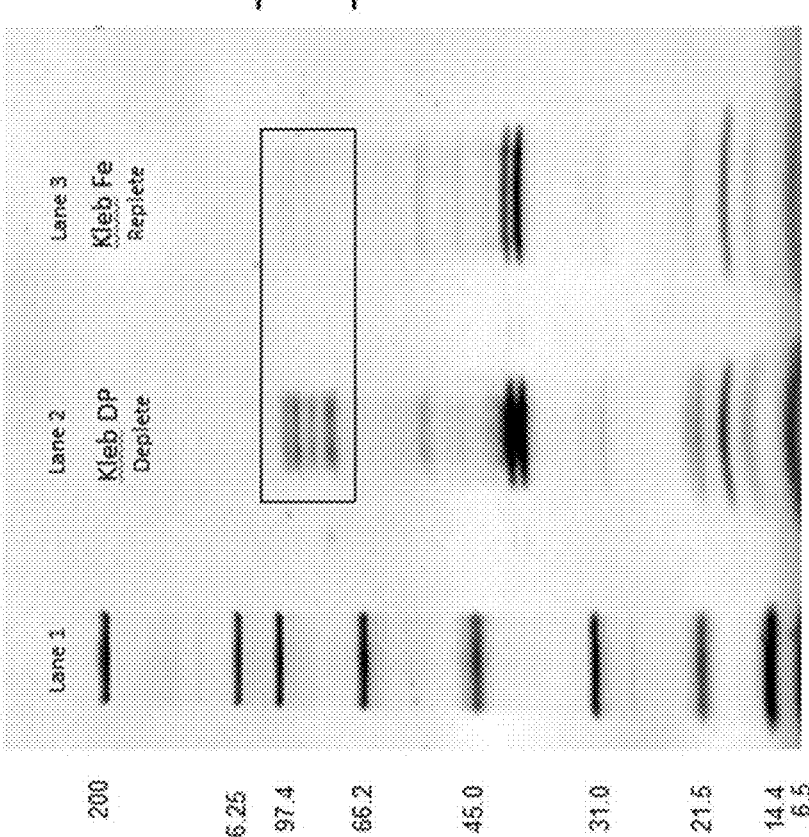
FIG. 3. Difference in outer membrane protein profiles comparing iron-replete and iron-deplete growth conditions of *Klebsiella pneumoniae* 1571 showing the expression of metal regulated proteins in the iron-replete condition as examined by SDS-PAGE. Lane 1, molecular weight marker; lane 2, iron deplete; lane 3, iron replete.

The protein-enriched extracts derived from each isolate were size-fractionated on SDS-PAGE gels using a 4% stacking gel and 10% resolving gel. Samples for electrophoresis were prepared by combining 10 µl of sample with 30 µl of SDS reducing sample buffer (62.5 mM Tris-HCL pH 6.8, 20% glycerol, 2% SDS, 5% β-mercaptoethanol) and boiled for 4 minutes. Samples were electrophoresed at 18 mA constant current for 5 hours at 4° C. using a Protein II xi cell power supply (BioRad Laboratories, Richmond, CA, model 1000/500). The electrophoretic profile comparing protein profiles derived from the *K. pneumonia*, grown under iron-replete and iron-deplete growth conditions are shown in FIG. 3.

Example 5

Large Scale Process for the Manufacture of Metal-Regulated Proteins Fermentation A cryogenic vial of the working seed (1 ml at $10^9$ CFU/ml) was used to inoculate 500 ml of 37° C. tryptic soy broth (TSB) without dextrose (Bacto) containing 34 micrograms/liter 2,2-dipyridyl (Sigma), 2.5 grams/liter yeast extract (Bacto) and glycerol (3% vol/vol). The culture was incubated at 37° C. for 16 hours while agitating at 160 rpm, and then divided between two 1.5 L bottles of the above media. This second culture was allowed to grow for an additional 2.5 hours at 37° C. This culture was used to inoculate a 400 L DCI-Biolafitte SIP fermentor, (DCI, St. Cloud, MN) charged with 300 liters of the above-described media with the addition of Mazu DF 204 defoamer (150 ml). The parameters of the fermentation were as follows: dissolved oxygen (DO) was maintained at 60%+/–20% by increasing agitation to 500 rev/minute sparged with 17-120 liters of air/minute, 0-60 liters of air/minute and 5 pounds per square inch (psi) back pressure. The pH was held constant between 6.9 and 7.2 by automatic titration with 50% NaOH and 25% H3PO4. The temperature was maintained at 37° C. The fermentation was allowed to continue growth for 5.5 hours at which point the fermentation was terminated by lowing the temperature of the fermentor to 15° C. and lowering pH to 5.0 with 25% H3PO4 (optical density 15 at 540 nanometers at a 1:20 dilution). The culture was sterilely transferred to a 200-liter tank (LEE Process Systems and Equipment model 2000LDBT) in preparation for harvest.

Harvest

The bacterial fermentation was concentrated and washed using a Pall Filtron Tangential Flow Maxisette-25 (Pall Filtron Corporation, Northboro, MA) equipped with four 30 ft$^2$ Alpha 0.1 um open channel filters (Pall Filtron, catalog No. PSM10C52) connected to a Waukesha Model 130 U2 feed pump (Waukesha Cherry-Burrell, Delevan, WI) The original culture volume of 300 liters was reduced to 60 liters using a filter inlet pressure of 30-40 psi and a retentate pressure of 2-15 psi. The bacterial retentate was then washed using 200 liters of a sodium acetate tryhidrate solution pH 5.0 which was composed of 2.72 grams/liter sodium acetate tryhidrate. The 60 liters of bacterial retentate was then washed with 100 liters of osmotic shock buffer (OMS) containing 14.52 grams/liter Tris-base and 1.86 grams/liter EDTA adjusted to a pH of 8.6. The EDTA in the OMS served to assist removal of much of LPS from the cell wall, while the elevated pH prevented much of the proteolytic degradation after freezing and disruption. Protease inhibitors may be used instead of, or in addition to, an elevated pH. The retentate was then concentrated down to 40 liters to help remove any contaminating exogenous proteins, 200 more liters of the above OMS was then added to wash all bacteria through the filters into the harvest tank. The retentate was mixed thoroughly while in the 200-liter tank using a bottom mount magnetically driven mixer. The retentate was sterilely dispensed (5 liters) into gamma irradiated 5 liter Invitro™ containers and placed into a –20° C. freezer for storage. Freezing the bacterial pellet served to weaken the cell wall structure making downstream disruption more efficient. The pellet mass was calculated by centrifuging 1 ml sample of the fermented culture and final harvest. Pre-weighted 1 ml conical tubes were centrifuged at 13,000 rpms for 10 minutes in a Microfuge 18. The supernatant was poured off and the pellet was re-suspended in sterile water. This mixture was again centrifuged at 13,000 rpms for 5 minutes before it was once again decanted. This washed pellet was placed in a 125° C. oven for 75 minutes before being weighed and extrapolated to determine harvest volume pellet mass. The fermentation process yielded a dry pellet mass of 2.3 kilograms.

Alternative methods for bacterial harvest can be used. Bacterial harvest may be performed by the use of hollow fiber filter methods. Bacterial culture is harvested using filter cartridges ranging in size from 0.2 µM to 5 kDa; preferably with a 750 kDa cartridge. Culture is reduced in volume from 2-20× and subsequently washed 1-5× by diafiltration with buffer prior to storage at 4° C. or freezing at −20° C. In this manner, undesired media proteins, bacterial proteins and LPS are removed from the culture. In another alternative, bacterial harvest may be performed by the use of industrial scale centrifugation, for example, by use of a disc-stack centrifuge.

Disruption (Homogenization)

Frozen bacterial cell slurry in OMS were thawed at 4° C. (2.3 kg of pellet mass). The liquid culture suspension from each container was aseptically aspirated into a 200 liter process tank (Model 200LDBT) with a bottom mounted mixer (LIGHTNIN Mixer Model MBI610H55) containing 13 liters OMS pH 8.5. The volume of OMS was determined by calculating the homogenizing volume by multiplying the pellet mass by 30.8 L/Kg and taking the homogenizing volume and subtracting the volume of bacteria from the fermentation harvest. The bulk bacterial suspension was chilled to 4° C. with continuous mixing for 18 hours at 18 Hz at which time it was disrupted by homogenization. Briefly, the 200 liter tank containing the bacterial suspension was connected to an AVESTIN Model EF-C500B Homogenizer (Avestin, Rosemont, IL). A second 200 liter process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of each pass, fluid was circulated at 60 psi via a Waukesha model 30U2 pump (Waukesha) through the homogenizer (500 Liters/hour) and back to the tank of origin, while the homogenizer pressure was adjusted to 11,000-30,000 psi. Prior to the first pass, two pre-homogenizing samples were withdrawn from the homogenizer to establish a baseline for determining the degree of disruption and monitoring of pH. The degree of disruption was monitored by transmittance (% T at 540 nm at 1:100 dilution) compared to the non-homogenized sample. The number of passes through the homogenizer was standardized for different organisms based on the integrity of the cell wall and variation in the degree of disruption, which had a direct correlation in the efficiency of solubilization and quality of end product. For example, the disruption of *Salmonella* passed two times through the homogenizer gave a final percent transmittance between 78-83% T at a 1:100 dilution. *E. coli* having the same pellet mass and starting OD gave a % T of 80-86% (at a 1:100 dilution) after the second pass. It has been observed that bacteria differ in their cell wall integrity and vary in their capacity of disruption under identical condition. This variation can affect the degree and efficiency of solubilization and recovery of metal regulated proteins. In general, cells were passed through the homogenizer until the transmittance of at least 80% was reached after a minimum of two passes.

After homogenization, sodium lauroyl sarcosinate (HAMPTOSYL L-30, Chem/Serv) was aseptically added to the homogenized bacterial suspension for solubilization. The amount of sarcosine (30%) added equaled 0.083 times the solubilizing volume, in liters, (solubilizing volume was determined by multiplying the fermentation dry pellet mass by 34.7 L/Kg). The tank was removed from the homogenizer and placed in a 2-7° C. cooler and mixed at 18 Hz for 12-96 hours. This time period was helpful to complete solubilization. It was discovered that increasing the solubilization time in OMS at an elevated pH (8.0-8.5) that metal regulated proteins aggregated together forming large insoluble aggregates that were easily removed by centrifugation. The optimal OD after solubilization was usually between 25-30% T at 540 nm. 12-24 hours prior to protein harvest 0.15% of formalin was added to the final solubilizing volume as a preservative.

Protein Harvest

The aggregated metal regulated proteins within the solubilized process fluid were collected by centrifugation using T-1 Sharples, (Alfa Laval Seperations, Warminster, PA). Briefly, the tank of solubilized homogenate was fed into twelve Sharples with a feed rate of 200 ml/minute at 11 psi at a centrifugal speed of 30,000 rpm. The effluent was collected into a second 200 liter process tank through a closed sterile loop allowing for multiple passes through the centrifuges while maintaining a closed system. The temperature during centrifugation was kept at 4° C. The solubilized homogenate was passed up to 12 times across the centrifuges with a feed rate of 150 ml/minute at 21 psi at a centrifugal speed of 50,000 rpm. Protein was collected after the first pass and discarded, at which point the solubilized fluid was concentrated to ⅓ of its original volume. This decrease in volume shortened the process time for passes 2-12. Briefly, the solubilized homogenate tank was connected to a Pall Filtron AT25 Holder, equipped with three 30.1 ft$^2$ screen-channel series Omega 10 kd Maxisette filters (Pall Filtron) connected to a Waukesha Model 130U2 feed pump for concentration. After concentration, centrifugation was continued until the process was completed. Protein was collected after each pass. The protein was collected, resuspended and dispensed into two 8 Liter containers containing Tris-buffer pH 8.5 containing 0.3% formalin (Sigma) as preservative. The containers were placed into a mixer Model Turbula T10B (M.O. Industries, Wippany, New Jersey) and mixed until the protein was re-suspended in the buffer solution.

Diafiltration

The protein suspension was washed by diafiltration at 4° C. to remove any contaminating sarcosine that may have been bound to the protein. The two containers of protein were aspirated into a 200 Liter tank containing 40 ml TBW/g protein harvested of Tris-Buffer pH 8.5 containing 0.3% formalin equipped with a bottom mount LIGHTNIN mixer, Model MBI610H55 mixing at 20 Hz. The process tank was placed in a 33° C. incubator for a minimum of 12 hours for protein inactivation. The process tank was sterilely connected to a MILLIPORE PELLICON Tangential Flow Filter assembly (Millipore Corporation, Bedford, MA), equipped with two 26.9 ft$^2$ screen-channel series Omega 10K Centrasette filter (Pall Filtron) connected to a Waukesha Model 30U2 feed pump. The solution was concentrated down to approximately 35 liters and was re-suspended with 200 liters of Tris-buffer, pH 7.4, containing 0.1% formalin solution. The solution was again concentrated down to approximately 35 liters and re-suspended again with 200 liters of a Tris-buffer, pH 7.4, containing 0.1% formalin solution. The solution was then concentrated down to approximately 35 liters and re-suspended with 80 liters of Tris-buffer, pH 7.4, containing 0.1% formalin solution. The solution was then concentrated by filtration to a target volume of 6.5 times the protein pellet mass. The protein concentrate was aseptically dispensed into sterile 20 liter Nalgene containers and placed into a 33° C. incubator for 12-24 hours for the final antigen inactivation.

This process produced a composition containing metal regulated proteins with a decrease in the amount of LPS and very little to no sarcosine residue. The protein was examined by SDS-PAGE for purity and banding profile, and also examined for bacterial contamination, residual sarcosine and LPS. The banding profile of the finished product showed consistent patterns as examined by electrophoresis. The composition was tested for sarcosine by the use of a modified agar gel diffusion test in which sheep red blood cells (5%) were incorporated into an agar base (1.5%). Wells were cut into the agar and samples of the finished product along with control samples of known concentrations of sarcosine at 0.05, 0.1, 0.2, 0.3, 0.4, 0.5 1.0 and 2.0% were placed into the wells. The gel was incubated at 25° C. for 24 hours and the degree of hemolysis was determined compared to the controls. The process removes the level of detectable sarcosine below 0.05%, which at this concentration showed minimal hemolysis in control samples. The concentration of LPS was examined by a *Limulus* amebocyte lysate (LAL) test available under the tradename PYROTELL (Associates of Cape Cod, Inc., East Falmouth, MA).

After cell lysis by freezing and homogenization, protein may be harvested by hollow fiber methods. Bacterial lysate is filtered to separate whole cells and large debris from small particulates and soluble protein. This may be accomplished using a range of sizes of hollow fiber cartridges from 0.2 μM to 5 kDa; preferably with a 0.65 μM nominal pore size. In this manner, whole unlysed cells and large debris are retained and possibly concentrated by the filter while protein and small particulates of interest are passed through the filter and collected. Additionally, it may be desirable to wash the retentate from 1-20× with buffer to increase the harvest of proteins of interest.

Subsequent to the primary harvest above, bacterial membranes of the small particulates are solubilized with sarcosine as described above, followed by further fractionation or protein harvest and wash by hollow fiber methods. This serves three functions: the removal of undesired cytosolic proteins, the removal of undesired membrane components including LPS and the hydrophobic aggregation of desired metal-regulated proteins and porin proteins into higher molecular weight forms. After the solubilizing step, the solution is filtered using hollow fiber cartridges ranging in size from 0.2 μM to 5 kDa; preferably with a Laboratory and/or Pilot Scale Ultrafiltration Cartridge (for example, (UFP-750-E-6A) size 6A Ultrafiltration Hollow Fiber Cartridge (63.5 cm L); Polysulfone membrane, optionally having a 750 000 NMWC pore size, GE Healthcare Pittsburgh, PA). This step can also include concentration (2-20×) and diafiltration wash steps (1×-20×) with buffer and ethanol to enhance the removal of undesired protein, membranous components, DNA and sarcosine and thus increase the purity of the harvested metal-regulated proteins and porin proteins.

An example of the proteins present in the composition prepared as described above is shown in FIG. 4. Five higher molecular weight proteins (four of which are identified in FIG. 4 as FepA, FecA, FhuA, and CirA, and one migrating above the band identified as FepA) and two lower molecular weight bands identified in FIG. 4 as OmpC and OmpA) were observed after resolving the proteins on an SDS-PAGE gel.

Example 6

Characterization of Metal Regulated Proteins of *Klebsiella pneumoniae* Isolate 1571

The proteins of the composition prepared as described in Example 5 from the *K. pneumoniae* strain 1571 were characterized using MALDI-TOF MS. These methods were also used for the *K. oxytoca* and *Enterobacter* isolates The proteins of the composition prepared as described in Example 5 from the *K. pneumoniae* strain 1571 was characterized using matrix assisted laser desorption/ionization time-of-flight spectrometry (MALDI-TOF MS). A portion of the composition was resolved using a sodium dodecyl sulfate-polyacrylamide gel. After the proteins of a composition had been resolved, the gel was stained with either coomasie brilliant blue or silver to visualize the proteins. This method was also used to characterize compositions obtained from *K. oxytoca* and *Enterobacter* isolates

Materials and Methods

Excision and washing. After resolving proteins using SDS-PAGE and staining to visualize the proteins, the gel was washed for 10 minutes with water twice. Each protein band of interest was excised by cutting as close to the protein band as possible to reduce the amount of gel present in the sample. Six gel fragments were prepared using the six bands identified in FIG. 4 as FepA, FecA, FhuA, CirA, OmpC, and OmpA.

Each gel slice was cut into 1×1 mm cubes and placed in 1.5 ml tube. The gel pieces were washed with water for 15 minutes. All the solvent volumes used in the wash steps were approximately equal to twice the volume of the gel slice. The gel slice was next washed with water/acetonitrile (1:1) for 15 minutes. When the proteins had been stained with silver, the water/acetonitrile mixture was removed, the gel pieces dried in a SPEEDVAC (ThermoSavant, Holbrook, NY) and then reduced and alkylated as described below. When the gel pieces were not silver-stained, the water/acetonitrile mixture was removed, and acetonitrile was added to cover until the gel pieces turned a sticky white, at which time the acetonitrile was removed. The gel pieces were rehydrated in 100 mM NH$_4$HCO$_3$, and after 5 minutes, a volume of acetonitrile equal to twice the volume of the gel pieces was added. This was incubated for 15 minutes, the liquid removed, and the gel pieces dried in a SPEEDVAC.

Reduction and alkylation. The dried gel pieces were rehydrated in 10 mM DTT and 100 mM NH$_4$HCO$_3$, and incubated for 45 minutes at 56° C. After allowing the tubes to cool to room temperature, the liquid was removed and the same volume of a mixture of 55 mM iodoacetamide and 100 mM NH$_4$HCO$_3$ was immediately added. This was incubated for 30 minutes at room temperature in the dark. The liquid was removed, acetonitrile was added to cover until the gel pieces turned a sticky white, at which time the acetonitrile was removed. The gel pieces were rehydrated in 100 mM NH$_4$HCO$_3$, and after 5 minutes, a volume of acetonitrile equal to twice the volume of the gel pieces was added. This was incubated for 15 minutes, the liquid removed, and the gel pieces dried in a SPEEDVAC. If the gel was stained with coomasie blue, and residual coomassie still remained, the wash with 100 mM NH$_4$HCO$_3$/acetonitrile was repeated.

In-gel digestion. Gel pieces were completely dried down in a SPEEDVAC. The pieces were rehydrated in digestion buffer (50 mM NH$_4$HCO$_3$, 5 mM CaCl$_2$), 12.5 nanograms per microliter (ng/μl) trypsin) at 4° C. Enough buffer was added to cover the gel pieces, and more was added as needed. The gel pieces were incubated on ice for 45 minutes, and the supernatant removed and replaced with 5-2 μl of same buffer without trypsin. This was incubated at 37° C. overnight in an air incubator.

Extraction of peptides. A sufficient volume of 25 mM NH$_4$HCO$_3$ was added to cover gel pieces, and incubated for 15 minutes (typically in a bath sonicator). The same volume of acetonitrile was added and incubated for 15 minutes (in a bath sonicator if possible), and the supernatant was recovered. The extraction was repeated twice, using 5% formic acid instead of NH$_4$HCO$_3$. A sufficient volume of 5% formic acid was added to cover gel pieces, and incubated for 15 minutes (typically in a bath sonicator). The same volume of acetonitrile was added and incubated for 15 minutes (typically in a bath sonicator), and the supernatant was recovered. The extracts were pooled, and 10 mM DTT was added to a final concentration of 1 mM DTT. The sample was dried in a SPEEDVAC to a final volume of approximately 5 μl.

Desalting of peptides. The samples were desalted using a ZIPTIP pipette tips (C18, Millipore, Billerica, MA) as suggested by the manufacturer. Briefly, a sample was reconstituted in reconstitution solution (5:95 acetonitrile:H$_2$O, 0.1%-0.5% trifluoroacetic acid), centrifuged, and the pH checked to verify that it was less than 3. A ZIPTIP was hydrated by aspirating 10 μl of solution 1 (50:50 acetonitrile: H$_2$O, 0.1% trifluoroacetic acid) and discarding the aspirated aliquots. This was followed by aspirating 10 μl of solution 2 (0.1% trifluoroacetic acid in deionized H$_2$O) and discarding the aspirated aliquots. The sample was loaded into the tip by aspirating 10 μl of the sample slowly into the tip, expelling it into the sample tube, and repeating this 5 to 6 times. Ten microliters of solution 2 was aspirated into the tip, the solution discarded by expelling, and this process was repeated 5-7 times to wash. The peptides were eluted by aspirating 2.5 μl of ice cold solution 3 (60:40, acetonitrile: H$_2$O, 0.1% trifluoroacetic acid), expelling, and then re-aspirating the same aliquot in and out of the tip 3 times. After the solution has been expelled from the tip, the tube was capped and stored on ice.

Mass spectrometric peptide mapping. The peptides were suspended in 10 μL to 30 μL of 5% formic acid, and analyzed by MALDI-TOF MS (Bruker Daltonics Inc., Billerica, MA). The mass spectrum of the peptide fragments was determined as suggested by the manufacturer. Briefly, a sample containing the peptides resulting from a tryptic digest were mixed with matrix cyano-4-hydroxycinnamic acid, transferred to a target, and allowed to dry. The dried sample was placed in the mass spectrometer, irradiated, and the time of flight of each ion detected and used to determine a peptide mass fingerprint for each protein present in the composition. Known polypeptides were used to standardize the machine.

Data analysis. The experimentally observed masses for the peptides in each mass spectrum were compared to the expected masses of proteins using the Peptide Mass Fingerprint search method of the MASCOT search engine (Matrix Science Ltd., London, UK, and www.matrixscience.com, see Perkins et al., 1999, Electrophoresis 20, 3551-3567). The search parameters included: database, NCBInr; taxonomy, bacteria (eubacteria); type of search, peptide mass fingerprint; enzyme, trypsin; fixed modifications, carbamidomethyl (C) or none; variable modifications, oxidation (M), carbamidomethyl (C), the combination, or none; mass values, monoisotopic; protein mass, unrestricted; peptide mass tolerance, between ±100 ppm and ±300 ppm or 450 ppm, or ±1 Da; peptide charge state, Mr; max missed cleavages, 0 or 1; number of queries, 25.

SDS-PAGE analysis of the polypeptides indicated that, under the SDS-PAGE conditions used, proteins migrated at 82 kDa, 78 kDa, 72 kDa, 68 kDa, 35 kDa and 33 kDa as determined by SDS-PAGE (Table 1). An additional protein was a light band and migrated at 87 kDa. MALDI analysis and predicted molecular weight based on amino acid sequence showed there was good agreement between the molecular weights of the proteins as estimated using SDS-PAGE and using MALDI (Table 1). The proteins in FIG. 4 were identified by MALDI. These analyses resulted in protein sequences that represent the best protein match for each peptide mass fingerprint. The best protein match for the band labeled FepA was NCBI Reference Sequence WP_012068422.1; the best protein match for the band labeled FecA was NCBI Reference Sequence NP_943400.1; best protein match for the band labeled FhuA was NCBI Reference Sequence WP_004178624.1; best protein match for the band labeled CirA was NCBI Reference Sequence WP_015958738.1; best protein match for the band labeled OmpC was NCBI Reference Sequence WP_015958749.1; and the best protein match for the band labeled OmpA was NCBI Reference Sequence WP_002898408.1.

Genomic Sequencing

Genomic DNA was isolated from the *Klebsiella pneumoniae* 1571 isolate using the CHARGESWITCH gDNA Mini Bacteria Kit (Life Technologies, Carlsbad, CA, product number: CS11301). Prior to extraction of the genomic DNA, a fresh culture of the isolate was grown on Trypticase Soy Agar II with 5% Sheep Blood (Becton, Dickinson and Company, Franklin Lakes, NJ, product code: 221261) overnight at 37° C. The procedure followed the manufacturer protocol. The final yield was 33.7 μg of genomic DNA, which was stored at −20° C. until sequencing. The genomic DNA was submitted to ACGT, Inc. for sequencing (Wheeling, IL).

Identifying Target Genes

After receiving the complete genomic sequence of the isolate, tblastn alignments were performed with the National Center for Biotechnology Information (NCBI) database to identify the possible genes of interest. The first analysis of the *Klebsiella pneumoniae* 1571 genomic sequence used the results of the data analysis of the six bands by MALDI. This analysis resulted in the identification of the following proteins encoded by genes present in the *Klebsiella pneumoniae* 1571 genomic sequence: FepA, FecA, FhuA, CirA, OmpC, and OmpA. These proteins, and the genes encoding them, are disclosed at FIGS. 10, 7, 8, 9, 20, and 21, respectively. Another analysis of the complete genomic sequence was based on Ton B dependent homologs within the sequence. The algorithm parameters were Matrix: BLOSUM62 and Gap Costs: Existence: 11 Extension: 1. A blastx search was used to identify the proteins translated by the homologous genes found with the tblastn alignment. The algorithm parameters were Matrix: BLOSUM62 and Gap Costs: Existence: 11 Extension: 1. Pairwise sequence alignments of the identified homologues of metal regulated polypeptides. The algorithm parameters were Matrix: BLOSUM62, Gap Open: 14, Gap Extend: 4, Alternative Matches: 1.

To identify possible homologues to other metal regulated proteins BtuB, YbiL, YncD, IroN, IutA, FitA, FcuA, Ferric Enterbactin Colicin B/D receptor and FoxA a "tblastn" alignment was performed against the sequenced genome of the *Klebsiella pneumoniae* isolate. Nine possible homologues were identified by looking at the sequences with highest identities respectively within the genome, and are disclosed at FIGS. 11-19. A partial nucleotide sequence and predicted amino acid sequence of three of the possible homologues were identified (YncD, IroN, and FitA, FIGS. 13, 14, and 16, respectively).

Example 7

Hyper-Immunization of Holstein Steers and Preparation of Polyclonal Antibody

Two Holstein Steers at four months of age were vaccinated subcutaneously three times at 28 day intervals using the *Klebsiella pneumoniae* 1571 composition as described in Examples 5 and 6. The immunizing composition included polypeptides having molecular weights of 87 kDa, 82 kDa, 78 kDa, 72 kDa, 68 kDa, 35 kDa, and 33 kDa as determined by SDS-PAGE. The proteins were emulsified into a single vaccine formulation. Briefly, 320 mg antigen (metal-regulated proteins and porins) was mixed into 355 ml of physiological saline. The antigen solution was emulsified into 80 ml of EMULSIGEN to give a final dose of 1500 µg total protein at a 22.5% EMULSIGEN concentration in a 2 ml injectable volume. Twenty eight days after the third vaccination 2.0 liters of blood from each steer was pooled and allowed to clot at 4° C. for 24 hours. The serum was separated from whole blood by centrifugation at 3000×g for 30 minutes. The serum; 800 ml was again centrifuged at 10,000×g for 30 minutes to remove any contaminating cell debris and then aliquoted into 25 ml volumes in sterile 50 ml conical tubes (Fisher Scientific) and frozen at −80° C. until use. Twenty five milliters of hyperimmunized serum was purified using standard ammonium sulfate precipitation. Briefly, exogenous serum proteins were removed first prior to antibody precipitation by adding 0.5 volumes of saturated ammonium sulfate pH 7.2. The solution was stirred at 100 rpm for 24 hours at 4° C. The solution was again centrifuged at 3000×g for 30 minutes. The supernatant was collected and precipitated again by adding enough saturated ammonium sulfate to bring the final concentration to 55% saturation. The solution was stirred at 100 rpm for 24 hours at 4° C. The precipitate was centrifuged at 3000×g for 30 minutes. The final pellet from each sample was resuspended into 2 ml PBS pH 7.2. The precipitated antibodies were then dialyzed using a 50,000 molecular cut off dialysis tubing (Pierce, Rockford Ill.) for 30 hours against three 1 liter changes of phosphate-buffered saline to remove ammonium sulfate. The first two liter changes were preserved with 0.02% sodium azide. The final 1 liter buffer change contained no preservative. The dialysate was collected and centrifuged again to remove any remaining debris at 3000×g for 30 minutes. The antibody solution was stored at 4° C. for less than 48 hours prior to use. Each sample was plated on blood agar to verify sterility.

Example 8

Cross-Reactivity of the *Klebsiella pneumoniae* 1571 Metal-Regulated Proteins with Other Strains of *Klebsiella, E. Coli* and *Enterobacter*

The hyperimmunized serum produced against the purified metal-regulated proteins of *Klebsiella pneumoniae* 1571 of Example 7 was examined for its cross-reactivity to bacteria from different genera and species. Metal-regulated proteins from Example 3 (*Klebsiella* 1564, 1569, 1571, LM21, *Enterobacter* 1568, and *E. coli* 0157) were subjected to electrophoresis followed by western blot analysis with the *Klebsiella pneumoniae* 1571 hyperimmunized serum as described in Example 7. Metal-regulated proteins from *E. coli* 0157 were also prepared as described in Example 3 and examined.

Figure 5A:
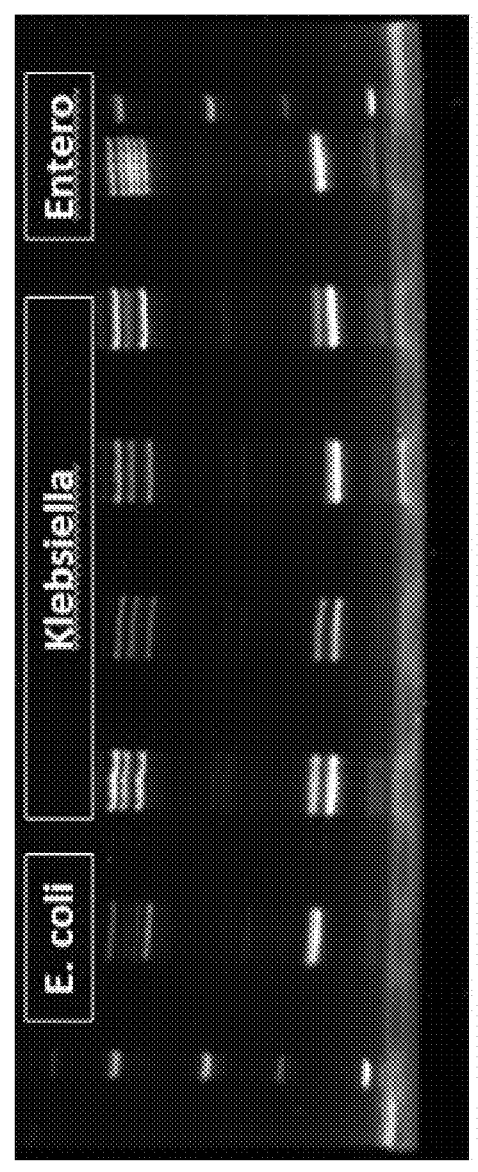
FIG. 5. Electrophoretic profile (FIG. 5A) and western Blot (FIG. 5B) of different genera and species of *E. coli, K. pneumoniae, K. oxytoca, Enterobacter* and *K. pneumoniae* LM21 showing the variation and cross-reactivity of metal regulated protein profiles. Hyperimmunized sera derived from *Klebsiella pneumonia* 1571 was used for the western blot.
Figure 5B:
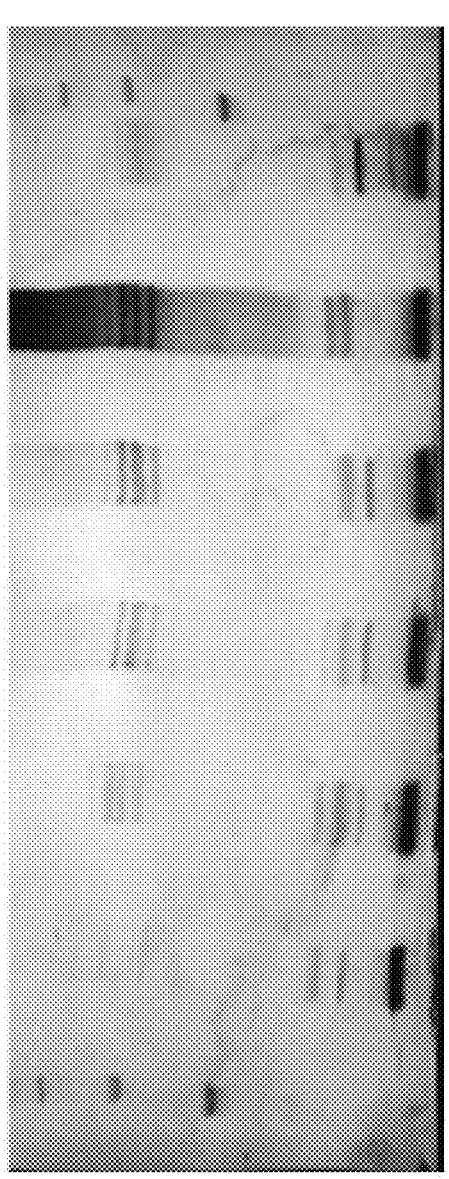

The purified metal-regulated proteins of *E. coli* 0157, *Klebsiella* of bovine and human origin, and *Enterobacter* were subjected to electrophoresis followed by western blot analysis with the hyperimmunized serum of *Klebsiella pneumoniae* 1571 as described in Example 7. Briefly, the outer membrane preps were size-fractionated on an SDS-PAGE gel using a 4% stacking gel and 7.5% resolving gel. A 10 µl sample was combined with 10 µl of SDS reducing sample buffer (62.5 mM Tris-HCL ph 6.8, 20% glycerol, 2% SDS, 5% β-mercaptoethanol) and boiled for 4 minutes. Samples were electrophoresed at 18 mA constant current for 5 hour at 4° C. using a Protein II xi cell and model 1000/500 power supply (BioRad Laboratories, Richmond, CA). Band migration was visualized using broad range kaleidoscope standards (BioRad) to aid in the electro-blot transfer while biotinylated broad range standards were used as molecular weight references on the blot (see FIGS. 5A and 5B). For Western blot analysis, proteins were electroblotted from the gel onto trans-blot nitrocellulose membranes (BioRad) overnight, at 4° C. at 50 V, in Towbin buffer (25 mM Tris, 192 mM glycine, 20% methanol) using a BioRad Trans-Blot transfer cell and a Pac 300 power supply (BioRad). The nitrocellulose membrane was blocked using 3% fish gelatin (Sigma Chemical, St. Louis, Mo) in Tris buffered saline (TBS—20 mM Tris, 500 mM NaCl, pH 7.5) for 1 hour while shaking at 37° C. The membrane was dried at 37° C. and blocked in TBS containing 3% fish gelatin and this process was repeated. The membrane was then probed with the polyclonal hyperimmunized sera collected from the immunized steers as described in example 7. The primary antibody was diluted 1/50 in TBS containing 1% fish gelatin, 0.05% TWEEN 20 and 0.2% sodium azide (Antibody Buffer). The membrane was incubated with the primary antibody solution overnight on a shaker at room temperature. The membrane was then washed two times in TBS containing 0.05% TWEEN 20 (TTBS) and transferred to antibody buffer containing a 1/10,000 dilution of Alkaline phosphatase-conjugated mouse anti-bovine IgG clone BG-18 (Sigma) and a 1/3000 dilution of avidin conjugated to alkaline phosphatase (BioRad). The membrane was incubated at 37° C. for 2 hours on a shaker, then washed in TTBS four times to remove unbound conjugate. The blot was resolved in substrate solution containing alkaline phosphate color reagent A and B in 1×AP color development Buffer (BioRad) for 30 min. at 37° C. on a shaker. The resulting Western immunoblot was documented using a BioRad GS-800 Densitometer (see FIGS. 5A and 5B).

Western blot analysis revealed that the positive antisera prepared against the purified metal-regulated proteins of example 5 reacted intensely with multiple metal-regulated proteins of 5 *E. coli* O157 (lane 2) *K. oxytoca* (lane 3), *K. pneumoniae* 1569 (lane 4) *K. pneumoniae* LM21 (lane 5), *Klebsiella pneumoniae* 1571 (lane 6) and *Enterobacter* 1568 (lane 7). These results show that the metal-regulated proteins of *Klebsiella pneumoniae* have a high degree of antigenic homology to different strains of *Klebsiella* and different genera and species of bacteria.

Example 9

Sequence Identity of Metal-Regulated Proteins

To further substantiate the homology of various metal-regulated proteins of the *Klebsiella pneumoniae* 1571 to other *Klebsiella, E. coli* and *Enterobacter* isolates, the amino acid sequence identity of multiple peptides (CirA, FcuA, FecA, FhuA, and IutA) was examined to determine the percent homology. Isolates were also selected based on specific disease conditions, such as mastitis in bovine species and septicemia, pneumonia, neonatal sepsis, liver abscesses, urinary tract infections, cerebrospinal infections and ETEC diarrhea in humans. Protein sequences were analyzed using the default settings of NCBI's protein BLAST (blastp). Matches with e-values equal to zero and query coverage >95% were considered for the homology. Table 3 shows the metal-regulated proteins that are shared between *Klebsiella pneumoniae* 1571 and other isolates of *Klebsiella, E. coli,* and *Enterobacter* that induced different disease conditions in both agricultural animals and humans. Not all isolates contain every iron regulated protein examined, but as can be seen from Table 3 most metal-regulated proteins approach 99-100% identity across the *Klebsiella* strains. In addition, most of the metal-regulated proteins found in the *Klebsiella pneumoniae* 1571 vaccine strain show significant identity of greater than 60% and up to 99% compared to other isolates of *E. coli* and *Enterobacter*. Considering that individual metal-regulated proteins are composed of more than 600 amino acids, and that the immune response recognizes epitopes that range from 5-20 amino acids, it clearly demonstrates that these proteins are excellent target antigens. Thus, a vaccine prepared using metal-regulated proteins would be expected to provide a broadly protective vaccine directed against multible gram negative pathogens responsible for a broad spectrum of disease conditions in both human and animal populations.

C. After the 2 hour time period 10 ml of the culture was transferred to 100 ml of pre-warmed TSB as described above except the concentration of 2,2-dipyridyl was 25 µg/l. This culture was allowed to grow until they reached an OD 1.0 at 540 nm at which point was centrifuged at 8000 rpm for 10 minutes and re-suspended into 90 ml cold TSB as described above; except it contained 20% glycerol. One ml aliquots of the bacterial suspension was dispensed into 2 ml cryovials; labeled and stored at −90° C. until use.

Example 11

Preparation of the Immunizing Compositions Derived from *Klebsiella pneumoniae* 1571

TABLE 3

Percent identity of the amino acid sequence for siderophore receptors proteins in *Klebsiella*, *Escherichia*, and *Enterobacter* genera and strains.

| Strain | Isolate ID | Disease | CirA | FcuA | FecA | FhuA | IutA |
|---|---|---|---|---|---|---|---|
| *Klebsiella pneumoniae* 1571 | | Mastitis (bovine) | 100 | 100 | 100 | 100 | 100 |
| *Klebsiella pneumoniae* KPN6 (KPNIH2) | 1087441 | septicemia | 100 | 99 | 99 | 99 | 99 |
| *Klebsiella pneumoniae* VA360 | 1236102 | neonatal sepsis | 100 | 99 | 99 | 99 | 99 |
| *Klebsiella pneumoniae* MP14 | 1341693 | pneumonia | 100 | 99 | | 99 | 99 |
| *Klebsiella pneumoniae* ST258-K28BO | 1185420 | pneumonia | 100 | 99 | 99 | 99 | 99 |
| *Klebsiella pneumoniae* JHCK1 | 1236101 | neonatal sepsis | 100 | 99 | 99 | 99 | 99 |
| *Klebsiella pneumoniae* CG43 | 1244085 | liver abscess | | 99 | 99 | 99 | 99 |
| *Klebsiella pneumoniae* ATCC BAA-2146 | 1263871 | urinary tract infection | 100 | 99 | | 99 | 99 |
| *Enterobacter cloacae* EC_38VIM1 | 1334630 | septicemia | 81 | 69 | 99 | 83 | 70 |
| *Enterobacter cloacae* UCICRE 11 | 1329855 | unknown | 36 | 69 | 99 | 83 | 71 |
| *Enterobacter cloacae* UCICRE 3 | 1329852 | unknown | 36 | 69 | 99 | 83 | 70 |
| *Enterobacter cloacae* ATCC 13047 | 716541 | cerebrospinal infection | 81 | 69 | | 61 | 71 |
| *Escherichia coli* EC958 O25b:H4-ST131 | 941322 | urinary tract infection | 81 | 27 | 99 | 60 | 73 |
| *Escherichia coli* CFT073 | 199310 | urinary tract infection | 36 | 27 | | 60 | 73 |
| *Escherichia coli* H10407 | 316401 | ETEC diarrhea | 81 | | 99 | 61 | |
| *Escherichia coli* ECC-1470 | 758831 | Mastitis (bovine) | 81 | | 99 | 61 | |

Percent identity is indicated by color intensity and the actual percentage. A blank cell indicates the gene is not encoded by that strain. Protein sequences were analyzed using the default settings of NCBI's protein BLAST (blastp). Matches with e-values equal to zero and query coverage >95% were considered for the homology. Bacterial isolates were also selected based on their clinical manifestation of disease to include mastitis in bovine and septicemia, pneumonia, neonatal sepsis, liver abscesses, urinary tract infections, cerebrospinal infections and ETEC diarrhea in humans.

Example 10

Serial Passage of *Klebsiella pneumoniae* 1571 in Mice to Enhance Virulence

To enhance virulence *Klebsiella pneumoniae* 1571 was serially passaged in the new host species, mouse. Briefly, using the culture as described above of example 1 two mice were subcutaneously injected with either 0.1 or 0.2 ml at $1.0 \times 10^9$ CFU/ml of the isolate. Twenty four hours post inoculation mice were morbid but did not die. Mice were euthanized by cervical dislocation and each liver was cultured using a flamed loop and plated onto Blood agar. Plates were incubated at 37° C. for 24 hours. A number of colonies from the 0.2 dose had grown on the Blood agar plates indicating the isolates had gone systemic. These colonies were streaked for isolation and again passed through mice using the same regiment. The final mouse passage resulted in all mice dying at 24 hours post challenge, clearly demonstrating that the isolate adapted to grow in the new host species by the enhancement of virulence with death as the outcome parameter. The isolate was sub-cultured from the final liver isolation and expanded into a frozen challenge seed. Briefly a single colony from the Blood plate was sub-cultured into 20 ml of TSB containing 32 gm TSB, 5 gm yeast extract, and 2,2-dipyridyl at 25 µg/liter. The culture was allowed to stir at 200 rpm for 2 hours at which point was sub-cultured in the same media that was pre-warmed to 37°

The proteins made from *Klebsiella pneumoniae* 1571 as described in Example 5 were used to prepare a composition for administration to mice to determine the efficacy of the vaccine against a live virulent homologous and heterologous challenge. Eighty female CF-1 mice obtained from Harlan Breeding Laboratories (Indianapolis, IN) weighing 16-22 grams were equally distributed into four groups (20 mice/group), two vaccinate groups and two placebo groups. Mice were housed in polycarbonate mouse cages (Ancore Corporation, Bellmore, NY). Four cages were used for each treatment group (5 mice/cage) to minimize the number of mice for each cage. Groups were designated as 1-4. Group 1 was designated as the *Klebsiella* Placebo, group 2 was designated as the *E. coli* Placebo while groups 3 and 4 were both vaccinated with the *Klebsiella pneumoniae* 1571 composition of Example 5. The vaccine composition contained the proteins illustrated in FIG. 4.

Example 12

Mouse Vaccination

The stock vaccine was prepared by emulsifying the aqueous protein suspension (1000 µg total protein/ml) into the commercial adjuvant, EMULSIGEN, (MVP Laboratories, Ralston, Nebraska) to give and adjuvant concentration of 22.5% vol/vol. A mouse dose was administered to give a final dose of 100 µg total protein in a 0.1 ml injectable volume. A placebo was prepared by replacing the antigen with physiological saline in the above formulation and emulsifying the suspension into EMULSIGEN to give and adjuvant concentration of 22.5%. Food and water were supplied ad libitum to all mice. Mice were vaccinated subcutaneously two times at 21 day intervals with the placebo and/or the *Klebsiella pneumoniae* vaccine.

Example 13

Preparation of Challenge Organisms

The *Klebsiella pneumoniae* isolate 1571 as described in Example 10 was used for the homologous challenge of groups 1 and 3 while mice in groups 2 and 4 were challenged with *E. coli* CFT073 (heterologous challenge). Briefly, the challenge isolates from frozen stocks was streaked onto blood agar plates and incubated at 37° C. for 18 hours. A single colony from either the *Klebsiella* plate or the *E. coli* plate was sub-cultured into one of two 50 ml bottles of Tryptic Soy Broth (Difco) containing 25 μg/ml 2,2' dipyridyl. The cultures were incubated at 37° C. for 6 hours while rotating at 200 rpm until an OD of 0.95-1.0 at 540 nm was reached at which point was centrifuged at 10,000×g for 10 minutes at 4° C. to pellet the bacteria. The bacterial pellet was washed twice by centrifugation in physiological saline at 4° C. The final pellet was resuspended back to 100 ml in physiological saline and used for challenge. Just prior to challenge, 1 ml of the above bacterial suspension was serially diluted ten-fold to enumerate the number of CFU/mouse dose.

Example 14

Challenge

Mice were challenged 28 days post second vaccination. Mice in groups 1 and 3 were challenged intraperitoneally with $5.7 \times 10^7$ CFU of *Klebsiella pneumoniae* 1571 in a 0.1 ml volume, while mice in groups 2 and 4 were challenged intraperitoneally with $1.3 \times 10^7$ CFU of *E. coli* CFT073 in a 0.1 ml volume. Mice were monitored daily for mortality for 10 days post-challenge.

Figure 6:
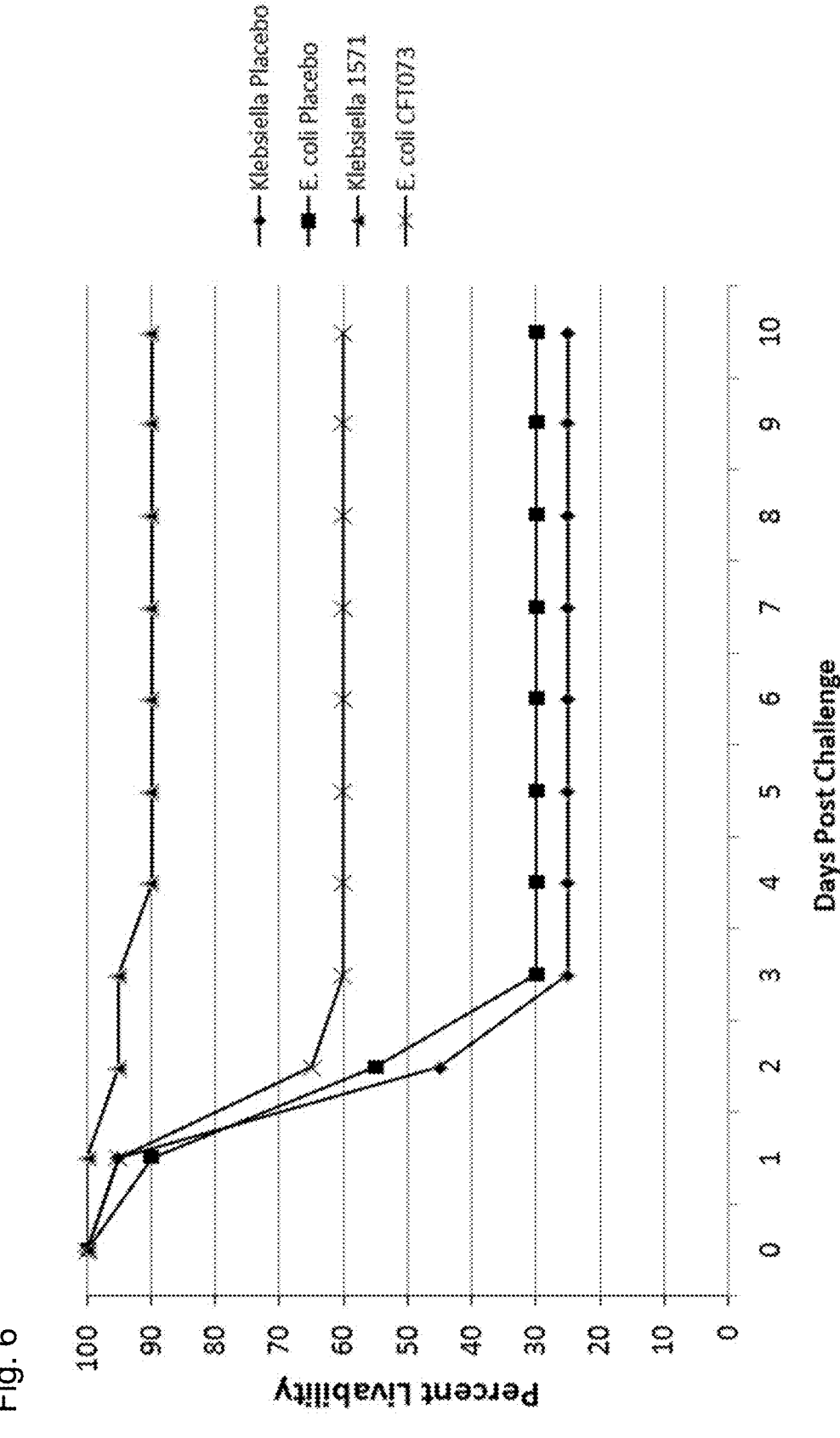
FIG. 6. Cross-protection of *Klebsiella pneumoniae* 1571 vaccine against a homologous and heterologous challenge in mice.

When comparing mortality in challenged mice in groups 1 and 3 (homologous challenge), vaccinated mice of group 3 showed a high degree of protection (90% livability) in contrast to its placebo control showing only 25% survival. In comparison, mice vaccinated with the *Klebsiella* 1571 composition and challenged with *E. coli* CFT073 (heterologous challenge) showed a significant degree of protection at 60% livability in contrast to its placebo control having only 30% livability at the dose of the vaccine given. It is expected that immunizing with a higher dose of antigen, e.g., 150 ug-200 ug, there would be a higher degree of protection. The results clearly demonstrate that the *Klebsiella pneumoniae* 1571 composition has the capability of protecting against another genera of bacteria FIG. 6.

Example 15

Construction of Expression Clones and Purification of Recombinant Metal-Regulated Proteins The amino acid sequences for the metal-regulated proteins FecA (from *Klebsiella pneumoniae* strain 1571) (SEQ ID NO.41 where the fourth amino acid is N), and CirA, FepA and IutA (from *E. coli* strain CFT073) (FIGS. 36-38) were submitted to GENEART (Life Technologies, Carlsbad, CA) for assembly. The GENEOPTIMIZER (Life Technologies) software was used to reverse translate the protein sequences into DNA for optimized gene synthesis. The sequences were cloned into the pQE30Xa expression vector (Qiagen, Valencia, CA), which adds an N-terminal 6× Histidine tag, and the vector was used to transform the XL-1 blue *E. coli* strain. Recombinant metal-regulated proteins were expressed and purified using standard methods. Frozen bacterial stocks (100 ul) were used to inoculate 20 ml of Luria-Bertani Broth with 100 ug/ml Ampicillin for plasmid maintenance, and the culture was grown at 37° C. in a shaking incubator (250 rpm). After 16 hours the culture was diluted 1:50 into 1 L of Luria-Bertani Broth with 100 ug/ml Ampicillin, grown to an optical density (600 nm) of 0.6, and then induced with 1 mM IPTG for 4 hours. Bacterial pellets were harvested by centrifugation at 4,000×g for 20 minutes at 4° C., washed in phosphate buffered saline, and then resuspended in 20 mM Tris buffer with 100 ug/ml lysozyme. The cells were then disrupted by sonication at 50% duty cycle and 5 output (Branson Sonifier, Danbury, CT) for 8 minutes on ice. The lysate was subjected to centrifugation for 10 min at 40,000×g at 4° C. to remove insoluble material. The soluble supernatants were processed by immobilized metal affinity chromatography (HisTrap FF 5 ml, GE Healthcare) to purify the Histidine-tagged recombinant protein, and then anion exchange chromatography to increase the purity and remove endotoxin. Protein concentration was estimated using the BCA method (Pierce) and protein purity was measured at greater than 70 percent by SDS-PAGE densitometry. Endotoxin was verified to be below 40 EU/mg proteins using the Kinetic-Turbidimetric Test for Bacterial Endotoxins using *Limulus* amoebocyte lysate. These results are summarized in Table 4.

TABLE 4

Results from purification of recombinant metal-regulated proteins.

| Protein | Protein concentration (mg/mL) | Purity (%) | Endotoxin Level (EU/mg) | Final Buffer |
|---|---|---|---|---|
| FecA | 1.9 | 85% | <10 | 50 mM Tris, 1 mM EDTA, 800 mM Urea, 51 mM n-OG |
| CirA | 16.7 | 70% | 38.6 | 20 mM Tris, 300 mM Urea, 0.5% ZWITTERGENT |
| FepA | 13.1 | 91% | 5 | 50 mM Tris, 300 mM Urea, 51 mM n-OG |
| IutA | 2.1 | 88% | 19 | 50 mM Tris, 300 mM Urea, 51 mM n-OG |

Example 16

Vaccine-Mediated Protection in a Mouse Sepsis Model Evaluating Multiple Vaccine Formulations A mouse sepsis model was chosen to evaluate the following vaccine compositions; *Klebsiella pneumoniae* bovine strain 1571, extracted metal-regulated proteins of *Klebsiella pneumoniae* human strain LM21 (prepared as described in Example 5), and a formulation containing four recombinant metal-regulated proteins FecA, CirA, FepA and IutA (prepared as described in Example 15). Eighty female CF-1 mice weighing 16-22 grams were purchased from Charles River Laboratory (Wilmington, MA) and randomly divided into 6 groups (15 mice per group except group 1, which contained 10 mice). Groups were designated as 1-6. Group 1, 2, and 3 were designated as controls. Group 1 was the naïve control (non-vaccinated/challenged), Group 2 was the adjuvant control having 50% incomplete Freunds adjuvant, 10 µg CpG and 2.5 µg monophosphoryl lipid A (MPLA) (vaccinated/challenged), and Group 3 was the adjuvant control having 50% incomplete Freunds adjuvant (vaccinated/challenged). Groups 4, 5, and 6 were vaccinated with their respective vaccine formulations that correlated to their appropriate adjuvant control groups (Table 5). Mice were housed in polycarbonate mouse cages (Ancore Corporation, Bellmore, NY). Three cages were used for each treatment group (5 mice/cage) to minimize the number of mice for each cage. All mice were allowed to acclimate one week prior to the first vaccination. The individual vaccine formulations were evaluated for their ability to protect against death in a mouse sepsis model using *Klebsiella pneumonia* 1571 as the challenge organism (Example 10).

Just prior to challenge, 1 ml of the above bacterial suspension was serially diluted ten-fold to enumerate the number of CFU/mouse dose.

Example 19

Challenge Results

Of the naïve and placebo controls, eighty percent (80%) of the naïve mice of Group 1 died following challenge compared to 73% death in mice of Group 2 and 80% death in mice of Group-3 (Table 6). These results demonstrate that the adjuvant alone did not provide protection against the challenge indicating there was no non-specific immunity induced by the adjuvant. By comparison, only three mice

TABLE 5

Experimental Design.

| Groups | Mice | Vaccine | Antigen (ug) | Adjuvant | Vaccine Volume (ul) | # Vaccines | Vaccine Route |
|---|---|---|---|---|---|---|---|
| 1 | 10 | Naïve | None | None | N/A | N/A | N/A |
| 2 | 15 | Placebo-1 | None | 50% IFA + 10 µg CpG + 2.5 µg MPLA | 100 | 3 | SC |
| 3 | 15 | Placebo-2 | None | 50% IFA | 100 | 3 | SC |
| 4 | 15 | 1571 Vaccine | 100 µg | 50% IFA | 100 | 3 | SC |
| 5 | 15 | 1748 Vaccine | 100 µg | 50% IFA | 100 | 3 | SC |
| 6 | 15 | Recombinant FecA, CirA, FepA and IutA | 20 µg each | 50% IFA + 10 µg CpG + 2.5 µg MPLA | 100 | 3 | SC |

Example 17

Vaccine Preparation and Vaccination

For vaccine preparation, 100 micrograms of the protein extracts derived from each of the *Klebsiella* strains 1571 and LM21 or 20 micrograms of each recombinant protein in phosphate buffered saline was formulated with their appropriate test adjuvant (see Table 5). Mice were immunized three times subcutaneously in the subscapular girdle with 0.1 ml of the appropriate vaccine at 14 day intervals. All mice were challenged 42 days post the second vaccination.

Example 18

Preparation of Challenge Organism

Figure 22:
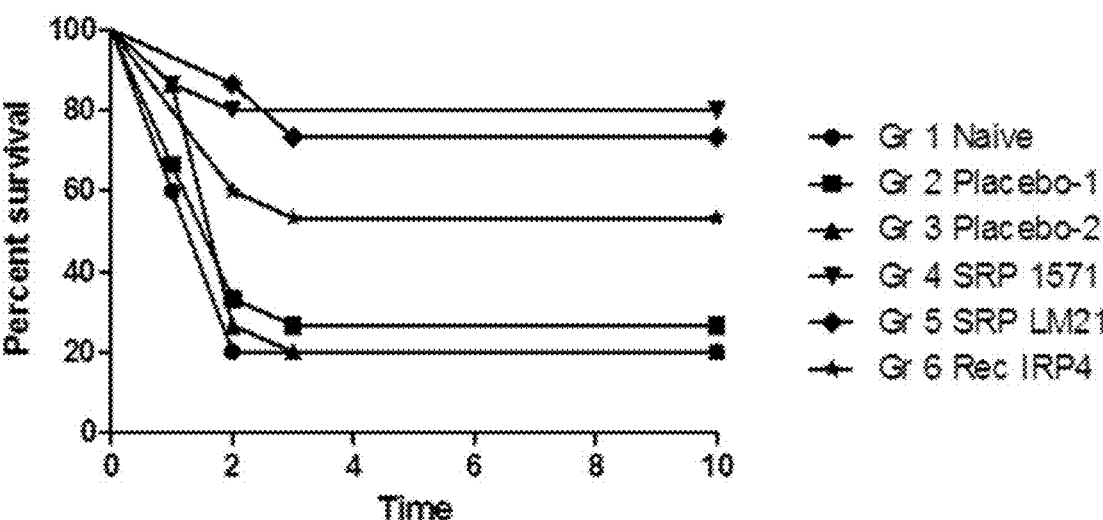
FIG. 22. Survival of mice after challenge with *Klebsiella pneumoniae* 1571.

The *Klebsiella pneumoniae* 1571 bacterial challenge isolate was prepared from a frozen stock described in Example 10. Briefly, the challenge isolate from the frozen stock was streaked onto a blood agar plate and incubated at 37° C. for 18 hours. A single colony was sub-cultured into 100 ml of Tryptic Soy Broth (Difco) containing 25 µg/ml 2,2' dipyridyl. The cultures were incubated at 37° C. for 6 hours while rotating at 200 rpm until an OD of 0.95-1.0 at 540 nm was reached at which point was centrifuged at 10,000×g for 10 minutes at 4° C. to pellet the bacteria. The bacterial pellet was washed once by centrifugation in physiological saline at 4° C. The final pellet was resuspended back to 100 ml in physiological saline and used for challenge. All mice were challenged intraperitoneally with $8.5 \times 10^7$ colony forming units of *Klebsiella pneumoniae* 1571 in a 0.1 ml volume.

died (80% survival) of Group 4 using the vaccine composition derived from *Klebsiella* 1571 (homologous to the challenge) (Table 6, FIG. 22). In comparison, only four mice died (74% survival) of Group 5 using the vaccine composition derived from *Klebsiella* 1748 (heterologous to the challenge) (Table 6, FIG. 22). These results clearly demonstrate that the vaccine composition prepared from *Klebsiella pneumonia* 1571 can provide protective immunity against a homologous and heterologous challenge or protection against multiple strains of *Klebsiella*.

In comparison, the vaccine composition of the recombinant proteins that were initially identified by MALDI and then cloned, expressed, and purified from *E. coli* including FecA, CirA, FepA and IutA also induced a significant degree of protection against the challenge. Fifty three percent (53%) of the mice vaccinated with the recombinant proteins (tested at a single dose of 20 µg of each protein) survived the challenge. It is expected that a higher concentration (e.g., a microgram dose) of the recombinant proteins would result in equivalent protection as compared to the extracted protein groups. In addition, the amount of endotoxin in this composition was less than 100 EU per dose. Taking this into consideration one could state that the LPS did not provide protection based on the presence of somatic antigens, since the somatic antigens that may contaminate the vaccine composition were derived from *E. coli* and not *Klebsiella*. Based on this information and the heterologous nature of the challenge strain, one can conclude that the degree of protection was due to the recombinant proteins in the vaccine composition.

TABLE 6

| Total Mortality and Percent Livability following *Klebsiella* 1571 Challenge | | | | | | | | | | | | |
|---|---|---|---|---|---|---|---|---|---|---|---|---|
| Treatments | Mortality-Days Post Challenge | | | | | | | | | | Total | Percent |
| Groups 1-6 | 1 | 2 | 3 | 4 | 5 | 6 | 7 | 8 | 9 | 10 | Mortality | Mortality (%) |
| 1) Naïve Control | 4 | 4 | 0 | 0 | 0 | 0 | 0 | 0 | 0 | 0 | 8 | 80 |
| 2) Placebo-1 Adjuvanted | 5 | 5 | 1 | 0 | 0 | 0 | 0 | 0 | 0 | 0 | 11 | 73 |
| 3 Placebo-2 Adjuvanted | 2 | 9 | 1 | 0 | 0 | 0 | 0 | 0 | 0 | 0 | 12 | 80 |
| 4) 1571 Vaccine | 2 | 1 | 0 | 0 | 0 | 0 | 0 | 0 | 0 | 0 | 3 | 20 |
| 5) LM21 vaccine | 0 | 2 | 2 | 0 | 0 | 0 | 0 | 0 | 0 | 0 | 4 | 26 |
| 6) Recombinant FecA, CirA, FepA and IutA (IRP4) | 0 | 6 | 1 | 0 | 0 | 0 | 0 | 0 | 0 | 0 | 7 | 47 |

Example 20

The Efficacy of Metal-Regulated Proteins Derived from *Klebsiella pneumonia* 1571 Against an Intramammary Challenge in Holstein Heifers Mastitis is the inflammation of the mammary gland and udder tissue, and is a major endemic disease of dairy cattle. It usually occurs as an immune response to bacterial invasion of the teat canal by variety of bacterial species such as *Klebsiella*. In this experimental study a subunit vaccine including metal-regulated proteins derived from *Klebsiella pneumonia* 1571 was used to evaluate the efficacy against a live intermammary challenge in Holstein heifers. The study parameters used for establishing vaccine efficacy between vaccinated and non-vaccinated placebo controls of this experimental study were 1) quantitative clearance following intramammary challenge, 2) somatic cell count, 3) serological response to vaccination, 4) quality of milk, 5) rectal temperature and 6) udder inflammation post challenge.

Example 21

Vaccine Preparation

The vaccine composition made from *Klebsiella pneumoniae* 1571 as described in Example 5 included polypeptides having molecular weights of 87 kDa, 82 kDa, 78 kDa, 72 kDa, 68 kDa, 35 kDa, and 33 kDa as determined by SDS-PAGE. The immunizing composition derived from strain 1571 was used to prepare the experimental vaccine by emulsifying the extracted protein suspension (600 µg total protein per milliliter) into a commercial adjuvant (EMULSIGEN, MVP Laboratories, Ralston Nebr.) using an IKA Process Pilot 2000/4-DR (TKA, Cincinnati, Ohio) to give a final dose of 1,200 µg total protein in a 2.0 ml injectable volume with an adjuvant concentration of 22.5% vol/vol. A placebo vaccine was prepared by substituting physiological saline for the aqueous protein suspension in the above protocol.

Example 22

Experimental Design and Herd Vaccination

Eight Holstein heifers at approximately 60-days precalving were randomly allocated to two groups consisting of 4 heifers per group. Heifers were identified by ear tags and left to co-mingle with approximately 500 cows on a large commercial dairy. Heifers in group-1 served as placebo controls while heifers in group-2 were vaccinated with the *Klebsiella pneumonia* 1571 vaccine composition of Example 21. Heifers were vaccinated subcutaneously in the upper right shoulder two times at 21 day intervals with 2 ml of the placebo and/or the *Klebsiella* pneumoniae 1571 vaccine. Heifers were fed twice daily a total mixed ration appropriate for their stage of production. All heifers had as libitum access to water during the study.

Blood was taken at the time of first vaccination, the second vaccination, and again two weeks post second vaccination. All blood was collected in sterile 13×75 millimeter (mm) VACUTAINER collection tubes, brand SST No. 369783, (Becton Dickinson, Franklin Lakes, N.J.). After clotting, the blood tubes were centrifuged at 800×g for 30 minutes and frozen at −80° C. until analysis. At approximately thirty days post-calving heifers were transported to a separate facility for intramammary challenge.

Example 23

Selection of Nalidixic Acid Resistance in *Klebsiella pneumonia* 1571

The *Klebsiella pneumoniae* 1571 isolate of Example 1 was made Nalidixic Acid resistant. Inducing resistance to a known antibiotic in the challenge strain aids in differentiation of the challenge strain from other *Klebsiella* strains that may contaminate challenged samples due to its prevalence in the environment. To induce antibiotic resistance the *Klebsiella* 1571 strain was grown in increasing concentrations of Nalidixic Acid. Briefly, two 1.0 liter stock solutions of TSB containing 35 gm Tryptic Soy, 5 gm yeast extract, and 2,2-dipyridyl at 25 µg was prepared and autoclaved for 30 minutes and then cooled to 4° C. Nalidixic acid was added to one of the 1 liter TSB stock solutions by membrane filtration through a 0.2 u filter to a final concentration of 150 µg/ml. The TSB now containing 150 µg Nalidixic acid was diluted in 20 ml stocks (50 ml Conical tubes) solution using the TSB without Nalidixic as the diluent to obtain the following concentrations; 0 (no Nalidixic acid), 25 µg/ml, 50 µg/ml, 75 µg/ml, 100 µg/ml, and non-diluted 150 µg.

The *Klebsiella* 1571 isolate of Example 1 was removed from frozen storage, plated onto Blood agar, and incubated at 37° C. for 24 hours at which point a single colony was picked and aseptically inoculated into one of the non-Nalidixic Acid TSB tubes and incubated for 3 hours at 37° C. while stirring at 200 rpm. At three hours post inoculation 2 ml of the culture was transferred into 20 ml of the 25 µg Nalidixic Acid tube that was pre-warmed to 37° C. The culture was allowed to grow at 37° C. while rapidly stirring at 200 rpm for 3 hours. This process was repeated two times and then transferred to the next concentration of Nalidixic Acid. If growth did not occur, the process was repeated in the previous concentration and then transferred to the next increasing concentration. This was done for each concentration until growth was established at the highest concentration of Nalidixic Acid. Once growth was established at the 150 μg/ml level, the culture was then plated onto EMB containing 150 μg/ml Nalidixic Acid. A single colony of the isolate was selected and transferred into 100 ml TSB containing 150 μg/ml Nalidixic acid (media as described above). The culture was allowed to grow at 37° C. for 4.5 hours or until an OD of 1.0 at 540 nm was achieved. The culture was then centrifuged at 8000 rpm for 20 minutes at which point the supernatant was discarded and the pellet re-suspended in 90 ml of TSB media as described above but containing 20% glycerol and 25 μg/ml 2,2-dipyridyl. One ml aliquots of the bacterial suspension was dispensed into 2 ml cryovials and stored at −90° C. until use.

Example 24

Intramammary Challenge with *Klebsiella pneumonia* 1571

Prior to challenge milk samples from all four quarters of each heifer were collected and bacteriological analysis was conducted to determine that no quarter was infected. On the day of challenge the Nalidixic acid resistant strain of *Klebsiella* 1571 from the frozen stock of Example 23 was diluted in Phosphate Buffered Saline (PBS) pH 7.2 to a previously determined level to yield a challenge dose of 100 Colony Forming Units (CFU) in a 1.0 ml volume. Using a teat cannula all heifers were challenged in one quarter through the teat canal of each udder. The challenged dose was then squeezed up the teat and into the udder by hand. Heifers were monitored at each milking for their rectal temperature, quality of milk, and differences in inflammation of the udder. In addition, a milk sample was collected from the challenged quarter of each heifer for the determination of somatic cell count and enumeration of the challenge organism. Heifers were milked twice daily for 7 days post challenge at which point the study was terminated.

Results

Serological Response to Vaccination

The serological response to vaccination was monitored by ELISA. Each serum sample was run individually using the *Klebsiella* Pneumonia 1571 antigen as the capture molecule. Briefly, 96-well plates were coated with a 1:1,000 dilution of turkey sera from turkeys that had been hyperimmunized with the *Klebsiella* Pneumonia 1571 antigen. After coating, the plates were blocked with PVA/PBS and antigen from *Klebsiella* 1571 antigen was added to the wells and incubated. The antigen was then removed, plates washed, and a 1:1,000 dilution of the bovine sera to be evaluated was added to the plate in duplicate. Sera were removed and the plate was washed. Sheep anti-bovine conjugate was added to the plate at a 1:20,000 dilution and incubated. Conjugate was removed from the plate. The plate was washed, and substrate was added for color development which was subsequently read with a spectrophotometer. For S/P calculations, average signal from the negative control sera was subtracted from all OD values. For samples being evaluated, the average OD of the sample was divided by the average positive control sample OD.

Figure 23:
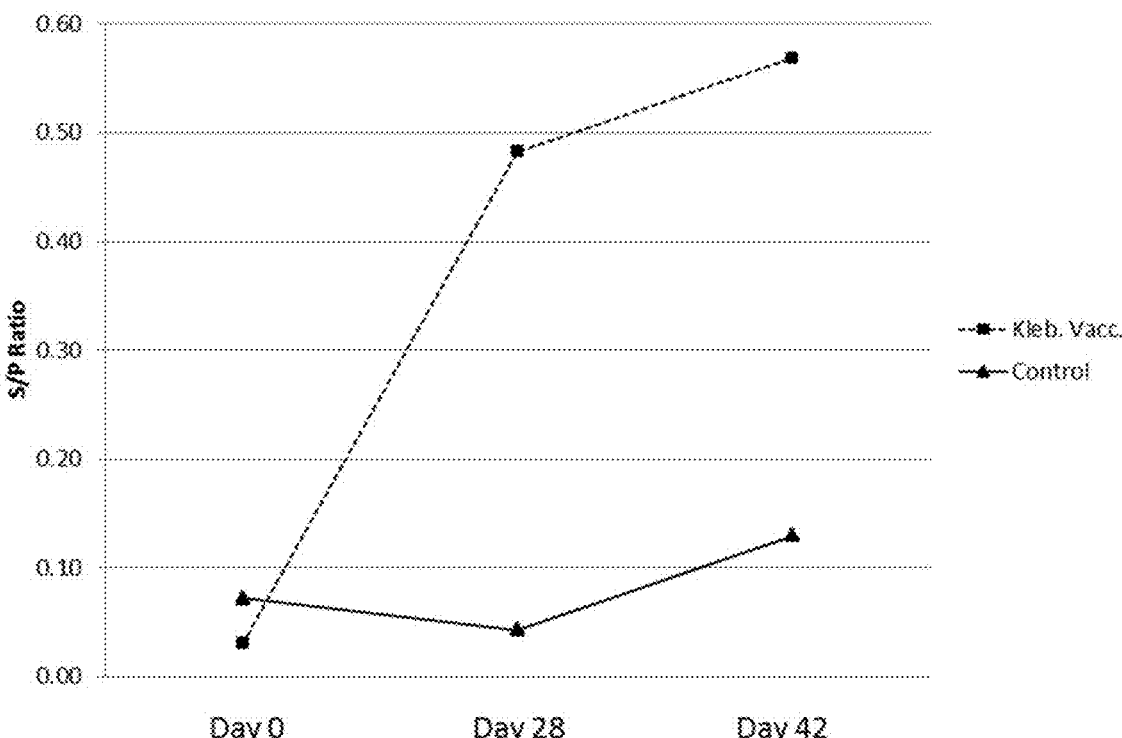
FIG. 23. Serological response of Heifers vaccinated with *Klebsiella pneumoniae* 1571 vaccine measured by ELISA.

FIG. 23 shows the serological response of heifers vaccinated with the *Klebsiella* Pneumonia 1571 vaccine composition. All heifers vaccinated showed an antibody response 21 days after the first vaccination in contrast to the placebo controls. This was followed by an anamnestic response with an increase in antibody 21 day after the second vaccination.

Figure 24:
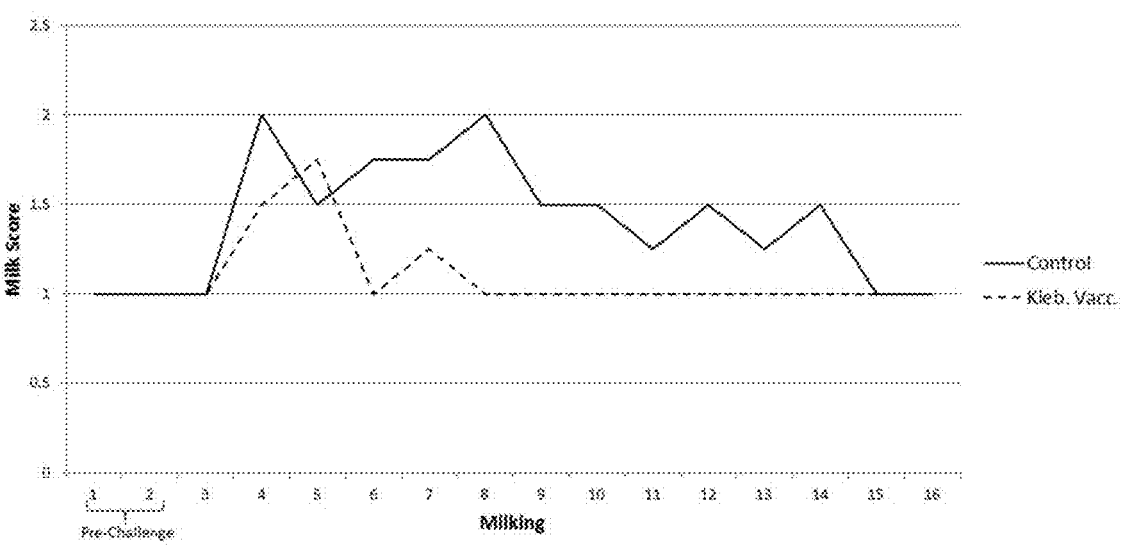
FIG. 24. Milk score of heifers vaccinated with *Klebsiella pneumoniae* 1571 vaccine versus controls following challenge with *K. pneumoniae*. Cumulative milk score after challenge with *Klebsiella pneumoniae* 1571. Difference in cumulative milk score between *Klebsiella pneumoniae* 1571 vaccinates and controls after challenge with *K. pneumoniae*.

Mastitis caused by *Klebsiella pneumonia* in the dairy industry is often responsible for a loss in milk quality often seen as abnormal milk. For example, cows with mastitis can often have milk that includes flakes, small slugs, large clots, or has a stringy watery consistency. These characteristics are indicative of clinical mastitis. FIG. 24 shows the milk score for each heifer over a period of 16 days. A score of 1 is normal, 2 refers to the presence of flakes, 3 refers to the presence of small slugs, 4 refers to the presence of large slugs or clots, and 5 refers to a consistency that is stringy or watery. The results illustrate that vaccinating with the *Klebsiella pneumonia* 1571 composition improved the overall quantitative measure of milk quality. Vaccination statistically improved milk quality over the non-vaccinated controls (p=0.042). This is a direct correlation to a decrease in Mastitis, as all four non-vaccinated controls developed clinical mastitis following challenge while only two of the vaccinated heifers met the definition of mastitis. The presence of mastitis was significantly reduced in vaccinates versus controls (p=0.046).

Figure 25:
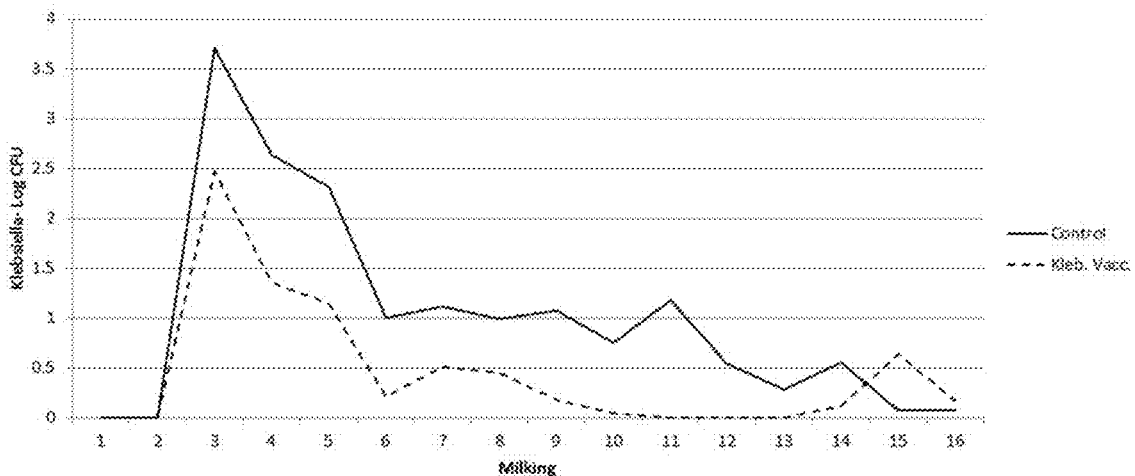
FIG. 25. Difference in quantitative clearance of *Klebsiella pneumoniae* 1571 between vaccinates and controls after homologous challenge.

At 30-days post calving heifers were intramammarily challenged through the teat canal with a 100 CFU of *Klebsiella pneumonia* 1571. Heifers were milked twice daily for 7 consecutive days post challenge. Milk samples from the challenged quarters was collected and frozen at −90° C. until enumerated. FIG. 25 shows the difference in the prevalence of the challenge organism in milk samples between vaccinates and the placebo controls for 2 samplings pre-challenge, and 14 consecutive samplings post challenge (i.e., two samplings per day for 7 consecutive days). There was a significant decrease in the amount of *Klebsiella* being shed in the milk derived from the infected udder of vaccinated heifers compared to controls. Averaged across the study period, the vaccinated heifers had only 15 positive *Klebsiella* milk samples out of 56 sampled or 27%. In contrast; the number of positive *Klebsiella* milk samples in the placebo controls was 64% or 36 positive out of 56 sampled.

Example 25

Evaluation of a Vaccine Composition Derived from *Klebsiella pneumoniae* in a Chronically Infected Dairy Herd A commercial dairy herd having a history of chronic mastitis attributable to *Klebsiella pneumonia* was chosen for the evaluation of a vaccine composition as described in Example 5. The criterion for establishing vaccine efficacy of this experimental study was based on an estimated prevented fraction with a 95% confidence interval of the following: 1) reduction of the prevalence and incidence of clinical mastitis caused by *Klebsiella pneumoniae* among *Klebsiella* vaccinates compared to placebo controls, 2) reduction of the prevalence and incidence of coliform mastitis among *Klebsiella* vaccinates compared to placebo controls, 3) improvement (i.e., a decrease) in somatic cell count among *Klebsiella* vaccinates compared to placebo controls and 4) improvement (i.e., an increase) in milk production among *Klebsiella* vaccinates and placebo controls.

Example 26

Vaccine Preparation

The vaccine composition made from *Klebsiella pneumoniae* 1571 as described in Example 5 included polypeptides having molecular weights of 87 kDa, 82 kDa, 78 kDa, 72 kDa, 68 kDa, 35 kDa, and 33 kDa as determined by SDS-PAGE. The immunizing composition derived from strain 1571 was used to prepare the experimental vaccine by emulsifying the extracted protein suspension (600 μg total protein per milliliter) into a commercial adjuvant (EMUL-SIGEN, MVP Laboratories, Ralston Nebr.) using an IKA Process Pilot 2000/4-DR (TKA, Cincinnati, Ohio) to give a final dose of 1,200 µg total protein in a 2.0 ml injectable volume with an adjuvant concentration of 22.5% vol/vol. A placebo vaccine was prepared by substituting physiological saline for the aqueous protein suspension in the above protocol.

Example 27

Experimental Design and Herd Vaccination

The study was conducted as a confirmatory, randomized, blinded, and placebo-controlled efficacy study of controlling *Klebsiella pneumoniae*. A total of 569 head of Holstein or jersey cows and heifers were enrolled in the study. The cows were housed in a single free-stall barn except when they were in their dry period. During the dry period, they were moved to a designated dry-cow barn. Heifers were in a heifer barn until close to calving at which point they were moved to the free-stall barn to join the milking herd. Cows were randomized to receive either the *Klebsiella pneumoniae* 1571 vaccine, or the placebo vaccine containing adjuvant only. Cows and heifers were injected subcutaneously with 2 ml on the day of enrollment, with a second dose administered 3 weeks later. With the exception of cows close to dry-off and cows close to calving, a whole-herd vaccination regimen was done to initiate the study followed by a booster dose 3 weeks later. A dry-cow protocol was set up to vaccinate all cows and heifers with 2 doses of vaccine, 3-4 weeks apart, once they achieved 217 days carrying calf (DCC). The experimental design is summarized in Table 7.

the known positive control sera (hyper-immunized sera of Example 7). These positive control wells served purposes of 1) internal plate control to ensure a valid test and 2) a means of calculating sera titers. Titer was defined as the point at which a sample's dilution curve intercepted 50% of the mean OD value of the positive control wells on the plate. Computer software was used to determine the intercept point to generate and report a calculated titer value for each serum sample tested on the plate.

Figure 26:
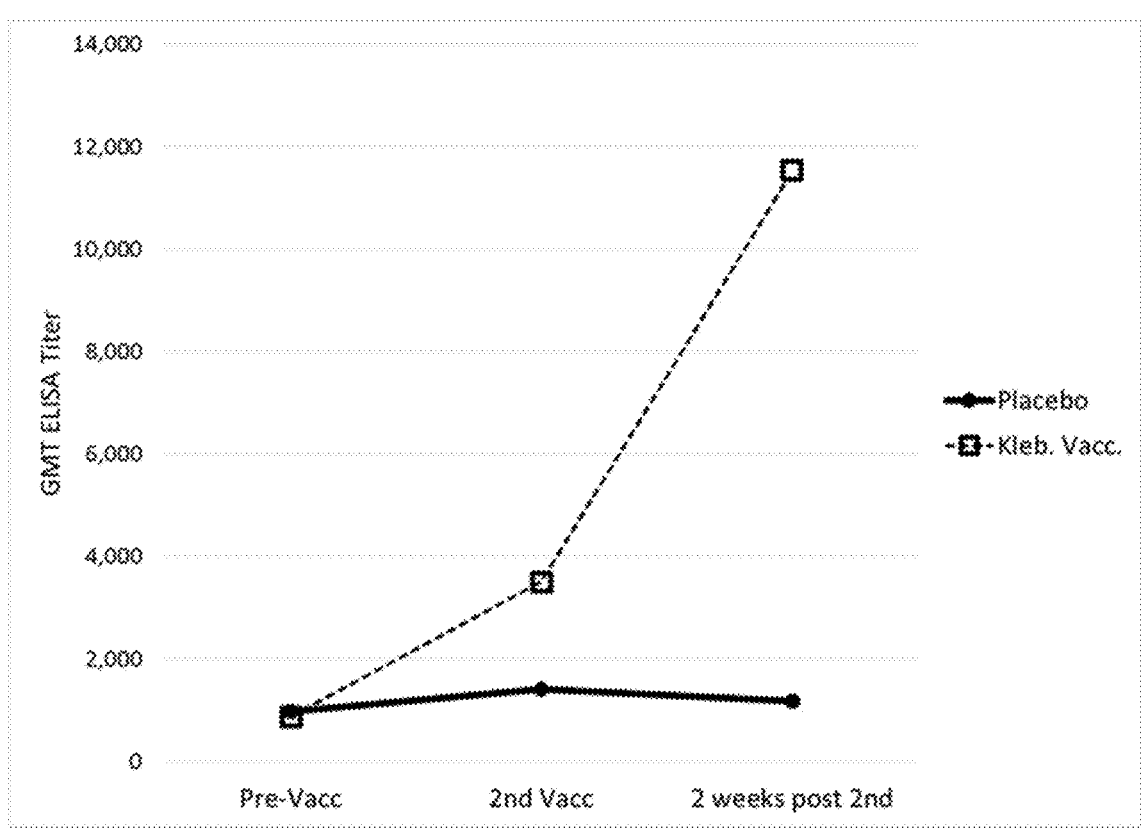
FIG. 26. ELISA serological response of cows vaccinated with the *Klebsiella pneumoniae* 1571 vaccine compared to placebo control cows.

Antibodies against the vaccine polypeptides was detectable in the *Klebsiella* pneumoniae 1571 vaccinates following one dose of vaccine and significantly increased after the second dose (FIG. 26). It is interesting to note that this dairy was chronically infected with *Klebsiella pneumoniae* resulting in continuous mortality through natural exposure. However this exposure did not induce immunity to metal-regulated proteins even though these proteins would have been expressed on the surface of the bacteria under natural field conditions and during infection. It was not until the cows were vaccinated with a vaccine composition of metal-regulated proteins prepared that an adaptive immune response was generated these target immunogens. This can be seen in FIG. 26, where the non-vaccinated animals show no antibody response even though they are continuously exposed to *Klebsiella pneumonia*, in contrast to those that have been vaccinated or primed to recognize the target immunogens in the vaccine composition.

The sera from Example 25 were analyzed by Western Blot to determine what proteins from the vaccine formulation were recognized. Western analysis was done using the WES Capillary Electrophoresis system (Protein Simple, San Jose,

TABLE 7

Summary of Animals in the Study

| | | Initiation | Month of Study | | | | | | | | | | |
|---|---|---|---|---|---|---|---|---|---|---|---|---|---|
| | | | 1 | 2 | 3 | 4 | 5 | 6 | 7 | 8 | 9 | 10 | Total |
| A | Controls | 165 | 47 | 15 | 7 | 4 | 5 | 6 | 10 | 5 | 10 | 7 | 281 |
| B | Vaccinates | 160 | 51 | 18 | 7 | 4 | 8 | 6 | 9 | 6 | 10 | 9 | 288 |
| C | Controls | | -4 | 0 | -3 | -3 | -4 | -8 | -10 | -5 | -6 | -4 | -47 |
| D | Vaccinates | | -2 | -1 | -6 | -9 | -3 | -11 | -8 | -2 | -5 | -1 | -48 |
| E | Controls | 165 | 208 | 223 | 227 | 228 | 229 | 227 | 227 | 227 | 231 | 234 | |
| F | Vaccinates | 160 | 209 | 226 | 227 | 222 | 227 | 222 | 223 | 227 | 232 | 240 | |

Table shows the number of animals enrolled and removed each month by treatment group. Rows A & B show original cows vaccinated and additional cows/heifers enrolled each month. Rows C & D shows the number of cows that died or were culled each month. Rows E & F show the total number of animals in the study each month (i.e., number of animals from the previous month minus animals removed each month, plus new animals enrolled each month).

Results

The serological response of each cow to vaccination was measured by an enzyme-linked immunosorbent assay (ELISA). Twenty cows from each group were randomly selected to assess the serological response following vaccination to the *Klebsiella pneumonia* 1571 composition compared to the placebo controls. Cows were bled and their serum harvested at the time of first vaccination, time of second vaccination, and two weeks after their second vaccination. Sera was frozen and stored until analysis by an enzyme-linked immunosorbent assay (ELISA).

Figure 27:
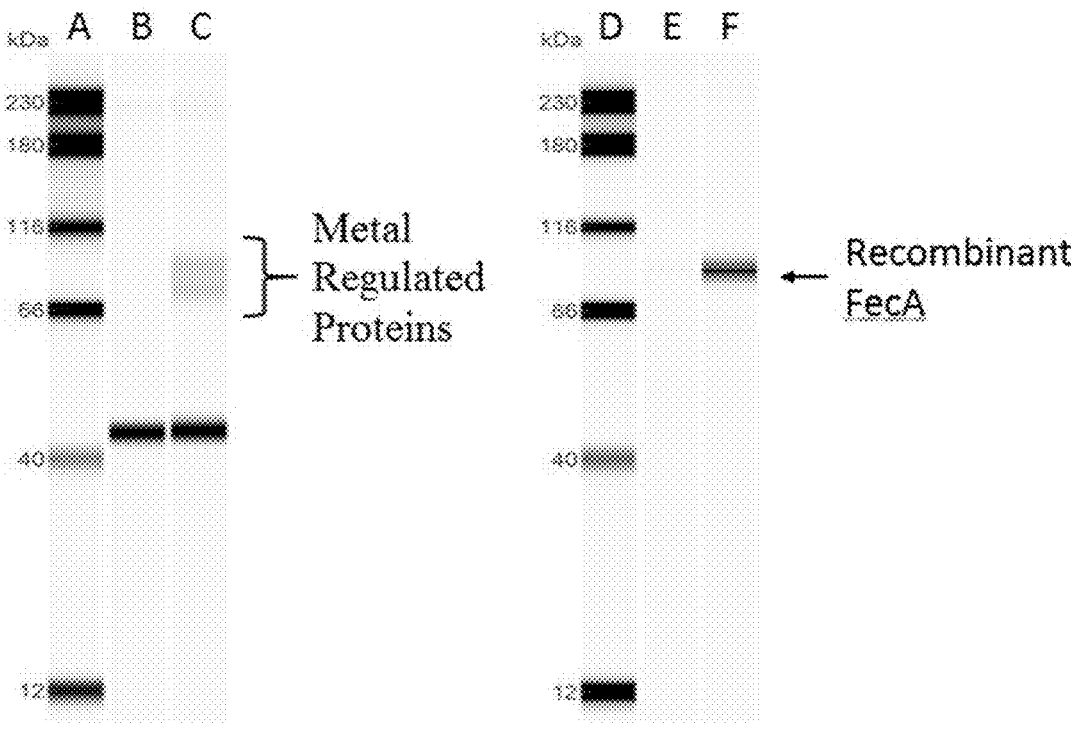
FIG. 27. Western blot using Protein Simple Capillary Electrophoresis System. Sample A, Molecular Weight Marker; Sample B, *Klebsiella pneumonia* 1571 vaccine antigen blotted with placebo sera; Sample C, *Klebsiella pneumonia* 1571 vaccine antigen blotted with sera from *Klebsiella pneumoniae* 1571 vaccinated cows; Sample D, Molecular Weight Marker; Sample E, recombinant FecA blotted with placebo sera; Sample F, recombinant FecA blotted with sera from *Klebsiella pneumoniae* 1571 vaccinated cows.

Ninety-six (96) well polystyrene plates were coated with *Klebsiella pneumoniae* 1571 polypeptides as the target antigens. The polypeptides had molecular weights of 87 kDa, 82 kDa, 78 kDa, 72 kDa, 68 kDa, 35 kDa, and 33 kDa as determined by SDS-PAGE. Each serum sample was diluted 4-fold from 1:400 to 1:409,600 and tested in duplicate. Each test plate contained two wells of a target dilution (1:400) of CA). Sera from cows vaccinated with the purified polypeptides reacted with the metal regulated proteins in the vaccine composition, whereas sera from cows vaccinated with placebo did not. In addition, cows vaccinated with the purified polypeptides reacted with the recombinant protein FecA, but the sera from placebo vaccinated cows did not (FIG. 27). These data confirm that the vaccine contained the metal-regulated protein FecA. Also, these data confirm that natural infections with *Klebsiella pneumoniae* fail to induce a strong immune response to these proteins.

Cows from Example 27 were milked three times per day and monitored for clinical signs of mastitis such as swollen udders, milk color change, flaky or clumpy milk, etc. In addition, a daily list of cows with a drop in milk production from normal levels was provided to the herdsmen by the farm manager as an extra alert to check for mastitis. If a cow was suspected of having mastitis, two duplicate, but independent milk samples were aseptically collected according to the recommended practices of the National Mastitis Council in case the first sample was contaminated (isolation of >2 organisms) the second sample can be tested.

Milk samples were submitted to the Veterinary Diagnostic Laboratory to determine the causative agent for the mastitis event. Aerobic culture was completed by plating 10 μl on blood and MacConkey agar plates to determine presence and identification of mastitis pathogens including *Klebsiella* spp., and other coliforms including *E. coli* spp, *Enterobacter* spp., *Citrobacter* spp., and *Serratia* spp. Bacterial identification procedures were performed by the state diagnostic laboratory with confirmation of bacterial identification by MALDI-TOF for all isolates. Mastitis events occurring 2 or more weeks after the second vaccination were considered eligible events for the study.

There were 53 cases of clinical mastitis that were confirmed to be due to coliforms and 20 cases of *Klebsiella* mastitis in the cows at 1-90 days in milk for this study. This incidence was sufficient to judge vaccine efficacy.

Figure 28:
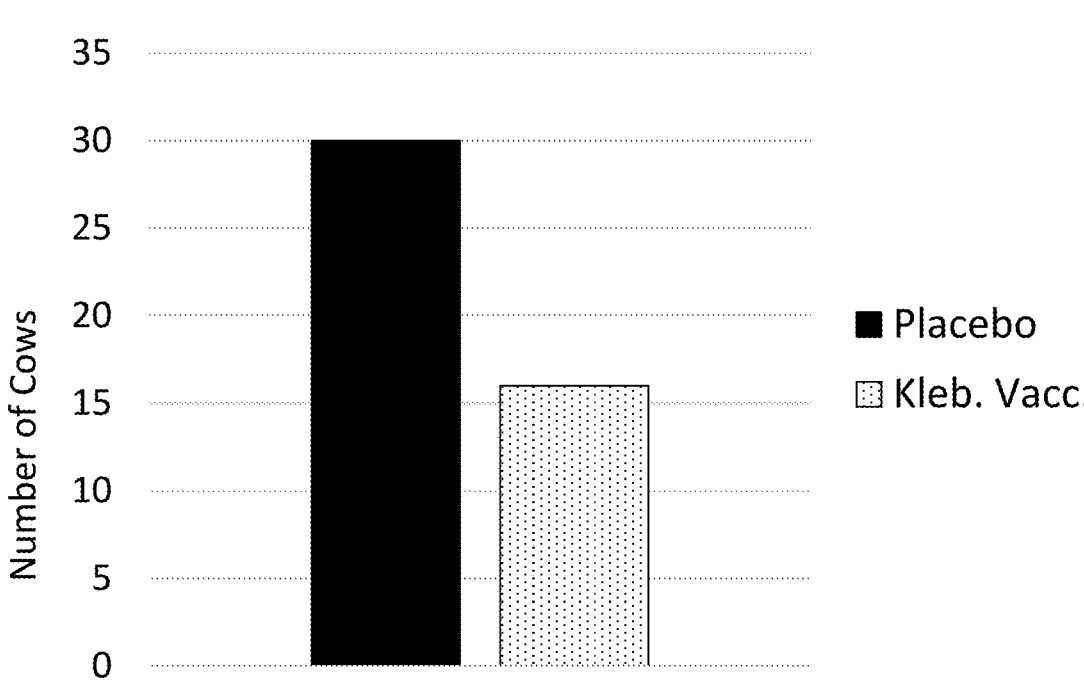
FIG. 28. Prevalence of coliform mastitis following vaccination with *Klebsiella pneumoniae* 1571 vaccine. Graph showing the number of cows 1-90 days in milk with clinical coliform mastitis in the placebo vaccinated group vs. the *Klebsiella pneumoniae* 1571 vaccinated group. Data provides a Prevented Fraction of 0.4667 (95% CI: 0.0494 to 0.7008); P=0.0305.

There were 46 cows that had coliform mastitis during their first 90 days in milk. The coliforms identified by culture of clinically-affected cows include *E. coli, Klebsiella, Enterobacter, Serratia* and *Citrobacter*. Thirty (30) of these cows were in the placebo group (out of 225), and 16 cows were in the *Klebsiella* Pneumoniae 1571 vaccine group (out of 225). The 47% reduction in the prevalence of coliform mastitis in the vaccinated cows was statistically significant (p=0.0305) (FIG. 28).

Figure 29:
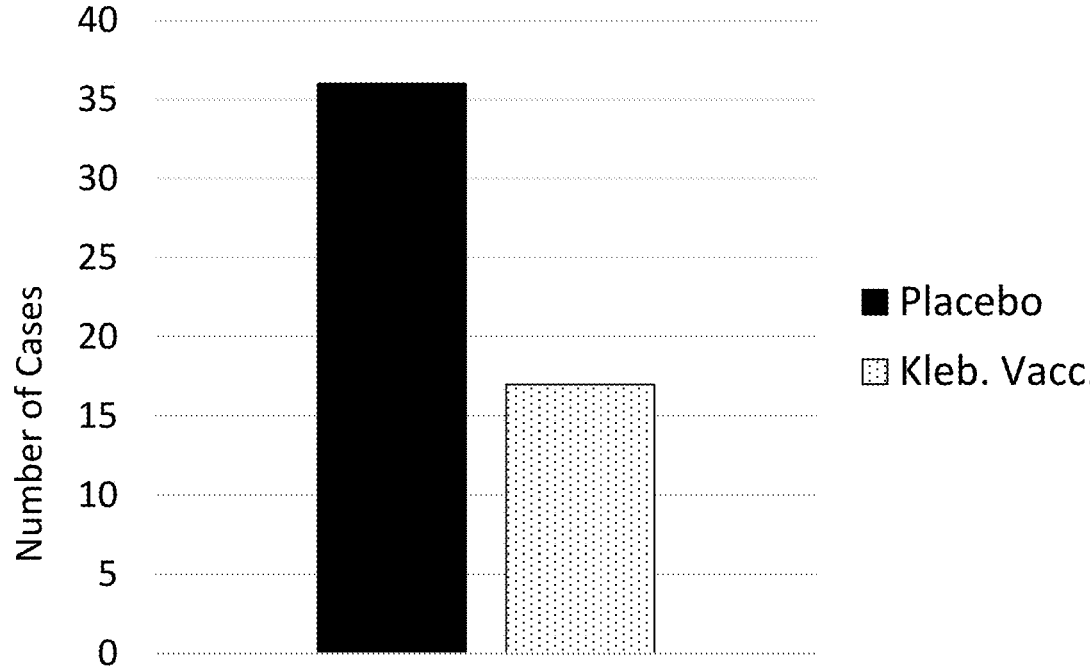
FIG. 29. Incidence of coliform mastitis following vaccination with *Klebsiella pneumoniae* 1571 vaccine. Graph showing the incidence of clinical coliform mastitis in the placebo vaccinated group vs. the *Klebsiella pneumoniae* 1571 vaccinated group. Data provides a Prevented Fraction of 0.5478 (95% CI: 0.1953 to 0.7549); P=0.0057.

There were 53 separate cases of coliform mastitis from cows 1-90 days in milk. Thirty-six (36) of these incidents were from cows in the placebo group, and 17 were from cows in the *Klebsiella* Pneumoniae 1571 vaccine group. The 55% reduction in the incidence of clinical mastitis in vaccinated cows was highly statistically significant (p=0.0057) (FIG. 29).

Figure 30:
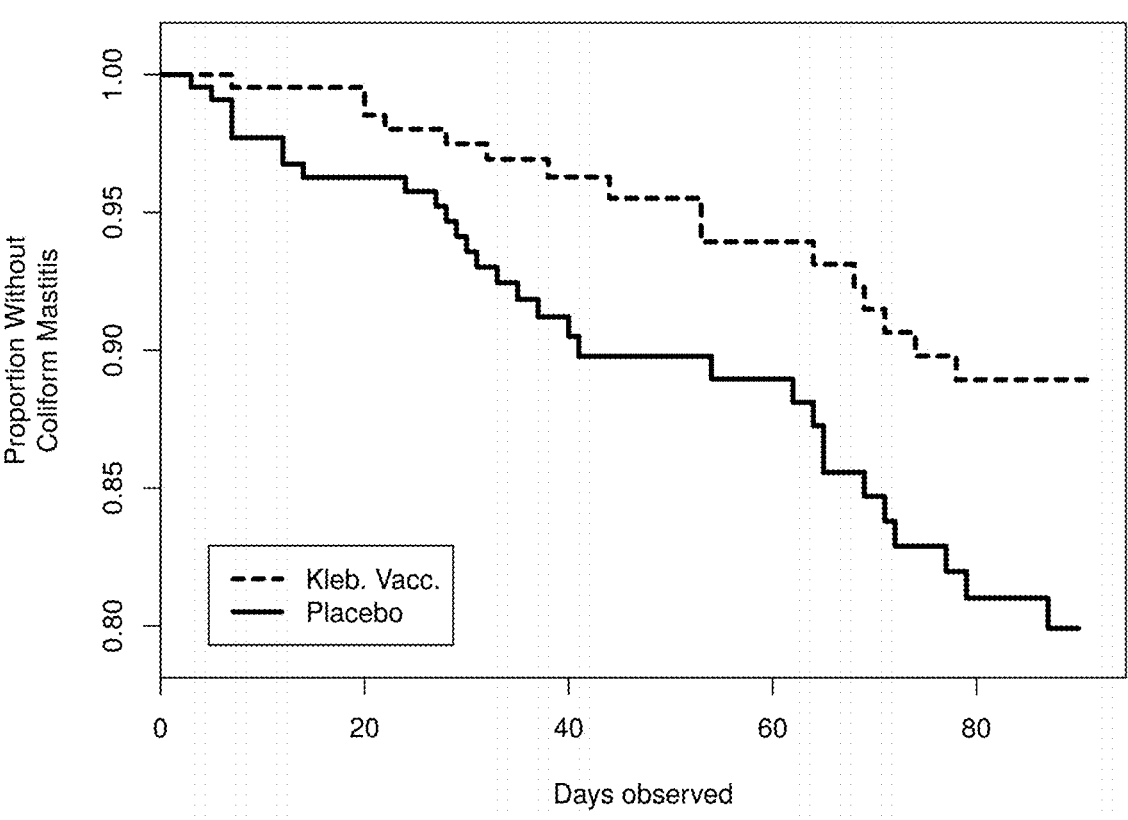
FIG. 30. Graph showings the proportion of cows without coliform mastitis over time. The estimate of the hazard ratio for mastitis caused by coliforms is 0.494 with a 95% confidence interval from 0.269 to 0.906. This suggests an approximately 50.6% decrease in the risk of mastitis from all coliform mastitis causing organisms and agrees with the significant p-value generated (p=0.02278). Each line represents the proportion of individuals that have not yet contracted Coliform mastitis. Each time the line drop represents an observed mastitis event.

With proper vaccine protection, the expectation of a dairy farm would be to see a high proportion of cows without coliform mastitis. FIG. 30 shows the proportion of cows without coliform mastitis over time and demonstrates cows in the Placebo group dropped at a faster rate (i.e., more cows with coliform mastitis) than the cows in the *Klebsiella* Pneumoniae 1571 vaccine group (p=0.02278).

The most common organism causing the coliform mastitis was *Klebsiella*, followed by *E. coli*. It was surprising to see this much coliform mastitis in a herd where cows were being vaccinated 4 times per lactation with a commercially available J5 vaccine. Bedding the cattle on dried manure solids may partly explain the high incidence. However, even in the face of the high challenge, cows vaccinated with the *Klebsiella pneumoniae* 1571 vaccine had significant protection versus cows vaccinated with placebo (FIGS. 28 and 29).

Another major problem with mastitis in the dairy industry are recurrent infections. While the actual costs of a single mastitis episode vary with cattle and milk prices, the economic losses from treatment costs, replacement costs and decreased saleable milk can be devastating. One study conducted in 1991 put the cost of one mastitis episode at $107/cow (Hoblet et al., 1991, J. Am Vet Med. Assoc., 199:190-196). These costs are of course amplified when there are recurrent infections in a single cow. In this study, recurrent infections occurred more often in the placebo group than in the *Klebsiella pneumoniae* 1571 vaccine group which can be seen in Table 8. Note how 9 cows in the placebo group had recurrent mastitis events with 5 cows having 3 or 4 recurrent infections. In comparison, only 4 cows in the vaccinated group had a single recurrence of mastitis during the monitoring period.

TABLE 8

| Number of cows with coliform mastitis during the first 90 Days In Milk that repeated with subsequent cases of coliform mastitis during the remainder of their lactation. | | | | | |
|---|---|---|---|---|---|
| | Total coliform | Number of cows with recurrent coliform mastitis | | | |
| | mastitis cows | 1 recurrence | 2 recurrences | 3 recurrences | 4 recurrences |
| Placebo | 30 | 2 | 2 | 4 | 1 |
| Kleb. Vacc. | 16 | 4 | 0 | 0 | 0 |

Figure 31:
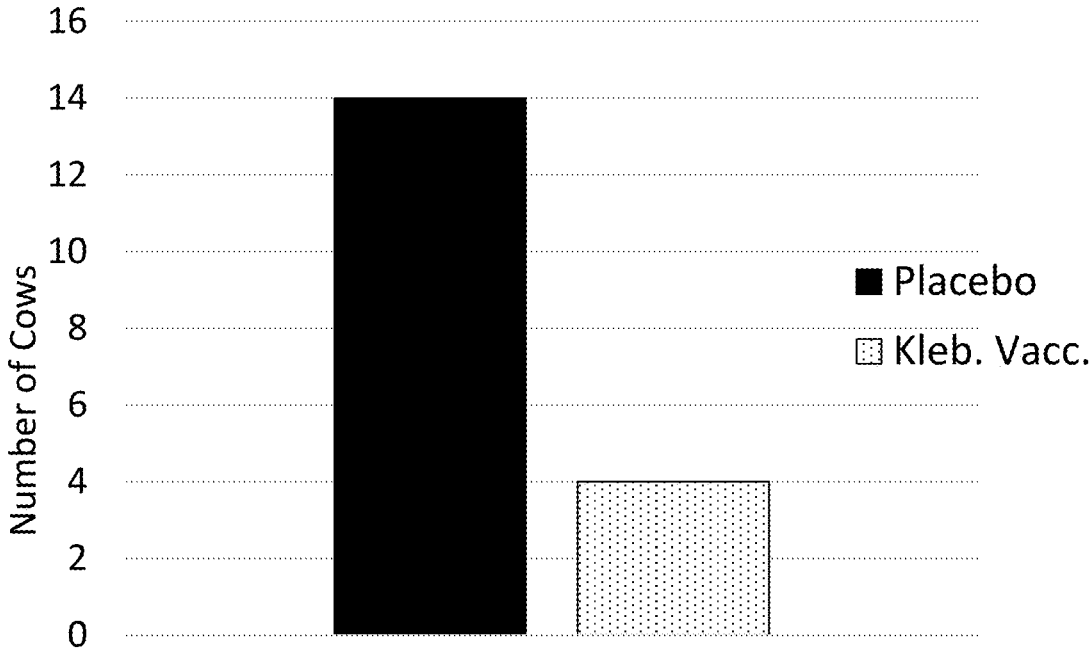
FIG. 31. Prevalence of *Klebsiella* mastitis following vaccination with *Klebsiella pneumoniae* 1571 vaccine. Graph showing the number of cows 1-90 days in milk with clinical *Klebsiella* mastitis in the placebo vaccinated group vs. the *Klebsiella pneumoniae* 1571 vaccinated group.

*Klebsiella* mastitis was the largest coliform problem in this herd. There were 18 cows that had *Klebsiella* mastitis during their first 90 days in milk. Fourteen (14) of these cows were in the placebo group (out of 225), and 4 cows were in the *Klebsiella* Pneumoniae 1571 vaccine group (out of 225) (FIG. 31). The 71% reduction in the prevalence of *Klebsiella* mastitis in the vaccinated group was highly statistically significant (p=0.0171). As mentioned previously, the experience of the ISU Dairy is that 60-80% of cows with *Klebsiella* mastitis leave the herd within that lactation. With only 4 cows diagnosed with clinical *Klebsiella* mastitis in the *Klebsiella* Pneumoniae 1571 vaccine group versus 14 cows in the placebo group, a predicted 6-8 more cows will be culled or die prior to the end of their lactation in the placebo group than the vaccinated group. Vaccination with the *Klebsiella* Pneumoniae 1571 vaccine reduces costs of mastitis episodes, including reducing culling.

Figure 33:
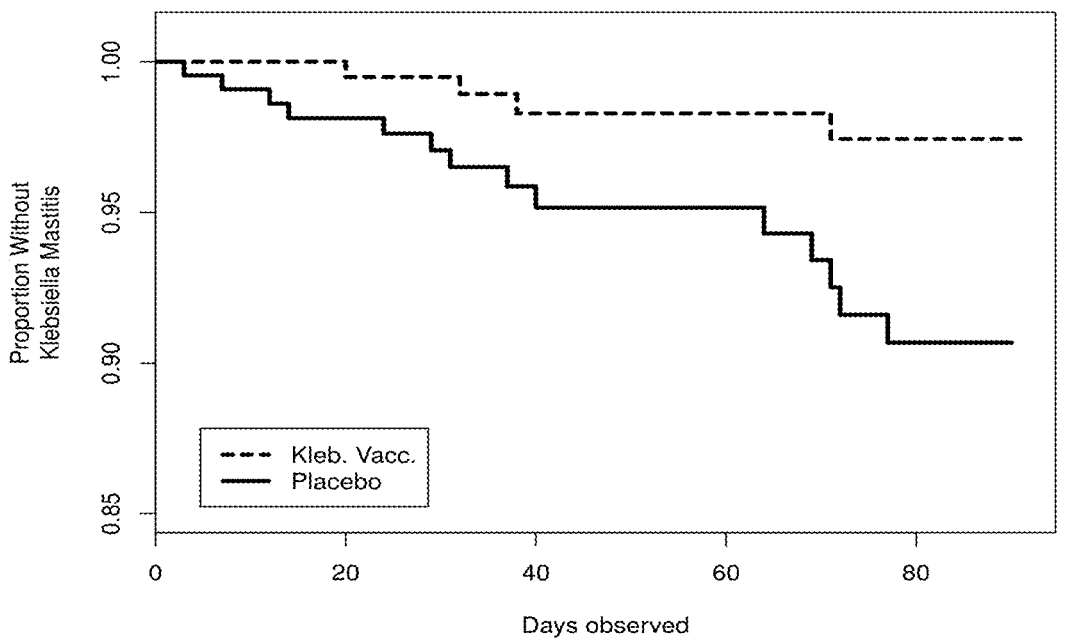
FIG. 33. Graph showing the proportion of cows without *Klebsiella* mastitis over time. The estimate of the hazard ratio for this *Klebsiella* data set is 0.272 with a 95% confidence interval from 0.089 to 0.825. This suggests an approximately 72.8% decrease in the risk of mastitis from *Klebsiella*, and agrees with the significant p-value generated (p=0.0215). Each line represents the proportion of individuals that have not yet contracted a qualifying mastitis. Each time the line drop represents an observed mastitis event.

With proper vaccine protection, the expectation of a dairy farm would be to see a high proportion of cows without *Klebsiella* mastitis. FIG. 33 shows the proportion of cows without *Klebsiella* mastitis over time and demonstrates cows in the Placebo group dropped at a faster rate (i.e., more cows with *Klebsiella* mastitis) than the cows in the *Klebsiella* Pneumoniae 1571 vaccine group (p=0.0215).

Figure 32:
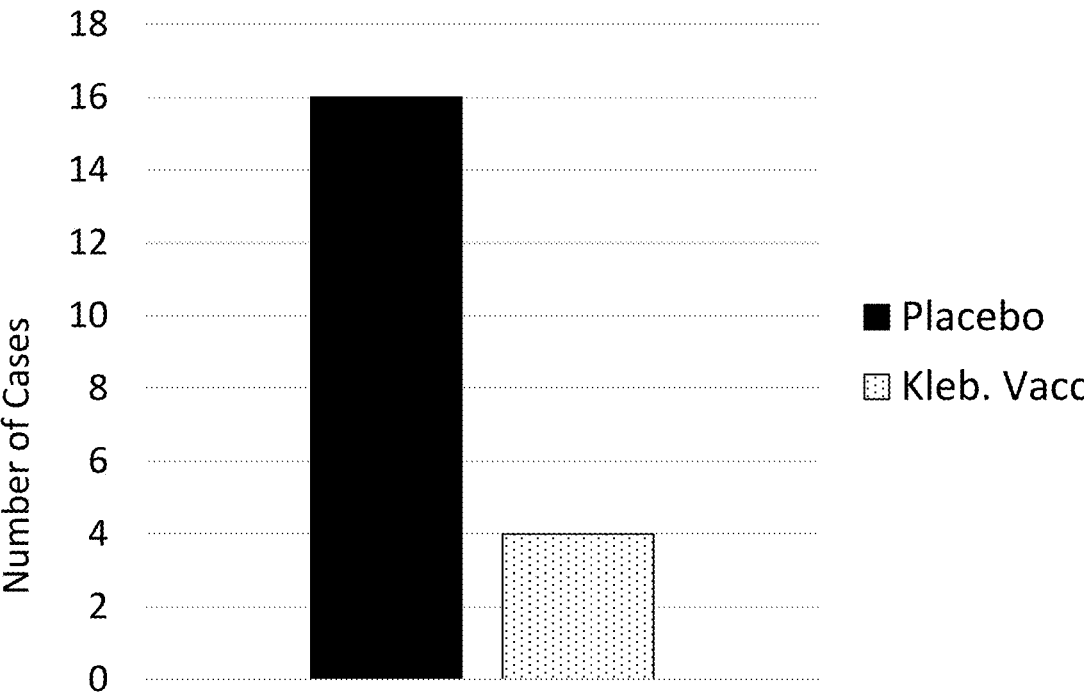
FIG. 32. Incidence of *Klebsiella* mastitis following vaccination with *Klebsiella pneumoniae* 1571 vaccine. Graph shows the number of cases of clinical *Klebsiella* mastitis from cows 1-90 days in milk in the placebo vaccinated group vs. the *Klebsiella pneumoniae* 1571 vaccinated group.

There were 20 separate cases of *Klebsiella* mastitis from cows 1-90 days in milk. Sixteen (16) of these incidents were from cows in the placebo group, where *Klebsiella* mastitis recurred in 2 cows during this short observation period. Only 4 cases of *Klebsiella* mastitis were observed in cows from the *Klebsiella* Pneumoniae 1571 vaccine vaccinated group and none of these animals had a recurrence during the observation period (FIG. 32). The 75% reduction of in the incidence of *Klebsiella* mastitis in the vaccinated cows was highly statistically significant (p=0.0056).

The cows were milked three times a day throughout the study and the pounds of milk produced was electronically recorded via software at the dairy. The cows were tested on approximately a monthly basis by the Dairy Herd Improvement Association (DHIA) and the somatic cell count in the milk for each cow was determined and recorded in Dairy Comp software.

Figure 34:
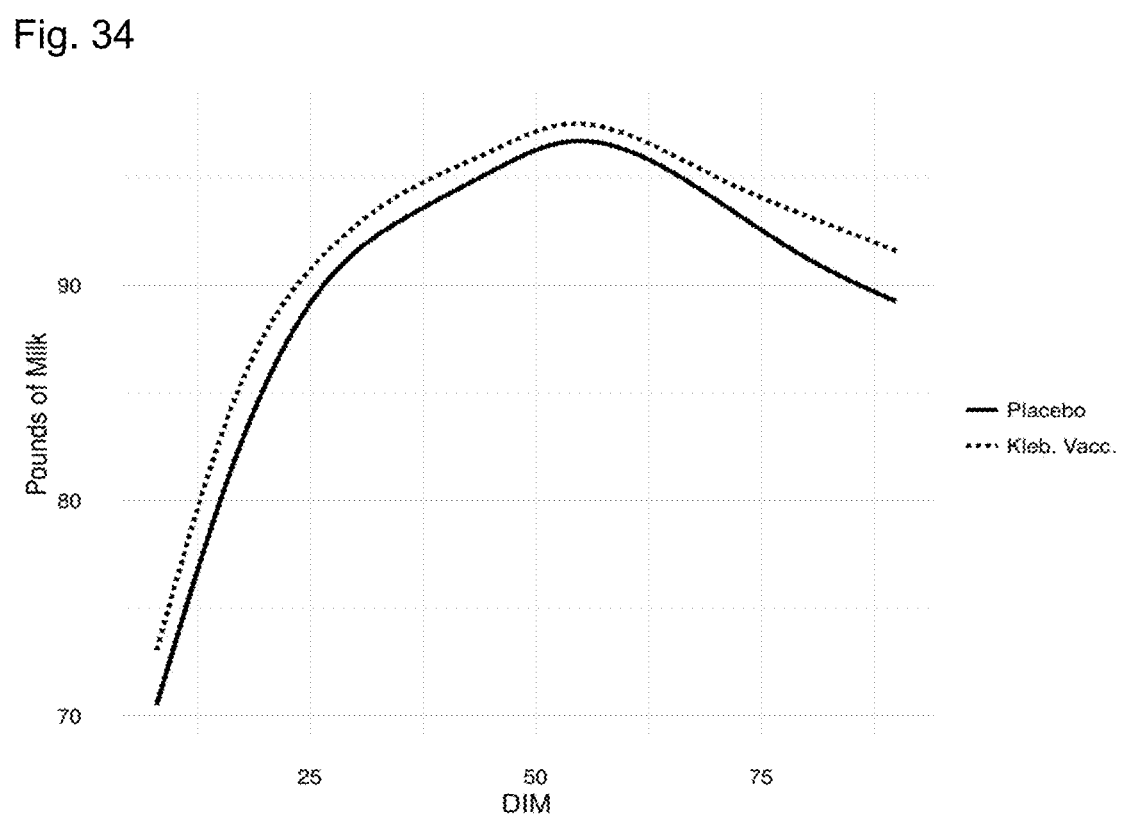

The amount of milk produced by a cow can be a useful indicator of overall health. It is well known in the dairy industry that clinical mastitis reduces milk production in affected cows (Grohn, et. al., 2004, J. Dairy Sci., 87:3358-3374; Pinzon-Sanchez et al., 2011, J. Dairy Sci., 94:1873-1892). In the present study, the *Klebsiella* Pneumoniae 1571 vaccinated cows averaged 2.0 pounds more milk per day than the placebo cows during the first 90 DIM. Over the 90 day period this amounts to a predicted 180 pounds of extra milk per cow, during a time when cows are expected to be in peak lactation. Typically, in the dairy industry each pound of milk increase at the time of peak milk yields an additional 200-250 pounds of milk in a typical 305 day lactation. Therefore, with a 2 pound increase in vaccinated cows at peak milk, this is predicted to yield an additional 400-500 pounds of milk in a typical 305 day lactation. A graph of the average pounds of milk produced per cow in this study up to 90 DIM is shown in FIG. 34.

Figure 35:
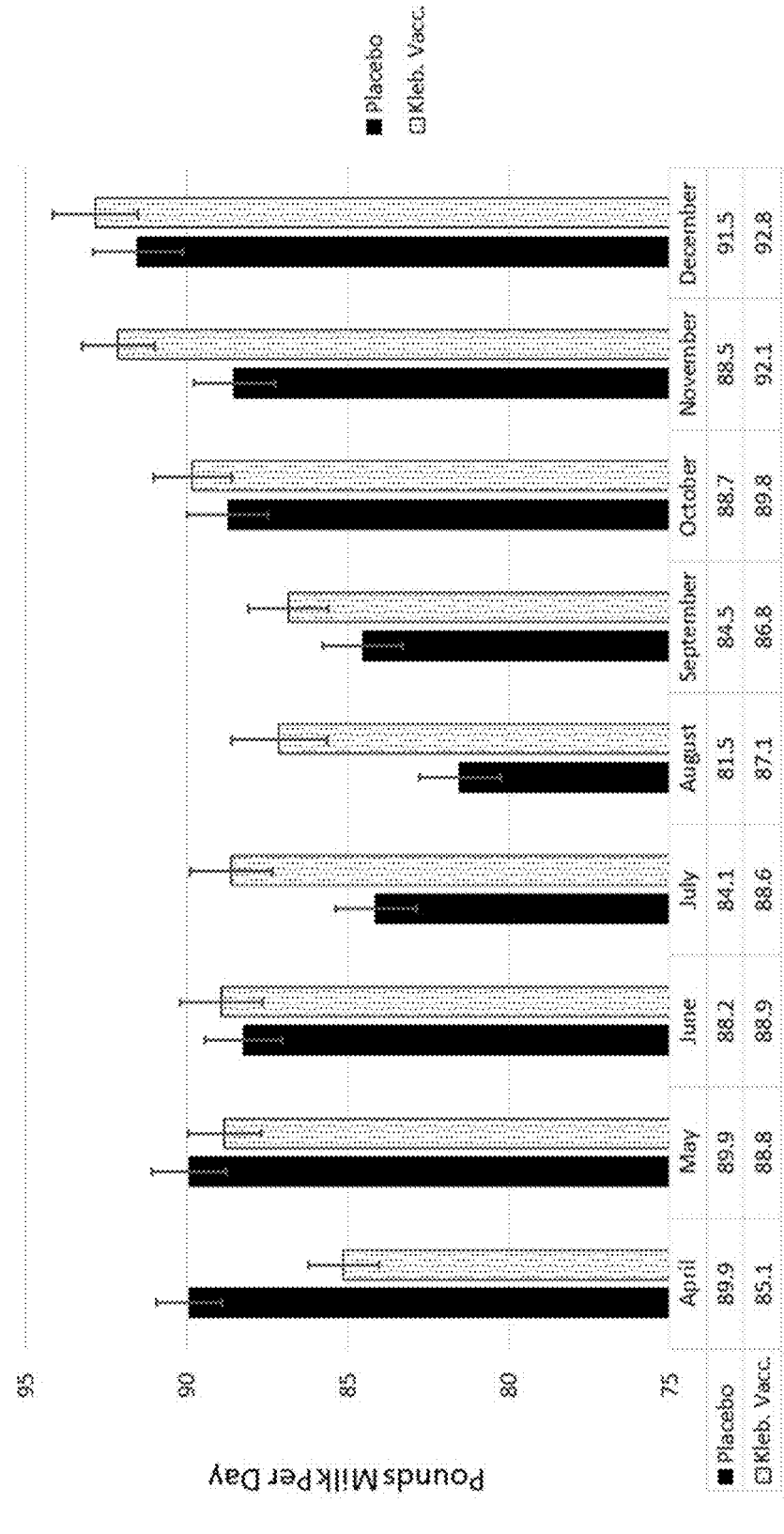
FIG. 35. Average daily milk production per cow from cows vaccinated with *Klebsiella pneumoniae* 1571 vaccine vs. placebo by month of the study. Error bars show 95% confidence interval.

The statistically significant increase in milk production by the *Klebsiella* Pneumoniae 1571 vaccinated cows (P=0.0000) is difficult to explain based solely on the differences in clinical mastitis between the two groups. A more detailed analysis of milk production differences by month (FIG. 35) shows the greatest differences in the summer months. Interestingly, summer conditions provide ideal conditions for coliforms to survive in manure and are associated with increased coliform infections.

Somatic cell counts (SCC) are routinely used to monitor milk quality and typically increase during clinical mastitis. In addition to clinical mastitis that was analyzed in this study, SCC is also a good indicator of sub-clinical mastitis. As mentioned in the milk results, it is surprising to see such a large increase in milk production from clinical mastitis alone. Therefore, SCC was used as an independent indicator of mammary health in the study animals. In this study, somatic cell counts were reduced in the *Klebsiella pneumoniae* 1571 vaccinated cows compared to placebo cows. The data can be analyzed categorically, and numerically. Categorically, the dairy industry uses a threshold of >200,000 cells/ml as an indication of mastitis, even if sub-clinical. Milk from cows vaccinated with placebo were above 200,000 SCC/ml 25.4% of the time, while milk from cows vaccinated with the *Klebsiella* pneumoniae 1571 vaccine were above this level only 11.7% of the time. The 54% reduction in the prevalence of clinically-significant SCC in *Klebsiella pneumoniae* 1571 vaccine group was highly statistically significant (P=0.0000). Quantitative comparison of SCC between groups shows an overall reduction of SCC in vaccinates of 42% which was also highly significant (P=0.0000; Appendix C). The reduction in SCC among vaccinated cows is consistent with the decreased clinical mastitis and provides insight to explain the increased milk production which may be attributable to not only clinical coliform mastitis, but also sub-clinical coliform mastitis.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising:

an isolated protein comprising an amino acid sequence that has at least 80% identity with SEQ ID NO:41 and an isolated protein comprising an amino acid sequence that has at least 80% identity with SEQ ID NO:42;

an effective amount of an adjuvant; and
a pharmaceutically acceptable carrier.

2. The composition of claim 1 further comprising a protein comprising an amino acid sequence that has at least 80% identity with SEQ ID NO:45, SEQ ID NO: 46, SEQ ID NO:49, SEQ ID NO:51, SEQ ID NO:52, SEQ ID NO:53, SEQ ID NO:58, SEQ ID NO: 61, or SEQ ID NO:64.

* * * * *